(12) United States Patent
Chiang et al.

(10) Patent No.: US 12,616,445 B2
(45) Date of Patent: May 5, 2026

(54) PORTABLE ULTRASOUND SYSTEM

(71) Applicant: Teratech Corporation, Burlington, MA (US)

(72) Inventors: Alice M. Chiang, Wayland, MA (US); Noah Berger, Sudbury, MA (US)

(73) Assignee: Teratech Corporation, Burlington, MA (US)

( * ) Notice: Subject to any disclaimer, the term of this patent is extended or adjusted under 35 U.S.C. 154(b) by 876 days.

(21) Appl. No.: 16/461,581

(22) PCT Filed: Nov. 16, 2017

(86) PCT No.: PCT/US2017/062109
§ 371 (c)(1),
(2) Date: May 16, 2019

(87) PCT Pub. No.: WO2018/094118
PCT Pub. Date: May 24, 2018

(65) Prior Publication Data
US 2019/0365350 A1      Dec. 5, 2019

Related U.S. Application Data

(60) Provisional application No. 62/565,846, filed on Sep. 29, 2017, provisional application No. 62/422,808, filed on Nov. 16, 2016.

(51) Int. Cl.
*A61B 8/00*        (2006.01)
*A61B 8/12*        (2006.01)
(Continued)

(52) U.S. Cl.
CPC .......... *A61B 8/4427* (2013.01); *A61B 8/4433* (2013.01); *A61B 8/461* (2013.01);
(Continued)

(58) Field of Classification Search
CPC ..... A61B 8/4427; A61B 8/4433; A61B 8/461; A61B 8/469; A61B 8/12; A61B 8/488;
(Continued)

(56) References Cited

U.S. PATENT DOCUMENTS 4,702,258 A      10/1987   Nicolas et al.
4,727,376 A      2/1988    Prenat
(Continued)

FOREIGN PATENT DOCUMENTS

CA        2902224 A1      9/2014
CN        1759327 A       4/2006
(Continued)

OTHER PUBLICATIONS

U.S. Appl. No. 17/520,150, filed Nov. 5, 2021, Pending.
(Continued)

*Primary Examiner* — Sanjay Cattungal
(74) *Attorney, Agent, or Firm* — McCarter & English, LLP

(57)        ABSTRACT

Exemplary embodiments provide systems and methods for portable medical ultrasound imaging. Preferred embodiments utilize a hand portable, battery powered system having a display and a user interface operative to control imaging and display operations. A keyboard control panel can be used alone or in combination with touchscreen controls to actuate a graphical user interface. Exemplary embodiments also provide an ultrasound engine circuit board including one or more multi-chip modules, and a portable medical ultrasound imaging system including an ultrasound engine circuit board.

36 Claims, 84 Drawing Sheets

(51) Int. Cl.

| | |
|---|---|
| *G06F 3/0481* | (2022.01) |
| *G06F 3/04842* | (2022.01) |
| *H10W 72/00* | (2026.01) |
| *H10W 74/00* | (2026.01) |
| *H10W 90/00* | (2026.01) |

(52) U.S. Cl.
CPC ............... *A61B 8/469* (2013.01); *A61B 8/12* (2013.01); *A61B 8/488* (2013.01); *G06F 3/0481* (2013.01); *G06F 3/04842* (2013.01); *H10W 72/884* (2026.01); *H10W 74/00* (2026.01); *H10W 90/732* (2026.01); *H10W 90/756* (2026.01)

(58) Field of Classification Search
CPC ..... A61B 8/4405; A61B 8/465; G06F 3/0481; G06F 3/04842; G06F 3/04886; H01L 2224/32145; H01L 2224/48247; H01L 2224/73265; H01L 2924/181; H01L 2224/32245; H01L 2224/48091
See application file for complete search history.

(56) References Cited

U.S. PATENT DOCUMENTS

| | | | |
|---|---|---|---|
| 4,991,604 A | | 2/1991 | Wurster et al. |
| 5,170,791 A | | 12/1992 | Boos et al. |
| 5,311,095 A | | 5/1994 | Smith et al. |
| 5,381,794 A | | 1/1995 | Tei et al. |
| 5,465,095 A | | 11/1995 | Bryant |
| 5,487,388 A | | 1/1996 | Rello et al. |
| 5,598,845 A | | 2/1997 | Chandraratna et al. |
| 5,653,236 A | | 8/1997 | Miller |
| 5,690,114 A | | 11/1997 | Chiang et al. |
| 5,722,411 A | | 3/1998 | Suzuki et al. |
| 5,735,797 A | | 4/1998 | Muzilla et al. |
| 5,844,140 A | | 12/1998 | Seale |
| 5,904,652 A | | 5/1999 | Gilbert et al. |
| 5,957,846 A | | 9/1999 | Chiang et al. |
| 5,964,709 A | | 10/1999 | Chiang et al. |
| 6,059,727 A | | 5/2000 | Fowlkes et al. |
| 6,063,030 A | * | 5/2000 | Vara ....................... A61B 8/465 |
| | | | 600/440 |
| 6,095,980 A | | 8/2000 | Burns et al. |
| 6,106,472 A | | 8/2000 | Chiang et al. |
| 6,111,816 A | | 8/2000 | Chiang et al. |
| 6,126,601 A | | 10/2000 | Gilling |
| 6,126,608 A | | 10/2000 | Kemme et al. |
| 6,131,459 A | | 10/2000 | Seale et al. |
| 6,139,501 A | | 10/2000 | Roundhill et al. |
| 6,146,331 A | | 11/2000 | Wong |
| 6,238,344 B1 | | 5/2001 | Gamelsky et al. |
| 6,248,073 B1 | | 6/2001 | Gilbert et al. |
| 6,261,234 B1 | | 7/2001 | Lin |
| 6,371,918 B1 | | 4/2002 | Bunce |
| 6,417,797 B1 | | 7/2002 | Cousins et al. |
| 6,417,857 B2 | | 7/2002 | Finger et al. |
| 6,425,865 B1 | | 7/2002 | Salcudean et al. |
| 6,436,040 B1 | | 8/2002 | Collamore et al. |
| 6,447,451 B1 | | 9/2002 | Wing et al. |
| 6,450,958 B1 | | 9/2002 | Linkhart et al. |
| 6,468,212 B1 | | 10/2002 | Scott et al. |
| 6,500,122 B1 | | 12/2002 | Washburn et al. |
| 6,500,126 B1 | | 12/2002 | Brock-Fisher |
| 6,516,667 B1 | | 2/2003 | Broad et al. |
| 6,519,632 B1 | | 2/2003 | Brackett et al. |
| 6,520,912 B1 | | 2/2003 | Brooks et al. |
| 6,530,887 B1 | | 3/2003 | Gilbert et al. |
| 6,540,682 B1 | | 4/2003 | Leavitt et al. |
| 6,558,326 B2 | | 5/2003 | Pelissier |
| 6,569,102 B2 | | 5/2003 | Imran et al. |
| 6,575,908 B2 | | 6/2003 | Barnes et al. |
| 6,599,256 B1 | | 7/2003 | Acker et al. |
| 6,603,494 B1 | | 8/2003 | Banks et al. |

| | | | |
|---|---|---|---|
| 6,638,226 B2 | | 10/2003 | He et al. |
| 6,648,825 B1 | | 11/2003 | Mesaros et al. |
| 6,663,567 B2 | | 12/2003 | Ji et al. |
| 6,669,633 B2 | | 12/2003 | Brodsky et al. |
| 6,682,483 B1 | | 1/2004 | Abend et al. |
| 6,689,055 B1 | | 2/2004 | Mullen et al. |
| 6,709,391 B2 | | 3/2004 | Mesaros et al. |
| 6,719,698 B2 | | 4/2004 | Manor et al. |
| 6,760,755 B1 | | 7/2004 | Brackett |
| 6,761,689 B2 | | 7/2004 | Salgo et al. |
| 6,980,419 B2 | | 12/2005 | Smith et al. |
| 7,022,075 B2 | | 4/2006 | Grunwald et al. |
| 7,115,093 B2 | | 10/2006 | Halmann et al. |
| 7,223,242 B2 | | 5/2007 | He et al. |
| 7,338,450 B2 | | 3/2008 | Kristoffersen et al. |
| 7,352,570 B2 | | 4/2008 | Smith et al. |
| 7,457,672 B2 | | 11/2008 | Katsman et al. |
| 7,604,601 B2 | | 10/2009 | Altmann et al. |
| 7,736,313 B2 | | 6/2010 | Luo et al. |
| 7,736,314 B2 | | 6/2010 | Beach et al. |
| 7,794,398 B2 | | 9/2010 | Salgo |
| 7,927,280 B2 | | 4/2011 | Davidsen |
| 8,012,092 B2 | | 9/2011 | Powers et al. |
| 8,128,563 B2 | | 3/2012 | Kristoffersen |
| 8,172,753 B2 | | 5/2012 | Halmann |
| 8,214,011 B2 | | 7/2012 | Friedman et al. |
| 8,235,903 B2 | | 8/2012 | Abraham |
| 8,241,220 B2 | | 8/2012 | Wilser et al. |
| 8,319,770 B2 | | 11/2012 | Friedman et al. |
| 8,357,094 B2 | | 1/2013 | Mo et al. |
| 8,394,023 B2 | | 3/2013 | Friedman et al. |
| 8,409,095 B1 | | 4/2013 | Marquis |
| 8,435,183 B2 | | 5/2013 | Barnes et al. |
| 8,659,507 B2 | | 2/2014 | Roncalez et al. |
| 8,925,386 B2 | | 1/2015 | Oshiki |
| 9,033,879 B2 | | 5/2015 | Urness et al. |
| 9,072,471 B2 | | 7/2015 | Kato et al. |
| 9,113,825 B2 | | 8/2015 | Chaggares et al. |
| 9,163,980 B2 | | 10/2015 | Herzog et al. |
| 9,173,639 B2 | | 11/2015 | Ichioka et al. |
| 9,198,680 B2 | | 12/2015 | Fraser et al. |
| 9,220,478 B2 | | 12/2015 | Smith et al. |
| 9,301,730 B2 | | 4/2016 | Poland |
| 9,314,225 B2 | | 4/2016 | Steen et al. |
| 9,327,142 B2 | | 5/2016 | Rothberg et al. |
| 9,351,706 B2 | | 5/2016 | Rothberg et al. |
| 9,386,964 B2 | | 7/2016 | Bagge |
| 9,460,499 B2 | | 10/2016 | McLaughlin et al. |
| 9,492,144 B1 | | 11/2016 | Chen et al. |
| 9,504,448 B2 | | 11/2016 | Cheng et al. |
| 9,597,008 B2 | | 3/2017 | Henkel et al. |
| 9,667,889 B2 | | 5/2017 | Rothberg |
| 9,848,849 B2 | | 12/2017 | Pfeiffer et al. |
| 9,877,699 B2 | | 1/2018 | Chiang et al. |
| 9,962,143 B2 | | 5/2018 | Funakubo |
| 9,983,905 B2 | | 5/2018 | Tobias et al. |
| 9,986,972 B2 | | 6/2018 | Halmann et al. |
| RE46,931 E | | 7/2018 | McLaughlin et al. |
| 10,014,871 B2 | | 7/2018 | Chen et al. |
| 10,082,488 B2 | | 9/2018 | Chen et al. |
| 10,426,430 B2 | | 10/2019 | Zagorchev et al. |
| 10,580,528 B2 | | 3/2020 | McLaughlin et al. |
| 10,667,790 B2 | | 6/2020 | Chiang et al. |
| 10,856,847 B2 | | 12/2020 | Rothberg et al. |
| 11,287,309 B2 | | 3/2022 | Schmid et al. |
| 11,660,003 B2 | | 5/2023 | Schmid |
| 11,865,287 B2 | | 1/2024 | Ignon et al. |
| 12,102,480 B2 | | 10/2024 | Chiang et al. |
| 12,115,023 B2 | | 10/2024 | Chiang et al. |
| 2002/0087061 A1 | | 7/2002 | Lifshitz et al. |
| 2002/0120193 A1 | | 8/2002 | Chiang et al. |
| 2002/0154727 A1 | | 10/2002 | Ning |
| 2002/0173721 A1 | | 11/2002 | Grunwald et al. |
| 2003/0013959 A1 | | 1/2003 | Grunwald et al. |
| 2003/0078501 A1 | | 4/2003 | Barnes et al. |
| 2003/0088182 A1 | | 5/2003 | He et al. |
| 2003/0097071 A1 | | 5/2003 | Halmann et al. |
| 2003/0139664 A1 | | 7/2003 | Hunt et al. |
| 2003/0195418 A1 | | 10/2003 | Barnes et al. |

(56) References Cited

U.S. PATENT DOCUMENTS

| | | |
|---|---|---|
| 2003/0212327 A1 | 11/2003 | Wang et al. |
| 2004/0015079 A1 | 1/2004 | Berger et al. |
| 2004/0059220 A1 | 3/2004 | Mourad et al. |
| 2004/0138569 A1 | 7/2004 | Grunwald et al. |
| 2004/0147840 A1* | 7/2004 | Duggirala ............ G06T 7/0012 |
| | | 600/437 |
| 2004/0150963 A1 | 8/2004 | Holmberg et al. |
| 2004/0152982 A1 | 8/2004 | Hwang et al. |
| 2004/0152986 A1 | 8/2004 | Fidel et al. |
| 2004/0158154 A1 | 8/2004 | Hanafy et al. |
| 2004/0193042 A1 | 9/2004 | Scampini et al. |
| 2005/0085730 A1 | 4/2005 | Flesch et al. |
| 2005/0101864 A1 | 5/2005 | Zheng et al. |
| 2005/0113690 A1 | 5/2005 | Halmann et al. |
| 2005/0119574 A1 | 6/2005 | Maerfeld et al. |
| 2005/0281444 A1 | 12/2005 | Lundberg et al. |
| 2006/0020204 A1 | 1/2006 | Serra et al. |
| 2006/0020206 A1 | 1/2006 | Serra et al. |
| 2006/0058609 A1 | 3/2006 | Olstad |
| 2006/0173326 A1 | 8/2006 | Thiele |
| 2007/0139873 A1 | 6/2007 | Thomas et al. |
| 2007/0140424 A1 | 6/2007 | Serceki |
| 2007/0161905 A1 | 7/2007 | Munrow |
| 2007/0167709 A1 | 7/2007 | Slayton et al. |
| 2007/0211064 A1 | 9/2007 | Buck et al. |
| 2007/0265531 A1 | 11/2007 | He et al. |
| 2008/0055826 A1 | 3/2008 | Smith et al. |
| 2008/0108899 A1 | 5/2008 | Halmann et al. |
| 2008/0119731 A1 | 5/2008 | Becerra et al. |
| 2008/0146922 A1 | 6/2008 | Steins et al. |
| 2008/0161686 A1 | 7/2008 | Halmann |
| 2008/0161688 A1 | 7/2008 | Poland et al. |
| 2008/0172383 A1 | 7/2008 | Lea et al. |
| 2008/0208047 A1 | 8/2008 | Delso |
| 2008/0208061 A1 | 8/2008 | Halmann |
| 2008/0215982 A1 | 9/2008 | Washburn et al. |
| 2008/0249414 A1 | 10/2008 | Yang et al. |
| 2008/0253589 A1 | 10/2008 | Trahms |
| 2008/0319316 A1 | 12/2008 | Powers et al. |
| 2009/0012401 A1 | 1/2009 | Steinbacher |
| 2009/0043195 A1 | 2/2009 | Poland |
| 2009/0054781 A1 | 2/2009 | Stonefield et al. |
| 2009/0099453 A1 | 4/2009 | Kristoffersen |
| 2009/0125840 A1 | 5/2009 | Squilla et al. |
| 2009/0131793 A1 | 5/2009 | Stonefield et al. |
| 2009/0177086 A1 | 7/2009 | Steen |
| 2009/0198132 A1 | 8/2009 | Pelissier et al. |
| 2009/0275835 A1 | 11/2009 | Hwang et al. |
| 2010/0022890 A1 | 1/2010 | Fukukita et al. |
| 2010/0094132 A1 | 4/2010 | Hansen et al. |
| 2010/0145195 A1 | 6/2010 | Hyun |
| 2010/0160787 A1 | 6/2010 | Gorzitze |
| 2010/0174189 A1 | 7/2010 | Abraham |
| 2010/0179428 A1 | 7/2010 | Pedersen et al. |
| 2010/0217123 A1 | 8/2010 | Eran et al. |
| 2010/0217128 A1 | 8/2010 | Betts |
| 2010/0305444 A1 | 12/2010 | Fujii et al. |
| 2011/0050594 A1 | 3/2011 | Kim et al. |
| 2011/0099513 A1 | 4/2011 | Ameline |
| 2011/0112399 A1* | 5/2011 | Willems ................ F16M 13/04 |
| | | 600/437 |
| 2011/0125022 A1 | 5/2011 | Lazebnik |
| 2011/0202889 A1 | 8/2011 | Ludwig et al. |
| 2011/0218436 A1 | 9/2011 | Dewey et al. |
| 2011/0230764 A1 | 9/2011 | Baba et al. |
| 2011/0237948 A1 | 9/2011 | Corn |
| 2011/0313292 A1 | 12/2011 | Kwak et al. |
| 2012/0010508 A1 | 1/2012 | Sokulin et al. |
| 2012/0029303 A1 | 2/2012 | Shaya |
| 2012/0053463 A1 | 3/2012 | Yoo |
| 2012/0065513 A1 | 3/2012 | Lee |
| 2012/0078108 A1 | 3/2012 | Kim et al. |
| 2012/0089024 A1 | 4/2012 | Hong |
| 2012/0095342 A1 | 4/2012 | Lee |
| 2012/0101378 A1 | 4/2012 | Lee |
| 2012/0108962 A1 | 5/2012 | Yoon |
| 2012/0108964 A1 | 5/2012 | Lee et al. |
| 2012/0112605 A1 | 5/2012 | Kim |
| 2012/0130244 A1 | 5/2012 | Kim |
| 2012/0133601 A1 | 5/2012 | Marshall et al. |
| 2012/0136252 A1 | 5/2012 | Cho |
| 2012/0136254 A1 | 5/2012 | Kim |
| 2012/0157836 A1 | 6/2012 | Kim |
| 2012/0157844 A1 | 6/2012 | Halmann |
| 2012/0157847 A1 | 6/2012 | Kim |
| 2012/0157848 A1 | 6/2012 | Kim |
| 2012/0179037 A1 | 7/2012 | Halmann |
| 2012/0179038 A1 | 7/2012 | Meurer et al. |
| 2012/0184849 A1 | 7/2012 | Sandstrom et al. |
| 2012/0190984 A1 | 7/2012 | Kim et al. |
| 2012/0209107 A1 | 8/2012 | Guo et al. |
| 2012/0215108 A1 | 8/2012 | Park et al. |
| 2012/0220873 A1 | 8/2012 | Hyun |
| 2012/0232399 A1 | 9/2012 | Lee |
| 2012/0265027 A1 | 10/2012 | Lee et al. |
| 2012/0265074 A1 | 10/2012 | Na et al. |
| 2012/0288172 A1 | 11/2012 | Perrey et al. |
| 2012/0289828 A1 | 11/2012 | Jensen et al. |
| 2012/0302883 A1 | 11/2012 | Kong et al. |
| 2012/0316444 A1 | 12/2012 | Shim et al. |
| 2013/0018265 A1 | 1/2013 | Kim et al. |
| 2013/0019193 A1 | 1/2013 | Rhee et al. |
| 2013/0072795 A1 | 3/2013 | Mo et al. |
| 2013/0072797 A1 | 3/2013 | Lee |
| 2013/0079627 A1 | 3/2013 | Lee |
| 2013/0144169 A1 | 6/2013 | Lee et al. |
| 2013/0144194 A1 | 6/2013 | Ahn et al. |
| 2013/0165783 A1 | 6/2013 | Kim et al. |
| 2013/0184578 A1 | 7/2013 | Lee et al. |
| 2013/0190624 A1 | 7/2013 | Beger et al. |
| 2013/0202169 A1 | 8/2013 | Lee et al. |
| 2013/0202174 A1 | 8/2013 | Lee |
| 2013/0218014 A1 | 8/2013 | Shim et al. |
| 2013/0218024 A1 | 8/2013 | Boctor et al. |
| 2013/0226001 A1 | 8/2013 | Steen et al. |
| 2013/0226004 A1 | 8/2013 | Lee |
| 2013/0237811 A1 | 9/2013 | Mihailescu et al. |
| 2013/0237824 A1 | 9/2013 | Kim |
| 2013/0237828 A1 | 9/2013 | Lee et al. |
| 2013/0239052 A1 | 9/2013 | Moody et al. |
| 2013/0245449 A1 | 9/2013 | Barnes et al. |
| 2013/0253316 A1 | 9/2013 | Choi |
| 2013/0253323 A1 | 9/2013 | Kim |
| 2013/0261434 A1 | 10/2013 | Kim et al. |
| 2013/0261448 A1 | 10/2013 | Hyun et al. |
| 2013/0261459 A1 | 10/2013 | Na et al. |
| 2013/0320485 A1 | 12/2013 | Ching Tee et al. |
| 2013/0324850 A1 | 12/2013 | Petruzzelli et al. |
| 2013/0328810 A1 | 12/2013 | Li et al. |
| 2013/0331694 A1 | 12/2013 | Barnes et al. |
| 2014/0005550 A1 | 1/2014 | Lu et al. |
| 2014/0009686 A1 | 1/2014 | Segal |
| 2014/0039277 A1 | 2/2014 | Abraham |
| 2014/0051984 A1 | 2/2014 | Berger et al. |
| 2014/0100440 A1 | 4/2014 | Cheline et al. |
| 2014/0107435 A1 | 4/2014 | Sharf et al. |
| 2014/0111451 A1 | 4/2014 | Park et al. |
| 2014/0114190 A1 | 4/2014 | Chiang et al. |
| 2014/0114194 A1 | 4/2014 | Kanayama et al. |
| 2014/0121524 A1* | 5/2014 | Chiang ................ A61B 8/0891 |
| | | 600/459 |
| 2014/0164965 A1 | 6/2014 | Lee et al. |
| 2014/0180111 A1 | 6/2014 | Gopinathan et al. |
| 2014/0187934 A1 | 7/2014 | Urness |
| 2014/0187946 A1 | 7/2014 | Miller et al. |
| 2014/0194742 A1 | 7/2014 | Sundaran Baby Sarojam et al. |
| 2014/0200452 A1 | 7/2014 | Chang et al. |
| 2014/0200456 A1 | 7/2014 | Owen |
| 2014/0237811 A1 | 8/2014 | Guercioni |
| 2014/0243614 A1 | 8/2014 | Rothberg et al. |
| 2014/0243669 A1 | 8/2014 | Halmann et al. |
| 2014/0257104 A1 | 9/2014 | Dunbar et al. |
| 2014/0275976 A1 | 9/2014 | Moro |
| 2014/0296711 A1 | 10/2014 | Lee |

US 12,616,445 B2

Page 4

(56) References Cited

U.S. PATENT DOCUMENTS

| | | | |
|---|---|---|---|
| 2014/0300720 A1 | 10/2014 | Rothberg |
| 2014/0378835 A1 | 12/2014 | Satoh et al. |
| 2015/0087982 A1 | 3/2015 | Mullick et al. |
| 2015/0094587 A1 | 4/2015 | Chen et al. |
| 2015/0173723 A1 | 6/2015 | Bates et al. |
| 2015/0182197 A1 | 7/2015 | Willems et al. |
| 2015/0238168 A1 | 8/2015 | Poland |
| 2015/0265252 A1 | 9/2015 | Chu et al. |
| 2015/0313578 A1 | 11/2015 | Yu et al. |
| 2015/0366536 A1 | 12/2015 | Courtney et al. |
| 2016/0110875 A1 | 4/2016 | Sugiyama et al. |
| 2016/0135786 A1 | 5/2016 | Mullen et al. |
| 2016/0174937 A1 | 6/2016 | Bakshi et al. |
| 2016/0228091 A1 | 8/2016 | Chiang et al. |
| 2016/0278739 A1 | 9/2016 | Pelissier et al. |
| 2016/0287214 A1 | 10/2016 | Ralovich et al. |
| 2017/0000464 A1 | 1/2017 | Chang et al. |
| 2017/0020483 A1 | 1/2017 | He et al. |
| 2017/0020490 A1 | 1/2017 | Ryu et al. |
| 2017/0028227 A1 | 2/2017 | Emery et al. |
| 2017/0055951 A1 | 3/2017 | Messina et al. |
| 2017/0079551 A1 | 3/2017 | Henkel et al. |
| 2017/0095228 A1 | 4/2017 | Richard et al. |
| 2017/0095230 A1 | 4/2017 | Richard et al. |
| 2017/0095231 A1 | 4/2017 | Richard et al. |
| 2017/0105700 A1 | 4/2017 | Bar-Zion et al. |
| 2017/0124700 A1 | 5/2017 | Sarojam et al. |
| 2017/0143307 A1 | 5/2017 | Tahmasebi Maraghoosh |
| 2017/0150948 A1 | 6/2017 | Kanayama |
| 2017/0249744 A1 | 8/2017 | Wang et al. |
| 2017/0360397 A1 | 12/2017 | Rothberg et al. |
| 2017/0360403 A1* | 12/2017 | Rothberg ............... A61B 8/065 |
| 2017/0360412 A1 | 12/2017 | Rothberg et al. |
| 2018/0085043 A1 | 3/2018 | Panicker et al. |
| 2018/0085090 A1 | 3/2018 | Park et al. |
| 2018/0125460 A1 | 5/2018 | Perrey et al. |
| 2018/0168548 A1 | 6/2018 | Chiang et al. |
| 2018/0182096 A1 | 6/2018 | Grady et al. |
| 2018/0365808 A1 | 12/2018 | Jiang et al. |
| 2019/0046158 A1 | 2/2019 | Kroon et al. |
| 2019/0086525 A1 | 3/2019 | Chen et al. |
| 2019/0156526 A1 | 5/2019 | Liu et al. |
| 2019/0196600 A1 | 6/2019 | Rothberg et al. |
| 2019/0336101 A1 | 11/2019 | Chiang et al. |
| 2020/0000428 A1 | 1/2020 | Kim et al. |
| 2020/0268351 A1 | 8/2020 | Chiang et al. |
| 2020/0383658 A1 | 12/2020 | Wang et al. |
| 2021/0015456 A1 | 1/2021 | Chiang et al. |
| 2022/0015741 A1 | 1/2022 | Amador Carrascal et al. |
| 2022/0125407 A1 | 4/2022 | Chiang et al. |
| 2022/0304661 A1 | 9/2022 | Chiang et al. |
| 2025/0195037 A1 | 6/2025 | Chiang et al. |
| 2025/0213221 A1 | 7/2025 | Chiang et al. |

FOREIGN PATENT DOCUMENTS

| | | | |
|---|---|---|---|
| CN | 101390778 A | 3/2009 |
| CN | 102178547 A | 9/2011 |
| CN | 102525556 A | 7/2012 |
| CN | 102626324 A | 8/2012 |
| CN | 102636787 A | 8/2012 |
| CN | 101742968 B | 1/2013 |
| CN | 102872542 A | 1/2013 |
| CN | 102930170 A | 2/2013 |
| CN | 102940507 A | 2/2013 |
| CN | 102988043 A | 3/2013 |
| CN | 101677805 B | 5/2013 |
| CN | 103140175 A | 6/2013 |
| CN | 103876781 A | 6/2014 |
| CN | 105611877 A | 5/2016 |
| EP | 1016875 A2 | 7/2000 |
| EP | 1239396 A2 | 9/2002 |
| EP | 1589878 B1 | 10/2009 |
| EP | 2422705 A1 | 2/2012 |
| EP | 2425784 A1 | 3/2012 |
| EP | 2453256 A2 | 5/2012 |
| EP | 2455753 A2 | 5/2012 |
| EP | 2468191 A1 | 6/2012 |
| EP | 2575628 A2 | 4/2013 |
| EP | 2599442 A1 | 6/2013 |
| EP | 2605035 A2 | 6/2013 |
| EP | 2637166 A2 | 9/2013 |
| EP | 2023820 B1 | 3/2019 |
| EP | 2967486 B1 | 7/2020 |
| JP | 62-97539 A | 5/1987 |
| JP | 10-73658 A | 3/1998 |
| JP | H11-508461 A | 7/1999 |
| JP | 2003-190159 A | 7/2003 |
| JP | 2004-530463 A | 10/2004 |
| JP | 2005-137747 A | 6/2005 |
| JP | 2006-68524 A | 3/2006 |
| JP | 2008-18107 A | 1/2008 |
| JP | 2008-515583 A | 5/2008 |
| JP | 2008-536555 A | 9/2008 |
| JP | 2009-45081 A | 3/2009 |
| JP | 2009-119259 A | 6/2009 |
| JP | 2009-525538 A | 7/2009 |
| JP | 2009-183720 A | 8/2009 |
| JP | 2009-240779 A | 10/2009 |
| JP | 2010-131396 A | 6/2010 |
| JP | 2010-220218 A | 9/2010 |
| JP | 2011-72746 A | 4/2011 |
| JP | 2011-87949 A | 5/2011 |
| JP | 2011-104079 A | 6/2011 |
| JP | 2011-200482 A | 10/2011 |
| JP | 2012-24133 A | 2/2012 |
| JP | 2012-101075 A | 5/2012 |
| JP | 2013-043082 A | 3/2013 |
| JP | 2013-111203 A | 6/2013 |
| JP | 2013-172959 A | 9/2013 |
| JP | 2013-188328 A | 9/2013 |
| JP | 2015-515312 A | 5/2015 |
| JP | 2016-087020 A | 5/2016 |
| KR | 20120043642 A | 5/2012 |
| KR | 20120047785 A | 5/2012 |
| KR | 20120071319 A | 7/2012 |
| KR | 20120097324 A | 9/2012 |
| KR | 20120117714 A | 10/2012 |
| KR | 20120137206 A | 12/2012 |
| KR | 20120138478 A | 12/2012 |
| KR | 20130011793 A | 1/2013 |
| KR | 20130012501 A | 2/2013 |
| KR | 20130012844 A | 2/2013 |
| KR | 20130020035 A | 2/2013 |
| KR | 20130020054 A | 2/2013 |
| KR | 20130020371 A | 2/2013 |
| KR | 20130022249 A | 3/2013 |
| KR | 20130026041 A | 3/2013 |
| KR | 20130030663 A | 3/2013 |
| KR | 20130033717 A | 4/2013 |
| KR | 20130036327 A | 4/2013 |
| KR | 101269459 B1 | 5/2013 |
| KR | 20130043702 A | 5/2013 |
| KR | 20130054013 A | 5/2013 |
| KR | 20130056676 A | 5/2013 |
| KR | 101273585 B1 | 6/2013 |
| KR | 20130059307 A | 6/2013 |
| KR | 20130060007 A | 6/2013 |
| KR | 20130066821 A | 6/2013 |
| KR | 20130074398 A | 7/2013 |
| KR | 20130074399 A | 7/2013 |
| KR | 20130075458 A | 7/2013 |
| KR | 20130075465 A | 7/2013 |
| KR | 20130075472 A | 7/2013 |
| KR | 20130075477 A | 7/2013 |
| KR | 20130075481 A | 7/2013 |
| KR | 20130075486 A | 7/2013 |
| KR | 20130076031 A | 7/2013 |
| KR | 20130076042 A | 7/2013 |
| KR | 20130076054 A | 7/2013 |
| KR | 20130076064 A | 7/2013 |
| KR | 20130076071 A | 7/2013 |
| KR | 20130076404 A | 7/2013 |
| KR | 20130076428 A | 7/2013 |

(56) References Cited

FOREIGN PATENT DOCUMENTS

| | | | |
|---|---|---|---|
| KR | 20130077118 A | 7/2013 |
| KR | 20130077121 A | 7/2013 |
| KR | 20130077406 A | 7/2013 |
| KR | 20130078935 A | 7/2013 |
| KR | 20130078972 A | 7/2013 |
| KR | 20130080640 A | 7/2013 |
| KR | 20130081067 A | 7/2013 |
| KR | 20130081626 A | 7/2013 |
| KR | 20130081684 A | 7/2013 |
| KR | 20130082267 A | 7/2013 |
| KR | 20130083725 A | 7/2013 |
| KR | 20130084049 A | 7/2013 |
| KR | 20130087291 A | 8/2013 |
| KR | 20130087478 | 8/2013 |
| KR | 20130088478 A | 8/2013 |
| KR | 20130089037 A | 8/2013 |
| KR | 20130090038 A | 8/2013 |
| KR | 20130094671 A | 8/2013 |
| KR | 20130095160 A | 8/2013 |
| KR | 20130095236 A | 8/2013 |
| KR | 20130095505 A | 8/2013 |
| TW | I378255 | 12/2012 |
| TW | I380014 | 12/2012 |
| TW | I406684 | 9/2013 |
| WO | 2000/31634 A1 | 6/2000 |
| WO | WO-2002/068992 A2 | 9/2002 |
| WO | 2003/027662 A2 | 4/2003 |
| WO | WO-2003/075769 A1 | 9/2003 |
| WO | 2005/058168 A2 | 6/2005 |
| WO | WO-2005/053664 A2 | 6/2005 |
| WO | 2006/030378 A1 | 3/2006 |
| WO | WO-2006/040697 A1 | 4/2006 |
| WO | 2006/111872 A2 | 10/2006 |
| WO | 2006/111874 A2 | 10/2006 |
| WO | WO-2006/111871 A1 | 10/2006 |
| WO | WO-2008/069021 A1 | 6/2008 |
| WO | WO-2008/115312 A2 | 9/2008 |
| WO | 2008/146208 A2 | 12/2008 |
| WO | WO-2009/129845 A1 | 10/2009 |
| WO | WO-2010/020939 A2 | 2/2010 |
| WO | 2010/032151 A1 | 3/2010 |
| WO | WO-2010/042282 A1 | 4/2010 |
| WO | WO-2010/051587 A1 | 5/2010 |
| WO | WO-2012/091518 A2 | 7/2012 |
| WO | 2012/101511 A2 | 8/2012 |
| WO | WO-2012/141550 A2 | 10/2012 |
| WO | WO-2013/030746 A1 | 3/2013 |
| WO | WO-2013/034175 A1 | 3/2013 |
| WO | WO-2013/055707 A1 | 4/2013 |
| WO | WO-2013/095032 A1 | 6/2013 |
| WO | WO-2013/122320 A1 | 8/2013 |
| WO | WO-2013/148730 A2 | 10/2013 |
| WO | WO-2013/162244 A1 | 10/2013 |
| WO | WO-2014/003404 A1 | 1/2014 |
| WO | WO-2014/014965 A1 | 1/2014 |
| WO | 2014/035567 A1 | 3/2014 |
| WO | WO-2014/134316 A1 | 9/2014 |
| WO | WO-2015/048327 A2 | 4/2015 |
| WO | WO-2015/114484 A1 | 8/2015 |
| WO | 2015/161157 A1 | 10/2015 |
| WO | WO-2016/001865 A1 | 1/2016 |
| WO | WO-2016/083985 A1 | 6/2016 |
| WO | 2016/149881 A1 | 9/2016 |
| WO | WO-2017/013511 A1 | 1/2017 |
| WO | 2017/096020 A1 | 6/2017 |
| WO | WO-2017/222970 A1 | 12/2017 |

OTHER PUBLICATIONS alibaba.com, Chison SonoTouch 10 B&W HAndled Ultrasound Tablet With CE FDA. Shaanxi Aipu Medical Instrument Co., Ltd. 6 pages, (2014).

Basoglu et al., Applications of a next-generation programmable ultrasound machine. Proceedings SPIE Medical Imaging. 1 page, Abstract 3031, May 7, 1997.

Basoglu et al., Computing requirements of modern medical diagnostic ultrasound machines. Parallel Computing. Sep. 1998;24(9-10):1407-1431.

Brattain LJ et al. Machine learning for medical ultrasound: status, methods, and future opportunities. Abdominal Radiology. Apr. 1, 2018;43(4):786-99.

Chison Medical Imaging Co., Ltd., Premarket Notification [510(k)] Summary. Sono Touch Series Diagnostic Ultrasound System. 11 pages, Aug. 2, 2012.

Esaote, MyLab Ultrasound Scanners, Dicom Conformance Statement, Document Version 6.3. May 21, 2010. 277 pages.

Esaote, MyLab Ultrasound Scanners, Dicom Conformance Statement, Document Version 6.5. Jul. 19, 2011. 278 pages.

Esaote, MyLab Ultrasound Scanners, Dicom Conformance Statement, Document Version 6.6. Mar. 1, 2012. 278 pages.

Felix et al., Biplane ultrasound arrays with integrated multiplexing solution for enhanced diagnostic accuracy in endorectal and transvaginal imaging. IEEE Ultrasonics Symposium, Sep. 18, 2005;4:2251-2254.

GE Healthcare Venue 40 Basic User Manual, Technical Publications Direction 5265930-100, Rev. 5. 288 pages (2008-2010).

Gray et al., Ultrasound-guided Regional Anesthesia, Current State of the Art. Anesthesiology. Feb. 2006;104:368-73.

Karadayi et al., Software-based Ultrasound Beamforming on Multi-core DSPs. IEEE International Ultrasonics. Oct. 18-21, 2011, 14 pages.

Khuri-Yakub et al., Capacitive micromachined ultrasonic transducers for medical imaging and therapy. J Micromech Microeng. May 2011;21(5):54004, 11 pages.

NanoMaxx Ultrasound System—Sonosite—User Guide. 100 pages (2010).

Soma, Access Systems, Introducing AxoTrack™ Needle visualization as you've never seen it. Retrieved online at: SomaAccessSystems. com, 6 pages.

SonoTouch, The Revolution is at Hand, catalog. Retrieved online at: www.sonatouch.com. 4 pages.

SonoTouch, The Revolution is at Hand, SonoTouch 20 Operation Manual. 68 pages.

Stolka et al., Needle guidance using handheld stereo vision and projection for ultrasound-based interventions. Med Image Comput Comput Assist Interv. 2014;17(Pt 2):684-91.

Wygant et al., Beamforming and hardware design for a multichannel front-end integrated circuit for real-time 3D catheter-based ultrasonic imaging. Proceedings of SPIE. 2006;6147:61470A-1.

York et al., Ultrasound Processing and Computing: Review and Future Directions. Annu Rev Biomed Eng. 1999;1:559-588.

York, Architecture and Algorithms for a Fully Programmable Ultrasound System. A dissertation in partial fulfillment of the requirements for the Degree of Doctor of Philosophy, University of Washington. 141 pages, (1999).

International Search Report and Written Opinion for Application No. PCT/US2017/062109, dated.

Kang et al., Stereoscopic augmented reality for laparoscopic surgery. Surg Endosc. 2014;28(7):2227-2235.

International Search Report and Written Opinion for Application No. PCT/US2019/032632, dated Dec. 12, 2019, 9 pages.

AMD Case Study. AMD embedded G-Series APU boosts 3-D visualization for portable ultrasound device. 3 pages. (2014).

Dickson, Wireless communication options for a mobile ultrasound system. Thesis Submitted to the Faculty of Worcester Polytechnic Institute. 2008. 252 pages.

Lee et al., A new smart probe system for a tablet PC-based point-of-care ultrasound imaging system: feasibility study. IEEE International Ultrasonics Symposium Proceedings. 2014;1611-14.

Lewandowski et al., Modular and scalable ultrasound platform with GPU processing. Conference Paper, Warsaw, Poland. 5 pages. (Oct. 2012).

Song et al., Tailored Holder for Continuous Echocardiographic Monitoring. Anesth Analg. Feb. 2018;126(2):435-437.

(56)            References Cited

OTHER PUBLICATIONS

Zhang et al., A software package for portavle three-dimensional ultrasound imaging. 2nd IEEE International Symposium on Biomedical Imaging: Nano to Macro. 2004;1:539-42.

U.S. Appl. No. 10/667,790, filed Mar. 15, 2013, U.S. Pat. No. 10,667,790, Issued.

U.S. Appl. No. 15/833,547, filed Dec. 6, 2017, 2018-0168548, Published.

U.S. Appl. No. 16/806,118, filed Mar. 2, 2020, Pending.

U.S. Appl. No. 16/938,515, filed Jul. 24, 2020, Pending.

Chengode, Left ventricular global systolic function assessment by echocardiography. Ann Card Anaesth. Oct. 2016;19(Supplement):S26-S34.

Tanter et al., Ultrafast imaging in biomedical ultrasound. IEEE Trans Ultrason Ferroelectr Freq Control. Jan. 2014;61(1):102-19.

Ultrasound Diagnostic System, Model: SonoTouch 20, Operator's Manual, Direction: CHUM-001a, Rev. 1.0, 98 pages, Oct. 13, 2012.

U.S. Appl. No. 13/838,694, filed Mar. 15, 2013, U.S. Pat. No. 10,667,790, Issued.

U.S. Appl. No. 14/037,106, filed Sep. 25, 2013, U.S. Pat. No. 9,877,699, Issued.

U.S. Appl. No. 15/025,058, filed Mar. 25, 2016, 2016-0228091, Published.

U.S. Appl. No. 15/833,547, filed Dec. 6, 2017, U.S. Pat. No. 11,179,138, Issued.

U.S. Appl. No. 16/806,118, filed Mar. 2, 2020, 2020-0268351, Published.

U.S. Appl. No. 17/520,150, filed Nov. 5, 2021, 2022-0125407, Allowed.

U.S. Appl. No. 17/834,771, filed Jun. 7, 2022, 2022-0304661, Published.

U.S. Appl. No. 16/414,215, filed May 16, 2019, 2019-0336101, Published.

U.S. Appl. No. 16/938,515, filed Jul. 24, 2020, 2021-0015456, Published.

U.S. Appl. No. 18/090,316, filed Dec. 28, 2022, 2023-0181160, Published.

Dewaraja et al., GPU engine enhances ultrasound-detected brain motion calculations. OpenSystems Media. Retrieved online at: https://embeddedcomputing.com/application/healthcare/gpu-engine-enhances-ultrasound-detected-brain-motion-calculations. 5 pages, May 1, 2009.

Kasai et al., Real-Time Two-Dimensional Blood Flow Imaging Using an Autocorrelation Technique. IEEE Transactions on Sonics and Ultrasonics. May 1985;32(3):458-464.

Shenzhen Mindray Bio-Medical Electronics Co., Ltd., Digital Ultrasonic Diagnostic Imaging System. installation Manual. 32 pages, (2007).

* cited by examiner

FIG. 3A
FIG. 3AA
302 —
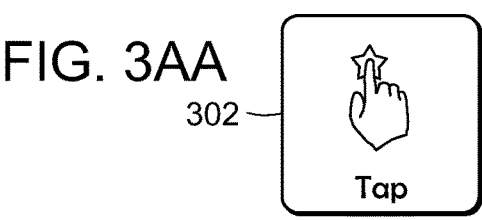
FIG. 3AG
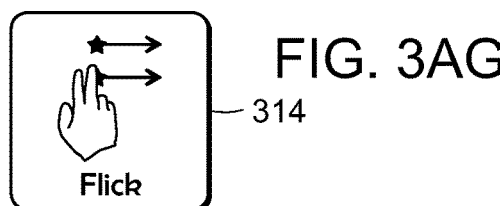
— 314
FIG. 3AB
304 —
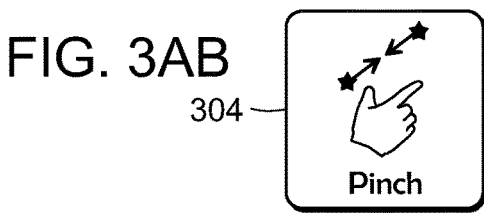
FIG. 3AH
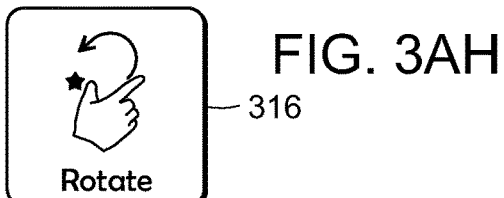
— 316
FIG. 3AC
306 —
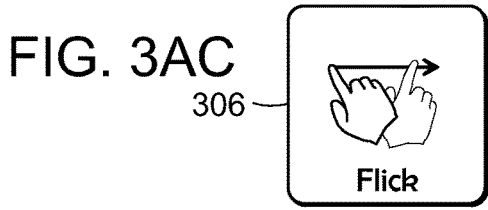
FIG. 3AI
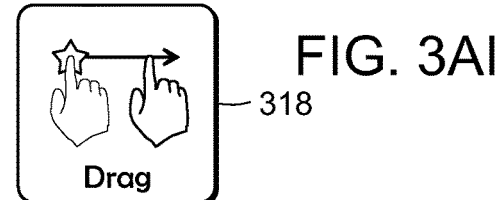
— 318
FIG. 3AD
308 —
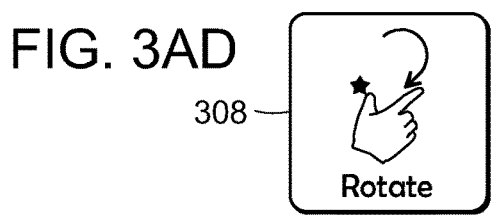
FIG. 3AJ
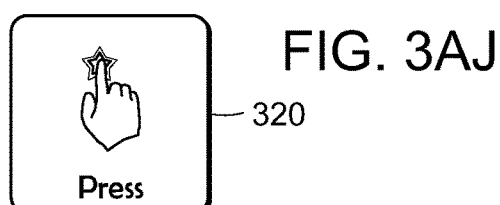
— 320
FIG. 3AE
310 —
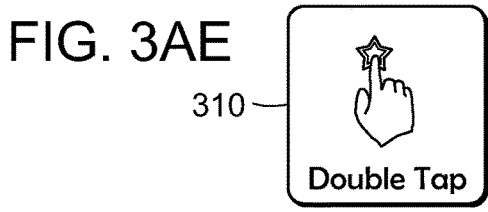
FIG. 3AK
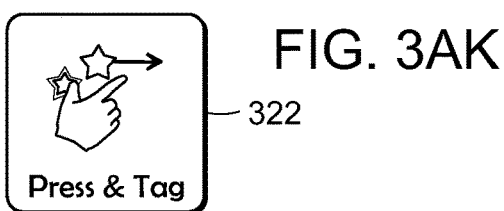
— 322
FIG. 3AF
312 —
FIG. 3AL
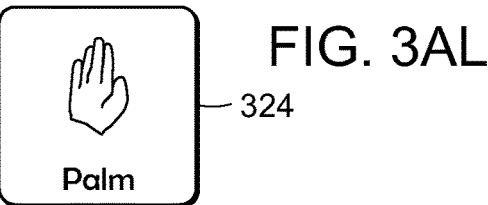
— 324

340

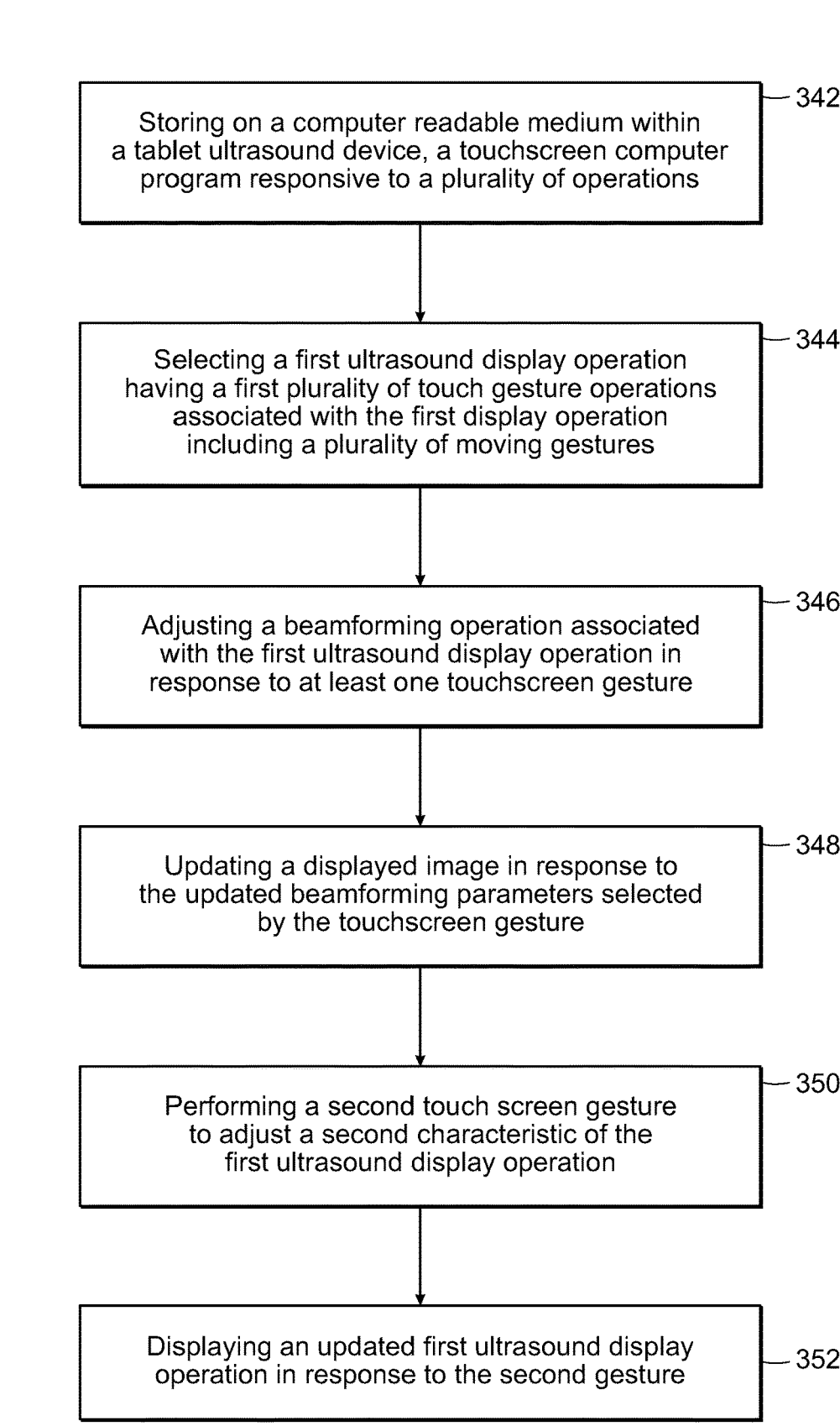

342 — Storing on a computer readable medium within a tablet ultrasound device, a touchscreen computer program responsive to a plurality of operations 344 — Selecting a first ultrasound display operation having a first plurality of touch gesture operations associated with the first display operation including a plurality of moving gestures 346 — Adjusting a beamforming operation associated with the first ultrasound display operation in response to at least one touchscreen gesture 348 — Updating a displayed image in response to the updated beamforming parameters selected by the touchscreen gesture 350 — Performing a second touch screen gesture to adjust a second characteristic of the first ultrasound display operation 352 — Displaying an updated first ultrasound display operation in response to the second gesture

FIG. 3B

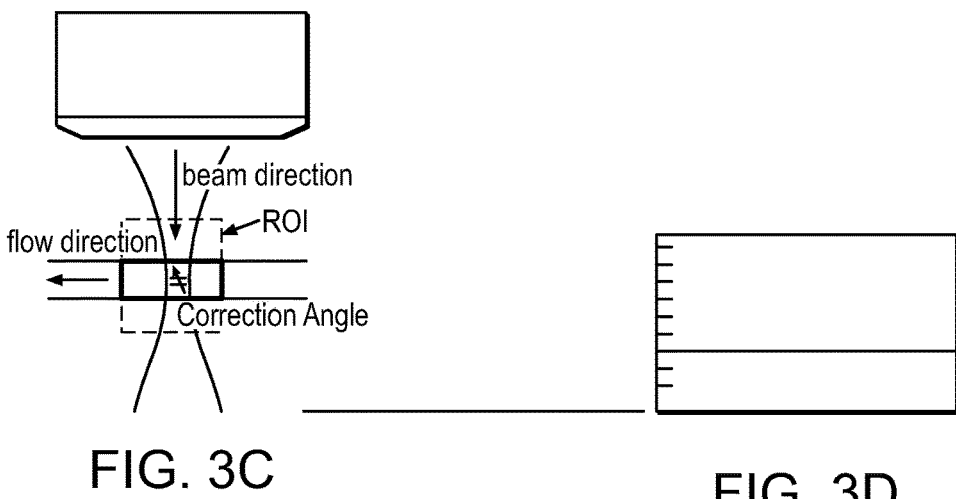
FIG. 3C
FIG. 3D
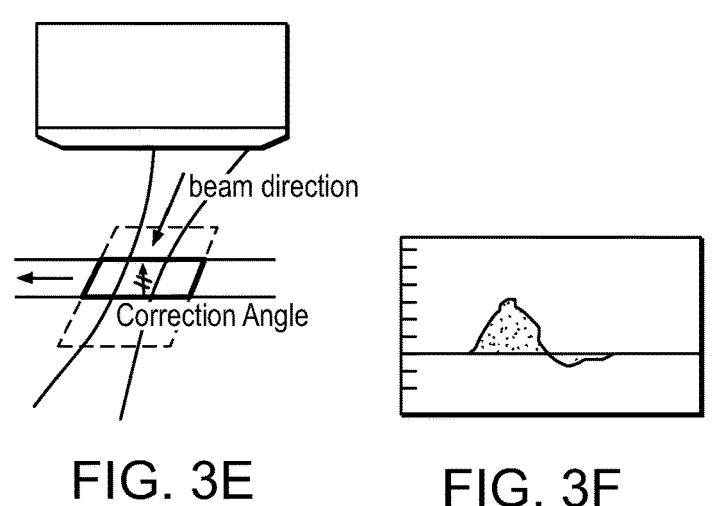
FIG. 3E
FIG. 3F
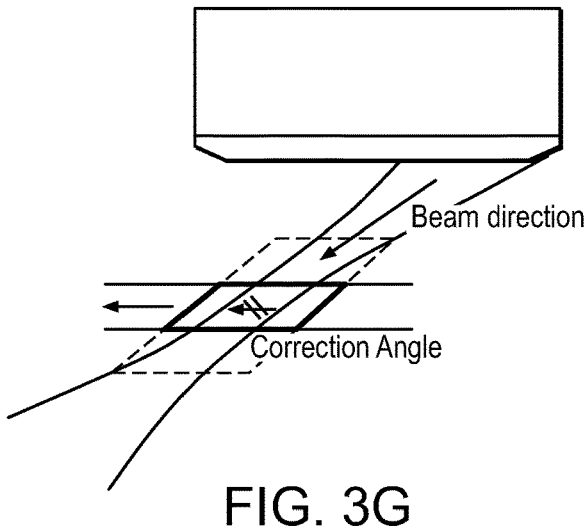
FIG. 3G
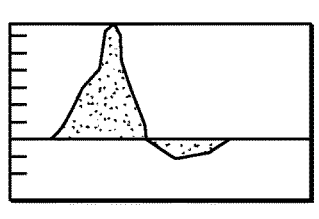
FIG. 3H Ultrasound imaging probe assembly 978

980

Ultrasound reflector disc 964

Ultrasound transducer elements 960

Needle Guide 962

966

Needle guide mounting bracket

982

Ultrasound imaging probe assembly for imaging the patient body

Ultrasound transducer array 984

Needle 956

986

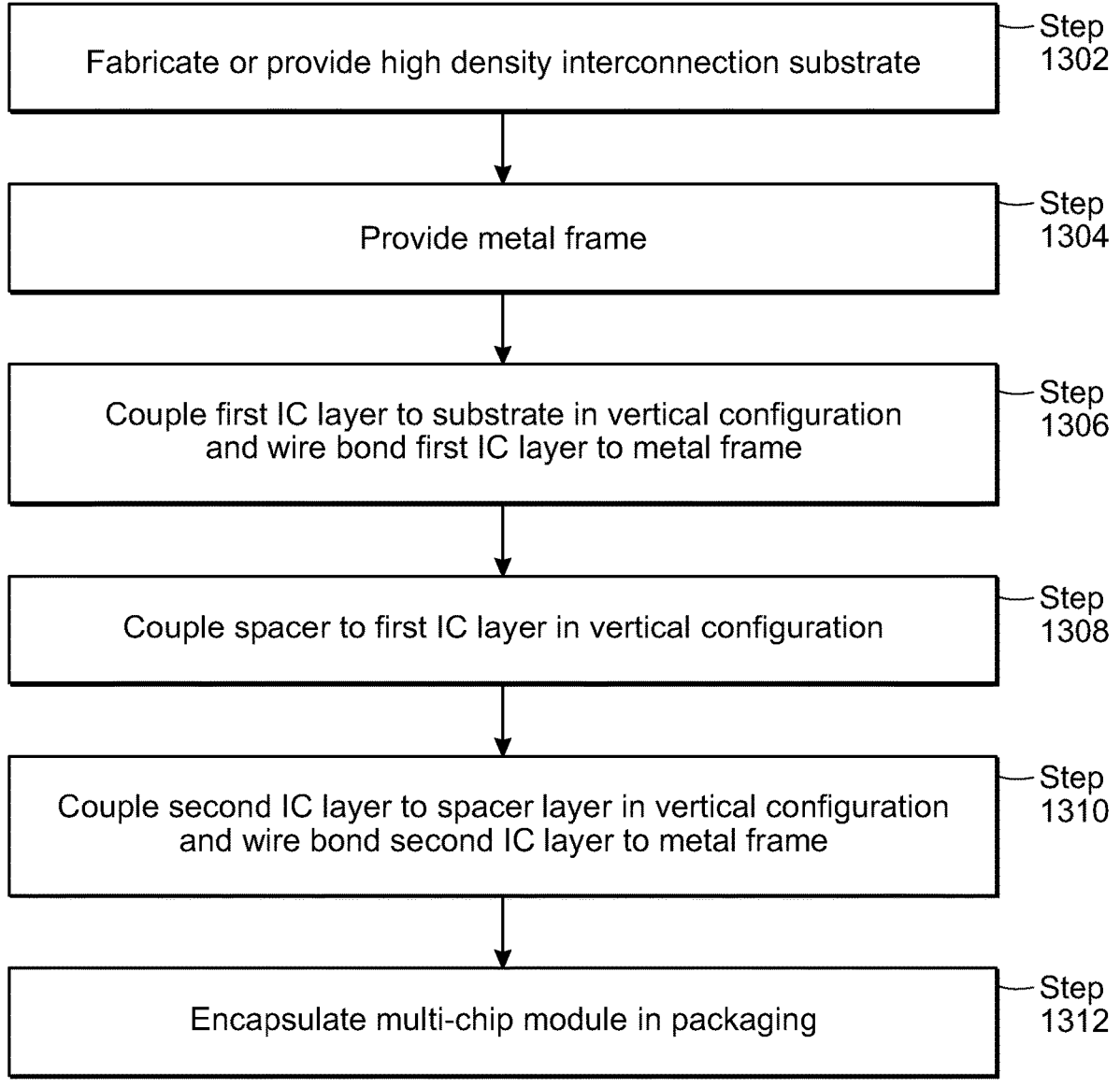

Fabricate or provide high density interconnection substrate — Step 1302

Provide metal frame — Step 1304

Couple first IC layer to substrate in vertical configuration and wire bond first IC layer to metal frame — Step 1306

Couple spacer to first IC layer in vertical configuration — Step 1308

Couple second IC layer to spacer layer in vertical configuration and wire bond second IC layer to metal frame — Step 1310

Encapsulate multi-chip module in packaging — Step 1312

FIG. 13

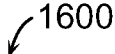
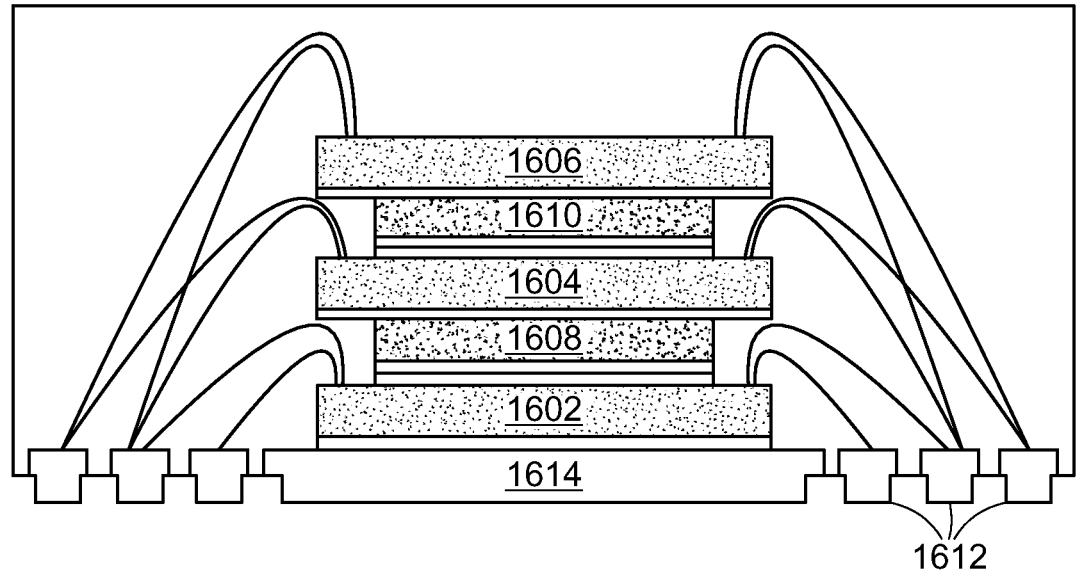
FIG. 16

Menu bar — 1902

Image display window — 1904

Image control bar — 1906

Tool bar 1908

1900

Transducer Port 2512

2510 Transducer Probe

2500

2508 Release Mechanism

2502 Docking Station

2506 Base Assembly

Tablet 2504

Adjustable Stand/Handle 2526

Tablet 2504

Transducer Port 2512

2510 Transducer Probe

2502 Docking Station

— 2606
Flexible Frequency

— 2602
 2D Image Window

— 2604
2D Scan Image

⟋ 2700
Tablet Display

— 2702
Flexible Frequency
Controls

— 2704
 2D Image Window

— 2706
2D Image

— 2708
Scan Time
Sores Window

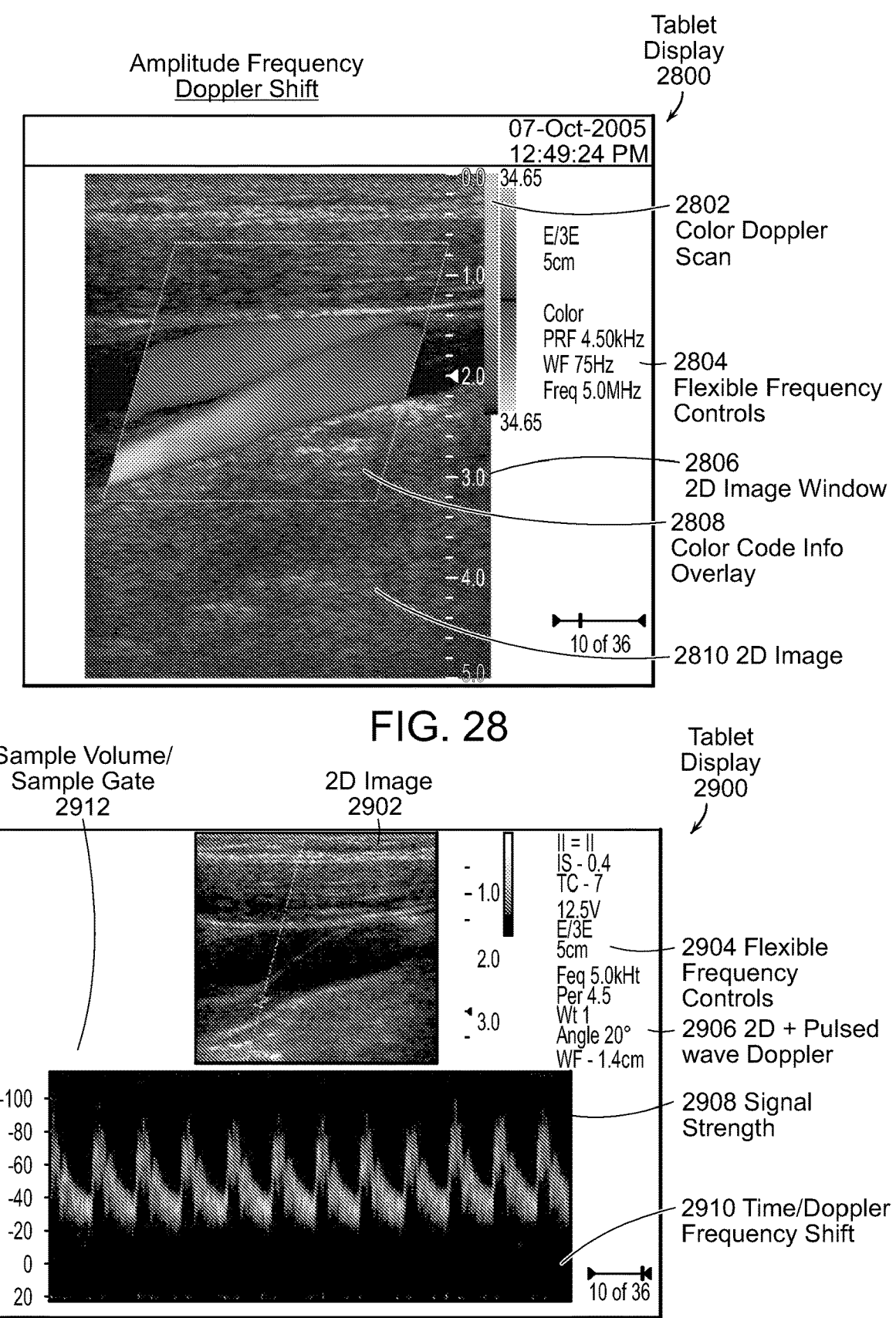

Amplitude Frequency
Doppler Shift

Tablet
Display
2800

07-Oct-2005
12:49:24 PM

2802
Color Doppler
Scan

E/3E
5cm

Color
PRF 4.50kHz
WF 75Hz
Freq 5.0MHz

2804
Flexible Frequency
Controls 2806
2D Image Window

2808
Color Code Info
Overlay 10 of 36

2810 2D Image

FIG. 28

Sample Volume/
Sample Gate
2912

2D Image
2902

Tablet
Display
2900

|| = ||
IS - 0.4
TC - 7
12.5V
E/3E
5cm
Feq 5.0kHt
Per 4.5
Wt 1
Angle 20°
WF - 1.4cm 2904 Flexible
Frequency
Controls 2906 2D + Pulsed
wave Doppler 2908 Signal
Strength 2910 Time/Doppler
Frequency Shift 10 of 36

FIG. 29

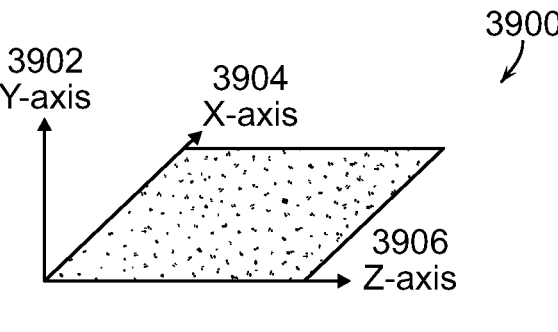
FIG. 39A
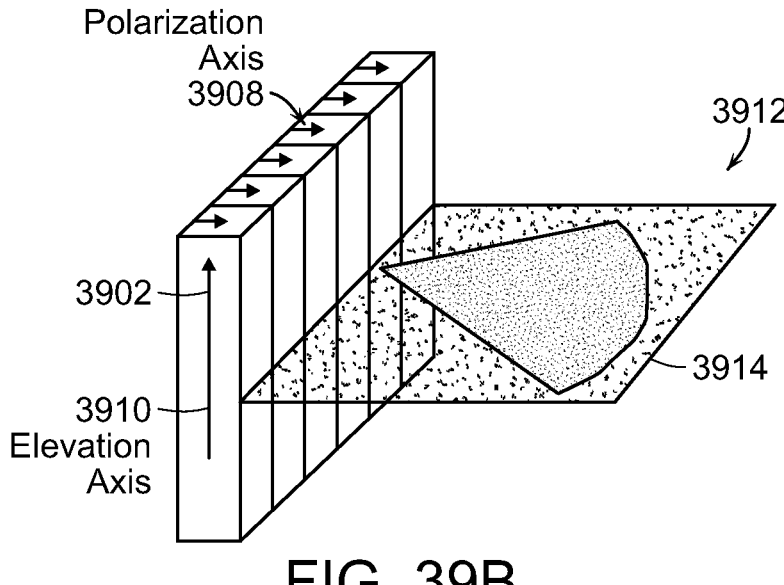
FIG. 39B
FIG. 39C

High-voltage driving pulses applying to elements of the transducer array with elevation axis in X-direction for forming images on the YZ plane.

Simultaneous bi-plane evaluation of left ventricular
mechanical dysschrony functions

4402     2CH

4404     4CH

Fundamental          Second Harmonics          Third Harmonics

SQUAREWAVE

Spectrum of 3 pulse

Harmonic Order

Spectrum of 3 cycles Modified Square Wave and Sinusoidal wave

TriLevel Square Wave

Sine Wave

MHZ

FIG. 53

Super Harmonic

Fundamental

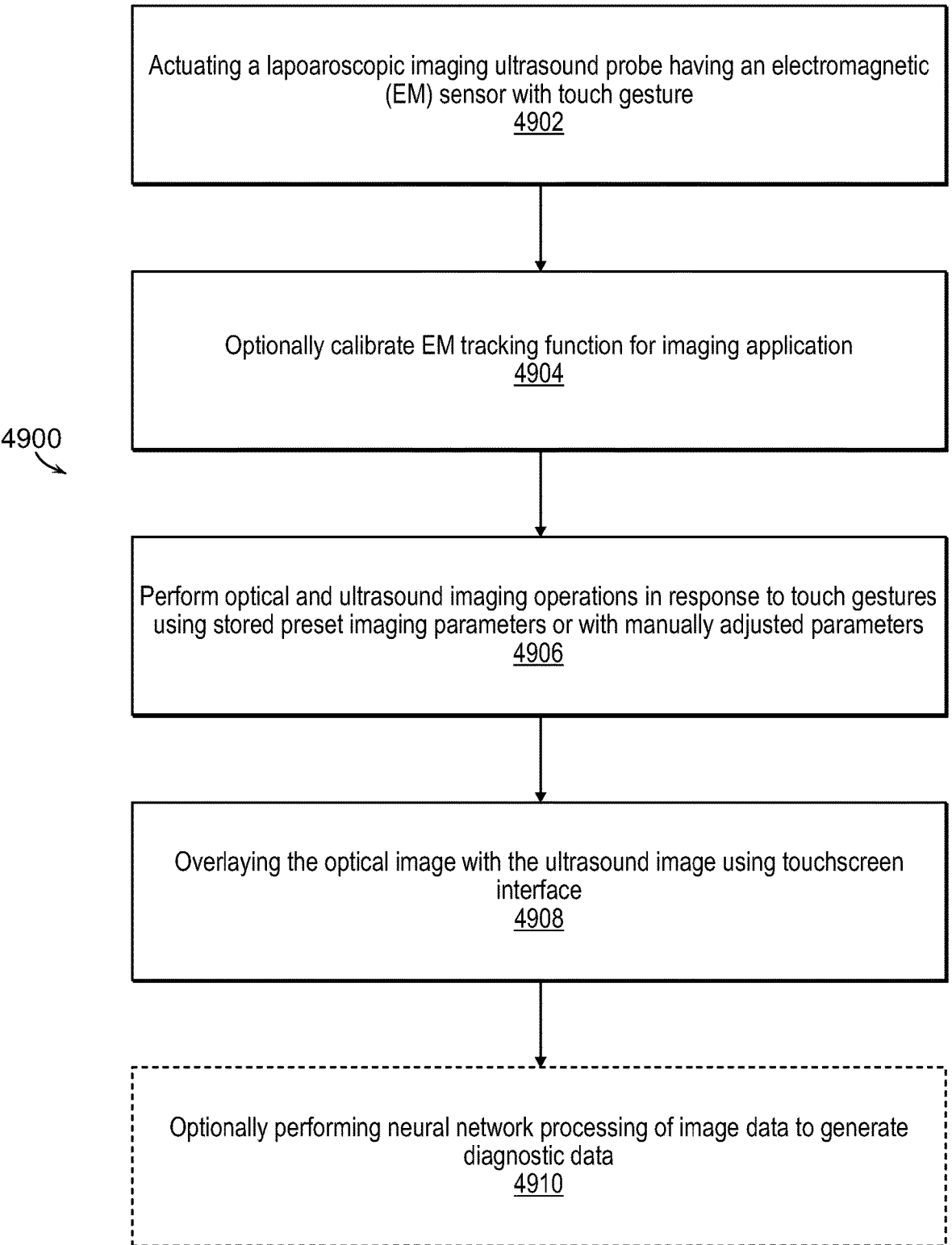

4900

Actuating a lapoaroscopic imaging ultrasound probe having an electromagnetic (EM) sensor with touch gesture
4902

Optionally calibrate EM tracking function for imaging application
4904

Perform optical and ultrasound imaging operations in response to touch gestures using stored preset imaging parameters or with manually adjusted parameters
4906

Overlaying the optical image with the ultrasound image using touchscreen interface
4908

Optionally performing neural network processing of image data to generate diagnostic data
4910

FIG. 57

1: Power button
2: Baseline key
3: Scale key
4: Page key
5: Unassigned
6: Steer key
7: Split key
8: Focus key
9: Depth key
10: Body Marker key
11: Text key
12: PW mode key
13: Color mode key
14: 2D mode key
15: CW mode key
16: Gain key
17: Clear key
18: Calcs key
19: Caliper key
20: Select key
21: Cursor key
22: M-Mode key
23: Zoom key
24: Update key
25: Left Enter key
26: Trackball
27: Right Enter key
28: Freeze key
29: Store key
30: Record key

PORTABLE ULTRASOUND SYSTEM

CROSS REFERENCE TO RELATED APPLICATIONS

This application is a 35 U.S.C. § 371 national stage filing of International Application No. PCT/US2017/062109, filed on Nov. 16, 2017, which claims priority to U.S. Provisional Application No. 62/565,846, filed on Sep. 29, 2017, and to U.S. Provisional Application No. 62/422,808 filed Nov. 16, 2016, all of the above applications being incorporated herein by reference in their entireties.

BACKGROUND OF THE INVENTION

Medical ultrasound imaging has become an industry standard for many medical imaging applications. In recent years, there has been an increasing need for medical ultrasound imaging equipment that is portable to allow medical personnel to easily transport the equipment to and from hospital and/or field locations, and more user-friendly to accommodate medical personnel who may possess a range of skill levels.

Conventional medical ultrasound imaging equipment typically includes at least one ultrasound probe/transducer, a keyboard and/or a knob, a computer, and a display. In a typical mode of operation, the ultrasound probe/transducer generates ultrasound waves that can penetrate tissue to different depths based on frequency level, and receives ultrasound waves reflected back from the tissue. Further, medical personnel can enter system inputs to the computer via the keyboard and/or the knob, and view ultrasound images of tissue structures on the display.

However, conventional medical ultrasound imaging equipment that employ such keyboards and/or knobs can be bulky, and therefore may not be amenable to portable use in hospital and/or field locations. Moreover, because such keyboards and/or knobs typically have uneven surfaces, they can be difficult to keep clean in hospital and/or field environments, where maintenance of a sterile field can be crucial to patient health. Some conventional medical ultrasound imaging equipment have incorporated touch screen technology to provide a partial user input interface. However, conventional medical ultrasound imaging equipment that employ such touch screen technology generally provide only limited touch screen functionality in conjunction with a traditional keyboard and/or knob, and can therefore not only be difficult to keep clean, but also complicated to use.

SUMMARY OF THE INVENTION

In accordance with the present application, systems and methods of medical ultrasound imaging are disclosed. The presently disclosed systems and methods of medical ultrasound imaging employ medical ultrasound imaging equipment that includes a handheld housing having a laptop or a tablet form factor. The user interface can include a keyboard control panel or a multi-touch touchscreen. The system can include a graphical processing unit within the system housing that is connected to the central processor that operates to perform ultrasound imaging operations. A preferred embodiment can employ a neural network for processing ultrasound image data and quantitative data generated by the system. A further embodiment can process image data from a second imaging modality such as a camera or other medical imaging system wherein the system processes the multimodal image data to provide overlaid images of a region of interest, for example.

Touchscreen embodiment can recognize and distinguish one or more single, multiple, and/or simultaneous touches on a surface of the touch screen display, thereby allowing the use of gestures, ranging from simple single point gestures to complex multipoint moving gestures, as user inputs to the medical ultrasound imaging equipment.

In accordance with one aspect, exemplary medical ultrasound imaging system includes a housing having a front panel and a rear panel rigidly mounted to each other in parallel planes, a touch screen display, a computer having at least one processor and at least one memory, an ultrasound beamforming system, and a battery. The housing of the medical ultrasound imaging equipment is implemented in a tablet form factor. The touch screen display is disposed on the front panel of the housing, and includes a multi-touch LCD touch screen that can recognize and distinguish one or more single, multiple, and/or simultaneous touches or gestures on a surface of the touch screen display. The computer, the ultrasound beamforming system or engine, and the battery are operatively disposed within the housing. The medical ultrasound imaging equipment can use a Firewire connection operatively connected between the computer and the ultrasound engine within the housing and a probe connector having a probe attach/detach lever to facilitate the connection of at least one ultrasound probe/transducer. In addition, the exemplary medical ultrasound imaging system includes an I/O port connector and a DC power input.

In an exemplary mode of operation, medical personnel can employ simple single point gestures and/or more complex multipoint gestures as user inputs to the multi-touch LCD touch screen for controlling operational modes and/or functions of the exemplary medical ultrasound imaging equipment. Such single point/multipoint gestures can correspond to single and/or multipoint touch events that are mapped to one or more predetermined operations that can be performed by the computer and/or the ultrasound engine. Medical personnel can make such single point/multipoint gestures by various finger, palm, and/or stylus motions on the surface of the touch screen display. The multi-touch LCD touch screen receives the single point/multipoint gestures as user inputs, and provides the user inputs to the computer, which executes, using the processor, program instructions stored in the memory to carry out the predetermined operations associated with the single point/multipoint gestures, at least at some times, in conjunction with the ultrasound engine. Such single point/multipoint gestures on the surface of the touch screen display can include, but are not limited to, a tap gesture, a pinch gesture, a flick gesture, a rotate gesture, a double tap gesture, a spread gesture, a drag gesture, a press gesture, a press and drag gesture, and a palm gesture. In contrast to existing ultrasound systems that rely on numerous control features operated by mechanical switching, keyboard elements, or touchpad trackball interface, preferred embodiments of the present invention employ a single on/off switch. All other operations have been implemented using touchscreen controls. Moreover, the preferred embodiments employ a capacitive touchscreen display that is sufficiently sensitive to detect touch gestures actuated by bare fingers of the user as well as gloved fingers of the user. Often medical personnel must wear sterilized plastic gloves during medical procedures. Consequently, it is highly desirable to provide a portable ultrasound device that can be used by gloved hands; however, this has previously prevented the use of touchscreen display control functions in ultrasound systems for many applications requiring sterile precautions. Preferred embodiments of the present invention provide control of all ultrasound imaging operations by gloved personnel on the touchscreen display using the programmed touch gestures.

In accordance with an exemplary aspect, at least one flick gesture may be employed to control the depth of tissue penetration of ultrasound waves generated by the ultrasound probe/transducer. For example, a single flick gesture in the "up" direction on the touch screen display surface can increase the penetration depth by one (1) centimeter or any other suitable amount, and a single flick gesture in the "down" direction on the touch screen display surface can decrease the penetration depth by one (1) centimeter or any other suitable amount. Further, a drag gesture in the "up" or "down" direction on the touch screen display surface can increase or decrease the penetration depth in multiples of one (1) centimeter or any other suitable amount. Additional operational modes and/or functions controlled by specific single point/multipoint gestures on the touch screen display surface can include, but are not limited to, freeze/store operations, 2-dimensional mode operations, gain control, color control, split screen control, PW imaging control, cine/time-series image clip scrolling control, zoom and pan control, full screen control, Doppler and 2-dimensional beam steering control, and/or body marking control. At least some of the operational modes and/or functions of the exemplary medical ultrasound imaging equipment can be controlled by one or more touch controls implemented on the touch screen display in which beamforming parameters can be reset by moving touch gestures. Medical personnel can provide one or more specific single point/multipoint gestures as user inputs for specifying at least one selected subset of the touch controls to be implemented, as required and/or desired, on the touch screen display. A larger number of touchscreen controls enable greater functionality when operating in full screen mode when a few or more virtual buttons or icons are available for use.

In accordance with another exemplary aspect, a press gesture can be employed inside a region of the touch screen display, and, in response to the press gesture, a virtual window can be provided on the touch screen display for displaying at least a magnified portion of an ultrasound image displayed on the touch screen display. In accordance with still another exemplary aspect, a press and drag gesture can be employed inside the region of the touch screen display, and, in response to the press and drag gesture, a predetermined feature of the ultrasound image can be traced. Further, a tap gesture can be employed inside the region of the touch screen display, substantially simultaneously with a portion of the press and drag gesture, and, in response to the tap gesture, the tracing of the predetermined feature of the ultrasound image can be completed. These operations can operate in different regions of a single display format, so that a moving gesture within a region of interest within the image, for example, may perform a different function than the same gesture executed within the image but outside the region of interest.

By providing medical ultrasound imaging equipment with a multi-touch touchscreen, medical personnel can control the equipment using simple single point gestures and/or more complex multipoint gestures, without the need of a traditional keyboard or knob. Because the multi-touch touch screen obviates the need for a traditional keyboard or knob, such medical ultrasound imaging equipment is easier to keep clean in hospital and/or field environments, provides an intuitive user friendly interface, while providing fully functional operations. Moreover, by providing such medical ultrasound imaging equipment in a tablet form factor, medical personnel can easily transport the equipment between hospital and/or field locations.

Certain exemplary embodiments provide a multi-chip module for an ultrasound engine of a portable medical ultrasound imaging system, in which a transmit/receive (TR) chip, a pre-amp/time gain compensation (TGC) chip and a beamformer chip are assembled in a vertically stacked configuration. The transmission circuit provides high voltage electrical driving pulses to the transducer elements to generate a transmit beam. As the transmit chip operates at voltages greater than 80V, a CMOS process utilizing a 1 micron design rule has been utilized for the transmit chip and a submicron design rule has been utilized for the low-voltage receiving circuits (less than 5V).

Preferred embodiments of the present invention utilize a submicron process to provide integrated circuits with sub-circuits operating at a plurality of voltages, for example, 2.5V, 5V and 60V or higher. These features can be used in conjunction with a bi-plane transducer probe in accordance with certain preferred embodiments of the invention.

Thus, a single IC chip can be utilized that incorporates high voltage transmission, low voltage amplifier/TGC and low voltage beamforming circuits in a single chip. Using a 0.25 micron design rule, this mixed signal circuit can accommodate beamforming of 32 transducer channels in a chip area less than $0.7 \times 0.7$ (0.49) cm². Thus, 128 channels can be processed using four 32 channel chips in a total circuit board area of less than $1.5 \times 1.5$ (2.25) cm².

The term "multi-chip module," as used herein, refers to an electronic package in which multiple integrated circuits (IC) are packaged with a unifying substrate, facilitating their use as a single component, i.e., as a higher processing capacity IC packaged in a much smaller volume. Each IC can comprise a circuit fabricated in a thinned semiconductor wafer. Exemplary embodiments also provide an ultrasound engine including one or more such multi-chip modules, and a portable medical ultrasound imaging system including an ultrasound engine circuit board with one or more multi-chip modules. Exemplary embodiments also provide methods for fabricating and assembling multi-chip modules as taught herein. Vertically stacking the TR chip, the pre-amp/TGC chip, and the beamformer chip on a circuit board minimizes the packaging size (e.g., the length and width) and the footprint occupied by the chips on the circuit board.

The TR chip, the pre-amp/TGC chip, and the beamformer chip in a multi-chip module may each include multiple channels (for example, 8 channels per chip to 64 channels per chip). In certain embodiments, the high-voltage TR chip, the pre-amp/TGC chip, and the sample-interpolate receive beamformer chip may each include 8, 16, 32, 64 channels. In a preferred embodiment, each circuit in a two layer beamformer module has 32 beamformer receive channels to provide a 64 channel receiving beamformer. A second 64 channel two layer module can be used to form a 128 channel handheld tablet ultrasound device having an overall thickness of less than 2 cm. A transmit multi-chip beamformer can also be used having the same or similar channel density in each layer.

Exemplary numbers of chips vertically integrated in a multi-chip module may include, but are not limited to, two, three, four, five, six, seven, eight, and the like. In one embodiment of an ultrasound device, a single multi-chip module is provided on a circuit board of an ultrasound engine that performs ultrasound-specific operations. In other embodiments, a plurality of multi-chip modules are provided on a circuit board of an ultrasound engine. The plurality of multi-chip modules may be stacked vertically on top of one another on the circuit board of the ultrasound engine to further minimize the packaging size and the footprint of the circuit board.

Providing one or more multi-chip modules on a circuit board of an ultrasound engine achieves a high channel count while minimizing the overall packaging size and footprint. For example, a 128-channel ultrasound engine circuit board can be assembled, using multi-chip modules, within exemplary planar dimensions of about 10 cm×about 10 cm, which is a significant improvement over the much larger space requirements of conventional ultrasound circuits. A single circuit board of an ultrasound engine including one or more multi-chip modules may have 16 to 128 channels in some embodiments. In certain embodiments, a single circuit board of an ultrasound engine including one or more multi-chip modules may have 16, 32, 64, 128 or 192 channels, and the like.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 3A illustrates exemplary single point and multipoint gestures that can be employed as user inputs to the medical ultrasound imaging system in accordance with preferred embodiments of the invention;

FIG. 3B illustrates a process flow diagram for operating a tablet ultrasound system in accordance with preferred embodiments of the invention;

FIG. 3C-3K illustrates details of touchscreen gestures to adjust beamforming and display operation;

FIG. 13 is a flowchart of an exemplary method for fabricating a circuit board including a multi-chip module assembled in a vertically stacked configuration;

FIG. 16 is a schematic side view of a multi-chip module including an ultrasound transmit/receive IC chip, an amplifier IC chip and an ultrasound beamformer IC chip vertically integrated in a vertically stacked configuration;

FIG. 28 illustrates a color Doppler mode of operation with a modular ultrasound imaging system in accordance with the invention;

FIG. 29 illustrates a pulsed-wave Doppler mode of operation with a modular ultrasound imaging system in accordance with the invention;

FIGS. 39A-39C illustrate XY bi-plane probe comprising a two one-dimensional, ID multi-element arrays in accordance with a preferred embodiment of the invention;

FIG. 53 shows a frequency spectral of a two Third square wave form and a sine wave, this modified waveform has a much lower third harmonic component than that of a regular square wave, and close to a pure sinewave;

FIG. 57 illustrates a flowchart for a procedure for imaging using multiple modalities in accordance with various embodiments of the present application.

DETAILED DESCRIPTION

Systems and methods of medical ultrasound imaging are disclosed. The presently disclosed systems and methods of medical ultrasound imaging employ medical ultrasound imaging equipment that includes housing in a tablet form factor, and a touch screen display disposed on a front panel of the housing. The touch screen display includes a multi-touch touch screen that can recognize and distinguish one or more single, multiple, and/or simultaneous touches on a surface of the touch screen display, thereby allowing the use of gestures, ranging from simple single point gestures to complex multipoint gestures, as user inputs to the medical ultrasound imaging equipment. Further details regarding tablet ultrasound systems and operations are described in U.S. application Ser. No. 10/997,062 filed on Nov. 11, 2004, Ser. No. 10/386,360 filed Mar. 11, 2003 and U.S. Pat. No. 6,969,352, the entire contents of these patents and applications are incorporated herein by reference.

Figure 1A:
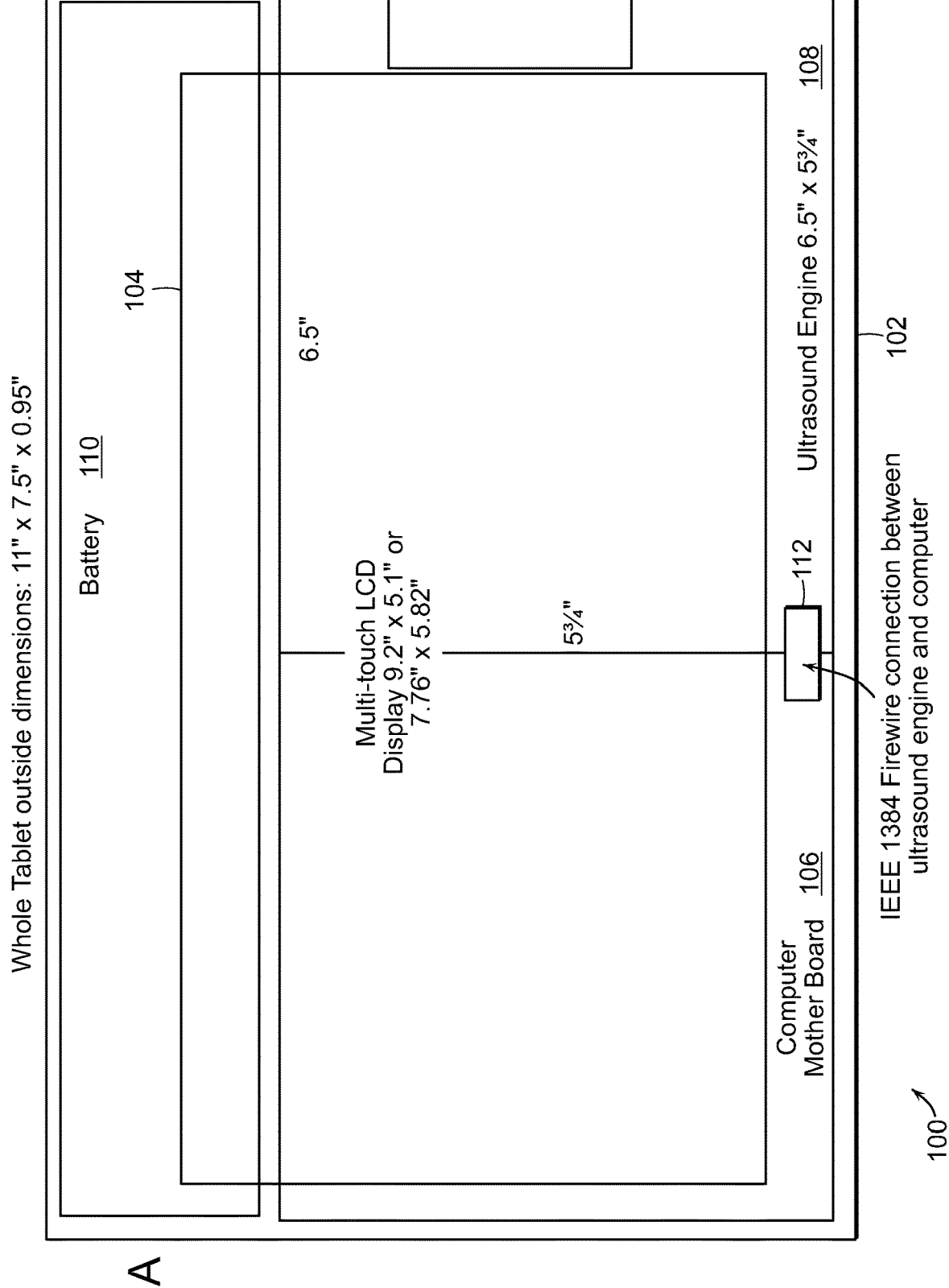
FIG. 1A is a plan view of exemplary medical ultrasound imaging equipment, in accordance with an exemplary embodiment of the present application.
Figure 1B:
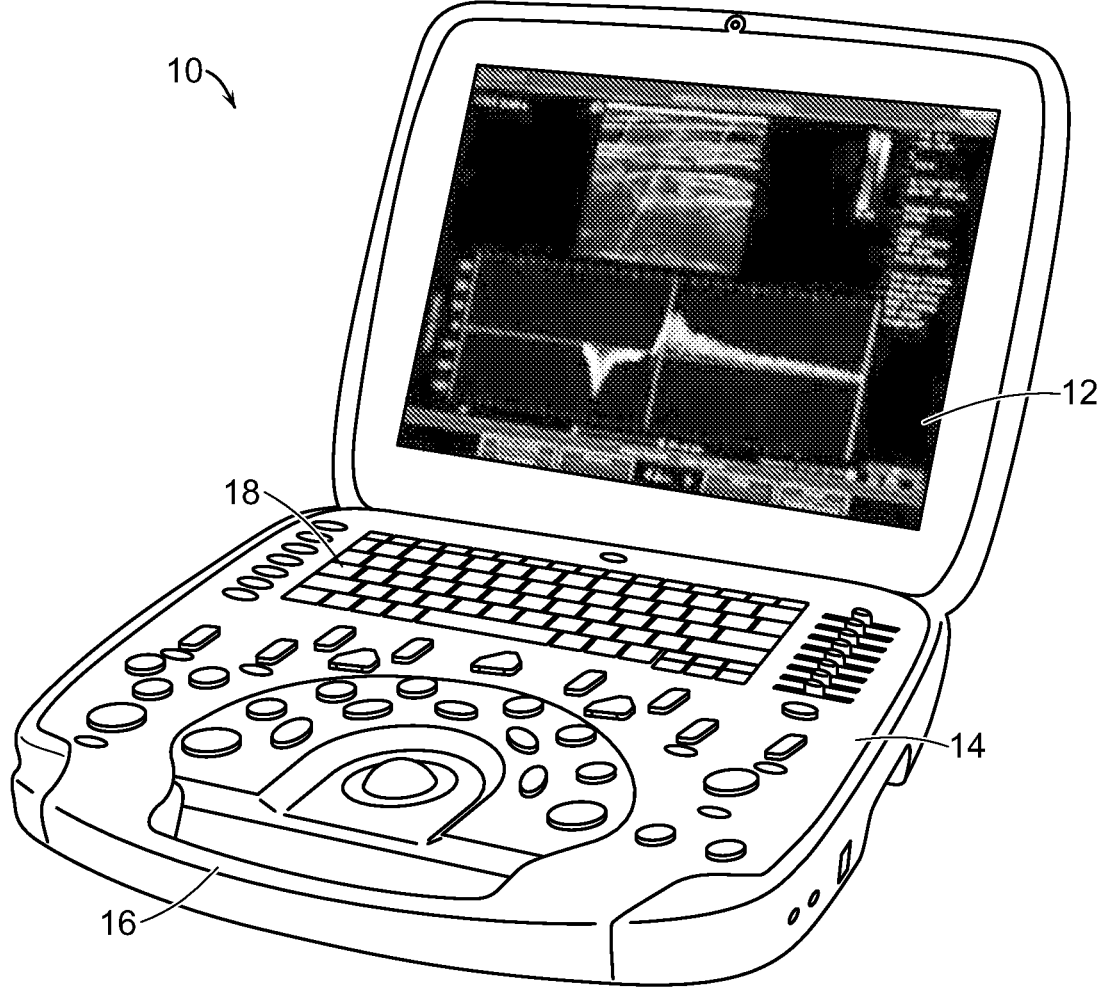
FIG. 1B shows a battery powered portable system having a keyboard control panel and a folding display.

FIGS. 1A and 1B depict illustrative embodiments of exemplary medical ultrasound imaging equipment 10, 100, in accordance with the present application. As shown in FIG. 1A, the medical ultrasound imaging equipment 100 includes a housing 102, a touch screen display 104, a computer having at least one processor and at least one memory implemented on a computer motherboard 106, an ultrasound engine 108, and a battery 110. For example, the housing 102 can be implemented in a tablet form factor, or any other suitable form factor. The housing 102 has a front panel 101 and a rear panel 103. The touch screen display 104 is disposed on the front panel 101 of the housing 102, and includes a multi-touch LCD touch screen that can recognize and distinguish one or more multiple and/or simultaneous touches on a surface 105 of the touch screen display 104. The computer motherboard 106, the ultrasound engine 108, and the battery 110 are operatively disposed within the housing 102. The medical ultrasound imaging equipment 100 further includes a Firewire connection 112 (see also FIG. 2A) operatively connected between the computer motherboard 106 and the ultrasound engine 108 within the housing 102, and a probe connector 114 having a probe attach/detach lever 115 (see also FIGS. 2A and 2B) to facilitate the connection of at least one ultrasound probe/transducer. The transducer probe housing can include circuit components including a transducer array, transmit and receive circuitry, as well as beamformer and beamformer control circuits in certain preferred embodiments. In addition, the medical ultrasound imaging equipment 100 has one or more I/O port connectors 116 (see FIG. 2A), which can include, but are not limited to, one or more USB connectors, one or more SD cards, one or more network ports, one or more mini display ports, and a DC power input. A further embodiment shown in FIG. 1B employs a battery powered hand portable system weighing less than 15 lbs that has a folding display 12 and a keyboard control panel 14 having a keyboard 14 controls and a handle 16.

In an exemplary mode of operation, medical personnel (also referred to herein as the "user" or "users") can employ simple single point gestures and/or more complex multi-point gestures as user inputs to the multi-touch LCD touch screen of the touch screen display 104 for controlling one or more operational modes and/or functions of the medical ultrasound imaging equipment 100. Such a gesture is defined herein as a movement, a stroke, or a position of at least one finger, a stylus, and/or a palm on the surface 105 of the touch screen display 104. For example, such single point/multipoint gestures can include static or dynamic gestures, continuous or segmented gestures, and/or any other suitable gestures. A single point gesture is defined herein as a gesture that can be performed with a single touch contact point on the touch screen display 104 by a single finger, a stylus, or a palm. A multipoint gesture is defined herein as a gesture that can be performed with multiple touch contact points on the touch screen display 104 by multiple fingers, or any suitable combination of at least one finger, a stylus, and a palm. A static gesture is defined herein as a gesture that does not involve the movement of at least one finger, a stylus, or a palm on the surface 105 of the touch screen display 104. A dynamic gesture is defined herein as a gesture that involves the movement of at least one finger, a stylus, or a palm, such as the movement caused by dragging one or more fingers across the surface 105 of the touch screen display 104. A continuous gesture is defined herein as a gesture that can be performed in a single movement or stroke of at least one finger, a stylus, or a palm on the surface 105 of the touch screen display 104. A segmented gesture is defined herein as a gesture that can be performed in multiple movements or stokes of at least one finger, a stylus, or a palm on the surface 105 of the touch screen display 104.

Such single point/multipoint gestures performed on the surface 105 of the touch screen display 104 can correspond to single or multipoint touch events, which are mapped to one or more predetermined operations that can be performed by the computer and/or the ultrasound engine 108. Users can make such single point/multipoint gestures by various single finger, multi-finger, stylus, and/or palm motions on the surface 105 of the touch screen display 104. The multi-touch LCD touch screen receives the single point/multipoint gestures as user inputs, and provides the user inputs to the processor, which executes program instructions stored in the memory to carry out the predetermined operations associated with the single point/multipoint gestures, at least at some times, in conjunction with the ultrasound engine 108. As shown in FIG. 3A, such single point/multipoint gestures on the surface 105 of the touch screen display 104 can include, but are not limited to, a tap gesture 302, a pinch gesture 304, a flick gesture 306, 314, a rotate gesture 308, 316, a double tap gesture 310, a spread gesture 312, a drag gesture 318, a press gesture 320, a press and drag gesture 322, and/or a palm gesture 324. For example, such single point/multipoint gestures can be stored in at least one gesture library in the memory implemented on the computer motherboard 106. The computer program operative to control system operations can be stored on a computer readable medium and can optionally be implemented using a touch processor connected to an image processor and a control processor connected to the system beamformer. Thus beamformer delays associated with both transmission and reception can be adjusted in response to both static and moving touch gestures.

In accordance with the illustrative embodiment of FIG. 1A, at least one flick gesture 306 or 314 may be employed by a user of the medical ultrasound imaging equipment 100 to control the depth of tissue penetration of ultrasound waves generated by the ultrasound probe/transducer. For example, a dynamic, continuous, flick gesture 306 or 314 in the "up" direction, or any other suitable direction, on the surface 105 of the touch screen display 104 can increase the penetration depth by one (1) centimeter, or any other suitable amount. Further, a dynamic, continuous, flick gesture 306 or 314 in the "down" direction, or any other suitable direction, on the surface 105 of the touch screen display 104 can decrease the penetration depth by one (1) centimeter, or any other suitable amount. Moreover, a dynamic, continuous, drag gesture 318 in the "up" or "down" direction, or any other suitable direction, on the surface 105 of the touch screen display 104 can increase or decrease the penetration depth in multiple centimeters, or any other suitable amounts.

Additional operational modes and/or functions controlled by specific single point/multipoint gestures on the surface 105 of the touch screen display 104 can include, but are not limited to, freeze/store operations, 2-dimensional mode operations, gain control, color control, split screen control, PW imaging control, cine/time-series image clip scrolling control, zoom and pan control, full screen display, Doppler and 2-dimensional beam steering control, and/or body marking control. At least some of the operational modes and/or functions of the medical ultrasound imaging equipment 100 can be controlled by one or more touch controls implemented on the touch screen display 104. Further, users can provide one or more specific single point/multipoint gestures as user inputs for specifying at least one selected subset of the touch controls to be implemented, as required and/or desired, on the touch screen display 104.

Shown in FIG. 3B is a process sequence in which ultrasound beamforming and imaging operations 340 are controlled in response to touch gestures entered on a touchscreen. Various static and moving touch gestures have been programmed into the system such that the data processor operable to control beamforming and image processing operations 342 within the tablet device. A user can select 344 a first display operation having a first plurality of touch gestures associated therewith. Using a static or moving gesture the user can perform one of the plurality of gestures operable to control the imaging operation and can specifically select one of a plurality of gestures that can adjust beamforming parameters 346 being used to generate image data associated with the first display operation. The displayed image is updated and displayed 348 response to the updated beamforming procedure. The user can further elect to perform a different gesture having a different velocity characteristic (direction or speed or both) to adjust 350 a second characteristic of the first ultrasound display operation. The displayed image is then updated 352 based on the second gesture, which can modify imaging processing parameters or beamforming parameters. Examples of this process are described in further detail herein where changes in velocity and direction of different gestures can be associated with distinct imaging parameters of a selected display operation.

Ultrasound images of flow or tissue movement, whether color flow or spectral Doppler, are essentially obtained from measurements of movement. In ultrasound scanners, a series of pulses is transmitted to detect movement of blood. Echoes from stationary targets are the same from pulse to pulse. Echoes from moving scatterers exhibit slight differences in the time for the signal to be returned to the scanner.

As can be seen from FIG. 3C-3H, there has to be motion in the direction of the beam; if the flow is perpendicular to the beam, there is no relative motion from pulse to pulse receive, there is no flow detected. These differences can be measured as a direct time difference or, more usually, in terms of a phase shift from which the 'Doppler frequency' is obtained. They are then processed to produce either a color flow display or a Doppler sonogram. In FIG. 3C-3D, the flow direction is perpendicular to the beam direction, no flow is measured by Pulse Wave spectral Doppler. In FIG. 3G-3H when the ultrasound beam is steered to an angle that is better aligned to the flow, a weak flow is shown in the color flow map, and in addition flow is measured by Pulse Wave Doppler. In FIG. 3H, when the ultrasound beam is steered to an angle much better aligned to the flow direction in response to a moving, the color flow map is stronger, in addition when the correction angle of the PWD is placed aligned to the flow, a strong flow is measured by the PWD.

Figure 3I:
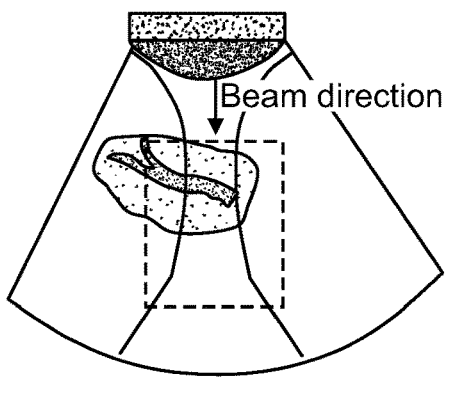
Figure 3J:
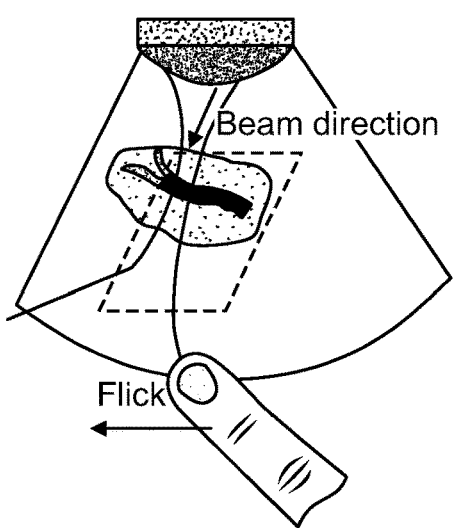

In this tablet ultrasound system, an ROI, region of interest, is also used to define the direction in response to a moving gesture of the ultrasound transmit beam. A liver image with a branch of renal flow in color flow mode is shown in FIG. 3I since the ROI is straight down from the transducer, the flow direction is almost normal to the ultrasound beam, so very week renal flow is detected. Hence, the color flow mode is used to image a renal flow in liver. As can be seen, the beam is almost normal to the flow and very weak flow is detected. A flick gesture with the finger outside of the ROI is used to steer the beam. As can be seen in FIG. 3J, the ROI is steered by resetting beamforming parameters so that the beam direction is more aligned to the flow direction, a much stronger flow within the ROI is detected. In FIG. 3J, a flick gesture with the finger outside of the ROI is used to steer the ultrasound beam into the direction more aligned to the flow direction. Stronger flow within the ROI can be seen. A panning gesture with the finger inside the ROI will move the ROI box into a position that covers the entire renal region, i.e., panning allows a translation movement of the ROI box such that the box covers the entire target area.

Figure 3K:
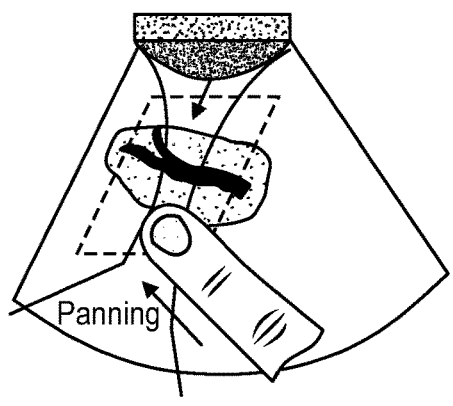

FIG. 3K demonstrates a panning gesture. With the finger inside the ROI, it can move the ROI box to any place within the image plane. In the above embodiment, it is easy to differentiate a "flick" gesture with a finger outside an "ROI" box is intended for steering a beam, and a "drag-and-move, panning" gesture with a finger inside the "ROI" is intended for moving the ROI box. However, there are applications in which no ROI as a reference region, then it is easy to see that it is difficult to differentiate a "flick" or a "panning" gesture, in this case, the touch-screen program needs to track the initial velocity or acceleration of the finger to determine it is a "flick" gesture or a "drag-and-move" gesture. Thus, the touch engine that receives data from the touchscreen sensor device is programmed to discriminate between velocity thresholds that indicate different gestures. Thus, the time, speed and direction associated with different moving gestures can have preset thresholds. Two and three finger static and moving gestures can have separate thresholds to differentiate these control operations. Note that preset displayed icons or virtual buttons can have distinct static pressure or time duration thresholds. When operated in full screen mode, the touchscreen processor, which is preferably operating on the systems central processing unit that performs other imaging operations such as scan conversion, switches off the static icons.

Figure 4A:
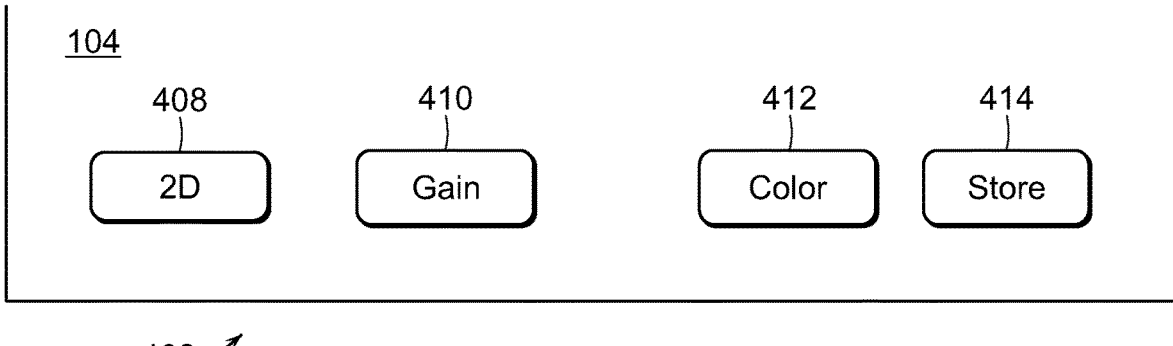
FIGS. 4A-4C illustrates exemplary subsets of touch controls that can be implemented on the medical ultrasound imaging system in accordance with preferred embodiments of the invention.
Figure 4B:
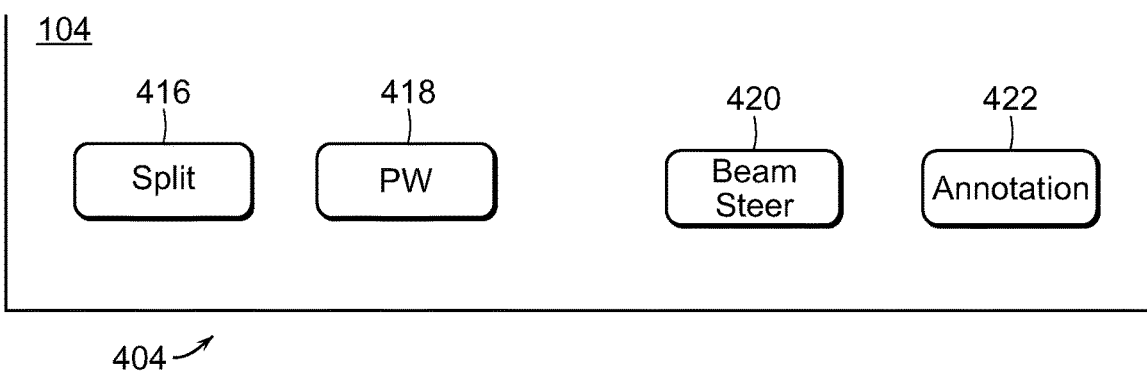
Figure 4C:
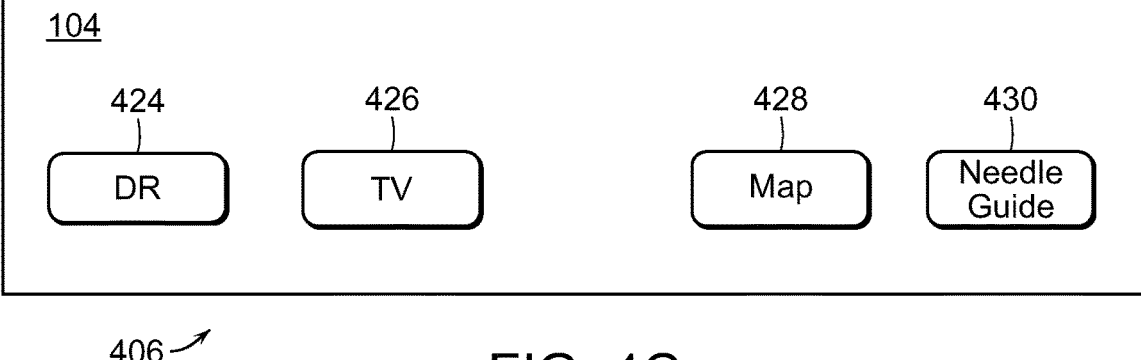

FIGS. 4A-4C depict exemplary subsets 402, 404, 406 of touch controls that can be implemented by users of the medical ultrasound imaging equipment 100 on the touch screen display 104. It is noted that any other suitable subset(s) of touch controls can be implemented, as required and/or desired, on the touch screen display 104. As shown in FIG. 4A, the subset 402 includes a touch control 408 for performing 2-dimensional (2D) mode operations, a touch control 410 for performing gain control operations, a touch control 412 for performing color control operations, and a touch control 414 for performing image/clip freeze/store operations. For example, a user can employ the press gesture 320 to actuate the touch control 408, returning the medical ultrasound imaging equipment 100 to 2D mode. Further, the user can employ the press gesture 320 against one side of the touch control 410 to decrease a gain level, and employ the press gesture 320 against another side of the touch control 410 to increase the gain level. Moreover, the user can employ the drag gesture 318 on the touch control 412 to identify ranges of densities on a 2D image, using a predetermined color code. In addition, the user can employ the press gesture 320 to actuate the touch control 414 to freeze/store a still image or to acquire a cine image clip.

As shown in FIG. 4B, the subset 404 includes a touch control 416 for performing split screen control operations, a touch control 418 for performing PW imaging control operations, a touch control 420 for performing Doppler and 2-dimensional beam steering control operations, and a touch control 422 for performing annotation operations. For example, a user can employ the press gesture 320 against the touch control 416, allowing the user to toggle between opposing sides of the split touch screen display 104 by alternately employing the tap gesture 302 on each side of the split screen. Further, the user can employ the press gesture 320 to actuate the touch control 418 and enter the PW mode, which allows (1) user control of the angle correction, (2) movement (e.g., "up" or "down") of a baseline that can be displayed on the touch screen display 104 by employing the press and drag gesture 322, and/or (3) an increase or a decrease of scale by employing the tap gesture 302 on a scale bar that can be displayed on the touch screen display 104. Moreover, the user can employ the press gesture 320 against one side of the touch control 420 to perform 2D beam steering to the "left" or any other suitable direction in increments of five (5) or any other suitable increment, and employ the press gesture 320 against another side of the touch control 420 to perform 2D beam steering to the "right" or any other suitable direction in increments of five (5) or any other suitable increment. In addition, the user can employ the tap gesture 302 on the touch control 422, allowing the user to enter annotation information via a pop-up keyboard that can be displayed on the touch screen display 104.

As shown in FIG. 4C, the subset 406 includes a touch control 424 for performing dynamic range operations, a touch control 426 for performing Teravision™ software operations, a touch control 428 for performing map operations, and a touch control 430 for performing needle guide operations. For example, a user can employ the press gesture 320 and/or the press and drag gesture 322 against the touch control 424 to control or set the dynamic range. Further, the user can employ the tap gesture 302 on the touch control 426 to choose a desired level of the Teravision™ software to be executed from the memory by the processor on the computer motherboard 106. Moreover, the user can employ the tap gesture 302 on the touch control 428 to perform a desired map operation. In addition, the user can employ the press gesture 320 against the touch control 430 to perform a desired needle guide operation.

In accordance with the present application, various measurements and/or tracings of objects (such as organs, tissues, etc.) displayed as ultrasound images on the touch screen display 104 of the medical ultrasound imaging equipment 100 (see FIG. 1) can be performed, using single point/multipoint gestures on the surface 105 of the touch screen display 104. The user can perform such measurements and/or tracings of objects directly on an original ultrasound image of the displayed object, on a magnified version of the ultrasound image of the displayed object, and/or on a magnified portion of the ultrasound image within a virtual window 506 (see FIGS. 5C and 5D) on the touch screen display 104.

Figure 5A:
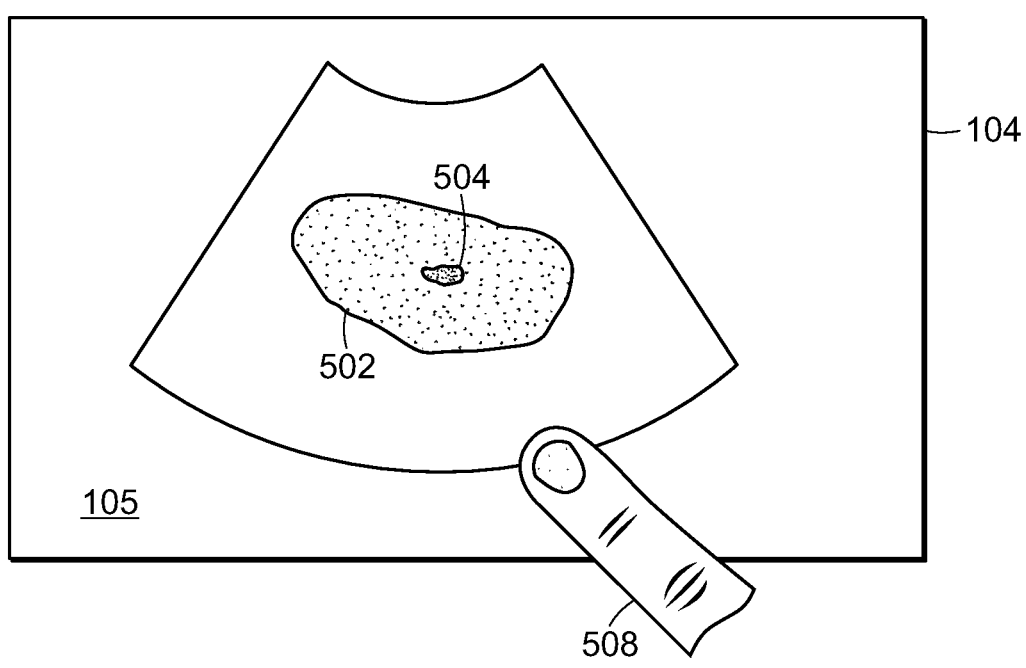
FIGS. 5A and 5B are exemplary representations of a liver with a cystic lesion on a touch screen display of the medical ultrasound imaging system in accordance with preferred embodiments of the invention.
Figure 5B:
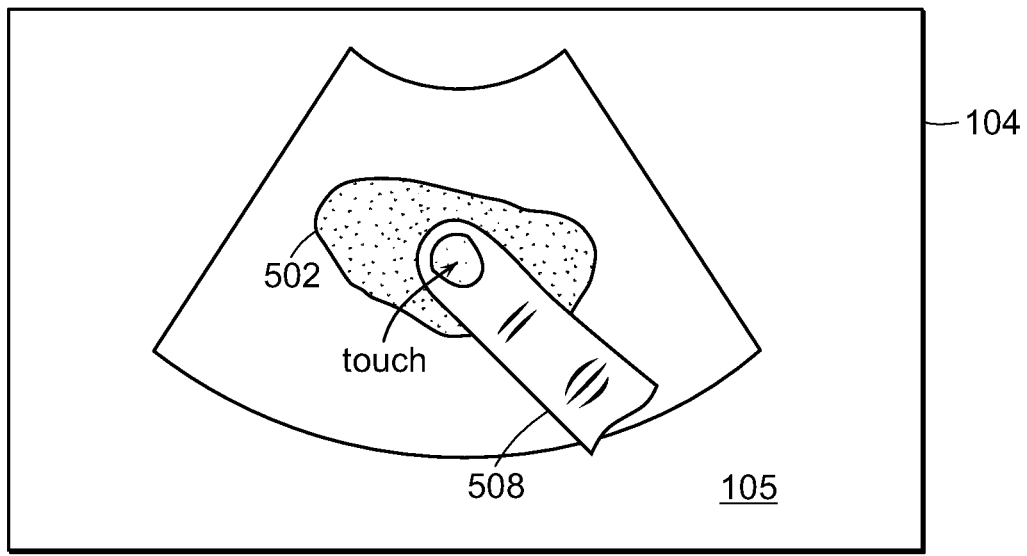
Figure 5C:
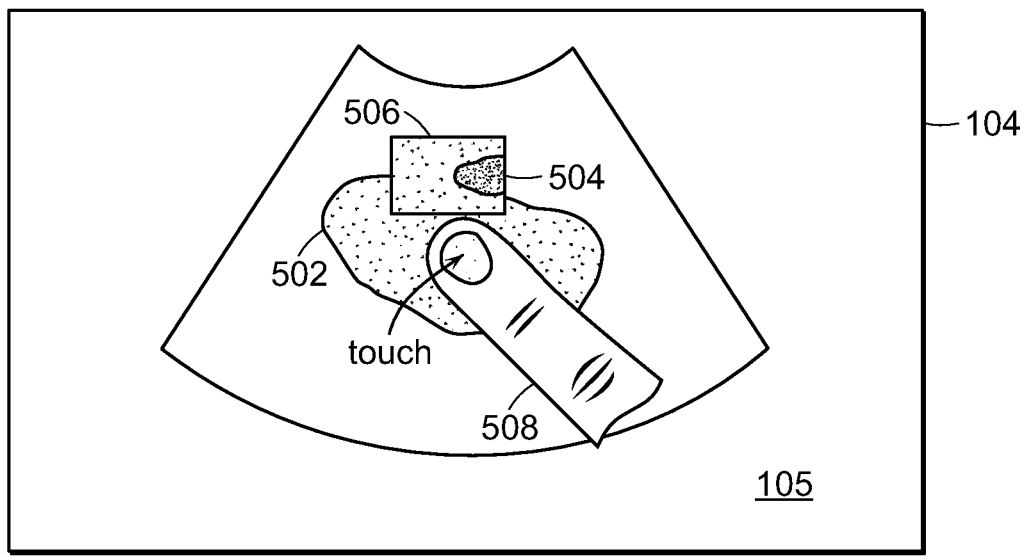
FIGS. 5C and 5D are exemplary representations of the liver and cystic lesion on the touch screen display of FIGS. 5A and 5B, including a virtual window that corresponds to a magnified portion of the liver.
Figure 5D:
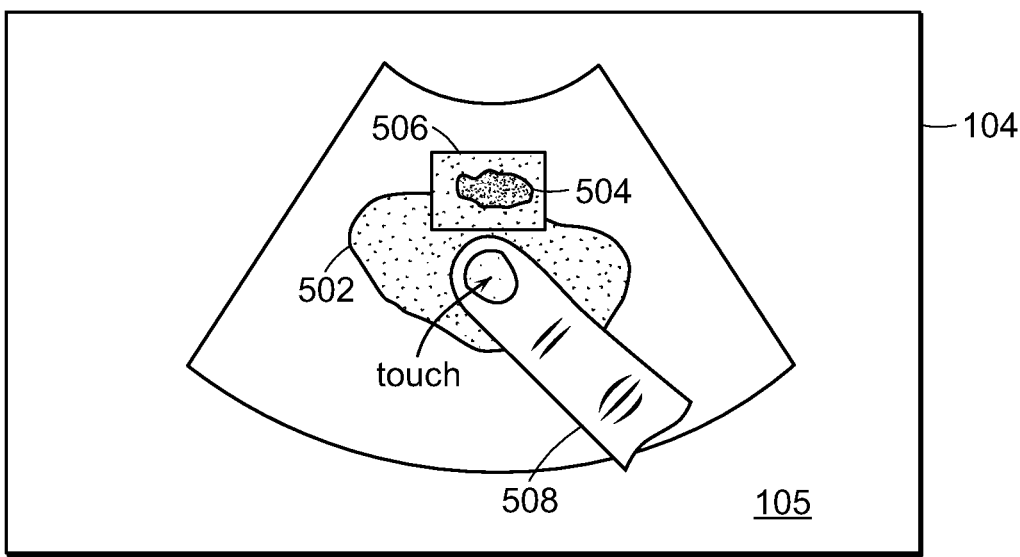

FIGS. 5A and 5B depict an original ultrasound image of an exemplary object, namely, a liver 502 with a cystic lesion 504, displayed on the touch screen display 104 of the medical ultrasound imaging equipment 100 (see FIG. 1). It is noted that such an ultrasound image can be generated by the medical ultrasound imaging equipment 100 in response to penetration of the liver tissue by ultrasound waves generated by an ultrasound probe/transducer operatively connected to the equipment 100. Measurements and/or tracings of the liver 502 with the cystic lesion 504 can be performed directly on the original ultrasound image displayed on the touch screen display 104 (see FIGS. 5A and 5B), or on a magnified version of the ultrasound image. For example, the user can obtain such a magnified version of the ultrasound image using a spread gesture (see, e.g., the spread gesture 312; FIG. 3) by placing two (2) fingers on the surface 105 of the touch screen display 104, and spreading them apart to magnify the original ultrasound image. Such measurements and/or tracings of the liver 502 and cystic lesion 504 can also be performed on a magnified portion of the ultrasound image within the virtual window 506 (see FIGS. 5C and 5D) on the touch screen display 104.

For example, using his or her finger (see, e.g., a finger 508; FIGS. 5A-5D), the user can obtain the virtual window 506 by employing a press gesture (see, e.g., the press gesture 320; FIG. 3) against the surface 105 of the touch screen display 104 (see FIG. 5B) in the vicinity of a region of interest, such as the region corresponding to the cystic lesion 504. In response to the press gesture, the virtual window 506 (see FIGS. 5C and 5D) is displayed on the touch screen display 104, possibly at least partially superimposed on the original ultrasound image, thereby providing the user with a view of a magnified portion of the liver 502 in the vicinity of the cystic lesion 504. For example, the virtual window 506 of FIG. 5C can provide a view of a magnified portion of the ultrasound image of the cystic lesion 504, which is covered by the finger 508 pressed against the surface 105 of the touch screen display 104. To re-position the magnified cystic lesion 504 within the virtual window 506, the user can employ a press and drag gesture (see, e.g., the press and drag gesture 322; FIG. 3) against the surface 105 of the touch screen display 104 (see FIG. 5D), thereby moving the image of the cystic lesion 504 to a desired position within the virtual window 506. In one embodiment, the medical ultrasound imaging equipment 100 can be configured to allow the user to select a level of magnification within the virtual window 506 to be 2 times larger, 4 times larger, or any other suitable number of times larger than the original ultrasound image. The user can remove the virtual window 506 from the touch screen display 104 by lifting his or her finger (see, e.g., the finger 508; FIGS. 5A-5D) from the surface 105 of the touch screen display 104.

Figure 6A:
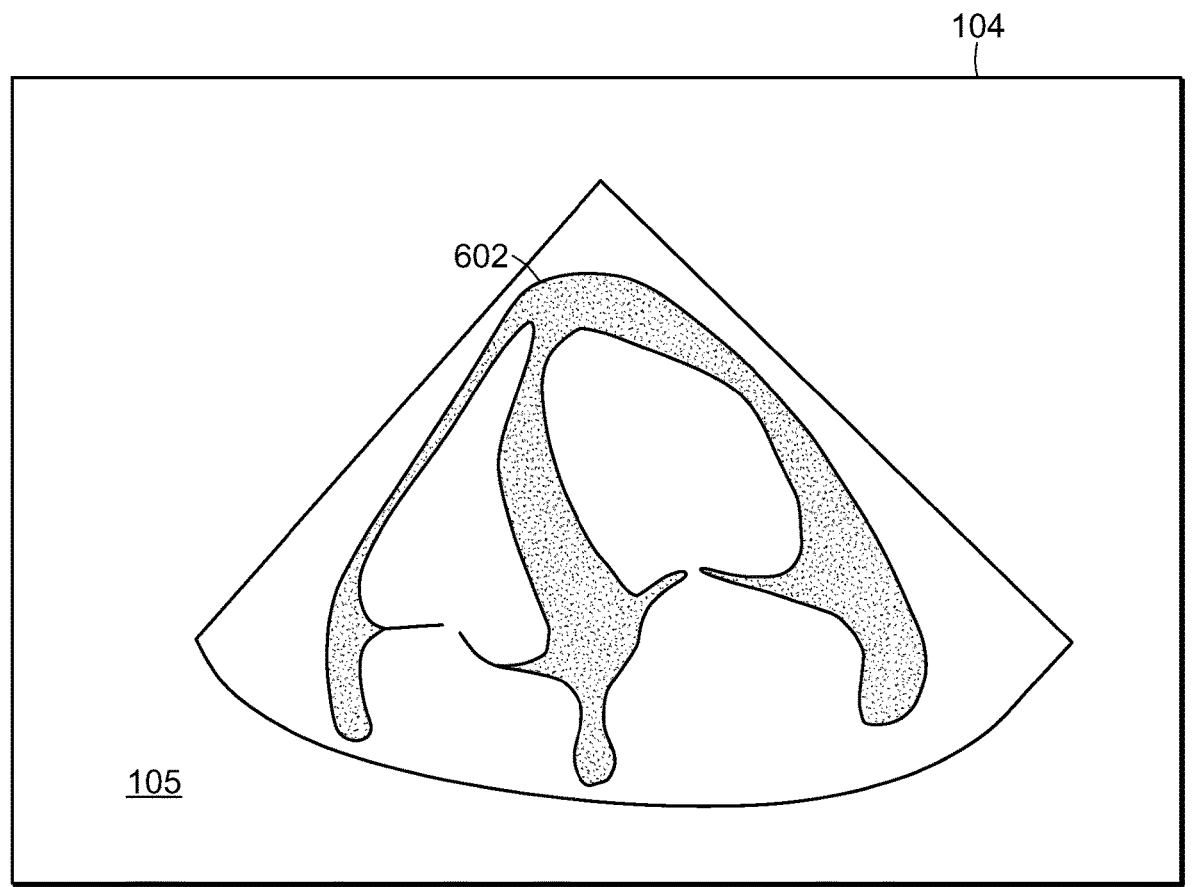
FIG. 6A is an exemplary representation of an apical four (4) chamber view of a heart on the touch screen display of the medical ultrasound imaging system.
Figure 6B:
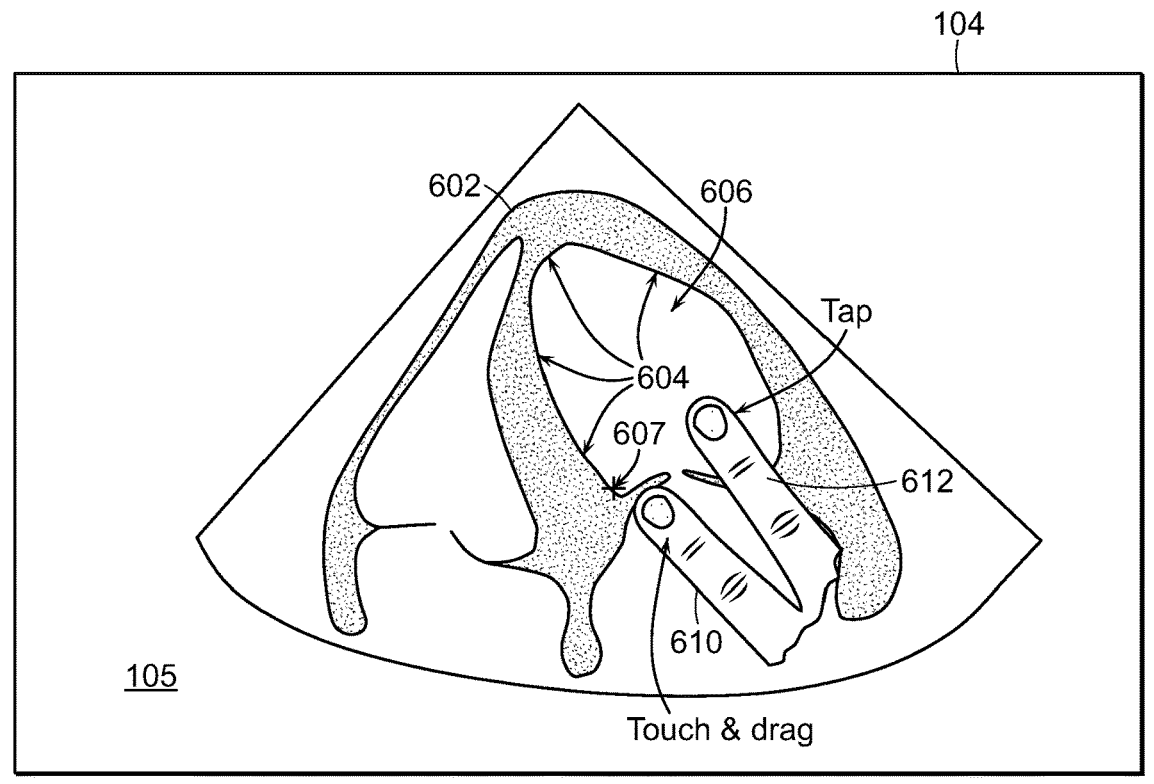
FIGS. 6B-6E illustrates an exemplary manual tracing of an endocardial border of a left ventricle of the heart on the touch screen display of FIG. 6A.

FIG. 6A depicts an ultrasound image of another exemplary object, namely, an apical four (4) chamber view of a heart 602, displayed on the touch screen display 104 of the medical ultrasound imaging equipment 100 (see FIG. 1). It is noted that such an ultrasound image can be generated by the medical ultrasound imaging equipment 100 in response to penetration of the heart tissue by ultrasound waves generated by an ultrasound probe/transducer operatively connected to the equipment 100. Measurements and/or tracings of the heart 602 can be performed directly on the original ultrasound image displayed on the touch screen display 104 (see FIGS. 6A-6E), or on a magnified version of the ultrasound image. For example, using his or her fingers (see, e.g., fingers 610, 612; FIGS. 6B-6E), the user can perform a manual tracing of an endocardial border 604 (see FIG. 6B) of a left ventricle 606 (see FIGS. 6B-6E) of the heart 602 by employing one or more multi-finger gestures on the surface 105 of the touch screen display 104. In one embodiment, using his or her fingers (see, e.g., the fingers 610, 612; FIGS. 6B-6E), the user can obtain a cursor 607 (see FIG. 6B) by employing a double tap gesture (see, e.g., the double tap gesture 310; FIG. 3A) on the surface 105 of the touch screen display 104, and can move the cursor 607 by employing a drag gesture (see, e.g., the drag gesture 318; FIG. 3A) using one finger, such as the finger 610, thereby moving the cursor 607 to a desired location on the touch screen display 104. The systems and methods described herein can be used for the quantitative measurement of heart wall motion and specifically for the measurement of ventricular dysynchrony as described in detail in U.S. application Ser. No. 10/817,316 filed on Apr. 2, 2004, the entire contents of which is incorporated herein by reference.

Figure 6C:
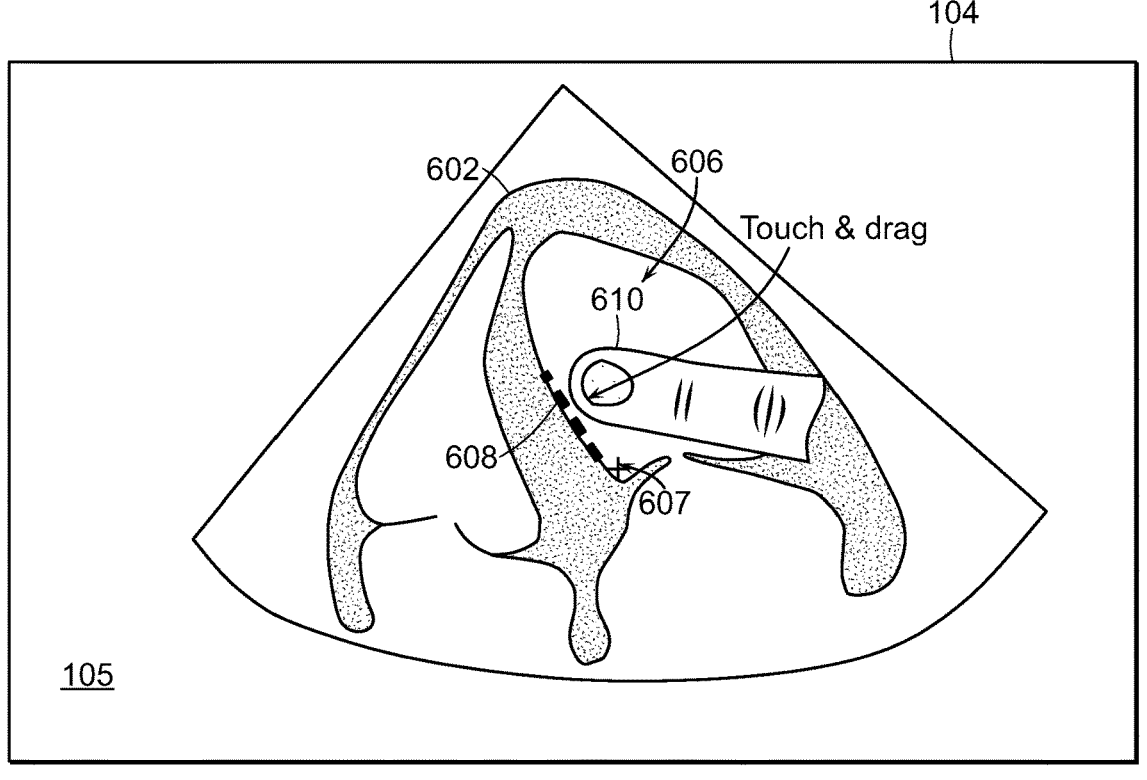
Figure 6D:
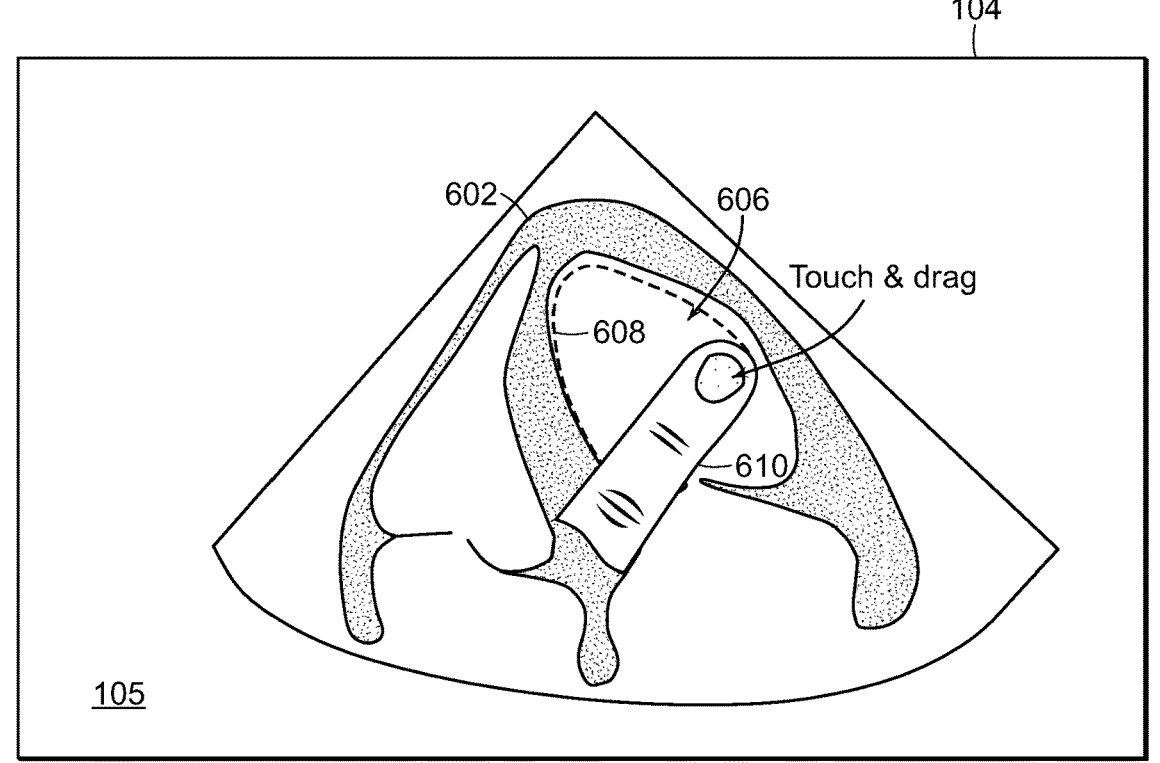
Figure 6E:
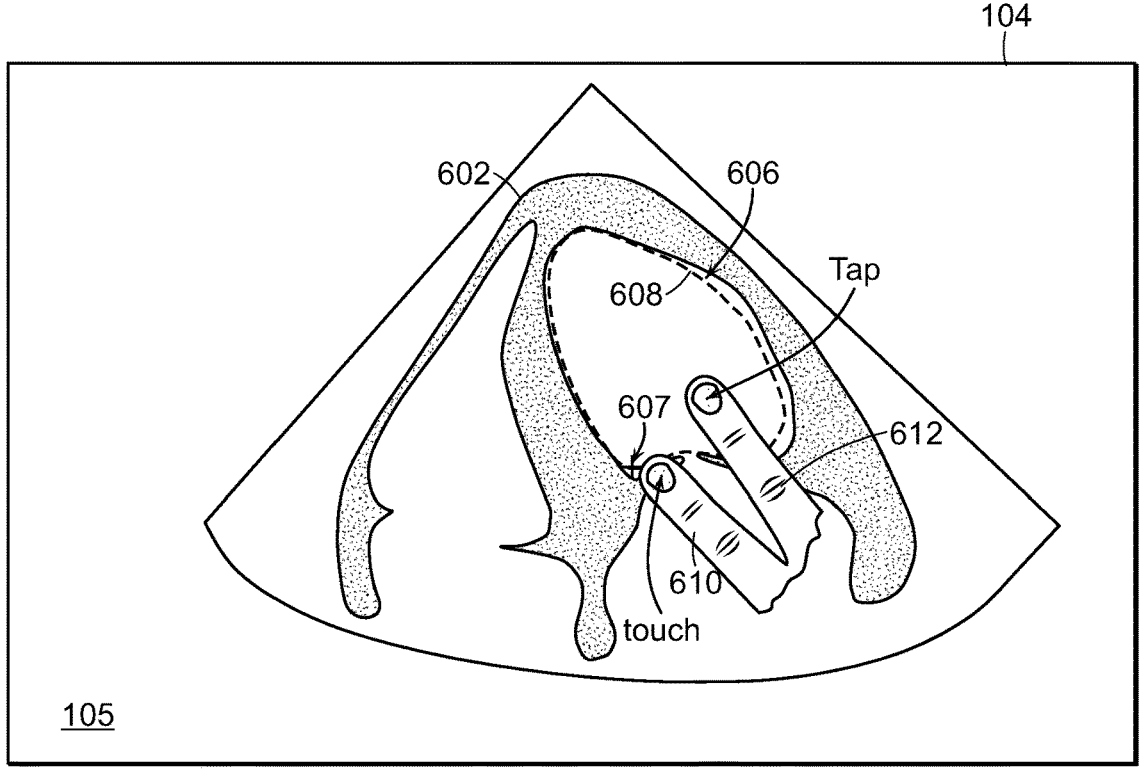

Once the cursor 607 is at the desired location on the touch screen display 104, as determined by the location of the finger 610, the user can fix the cursor 607 at that location by employing a tap gesture (see, e.g., the tap gesture 302; see FIG. 3) using another finger, such as the finger 612. To perform a manual tracing of the endocardial border 604 (see FIG. 6B), the user can employ a press and drag gesture (see, e.g., the press and drag gesture 322; FIG. 3) using the finger 610, as illustrated in FIGS. 6C and 6D. Such a manual tracing of the endocardial border 604 can be highlighted on the touch screen display 104 in any suitable fashion, such as by a dashed line 608 (see FIGS. 6C-6E). The manual tracing of the endocardial border 604 can continue until the finger 610 arrives at any suitable location on the touch screen display 104, or until the finger 610 returns to the location of the cursor 607, as illustrated in FIG. 6E. Once the finger 610 is at the location of the cursor 607, or at any other suitable location, the user can complete the manual tracing operation by employing a tap gesture (see, e.g., the tap gesture 302; see FIG. 3) using the finger 612. It is noted that such a manual tracing operation can be employed to trace any other suitable feature(s) and/or waveform(s), such as a pulsed wave Doppler (PWD) waveform. In one embodiment, the medical ultrasound imaging equipment 100 can be configured to perform any suitable calculation(s) and/or measurement(s) relating to such feature(s) and/or waveform(s), based at least in part on a manual tracing(s) of the respective feature(s)/ waveform(s).

Figures 7A, 7B, 7C:
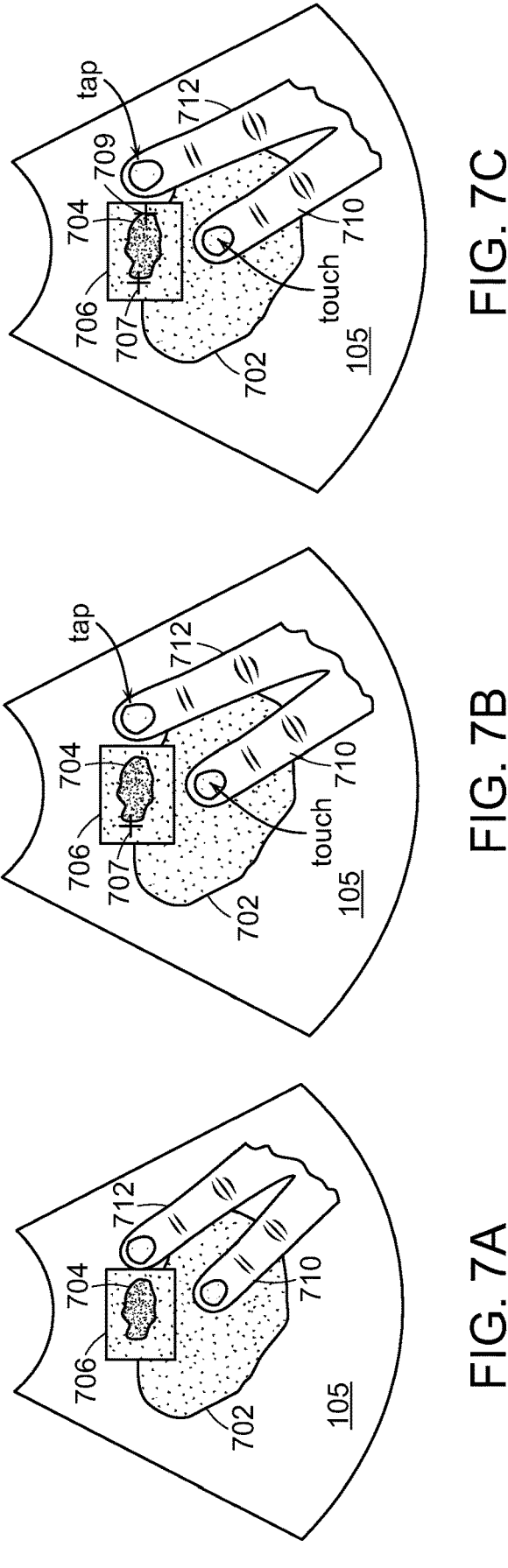
FIGS. 7A-7C illustrates an exemplary measurement of the size of the cystic lesion on the liver within the virtual window of FIGS. 5C and 5D.

As described above, the user can perform measurements and/or tracings of objects on a magnified portion of an original ultrasound image of a displayed object within a virtual window on the touch screen display 104. FIGS. 7A-7C depict an original ultrasound image of an exemplary object, namely, a liver 702 with a cystic lesion 704, displayed on the touch screen display 104 of the medical ultrasound imaging equipment 100 (see FIG. 1). FIGS. 7A-7C further depict a virtual window 706 that provides a view of a magnified portion of the ultrasound image of the cystic lesion 704, which is covered by one of the user's fingers, such as a finger 710, pressed against the surface 105 of the touch screen display 104. Using his or her fingers (see, e.g., fingers 710, 712; FIGS. 7A-7C), the user can perform a size measurement of the cystic lesion 704 within the virtual window 706 by employing one or more multi-finger gestures on the surface 105 of the touch screen display 104.

For example, using his or her fingers (see, e.g., the fingers 710, 712; FIGS. 7A-7C), the user can obtain a first cursor 707 (see FIGS. 7B, 7C) by employing a double tap gesture (see, e.g., the double tap gesture 310; FIG. 3) on the surface 105, and can move the first cursor 707 by employing a drag gesture (see, e.g., the drag gesture 318; FIG. 3) using one finger, such as the finger 710, thereby moving the first cursor 707 to a desired location. Once the first cursor 707 is at the desired location, as determined by the location of the finger 710, the user can fix the first cursor 707 at that location by employing a tap gesture (see, e.g., the tap gesture 302; see FIG. 3) using another finger, such as the finger 712. Similarly, the user can obtain a second cursor 709 (see FIG. 7C) by employing a double tap gesture (see, e.g., the double tap gesture 310; FIG. 3) on the surface 105, and can move the second cursor 709 by employing a drag gesture (see, e.g., the drag gesture 318; FIG. 3) using the finger 710, thereby moving the second cursor 709 to a desired location. Once the second cursor 709 is at the desired location, as determined by the location of the finger 710, the user can fix the second cursor 709 at that location by employing a tap gesture (see, e.g., the tap gesture 302; see FIG. 3) using the finger 712. In one embodiment, the medical ultrasound imaging equipment 100 can be configured to perform any suitable size calculation(s) and/or measurement(s) relating to the cystic lesion 704, based at least in part on the locations of the first and second cursors 707, 709.

Figures 8A, 8B, 8C:
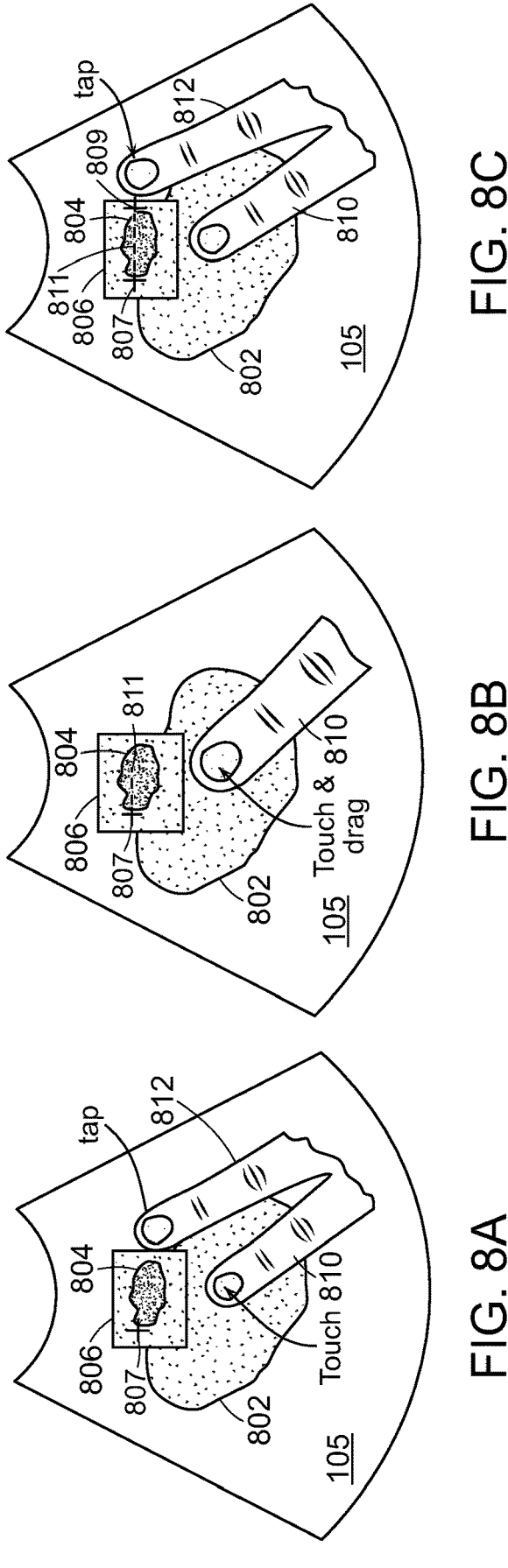
FIGS. 8A-8C illustrates an exemplary caliper measurement of the cystic lesion on the liver within the virtual window of FIGS. 5C and 5D.

FIGS. 8A-8C depict an original ultrasound image of an exemplary object, namely, a liver 802 with a cystic lesion 804, displayed on the touch screen display 104 of the medical ultrasound imaging equipment 100 (see FIG. 1). FIGS. 8a-8c further depict a virtual window 806 that provides a view of a magnified portion of the ultrasound image of the cystic lesion 804, which is covered by one of the user's fingers, such as a finger 810, pressed against the surface 105 of the touch screen display 104. Using his or her fingers (see, e.g., fingers 810, 812; FIGS. 8A-8C), the user can perform a caliper measurement of the cystic lesion 804 within the virtual window 806 by employing one or more multi-finger gestures on the surface 105 of the touch screen display 104.

For example, using his or her fingers (see, e.g., the fingers 810, 812; FIGS. 8A-8C), the user can obtain a first cursor 807 (see FIGS. 8B, 8C) by employing a double tap gesture (see, e.g., the double tap gesture 310; FIG. 3) on the surface 105, and can move the cursor 807 by employing a drag gesture (see, e.g., the drag gesture 318; FIG. 3) using one finger, such as the finger 810, thereby moving the cursor 807 to a desired location. Once the cursor 807 is at the desired location, as determined by the location of the finger 810, the user can fix the cursor 807 at that location by employing a tap gesture (see, e.g., the tap gesture 302; see FIG. 3) using another finger, such as the finger 812. The user can then employ a press and drag gesture (see, e.g., the press and drag gesture 322; FIG. 3) to obtain a connecting line 811 (see FIGS. 8B, 8C), and to extend the connecting line 811 from the first cursor 807 across the cystic lesion 804 to a desired location on another side of the cystic lesion 804. Once the connecting line 811 is extended across the cystic lesion 804 to the desired location on the other side of the cystic lesion 804, the user can employ a tap gesture (see, e.g., the tap gesture 302; see FIG. 3) using the finger 812 to obtain and fix a second cursor 809 (see FIG. 8C) at that desired location. In one embodiment, the medical ultrasound imaging equipment 100 can be configured to perform any suitable caliper calculation(s) and/or measurement(s) relating to the cystic lesion 804, based at least in part on the connecting line 811 extending between the locations of the first and second cursors 807, 809.

Figure 9A:
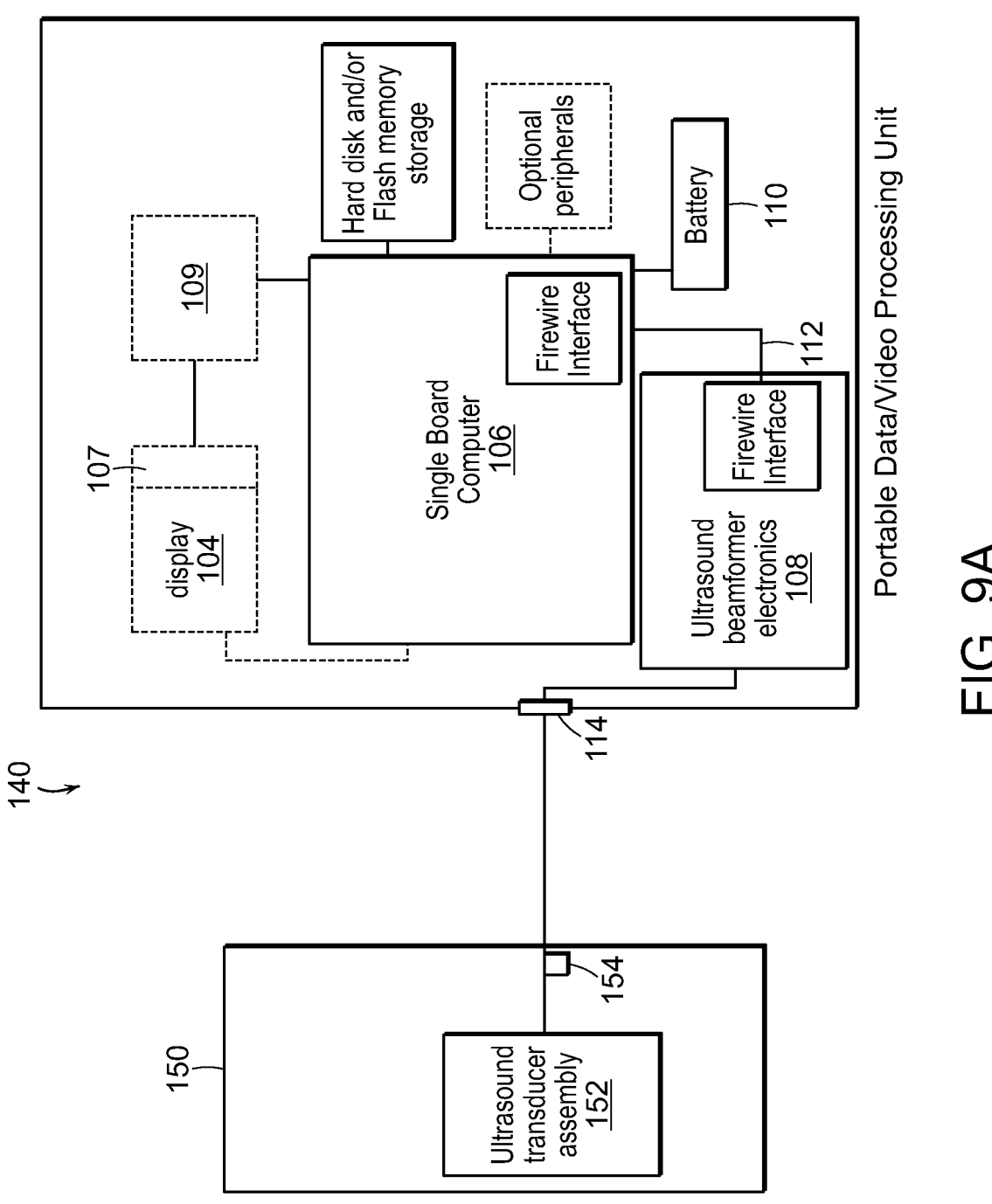
FIG. 9A illustrates one of a plurality of transducer arrays attached to the processor housing.

FIG. 9A shows a system 140 in which a transducer housing 150 with an array of transducer elements 152 can be attached at connector 114 to housing 102. Each probe 150 can have a probe identification circuit 154 that uniquely identifies the probe that is attached. When the user inserts a different probe with a different array, the system identifies the probe operating parameters. Note that preferred embodiments can include a display 104 having a touch sensor 107 which can be connected to a touch processor 109 that analyzes touchscreen data from the sensor 107 and transmits commands to both image processing operations and to a beamformer control processor (1116, 1124). In a preferred embodiment, the touch processor can include a computer readable medium that stores instructions to operate an ultrasound touchscreen engine that is operable to control display and imaging operations described herein.

Figure 9B:
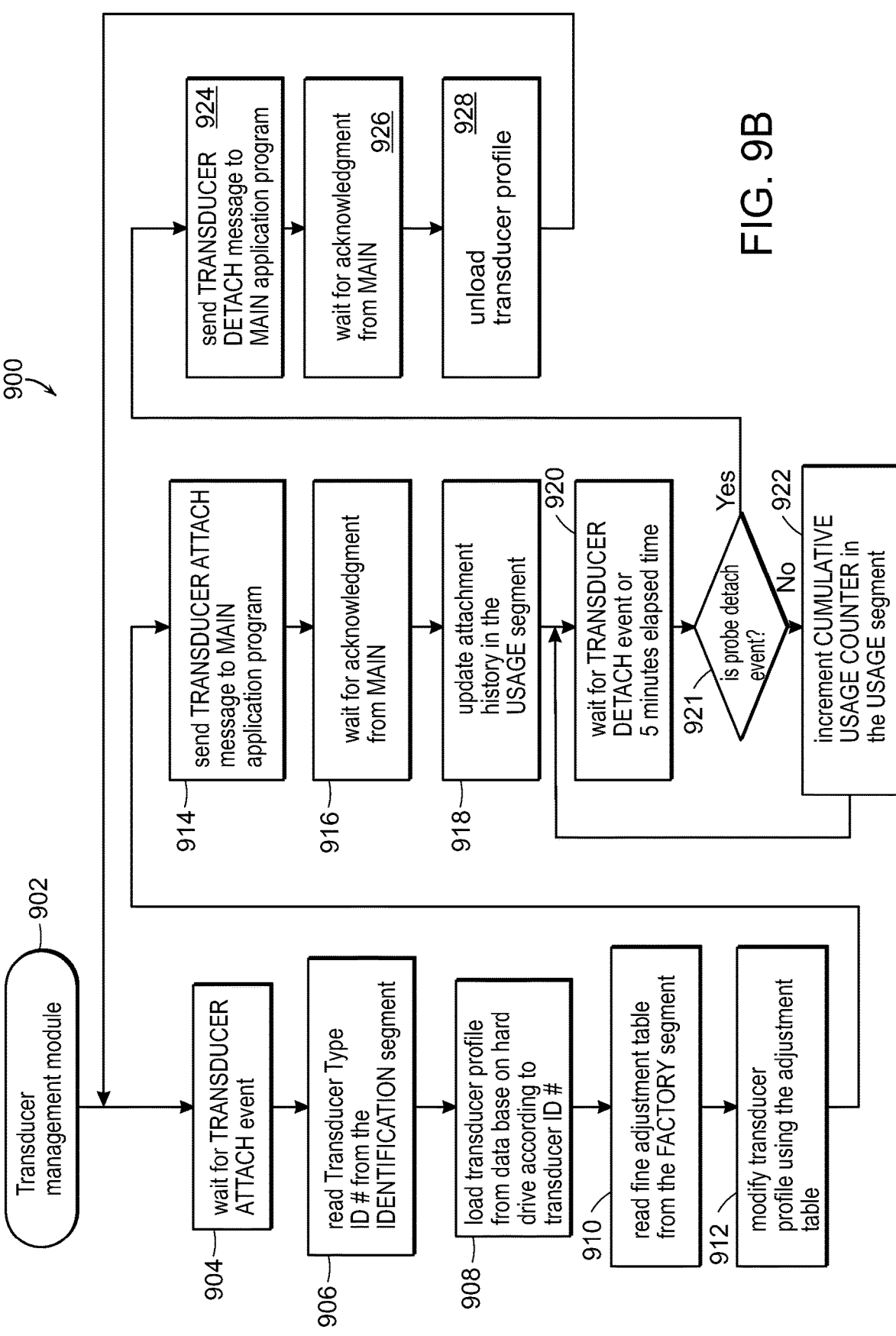
FIG. 9B shows a transducer attach sequence in accordance with exemplary embodiments.

FIG. 9B shows a software flowchart 900 of a typical transducer management module 902 within the ultrasound application program. When a TRANSDUCER ATTACH 904 event is detected, the Transducer Management Software Module 902 first reads the Transducer type ID 906 and hardware revision information from the IDENTIFICATION Segment. The information is used to fetch the particular set of transducer profile data 908 from the hard disk and load it into the memory of the application program. The software then reads the adjustment data from the FACTORY Segment 910 and applies the adjustments to the profile data just loaded into memory 912. The software module then sends a TRANSDUCER ATTACH Message 914 to the main ultrasound application program, which uses the transducer profile already loaded. After acknowledgment 916, an ultrasound imaging sequence is performed and the USAGE segment is updated 918. The Transducer Management Software Module then waits for either a TRANSDUCER DETACH event 920, or the elapse of 5 minutes. If a TRANSDUCER DETACH event is detected 921, a message 924 is sent and acknowledged 926, the transducer profile data set is removed 928 from memory and the module goes back to wait for another TRANSDUCER ATTACH event. If a 5 minutes time period expires without detecting a TRANSDUCER DETACH event, the software module increments a Cumulative Usage Counter in the USAGE Segment 922, and waits for another 5 minutes period or a TRANSDUCER DETACH event. The cumulative usage is recorded in memory for maintenance and replacement records.

There are many types of ultrasound transducers. They differ by geometry, number of elements, and frequency response. For example, a linear array with center frequency of 10 to 15 MHz is better suited for breast imaging, and a curved array with center frequency of 3 to 5 MHz is better suited for abdominal imaging.

It is often necessary to use different types of transducers for the same or different ultrasound scanning sessions. For ultrasound systems with only one transducer connection, the operator will change the transducer prior to the start of a new scanning session.

In some applications, it is necessary to switch among different types of transducers during one ultrasound scanning session. In this case, it is more convenient to have multiple transducers connected to the same ultrasound system, and the operator can quickly switch among these connected transducers by hitting a button on the operator console, without having to physically detach and re-attach the transducers, which takes a longer time. Preferred embodiments of the invention can include a multiplexor within the tablet housing that can select between a plurality of probe connector ports within the tablet housing, or alternatively, the tablet housing can be connected to an external multiplexor that can be mounted on a cart as described herein.

Figure 9C:
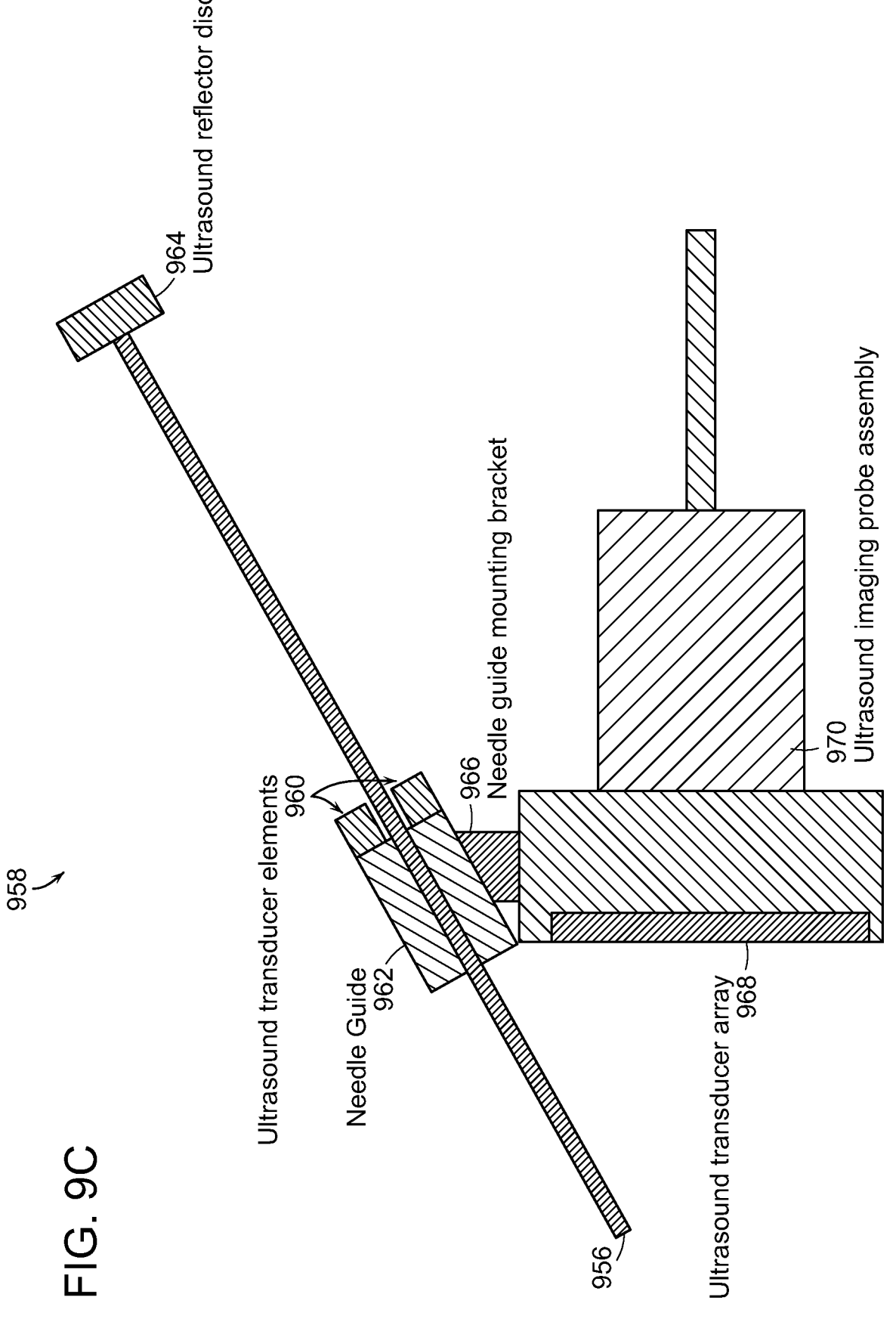
FIG. 9C shows a perspective view of a needle sensing positioning system with exemplary embodiments.

FIG. 9C is a perspective view of an exemplary needle sensing positioning system using ultrasound transducers without the requirement of any active electronics in the sensor assembly. The sensor transducer may include a passive ultrasound transducer element. The elements may be used in a similar way as a typical transducer probe, utilizing the ultrasound engine electronics. The system 958 includes the addition of ultrasound transducer elements 960, added to a needle guide 962, that is represented in FIG. 9C but that may be any suitable form factor. The ultrasound transducer element 960, and needle guide 962, may be mounted using a needle guide mounting bracket 966, to an ultrasound transducer probe acoustic handle or an ultrasound imagining probe assembly 970. The needle with a disc mounted on the exposed end, the ultrasound reflector disc 964, is reflective to ultrasonic waves.

The ultrasound transducer element 960, on the needle guide 962, may be connected to the ultrasound engine. The connection may be made through a separate cable to a dedicated probe connector on the engine, similar to a sharing the pencil CW probe connector. In an alternate embodiment, a small short cable may be plugged into the larger image transducer probe handle or a split cable connecting to the same probe connector at the engine. In another alternate embodiment the connection may be made via an electrical connector between the image probe handle and the needle guide without a cable in between. In an alternate embodiment the ultrasound transducer elements on the needle guide may be connected to the ultrasound engine by enclosing the needle guide and transducer elements in the same mechanical enclosure of the imagining probe handle.

Figure 9D:
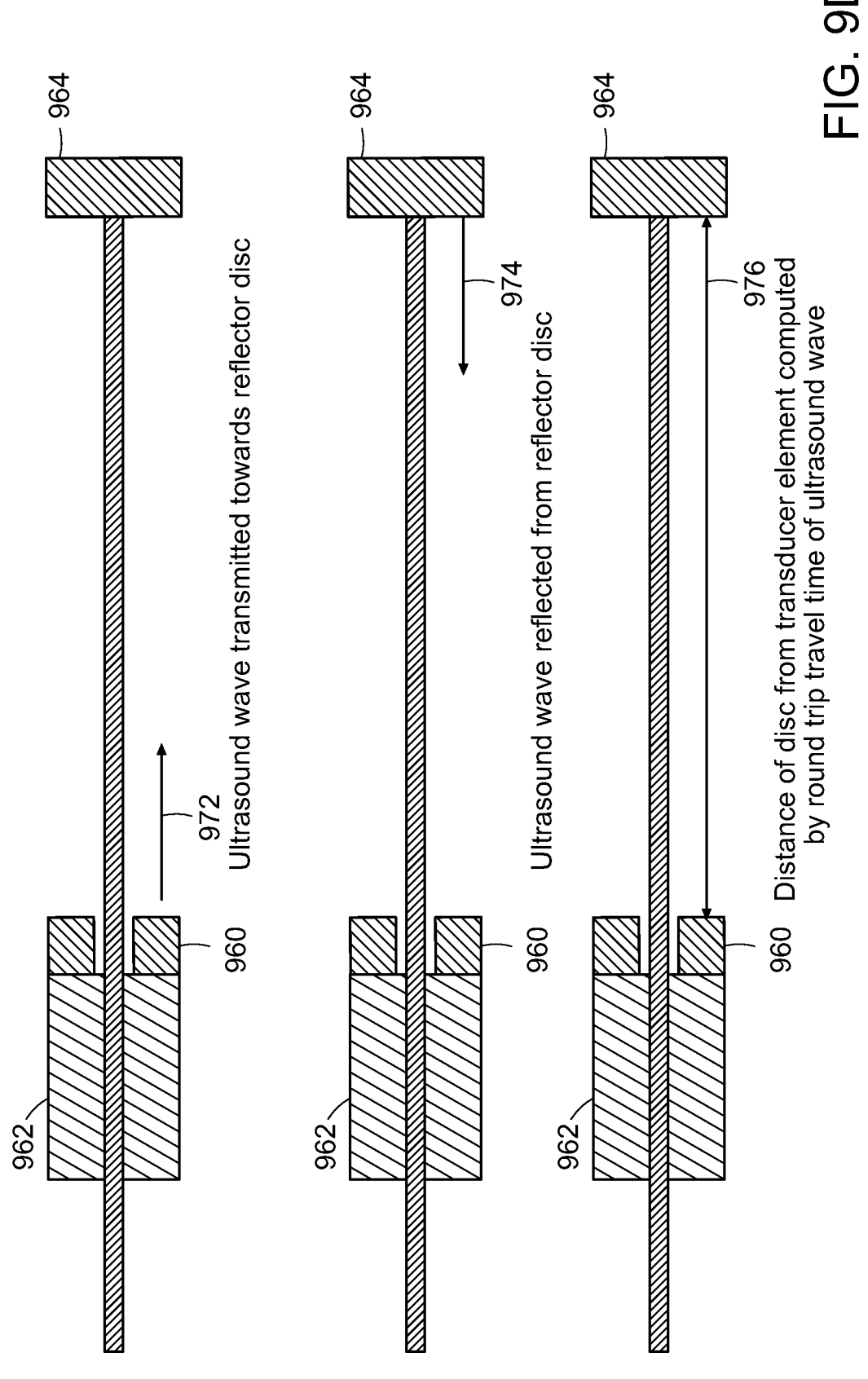
FIG. 9D shows a perspective view of a needle guide with exemplary embodiments.

FIG. 9D is a perspective view of a needle guide 962, positioned with transducer elements 960 and the ultrasound reflector disc 964. The position of the reflector disc 964 is located by transmitting ultrasonic wave 972, from the transducer element 960 on the needle guide 962. The ultrasound wave 972 travels through the air towards reflector disc 964 and is reflected by the reflector disc 964. The reflected ultrasound wave 974, reaches the transducer element 960 on the needle guide 962. The distance 976, between the reflector disc 964, and the transducer element 960 is calculated from the time elapsed and the speed of sound in the air.

Figure 9E:
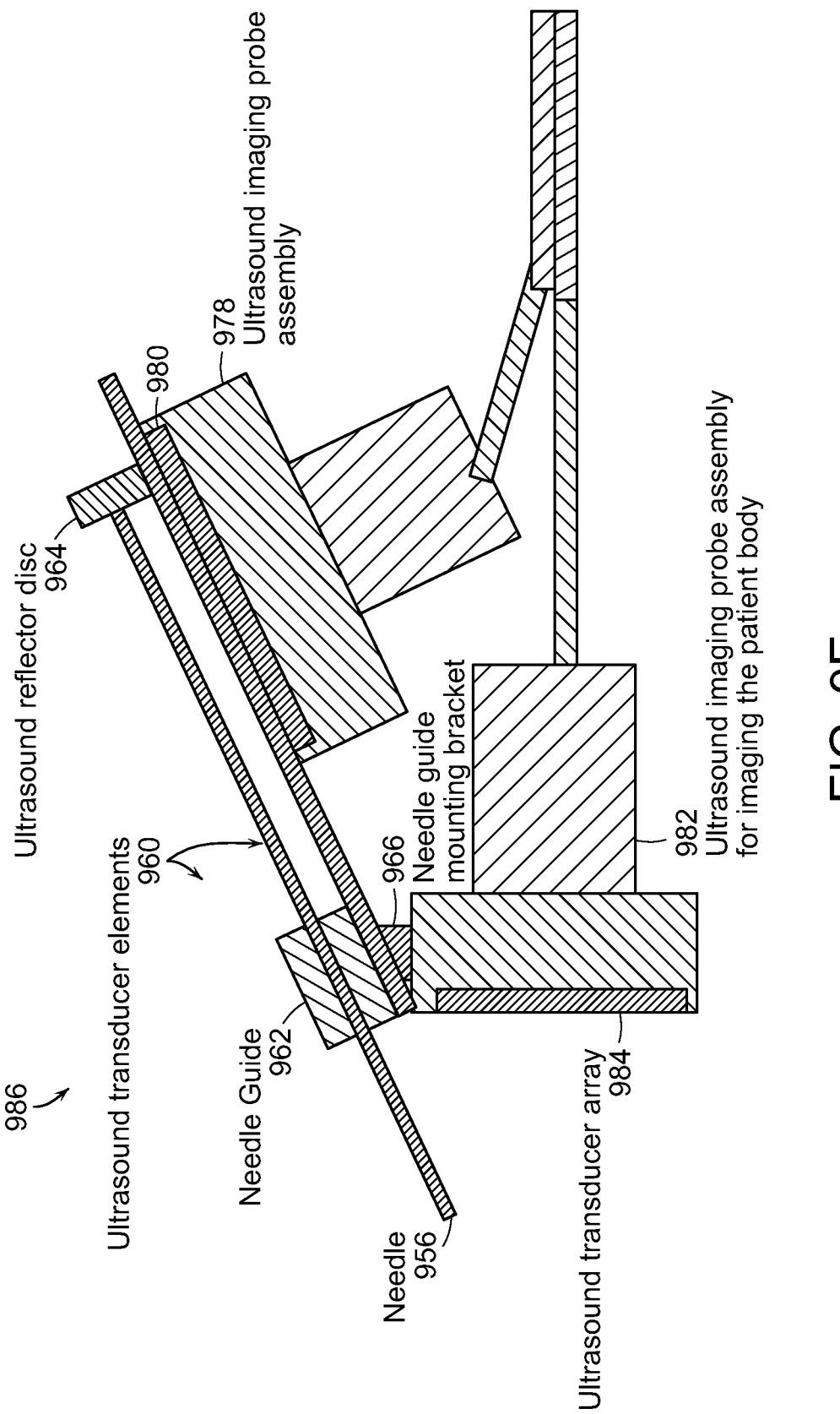
FIG. 9E shows a perspective view of a needle sensing positioning system with exemplary embodiments.

FIG. 9E is a perspective view of an alternate embodiment of the exemplary needle sensing positioning system using ultrasound transducers without the requirement of any active electronics in the sensor assembly. The sensor transducer may include a passive ultrasound transducer element. The elements may be used in a similar way as a typical transducer probe, utilizing the ultrasound engine electronics.

The system 986 includes needle guide 962 that may be mounted to a needle guide mounting bracket 966 that may be coupled to an ultrasound imaging probe assembly for imaging the patient's body 982, or alternative suitable form factors. The ultrasound reflector disc 964 may be mounted at the exposed end of the needle 956. In this embodiment a linear ultrasound acoustic array 978, is mounted parallel to the direction of movement of the needle 956. The linear ultrasound acoustic array 978 includes an ultrasound transducer array 980 positioned parallel to the needle 956. In this embodiment an ultrasound imagining probe assembly 982, is positioned for imagining the patient body. The ultrasound imaging probe assembly for imaging the patient body 982 is configured with an ultrasound transducer array 984.

In this embodiment, the position of the ultrasound reflector disc 964 can be detected by using the ultrasound transducer array 980 coupled to an ultrasound imaging probe assembly for imaging 978. The position of the reflector disc 964 is located by transmitting ultrasonic wave 972, from the transducer element 980 on the ultrasound imaging probe assembly for imaging 978. The ultrasound wave 972 travels through the air towards reflector disc 964 and is reflected by the reflector disc 964. The reflected ultrasound wave 974, reaches the transducer element 980 on the ultrasound imaging probe assembly for imaging 978. The distance 976, between the reflector disc 964, and the transducer element 980 is calculated from the time elapsed and the speed of sound in the air. In an alternate embodiment an alternate algorithm may be used to sequentially scan the polarity of elements in the transducer array and analyze the reflections produced per transducer array element. In an alternate embodiment a plurality of scans may occur prior to forming an ultrasound image.

Figure 9F:
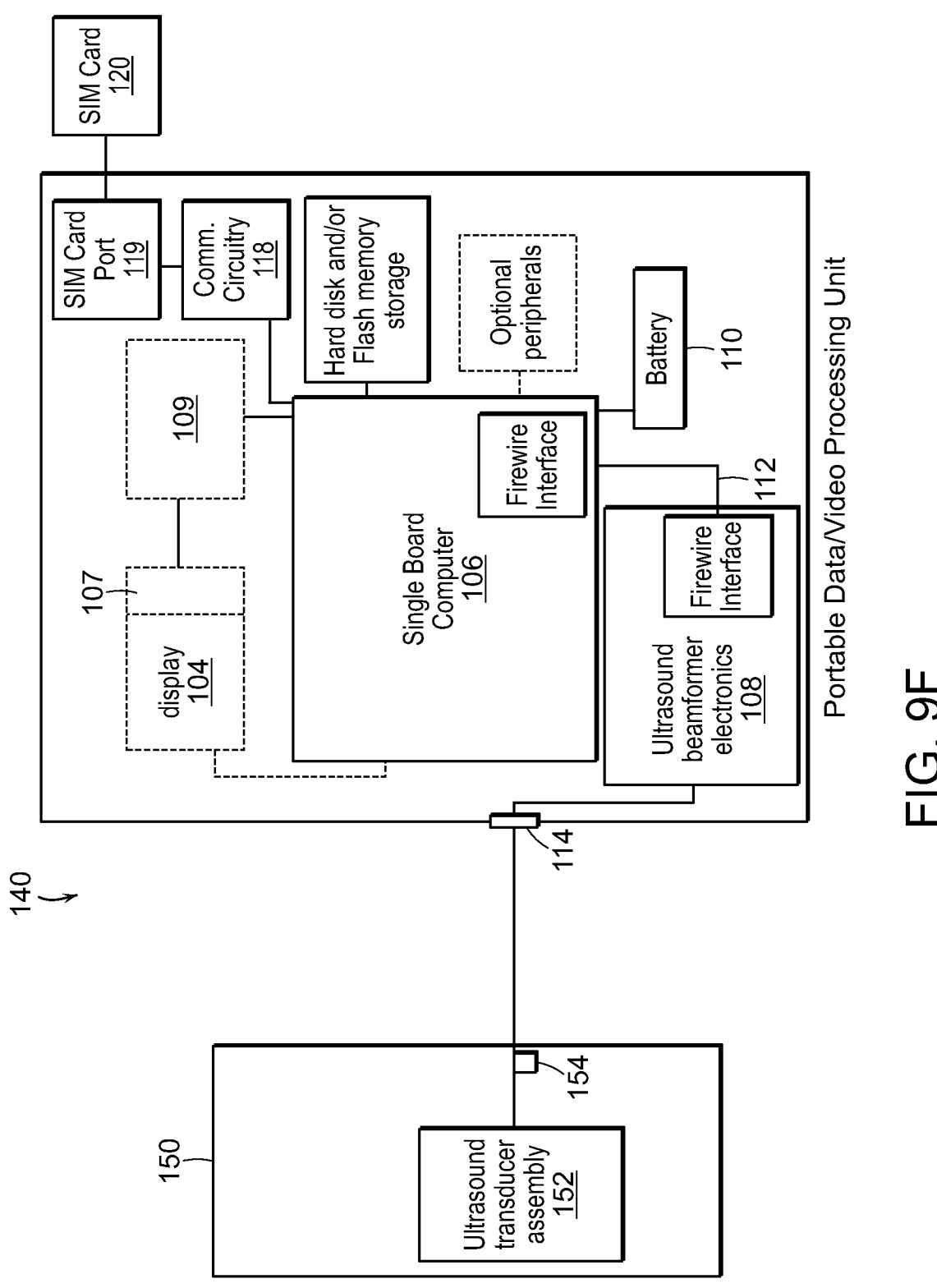
FIG. 9F illustrates a system having a cellular communications card.

FIG. 9F illustrates a system in which a SIM card 120 can be used for wireless 36/46 cellular services for communication with the portable ultrasound systems as described herein including the systems illustrated in FIGS. 1A and 1B. The card 120 can be inserted into a housing port 119 which communicates using circuitry 118 with system processor 106.

Figure 10A:
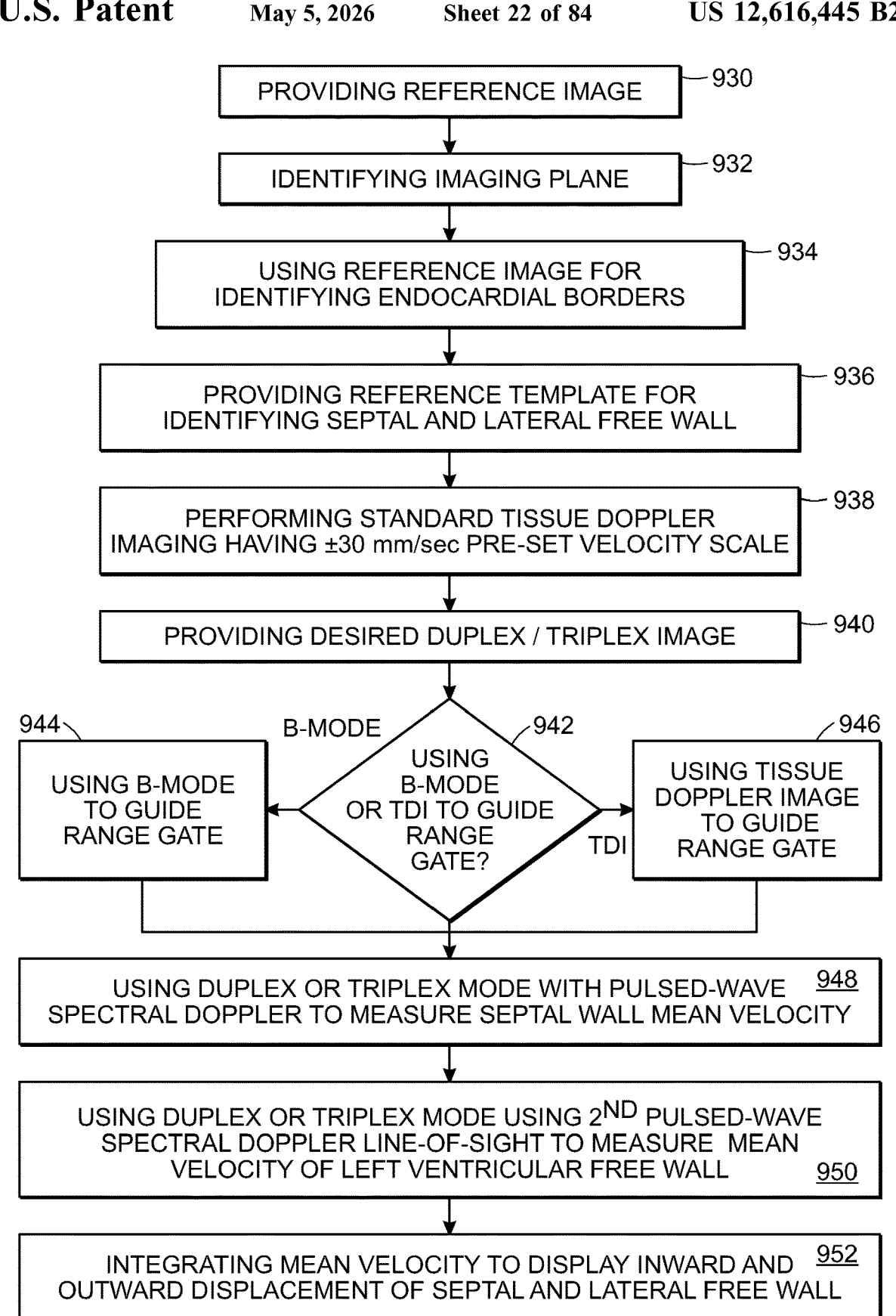
FIG. 10A shows a method of measuring heart wall motion.

FIG. 10A illustrates an exemplary method for monitoring the synchrony of a heart in accordance with exemplary embodiments. In the method, a reference template is loaded into memory and used to guide a user in identifying an imaging plane (per step 930). Next a user identifies a desired imaging plane (per step 932). Typically an apical 4-chamber view of the heart is used; however, other views may be used without departing from the spirit of the invention.

At times, identification of endocardial borders may be difficult, and when such difficulties are encountered tissue Doppler imaging of the same view may be employed (per step 934). A reference template for identifying the septal and lateral free wall is provided (per step 936). Next, standard tissue Doppler imaging (TDI) with pre-set velocity scales of, say, ±30 cm/sec may be used (per step 938).

Then, a reference of the desired triplex image may be provided (per step 940). Either B-mode or TDI may be used to guide the range gate (per step 942). B-mode can be used for guiding the range gate (per step 944) or TDI for guiding the range gate (per step 946). Using TDI or B-mode for guiding the range gate also allows the use of a direction correction angle for allowing the Spectral Doppler to display the radial mean velocity of the septal wall. A first pulsed-wave spectral Doppler is then used to measure the septal wall mean velocity using duplex or triplex mode (per step 948). The software used to process the data and calculate dysychrony can utilize a location (e.g. a center point) to automatically set an angle between dated locations on a heart wall to assist in simplifying the setting of parameters.

A second range-gate position is also guided using a duplex image or a TDI (per step 950), and a directional correction angle may be used if desired. After step 950, the mean velocity of the septal wall and lateral free wall are being tracked by the system. Time integration of the Spectral Doppler mean velocities 952 at regions of interest (e.g., the septum wall and the left ventricular free wall) then provides the displacement of the septal and left free wall, respectively.

The above method steps may be utilized in conjunction with a high pass filtering means, analog or digital, known in the relevant arts for removing any baseline disturbance present in collected signals. In addition, the disclosed method employs multiple simultaneous PW Spectral Doppler lines for tracking movement of the interventricular septum and the left ventricular fee wall. In additional, a multiple gate structure may be employed along each spectral line, thus allowing quantitative measurement of regional wall motion. Averaging over multiple gates may allow measurement of global wall movement.

Figure 10B:
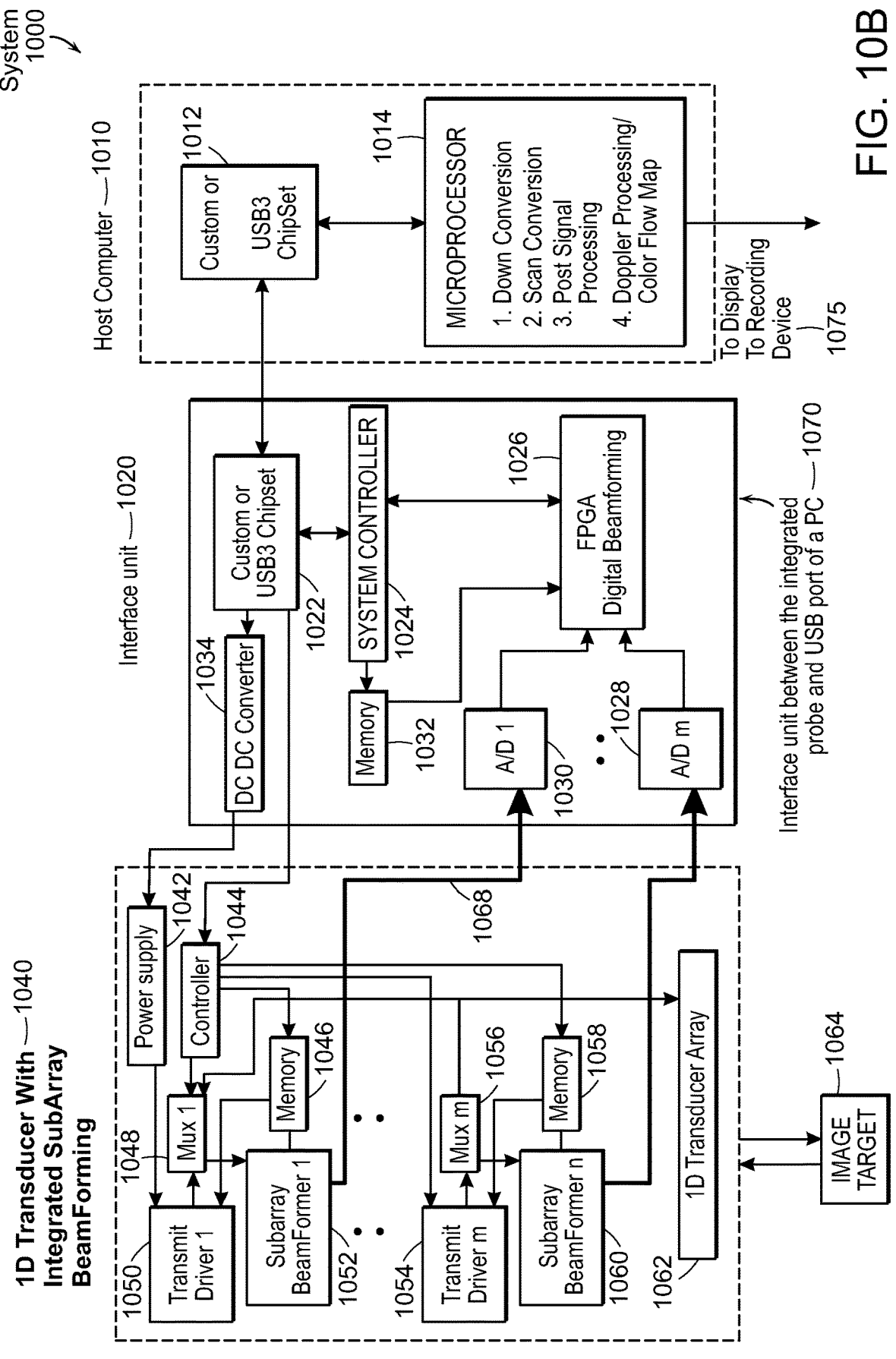
FIG. 10B shows a schematic block diagram for an integrated ultrasound probe with exemplary embodiments.

FIG. 10B is a detailed schematic block diagram for an exemplary embodiment of the integrated ultrasound probe 1040 can be connected to any PC 1010 through an Interface unit 1020. The ultra sound probe 1040 is configured to transmit ultrasound waves to and reduce reflected ultrasound waves from on ore more image targets 1064. The transducer 1040 can be coupled to the interface unit 1020 using one or more cables 1066, 1068. The interface unit 1020 can be positioned between the integrated ultrasound probe 1040 and the host computer 1010. The two stage beam forming system 1040 and 1020 can be connected to any PC through a USB connection 1022, 1012.

The ultrasound probe 1040, can include sub-arrays/apertures 1052 consisting of neighboring elements with an aperture smaller than that of the whole array. Returned echoes are received by the 1D transducer array 1062 and transmitted to the controller 1044. The controller initiates formation of a coarse beam by transmitting the signals to memory 1058, 1046. The memory 1058, 1046 transmits a signal to a transmit Driver 1 1050, and Transmit Driver m 1054. Transmit Driver 1 1050 and Transmit Driver m 1054 then send the signal to mux1 1048 and mux m 1056, respectively. The signal is transmitted to sub-array beamformer 1 1052 and sub-array beamformer n 1060.

The outputs of each coarse beam forming operation can include further processing through a second stage beam forming in the interface unit 1020 to convert the beam forming output to digital representation. The coarse beam forming operations can be coherently summed to form a fine beam output for the array. The signals can be transmitted from the ultrasound probe 1040 sub-array beam former 1 1052 and sub-array beam former n 1060 to the A/D convertors 1030 and 1028 within the interface unit 1020. Within the interface unit 1020 there are A/D converters 1028, 1030 for converting the first stage beam forming output to digital representation. The digital conversion can be received from the A/D convertors 1030, 1028 by a customer ASIC such as a FPGA 1026 to complete the second stage beam forming. The FPGA Digital beam forming 1026 can transmit information to the system controller 1024. The system controller can transmit information to a memory 1032 which may send a signal back to the FPGA Digital Beam forming 1026. Alternatively, the system controller 1024 may transmit information to the custom USB3 Chipset 1022. The USB3 Chipset 1022 may then transmit information to a DC-DC convertor 1034. In turn, the DC-DC convertor 1034 may transmit power from the interface unit 1020 to the ultrasound probe 1040. Within the ultrasound probe 1040 a power supply 1042 may receive the power signal and interface with the transmit driver 1 1050 to provide the power to the front end integration probe.

The Interface unit 1020 custom or USB3 Chipset 1022 may be used to provide a communication link between the interface unit 10220 and the host computer 1010. The custom or USB3 Chipset 1022 transmits a signal to the host computer's 1010 custom or USB3 Chipset 1012. The custom or the USB3 Chipset 1012 then interfaces with the microprocessor 1014. The microprocessor 1014 then may display information or send information to a device 1075.

In an alternate embodiment, a narrow band beamformer can be used. For example, an individual analog phase shifter is applied to each of the received echoes. The phase shifted outputs within each sub-array are then summed to form a coarse beam. The A/D converts can be used to digitize each of the coarse beams; a digital beam former is then used to form the fine beam.

In another embodiment, forming a 64 element linear array may use eight adjacent elements to form a coarse beam output. Such arrangement may utilize eight output analog cables connecting the outputs of the integrated probe to the interface units. The coarse beams may be sent through the cable to the corresponding A/D convertors located in the interface unit. The digital delay is used to form a fine beam output. Eight A/D convertors may be required to form the digital representation.

In another embodiment, forming a 128 element array may use sixteen sub-array beam forming circuits. Each circuit may form a coarse beam from an adjacent eight element array provided in the first stage output to the interface unit. Such arrangement may utilize sixteen output analog cables connecting the outputs of the integrated probe to the interface units to digitize the output. A PC microprocessor or a DSP may be used to perform the down conversion, basebanding, scan conversion and post image processing functions. The microprocessor or DSP can also be used to perform all the Doppler processing functions.

Figure 10C:
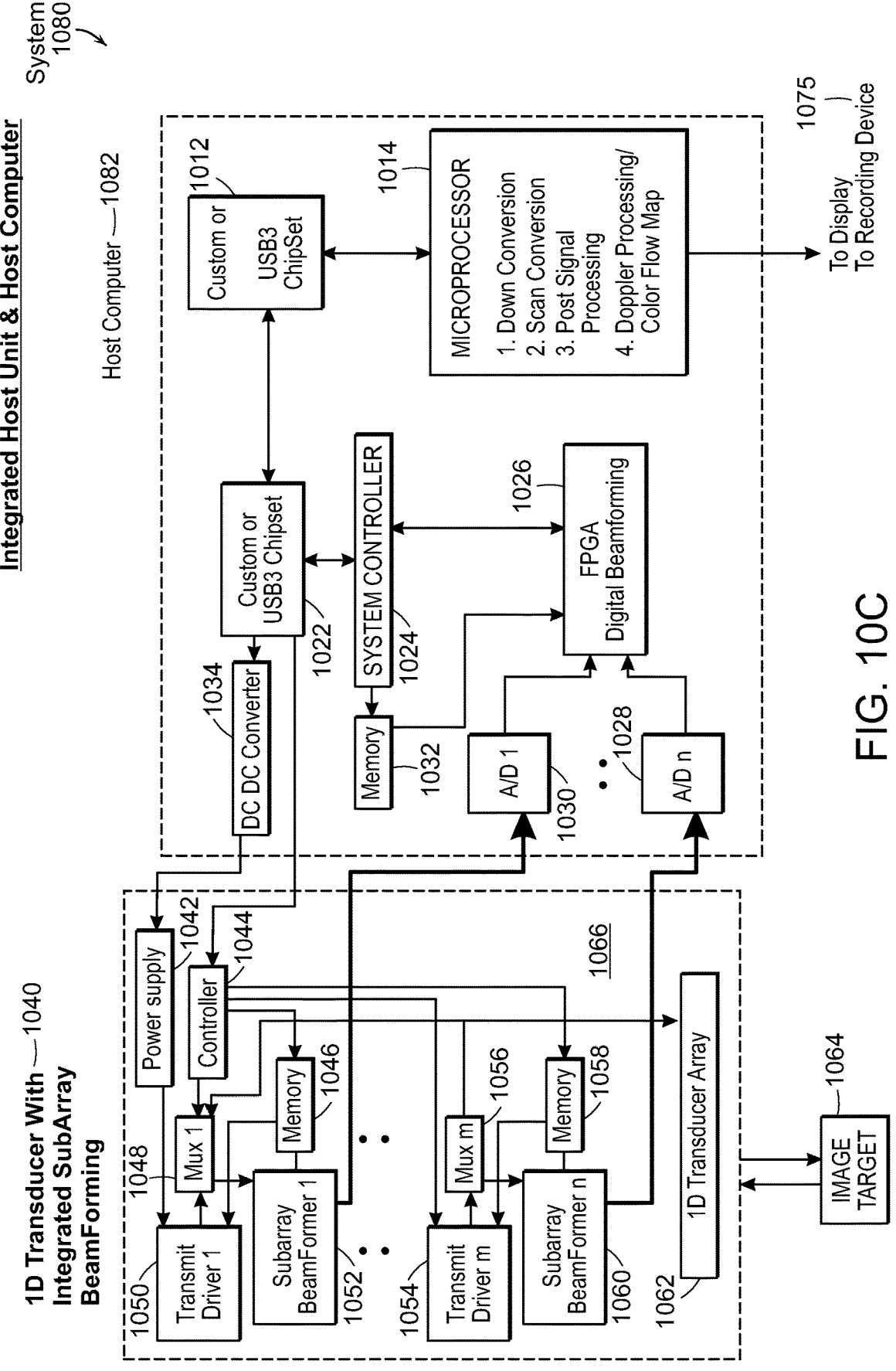
FIG. 10C shows a schematic block diagram for an integrated ultrasound probe with exemplary embodiments.

FIG. 10C is a detailed schematic block diagram for an exemplary embodiment of the integrated ultrasound probe 1040 with the first sub array beamforming circuit, and the second stage beamforming circuits are integrated inside the host computer 1082. The back end computer with the second stage beamforming circuit may be a PDA, tablet or mobile device housing. The ultra sound probe 1040 is configured to transmit ultrasound waves to and reduce reflected ultrasound waves from on ore more image targets 1064. The transducer 1040 is coupled to the host computer 1082 using one or more cables 1066, 1068. Note that A/D circuit elements can also be placed in the transducer probe housing.

The ultrasound probe 1040 includes subarray/apertures 1052 consisting of neighboring elements with an aperture smaller than that of the whole array. Returned echoes are received by the 1D transducer array 1062 and transmitted to the controller 1044. The controller initiates formation of a coarse beam by transmitting the signals to memory 1058, 1046. The memory 1058, 1046 transmits a signal to a transmit Driver 1 1050, and Transmit Driver m 1054. Transmit Driver 1 1050 and Transmit Driver m 1054 then send the signal to mux1 1048 and mux m 1056, respectively. The signal is transmitted to subarray beamformer 1 1052 and subarray beamformer n 1060.

The outputs of each coarse beam forming operation then go through a second stage beam forming in the interface unit 1020 to convert the beam forming output to digital representation. The coarse beamforming operations are coherently summed to form a fine beam output for the array. The signals are transmitted from the ultrasound probe 1040 subarray beamformer 1 1052 and subarray beamformer n 1060 to the A/D convertors 1030 and 1028 within the host computer 1082. Within the host computer 1082 there are A/D converters 1028, 1030 for converting the first stage beamforming output to digital representation. The digital conversion is received from the A/D convertors 1030, 1028 by a customer ASIC such as a FPGA 1026 to complete the second stage beamforming. The FPGA Digital beamforming 1026 transmits information to the system controller 1024. The system controller transmits information to a memory 1032 which may send a signal back to the FPGA Digital Beam forming 1026. Alternatively, the system controller 1024 may transmit information to the custom USB3 Chipset 1022. The USB3 Chipset 1022 may then transmit information to a DC-DC convertor 1034. In turn, the DC-DC convertor 1034 may transmit power from the interface unit 1020 to the ultrasound probe 1040. Within the ultrasound probe 1040 a power supply 1042 may receive the power signal and interface with the transmit driver 1 1050 to provide the power to the front end integration probe. The power supply can include a battery to enable wireless operation of the transducer assembly. A wireless transceiver can be integrated into controller circuit or a separate communications circuit to enable wireless transfer of image data and control signals.

The host computer's 1082 custom or USB3 Chipset 1022 may be used to provide a communication link between the custom or USB3 Chipset 1012 to transmits a signal to the microprocessor 1014. The microprocessor 1014 then may display information or send information to a device 1075.

Figures 2A, 2B:
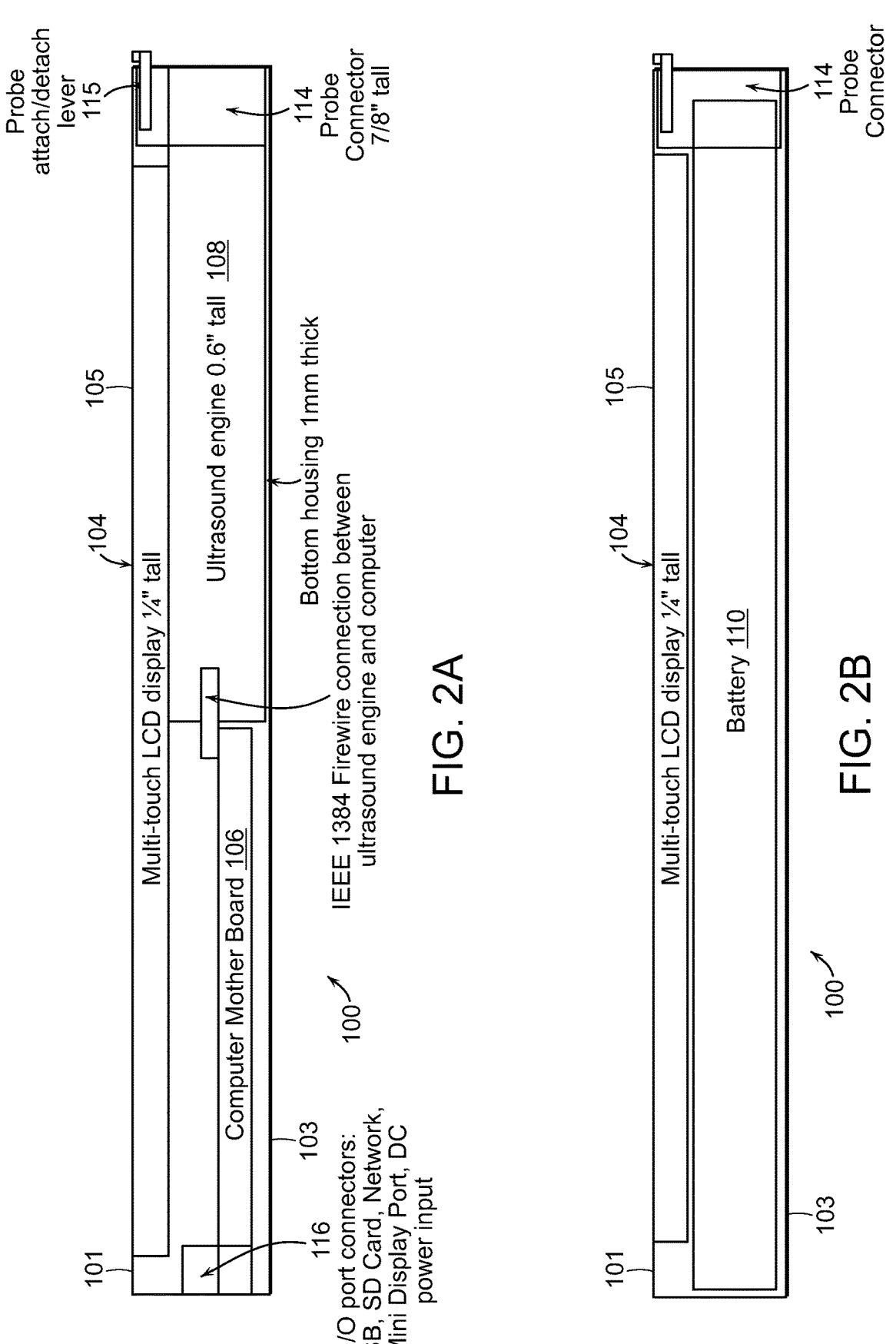
FIGS. 2A and 2B are side views of the medical ultrasound imaging system in accordance with preferred embodiments of the invention.
Figure 11:
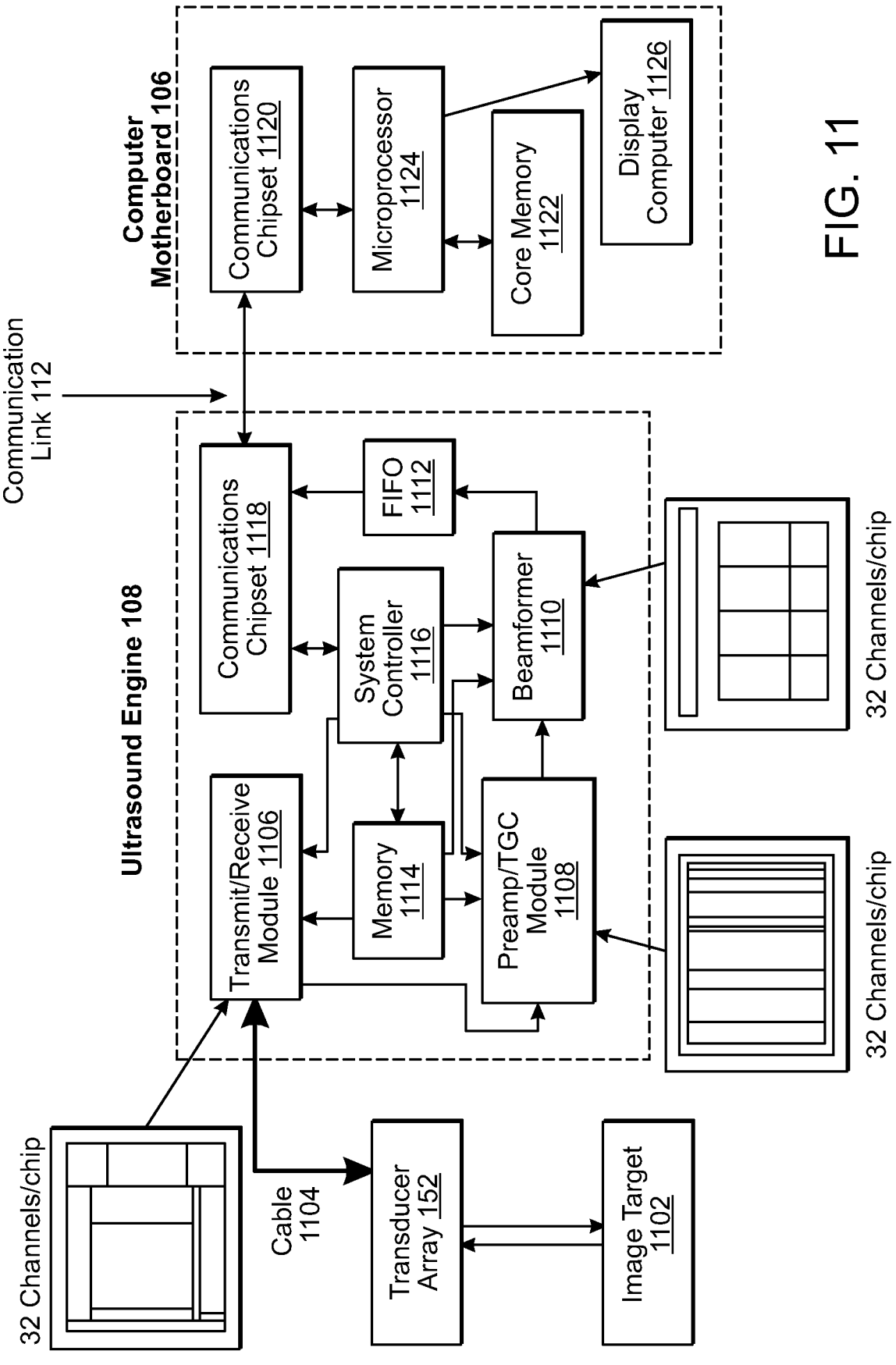
FIG. 11 is a detailed schematic block diagram of an exemplary embodiment of an ultrasound engine (i.e., the front-end ultrasound specific circuitry) and an exemplary embodiment of a computer motherboard (i.e., the host computer) of the exemplary ultrasound device.

FIG. 11 is a detailed schematic block diagram of an exemplary embodiment of the ultrasound engine 108 (i.e., the front-end ultrasound specific circuitry) and an exemplary embodiment of the computer motherboard 106 (i.e., the host computer) of the ultrasound device illustrated in FIGS. 1 and 2A. The components of the ultrasound engine 108 and/or the computer motherboard 106 may be implemented in application-specific integrated circuits (ASICs). Exemplary ASICs have a high channel count and can pack 32 or more channels per chip in some exemplary embodiments. One of ordinary skill in the art will recognize that the ultrasound engine 108 and the computer motherboard 106 may include more or fewer modules than those shown. For example, the ultrasound engine 108 and the computer motherboard 106 may include the modules shown in FIG. 17.

A transducer array 152 is configured to transmit ultrasound waves to and receive reflected ultrasound waves from one or more image targets 1102. The transducer array 152 is coupled to the ultrasound engine 108 using one or more cables 1104.

The ultrasound engine 108 includes a high-voltage transmit/receive (TR) module 1106 for applying drive signals to the transducer array 152 and for receiving return echo signals from the transducer array 152. The ultrasound engine 108 includes a pre-amp/time gain compensation (TGC) module 1108 for amplifying the return echo signals and applying suitable TGC functions to the signals. The ultrasound engine 108 includes a sampled-data beamformer 1110 that the delay coefficients used in each channel after the return echo signals have been amplified and processed by the pre-amp/TGC module 1108.

In some exemplary embodiments, the high-voltage TR module 1106, the pre-amp/TGC module 1108, and the sample-interpolate receive beamformer 1110 may each be a silicon chip having 8 to 64 channels per chip, but exemplary embodiments are not limited to this range. In certain embodiments, the high-voltage TR module 1106, the pre-amp/TGC module 1108, and the sample-interpolate receive beamformer 1110 may each be a silicon chip having 8, 16, 32, 64 channels, and the like. As illustrated in FIG. 11, an exemplary TR module 1106, an exemplary pre-amp/TGC module 1108 and an exemplary beamformer 1110 may each take the form of a silicon chip including 32 channels.

The ultrasound engine 108 includes a first-in first-out (FIFO) buffer module 1112 which is used for buffering the processed data output by the beamformer 1110. The ultra-sound engine 108 also includes a memory 1114 for storing program instructions and data, and a system controller 1116 for controlling the operations of the ultrasound engine modules.

The ultrasound engine 108 interfaces with the computer motherboard 106 over a communications link 112 which can follow a standard high-speed communications protocol, such as the Fire Wire (IEEE 1394 Standards Serial Interface) or fast (e.g., 200-400 Mbits/second or faster) Universal Serial Bus (USB 2.0 USB 3.0), protocol. The standard communication link to the computer motherboard operates at least at 400 Mbits/second or higher, preferably at 800 Mbits/second or higher. Alternatively, the link 112 can be a wireless connection such as an infrared (IR) link. The ultrasound engine 108 includes a communications chipset 1118 (e.g., a Fire Wire chipset) to establish and maintain the communications link 112.

Similarly, the computer motherboard 106 also includes a communications chipset 1120 (e.g., a Fire Wire chipset) to establish and maintain the communications link 112. The computer motherboard 106 includes a core computer-read-able memory 1122 for storing data and/or computer-execut-able instructions for performing ultrasound imaging opera-tions. The memory 1122 forms the main memory for the computer and, in an exemplary embodiment, may store about 4 GB of DDR3 memory. The computer motherboard 106 also includes a microprocessor 1124 for executing computer-executable instructions stored on the core com-puter-readable memory 1122 for performing ultrasound imaging processing operations. An exemplary microproces-sor 1124 may be an off-the-shelf commercial computer processor, such as an Intel Core-i5 processor. Another exem-plary microprocessor 1124 may be a digital signal processor (DSP) based processor, such as one or more DaVinci™ processors from Texas Instruments. The computer mother-board 106 also includes a display controller 1126 for con-trolling a display device that may be used to display ultra-sound data, scans and maps.

Exemplary operations performed by the microprocessor 1124 include, but are not limited to, down conversion (for generating I, Q samples from received ultrasound data), scan conversion (for converting ultrasound data into a display format of a display device), Doppler processing (for deter-mining and/or imaging movement and/or flow information from the ultrasound data), Color Flow processing (for gen-erating, using autocorrelation in one embodiment, a color-coded map of Doppler shifts superimposed on a B-mode ultrasound image), Power Doppler processing (for determin-ing power Doppler data and/or generating a power Doppler map), Spectral Doppler processing (for determining spectral Doppler data and/or generating a spectral Doppler map), and post signal processing. These operations are described in further detail in WO 03/079038 A2, filed Mar. 11, 2003, titled "Ultrasound Probe with Integrated Electronics," the entire contents of which are expressly incorporated herein by reference.

To achieve a smaller and lighter portable ultrasound devices, the ultrasound engine 108 includes reduction in overall packaging size and footprint of a circuit board providing the ultrasound engine 108. To this end, exemplary embodiments provide a small and light portable ultrasound device that minimizes overall packaging size and footprint while providing a high channel count. In some embodi-ments, a high channel count circuit board of an exemplary ultrasound engine may include one or more multi-chip modules in which each chip provides multiple channels, for example, 32 channels. The term "multi-chip module," as used herein, refers to an electronic package in which mul-tiple integrated circuits (IC) are packaged into a unifying substrate, facilitating their use as a single component, i.e., as a larger IC. A multi-chip module may be used in an exem-plary circuit board to enable two or more active IC compo-nents integrated on a High Density Interconnection (HDI) substrate to reduce the overall packaging size. In an exem-plary embodiment, a multi-chip module may be assembled by vertically stacking a transmit/receive (TR) silicon chip, an amplifier silicon chip and a beamformer silicon chip of an ultrasound engine. A single circuit board of the ultrasound engine may include one or more of these multi-chip modules to provide a high channel count, while minimizing the overall packaging size and footprint of the circuit board.

Figure 12:
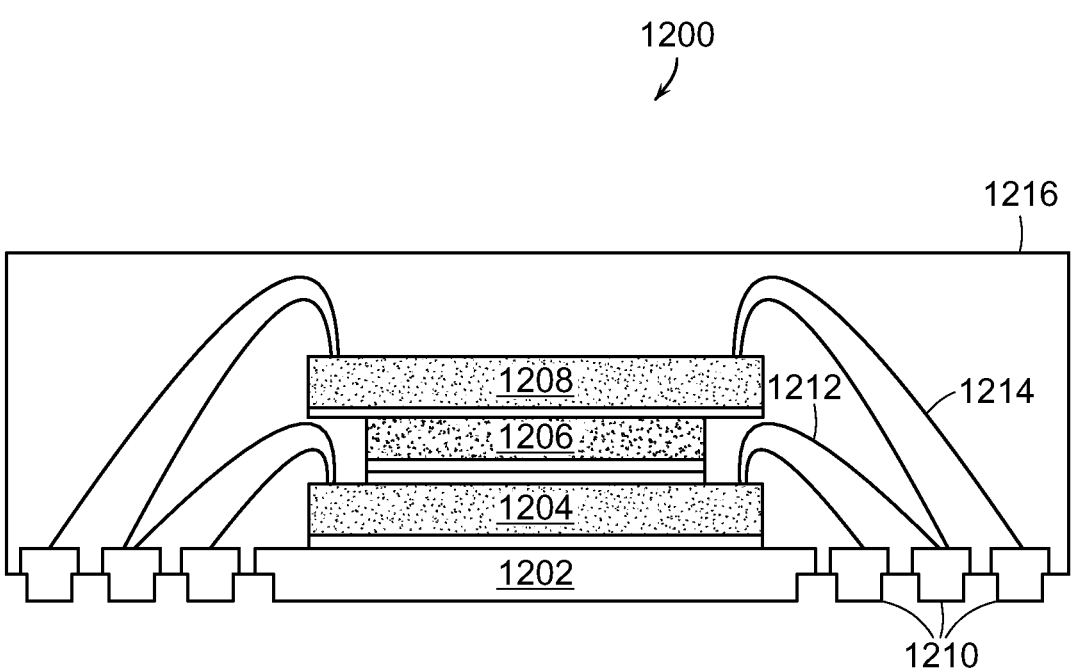
FIG. 12 depicts a schematic side view of a circuit board including a multi-chip module assembled in a vertically stacked configuration.

FIG. 12 depicts a schematic side view of a portion of a circuit board 1200 including a multi-chip module assembled in a vertically stacked configuration. Two or more layers of active electronic integrated circuit components are inte-grated vertically into a single circuit. The IC layers are oriented in spaced planes that extend substantially parallel to one another in a vertically stacked configuration. In FIG. 12, the circuit board includes an HDI substrate 1202 for sup-porting the multi-chip module. A first integrated circuit chip 1204 including, for example, a first beamformer device is coupled to the substrate 1202 using any suitable coupling mechanism, for example, epoxy application and curing. A first spacer layer 1206 is coupled to the surface of the first integrated circuit chip 1204 opposite to the substrate 1202 using, for example, epoxy application and curing. A second integrated circuit chip 1208 having, for example, a second beamforer device is coupled to the surface of the first spacer layer 1206 opposite to the first integrated circuit chip 1204 using, for example, epoxy application and curing. A metal frame 1210 is provided for mechanical and/or electrical connection among the integrated circuit chips. An exem-plary metal frame 1210 may take the form of a leadframe. The first integrated circuit chip 1204 may be coupled to the metal frame 1210 using wiring 1212. The second integrated circuit chip 1208 may be coupled to the same metal frame 1210 using wiring 1214. A packaging 1216 is provided to encapsulate the multi-chip module assembly and to maintain the multiple integrated circuit chips in substantially parallel arrangement with respect to one another.

As illustrated in FIG. 12, the vertical three-dimensional stacking of the first integrated circuit chip 1204, the first spacer layer 1206 and the second integrated circuit chip 1208 provides high-density functionality on the circuit board while minimizing overall packaging size and footprint (as compared to an ultrasound engine circuit board that does not employ a vertically stacked multi-chip module). One of ordinary skill in the art will recognize that an exemplary multi-chip module is not limited to two stacked integrated circuit chips. Exemplary numbers of chips vertically integrated in a multi-chip module may include, but are not limited to, two, three, four, five, six, seven, eight, and the like.

In one embodiment of an ultrasound engine circuit board, a single multi-chip module as illustrated in FIG. 12 is provided. In other embodiments, a plurality of multi-chip modules also illustrated in FIG. 12. In an exemplary embodiment, a plurality of multi-chip modules (for example, two multi-chip modules) may be stacked vertically on top of one another on a circuit board of an ultrasound engine to further minimize the packaging size and footprint of the circuit board.

In addition to the need for reducing the footprint, there is also a need for decreasing the overall package height in multi-chip modules. Exemplary embodiments may employ wafer thinning to sub-hundreds micron to reduce the package height in multi-chip modules.

Any suitable technique can be used to assemble a multi-chip module on a substrate. Exemplary assembly techniques include, but are not limited to, laminated MCM (MCM-L) in which the substrate is a multi-layer laminated printed circuit board, deposited MCM (MCM-D) in which the multi-chip modules are deposited on the base substrate using thin film technology, and ceramic substrate MCM (MCM-C) in which several conductive layers are deposited on a ceramic substrate and embedded in glass layers that layers are co-fired at high temperatures (HTCC) or low temperatures (LTCC).

FIG. 13 is a flowchart of an exemplary method for fabricating a circuit board including a multi-chip module assembled in a vertically stacked configuration. In step 1302, a HDI substrate is fabricated or provided. In step 1304, a metal frame (e.g., leadframe) is provided. In step 1306, a first IC layer is coupled or bonded to the substrate using, for example, epoxy application and curing. The first IC layer is wire bonded to the metal frame. In step 1308, a spacer layer is coupled to the first IC layer using, for example, epoxy application and curing, so that the layers are stacked vertically and extend substantially parallel to each other. In step 1310, a second IC layer is coupled to the spacer layer using, for example, epoxy application and curing, so that all of the layers are stacked vertically and extend substantially parallel to one another. The second IC layer is wire bonded to the metal frame. In step 1312, a packaging is used to encapsulate the multi-chip module assembly.

Exemplary chip layers in a multi-chip module may be coupled to each other using any suitable technique. For example, in the embodiment illustrated in FIG. 12, spacer layers may be provided between chip layers to spacedly separate the chip layers. Passive silicon layers, die attach paste layers and/or die attach film layers may be used as the spacer layers. Exemplary spacer techniques that may be used in fabricating a multi-chip module is further described in Toh C H et al., "Die Attach Adhesives for 3D Same-Sized Dies Stacked Packages," the 58th Electronic Components and Technology Conference (ECTC2008), pp. 1538-43, Florida, US (27-30 May 2008), the entire contents of which are expressly incorporated herein by reference.

Important requirements for the die attach (DA) paste or film is excellent adhesion to the passivation materials of adjacent dies. Also, a uniform bond-link thickness (BLT) is required for a large die application. In addition, high cohesive strength at high temperatures and low moisture absorption are preferred for reliability.

Figure 14A:
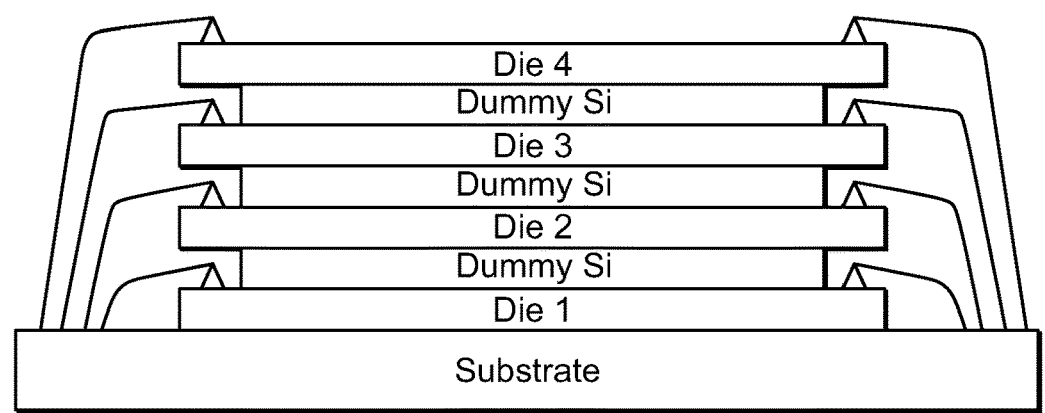
FIG. 14A is a schematic side view of a multi-chip module including four vertically stacked dies in which the dies are spacedly separated from one another by passive silicon layers with a 2-in-1 dicing die attach film (D-DAF)
Figure 14B:
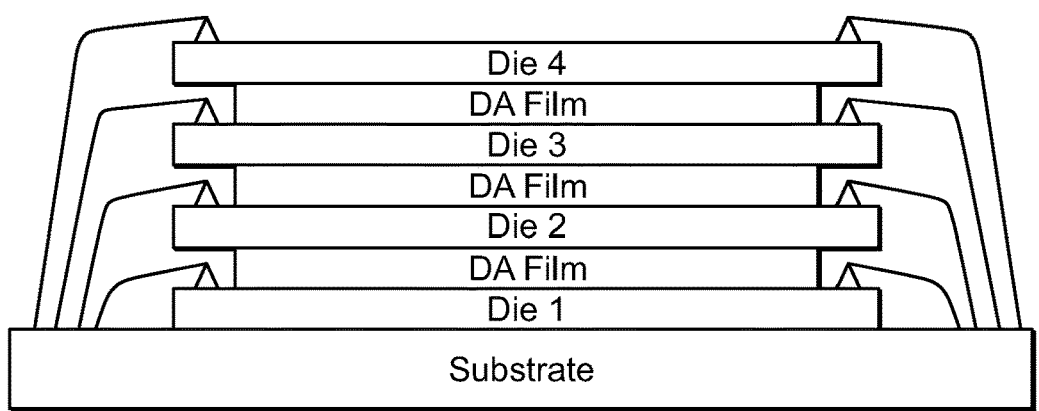
FIG. 14B is a schematic side view of a multi-chip module including four vertically stacked dies in which the dies are spacedly separated from one another by DA film-based adhesives acting as die-to-die spacers.
Figure 14C:
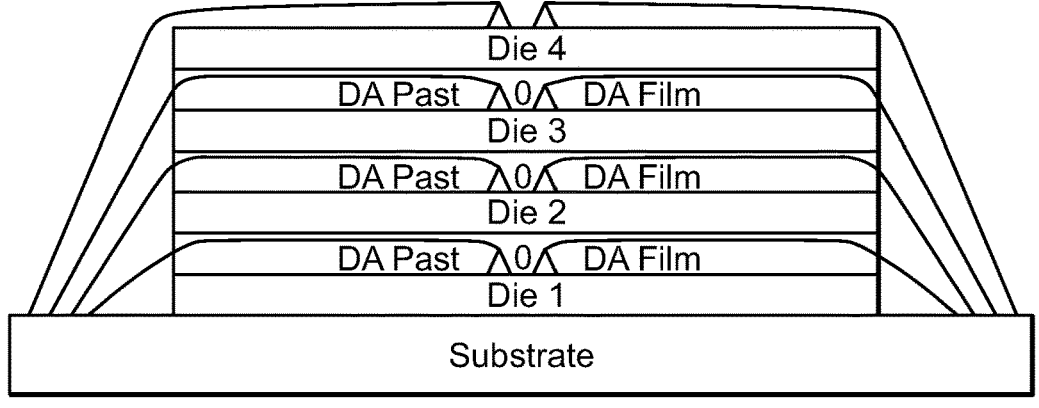
FIG. 14C is a schematic side view of a multi-chip module including four vertically stacked dies in which the dies are spacedly separated from one another by DA paste or film-based adhesives acting as die-to-die spacers.

FIGS. 14A-14C are schematic side views of exemplary multi-chip modules, including vertically stacked dies, that may be used in accordance with exemplary embodiments. Both peripheral and center pads wire bond (WB) packages are illustrated and may be used in wire bonding exemplary chip layers in a multi-chip module. FIG. 14A is a schematic side view of a multi-chip module including four vertically stacked dies in which the dies are spacedly separated from one another by passive silicon layers with a 2-in-1 dicing die attach film (D-DAF). FIG. 14B is a schematic side view of a multi-chip module including four vertically stacked dies in which the dies are spacedly separated from one another by DA film-based adhesives acting as die-to-die spacers. FIG. 14C is a schematic side view of a multi-chip module including four vertically stacked dies in which the dies are spacedly separated from one another by DA paste or film-based adhesives acting as die-to-die spacers. The DA paste or film-based adhesives may have wire penetrating capability in some exemplary embodiments. In the exemplary multi-chip module of FIG. 14C, film-over wire (FOW) is used to allow long wire bonding and center bond pads stacked die packages. FOW employs a die-attach film with wire penetrating capability that allows the same or similar-sized wire-bonded dies to be stacked directly on top of one another without passive silicon spacers. This solves the problem of stacking same or similar-sized dies directly on top of each other, which otherwise poses a challenge as there is no or insufficient clearance for the bond wires of the lower dies.

The DA material illustrated in FIGS. 14B and 14C preferably maintain a bond-line thickness (BLT) with little to no voiding and bleed out through the assembly process. Upon assembly, the DA materials sandwiched between the dies maintain an excellent adhesion to the dies. The material properties of the DA materials are tailored to maintain high cohesive strength for high temperature reliability stressing without bulk fracture. The material properties of the DA materials are tailored to also minimize or preferably eliminate moisture accumulation that may cause package reliability failures (e.g., popcorning whereby interfacial or bulk fractures occur as a result of pressure build-up from moisture in the package).

Figure 15:
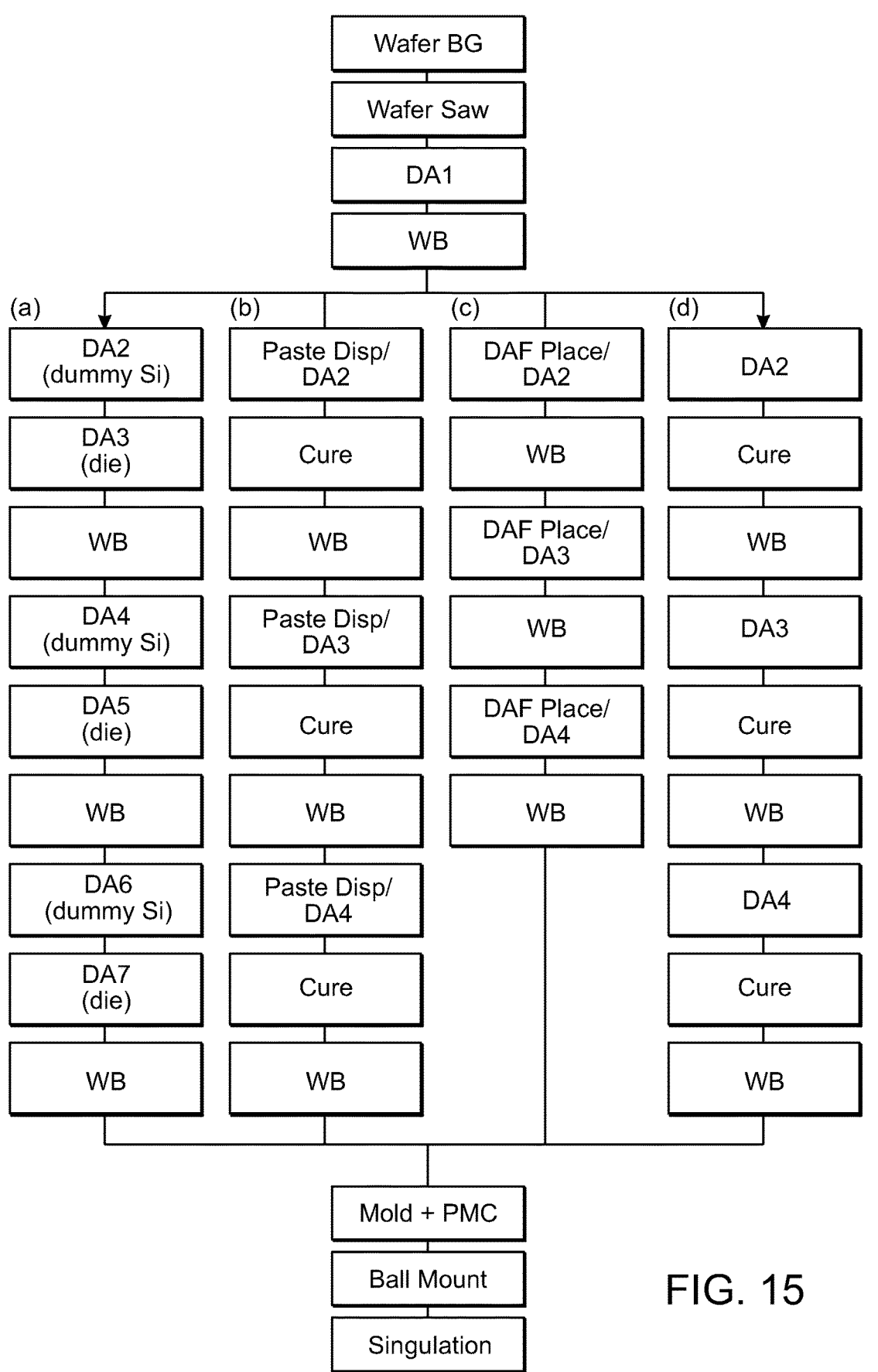
FIG. 15 is a flowchart of another exemplary method of die-to-die stacking using (a) passive silicon layers with a 2-in-1 dicing die attach film (D-DAF), (b) DA paste, (c) thick DA-film, and (d) film-over wire (FOW) including a 2-in-1 D-DAF.

FIG. 15 is a flowchart of certain exemplary methods of die-to-die stacking using (a) passive silicon layers with a 2-in-1 dicing die attach film (D-DAF), (b) DA paste, (c) thick DA-film, and (d) film-over wire (FOW) that employs a die-attach film with wire penetrating capability that allows the same or similar-sized wire-bonded dies to be stacked directly on top of one another without passive silicon spacers. Each method performs backgrinding of wafers to reduce the wafer thickness to enable stacking and high density packaging of integrated circuits. The wafers are sawed to separate the individual dies. A first die is bonded to a substrate of a multi-chip module using, for example, epoxy application and curing in an oven. Wire bonding is used to couple the first die to a metal frame.

In method (A), a first passive silicon layer is bonded to the first die in a stacked manner using a dicing die-attach film (D-DAF). A second die is bonded to the first passive layer in a stacked manner using D-DAF. Wire bonding is used to couple the second die to the metal frame. A second passive silicon layer is bonded to the second die in a stacked manner using D-DAF. A third die is bonded to the second passive layer in a stacked manner using D-DAF.

Wire bonding is used to couple the third die to the metal frame. A third passive silicon layer is bonded to the third die in a stacked manner using D-DAF. A fourth die is bonded to the third passive layer in a stacked manner using D-DAF. Wire bonding is used to couple the fourth die to the metal frame.

In method (B), die attach (DA) paste dispensing and curing is repeated for multi-thin die stack application. DA paste is dispensed onto a first die, and a second die is provided on the DA paste and cured to the first die. Wire bonding is used to couple the second die to the metal frame. DA paste is dispensed onto the second die, and a third die is provided on the DA paste and cured to the second die. Wire bonding is used to couple the third die to the metal frame. DA paste is dispensed onto the third die, and a fourth die is provided on the DA paste and cured to the third die. Wire bonding is used to couple the fourth die to the metal frame.

In method (C), die attach films (DAF) are cut and pressed to a bottom die and a top die is then placed and thermal compressed onto the DAF. For example, a DAF is pressed to the first die and a second die is thermal compressed onto the DAF. Wire bonding is used to couple the second die to the metal frame. Similarly, a DAF is pressed to the second die and a third die is thermal compressed onto the DAF. Wire bonding is used to couple the third die to the metal frame. A DAF is pressed to the third die and a fourth die is thermal compressed onto the DAF.

Wire bonding is used to couple the fourth die to the metal frame.

In method (D), film-over wire (FOW) employs a die-attach film with wire penetrating capability that allows the same or similar-sized wire-bonded dies to be stacked directly on top of one another without passive silicon spacers. A second die is bonded and cured to the first die in a stacked manner. Film-over wire bonding is used to couple the second die to the metal frame. A third die is bonded and cured to the first die in a stacked manner. Film-over wire bonding is used to couple the third die to the metal frame. A fourth die is bonded and cured to the first die in a stacked manner. Film-over wire bonding is used to couple the fourth die to the metal frame.

After the above-described steps are completed, in each method (a)-(d), wafer molding and post-mold curing (PMC) are performed. Subsequently, ball mount and singulation are performed.

Further details on the above-described die attachment techniques are provided in TOH C H et al., "Die Attach Adhesives for 3D Same-Sized Dies Stacked Packages," the 58th Electronic Components and Technology Conference (ECTC2008), pp. 1538-43, Florida, US (27-30 May 2008), the entire contents of which are expressly incorporated herein by reference.

FIG. 16 is a schematic side view of a multi-chip module 1600 including a TR chip 1602, an amplifier chip 1604 and a beamformer chip 1606 vertically integrated in a vertically stacked configuration on a substrate 1614. Any suitable technique illustrated in FIGS. 12-15 may be used to fabricate the multi-chip module. One of ordinary skill in the art will recognize that the particular order in which the chips are stacked may be different in other embodiments. First and second spacer layers 1608, 1610 are provided to spacedly separate the chips 1602, 1604, 1606.

Each chip is coupled to a metal frame (e.g., a leadframe) 1612. In certain exemplary embodiments, heat transfer and heat sink mechanisms may be provided in the multi-chip module to sustain high temperature reliability stressing without bulk failure. Other components of FIG. 16 are described with reference to FIGS. 12 and 14.

In this exemplary embodiment, each multi-chip module may handle the complete transmit, receive, TGC amplification and beam forming operations for a large number of channels, for example, 32 channels. By vertically integrating the three silicon chips into a single multi-chip module, the space and footprint required for the printed circuit board is further reduced. A plurality of multi-chip modules may be provided on a single ultrasound engine circuit board to further increase the number of channels while minimizing the packaging size and footprint. For example, a 128 channel ultrasound engine circuit board 108 can be fabricated within exemplary planar dimensions of about 10 cm×about 10 cm, which is a significant improvement of the space requirements of conventional ultrasound circuits. A single circuit board of an ultrasound engine including one or more multi-chip modules may have 16 to 128 channels in preferred embodiments. In certain embodiments, a single circuit board of an ultrasound engine including one or more multi-chip modules may have 16, 32, 64, 128 channels, and the like.

Figure 17:
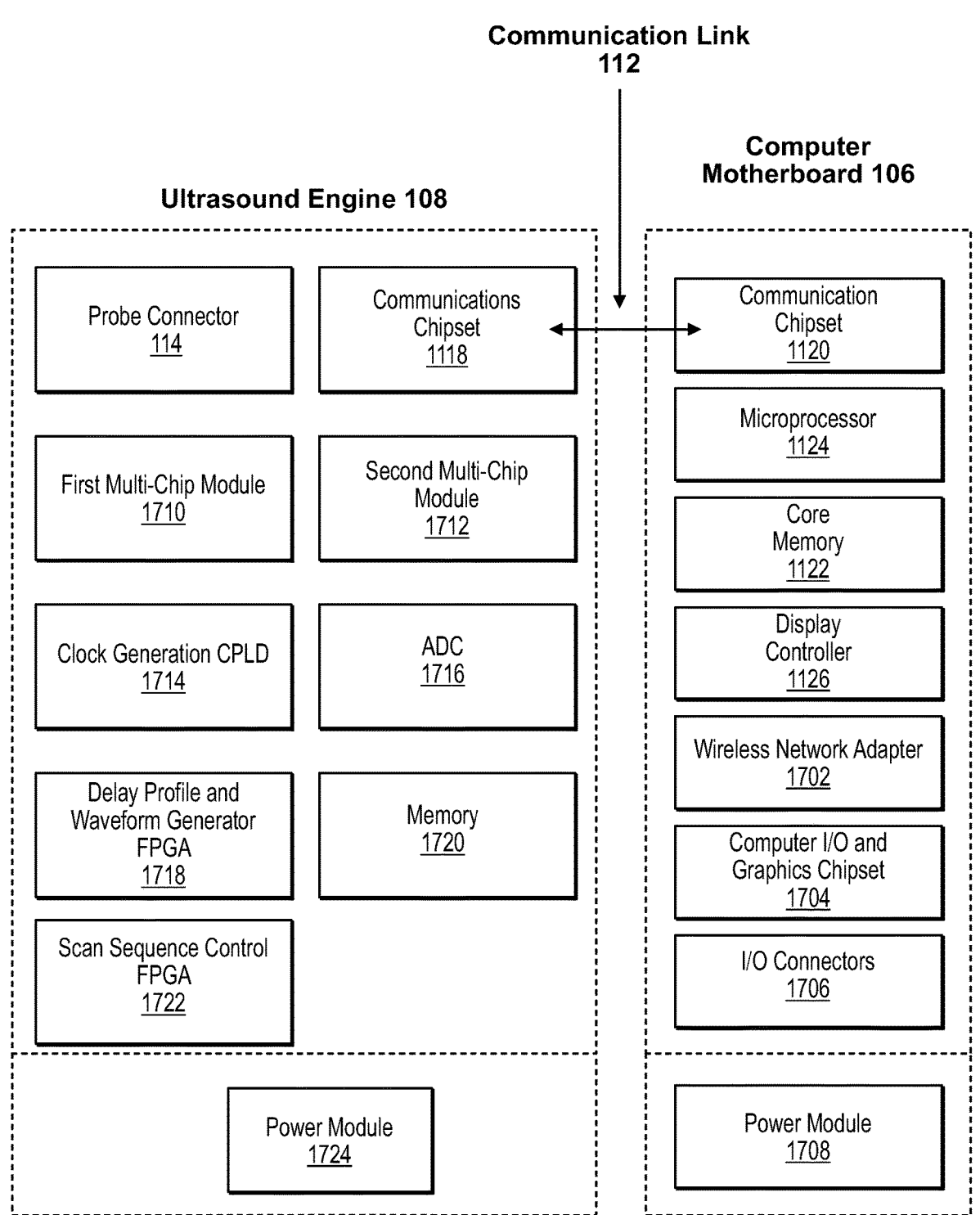
FIG. 17 is a detailed schematic block diagram of an exemplary embodiment of an ultrasound engine (i.e., the front-end ultrasound specific circuitry) and an exemplary embodiment of a computer motherboard (i.e., the host computer) provided as a single board complete ultrasound system.

FIG. 17 is a detailed schematic block diagram of an exemplary embodiment of the ultrasound engine 108 (i.e., the front-end ultrasound specific circuitry) and an exemplary embodiment of the computer motherboard 106 (i.e., the host computer) provided as a single board complete ultrasound system. An exemplary single board ultrasound system as illustrated in FIG. 17 may have exemplary planar dimensions of about 25 cm×about 18 cm, although other dimensions are possible. The single board complete ultrasound system of FIG. 17 may be implemented in the ultrasound device illustrated in FIGS. 1, 2A, 2B, and 9A, and may be used to perform the operations depicted in FIGS. 3-8, 9B, and 10.

The ultrasound engine 108 includes a probe connector 114 to facilitate the connection of at least one ultrasound probe/transducer. In the ultrasound engine 108, a TR module, an amplifier module and a beamformer module may be vertically stacked to form a multi-chip module as shown in FIG. 16, thereby minimizing the overall packaging size and footprint of the ultrasound engine 108. The ultrasound engine 108 may include a first multi-chip module 1710 and a second multi-chip module 1712, each including a TR chip, an ultrasound pulser and receiver, an amplifier chip including a time-gain control amplifier, and a sample-data beamformer chip vertically integrated in a stacked configuration as shown in FIG. 16. The first and second multi-chip modules 1710, 1712 may be stacked vertically on top of each other to further minimize the area required on the circuit board. Alternatively, the first and second multi-chip modules 1710, 1712 may be disposed horizontally on the circuit board. In an exemplary embodiment, the TR chip, the amplifier chip and the beamformer chip is each a 32-channel chip, and each multi-chip module 1710, 1712 has 32 channels. One of ordinary skill in the art will recognize that exemplary ultrasound engines 108 may include, but are not limited to, one, two, three, four, five, six, seven, eight multi-chip modules. Note that in a preferred embodiment the system can be configured with a first beamformer in the transducer housing and a second beamformer in the tablet housing.

The ASICs and the multi-chip module configuration enable a 128-channel complete ultrasound system to be implemented on a small single board in a size of a tablet computer format. An exemplary 128-channel ultrasound engine 108, for example, can be accommodated within exemplary planar dimensions of about 10 cm×about 10 cm, which is a significant improvement of the space requirements of conventional ultrasound circuits. An exemplary 128-channel ultrasound engine 108 can also be accommodated within an exemplary area of about 100 cm$^2$.

The ultrasound engine 108 also includes a clock generation complex programmable logic device (CPLD) 1714 for generating timing clocks for performing an ultrasound scan using the transducer array. The ultrasound engine 108 includes an analog-to-digital converter (ADC) 1716 for converting analog ultrasound signals received from the transducer array to digital RF formed beams. The ultrasound engine 108 also includes one or more delay profile and waveform generator field programmable gate arrays (FPGA) 1718 for managing the receive delay profiles and generating the transmit waveforms. The ultrasound engine 108 includes a memory 1720 for storing the delay profiles for ultrasound scanning. An exemplary memory 1720 may be a single DDR3 memory chip. The ultrasound engine 108 includes a scan sequence control field programmable gate array (FPGA) 1722 configured to manage the ultrasound scan sequence, transmit/receiving timing, storing and fetching of profiles to/from the memory 1720, and buffering and moving of digital RF data streams to the computer motherboard 106 via a high-speed serial interface 112. The high-speed serial interface 112 may include Fire Wire or other serial or parallel bus interface between the computer motherboard 106 and the ultrasound engine 108. The ultrasound engine 108 includes a communications chipset 1118 (e.g., a Fire Wire chipset) to establish and maintain the communications link 112.

A power module 1724 is provided to supply power to the ultrasound engine 108, manage a battery charging environment and perform power management operations. The power module 1724 may generate regulated, low noise power for the ultrasound circuitry and may generate high voltages for the ultrasound transmit pulser in the TR module.

The computer motherboard 106 includes a core computer-readable memory 1122 for storing data and/or computer-executable instructions for performing ultrasound imaging operations. The memory 1122 forms the main memory for the computer and, in an exemplary embodiment, may store about 4 Gb of DDR3 memory. The memory 1122 may include a solid state hard drive (SSD) for storing an operating system, computer-executable instructions, programs and image data. An exemplary SSD may have a capacity of about 128 GB.

The computer motherboard 106 also includes a microprocessor 1124 for executing computer-executable instructions stored on the core computer-readable memory 1122 for performing ultrasound imaging processing operations. Exemplary operations include, but are not limited to, down conversion, scan conversion, Doppler processing, Color Flow processing, Power Doppler processing, Spectral Doppler processing, and post signal processing. An exemplary microprocessor 1124 may be an off-the-shelf commercial computer processor, such as an Intel Core-i5 processor. Another exemplary microprocessor 1124 may be a digital signal processor (DSP) based processor, such as DaVinci™ processors from Texas Instruments.

The computer motherboard 106 includes an input/output (I/O) and graphics chipset 1704 which includes a co-processor configured to control I/O and graphic peripherals such as USB ports, video display ports and the like. The computer motherboard 106 includes a wireless network adapter 1702 configured to provide a wireless network connection. An exemplary adapter 1702 supports 802.11g and 802.11n standards. The computer motherboard 106 includes a display controller 1126 configured to interface the computer motherboard 106 to the display 104. The computer motherboard 106 includes a communications chipset 1120 (e.g., a Fire Wire chipset or interface) configured to provide a fast data communication between the computer motherboard 106 and the ultrasound engine 108. An exemplary communications chipset 1120 may be an IEEE 1394b 800

Mbit/sec interface. Other serial or parallel interfaces 1706 may alternatively be provided, such as USB3, Thunder-Bolt, PCIe, and the like. A power module 1708 is provided to supply power to the computer motherboard 106, manage a battery charging environment and perform power management operations.

An exemplary computer motherboard 106 may be accommodated within exemplary planar dimensions of about 12 cm×about 10 cm. An exemplary computer motherboard 106 can be accommodated within an exemplary area of about 120 cm².

Figure 18:
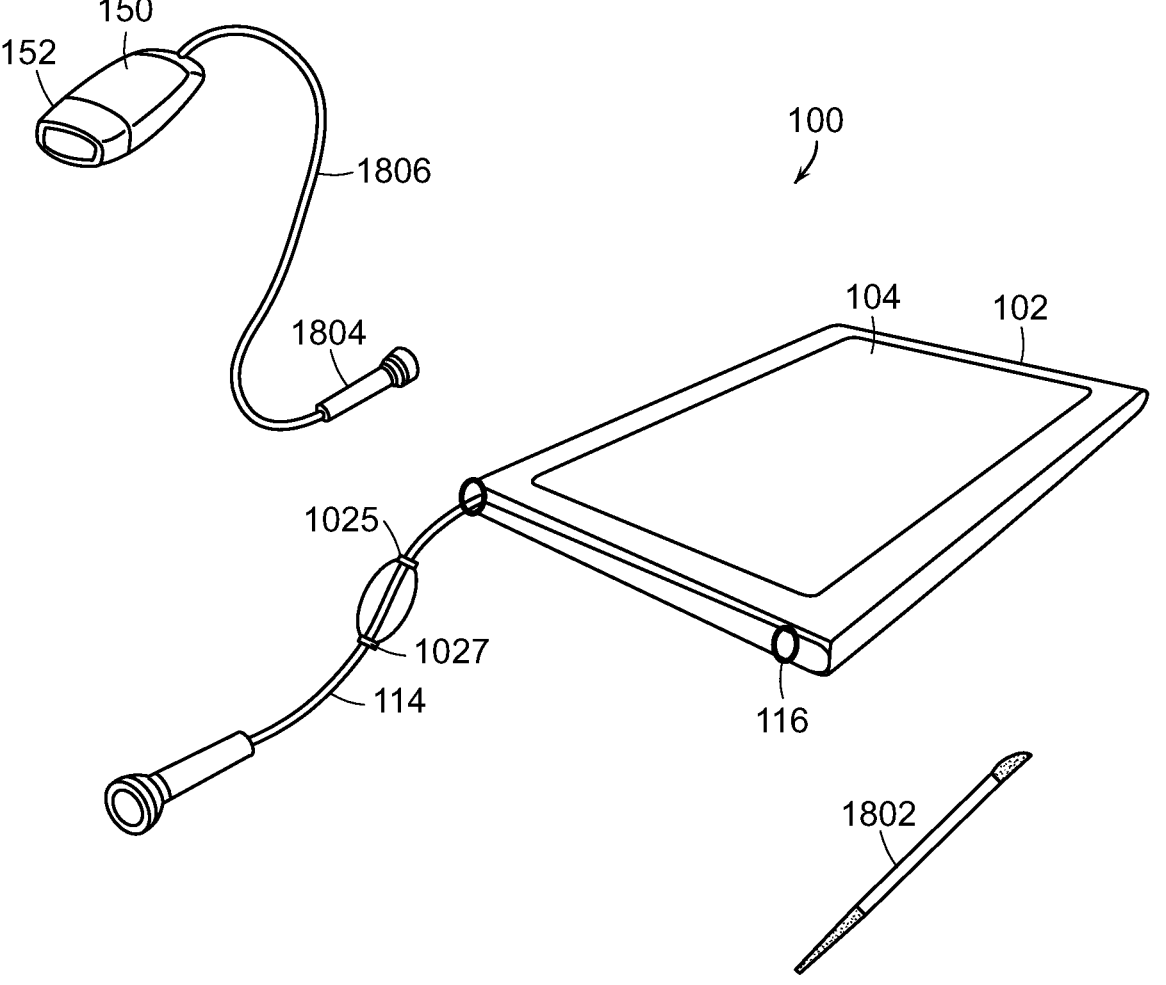
FIG. 18 is a perspective view of an exemplary portable ultrasound system provided in accordance with exemplary embodiments.

FIG. 18 is a perspective view of an exemplary portable ultrasound system 100 provided in accordance with exemplary embodiments. The system 100 includes a housing 102 that is in a tablet form factor as illustrated in FIG. 18, but that may be in any other suitable form factor. An exemplary housing 102 may have a thickness below 2 cm and preferably between 0.5 and 1.5 cm. A front panel of the housing 102 includes a multi-touch LCD touch screen display 104 that is configured to recognize and distinguish one or more multiple and/or simultaneous touches on a surface of the touch screen display 104. The surface of the display 104 may be touched using one or more of a user's fingers, a user's hand or an optional stylus 1802. The housing 102 includes one or more I/O port connectors 116 which may include, but are not limited to, one or more USB connectors, one or more SD cards, one or more network mini display ports, and a DC power input. The embodiment of housing 102 in FIG. 18 can also be configured within a palm-carried form factor having dimensions of 150 mm×100 mm×15 mm (a volume of 225000 mm³) or less. The housing 102 can have a weight of less than 200 g. Optionally, cabling between the transducer array and the display housing can include interface circuitry 1020 as described herein. The interface circuitry 1020 can include, for example, beamforming circuitry and/or A/D circuitry in a pod that dangles from the tablet. Separate connectors 1025, 1027 can be used to connect the dangling pod to the transducer probe cable. The connector 1027 can include probe identification circuitry as described herein. The unit 102 can include a camera, a microphone and a speaker as well as wireless telephone circuitry for voice and data communications as well as voice activated software that can be used to control the ultrasound imaging operations described herein.

The housing 102 includes or is coupled to a probe connector 114 to facilitate connection of at least one ultrasound probe/transducer 150. The ultrasound probe 150 includes a transducer housing including one or more transducer arrays 152. The ultrasound probe 150 is couplable to the probe connector 114 using a housing connector 1804 provided along a flexible cable 1806. One of ordinary skill in the art will recognize that the ultrasound probe 150 may be coupled to the housing 102 using any other suitable mechanism, for example, an interface housing that includes circuitry for performing ultrasound-specific operations like beamforming. Other exemplary embodiments of ultrasound systems are described in further detail in WO 03/079038 A2, filed Mar. 11, 2003, titled "Ultrasound Probe with Integrated Electronics," the entire contents of which is expressly incorporated herein by reference. Preferred embodiments can employ a wireless connection between the hand-held transducer probe 150 and the display housing. Beamformer electronics can be incorporated into probe housing 150 to provide beamforming of subarrays in a 1D or 2D transducer array as described herein. The display housing can be sized to be held in the palm of the user's hand and can include wireless network connectivity to public access networks such as the internet.

Figure 19:
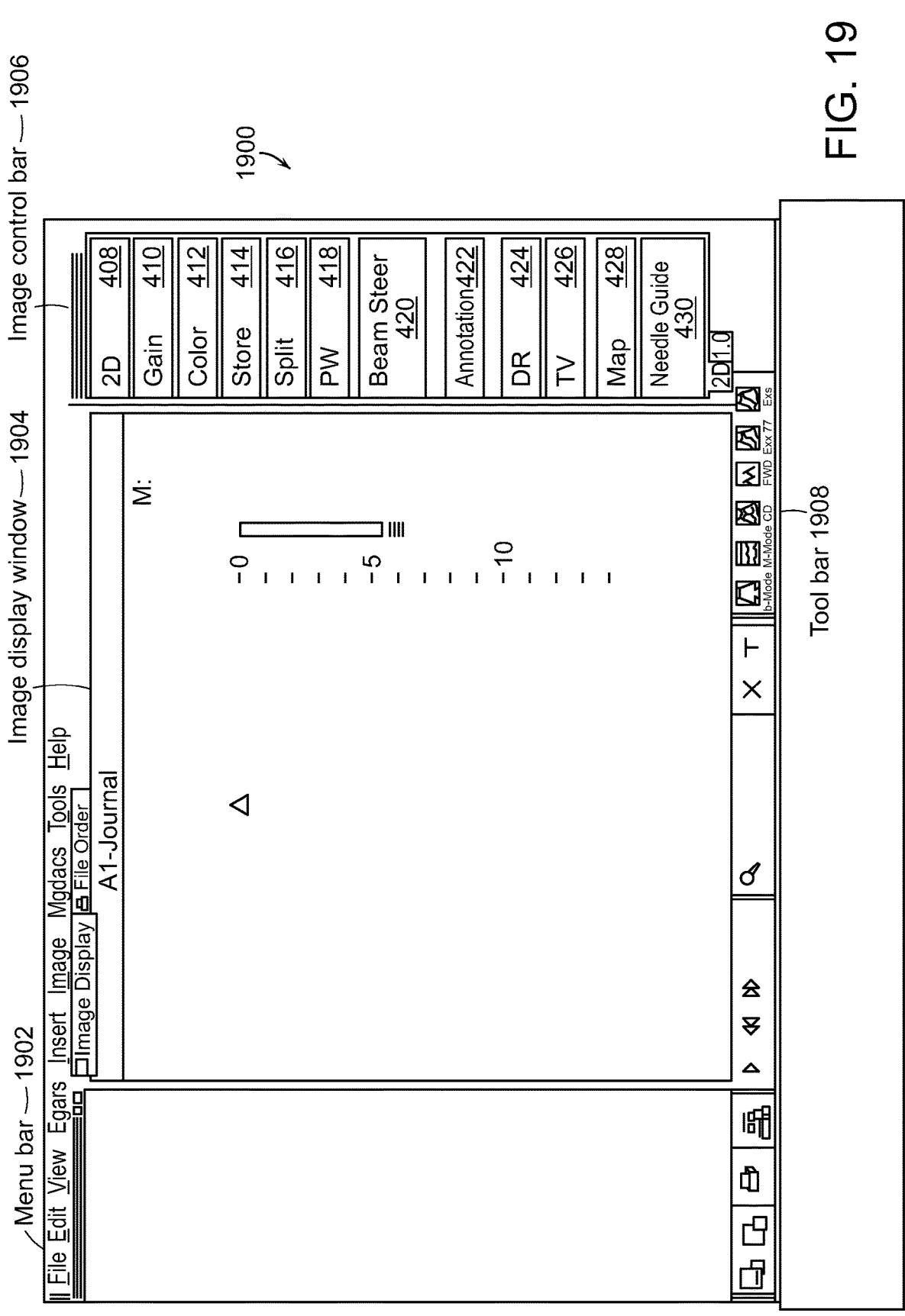
FIG. 19 illustrates an exemplary view of a main graphical user interface (GUI) rendered on a touch screen display of the exemplary portable ultrasound system of FIG. 18.

FIG. 19 illustrates an exemplary view of a main graphical user interface (GUI) 1900 rendered on the touch screen display 104 of the portable ultrasound system 100 of FIG. 18. The main GUI 1900 may be displayed when the ultrasound system 100 is started. To assist a user in navigating the main GUI 1900, the GUI may be considered as including four exemplary work areas: a menu bar 1902, an image display window 1904, an image control bar 1906, and a tool bar 1908. Additional GUI components may be provided on the main GUI 1900 to, for example, enable a user to close, resize and exit the GUI and/or windows in the GUI.

The menu bar 1902 enables a user to select ultrasound data, images and/or videos for display in the image display window 1904. The menu bar 1902 may include, for example, GUI components for selecting one or more files in a patient folder directory and an image folder directory. The image display window 1904 displays ultrasound data, images and/or videos and may, optionally, provide patient information. The tool bar 1908 provides functionalities associated with an image or video display including, but not limited to, a save button for saving the current image and/or video to a file, a save Loop button that saves a maximum allowed number of previous frames as a Cine loop, a print button for printing the current image, a freeze image button for freezing an image, a playback toolbar for controlling aspects of playback of a Cine loop, and the like. Exemplary GUI functionalities that may be provided in the main GUI 1900 are described in further detail in WO 03/079038 A2, filed Mar. 11, 2003, titled "Ultrasound Probe with Integrated Electronics," the entire contents of which are expressly incorporated herein by reference.

The image control bar 1906 includes touch controls that may be operated by touch and touch gestures applied by a user directly to the surface of the display 104. Exemplary touch controls may include, but are not limited to, a 2D touch control 408, a gain touch control 410, a color touch control 412, a storage touch control 414, a split touch control 416, a PW imaging touch control 418, a beamsteering touch control 20, an annotation touch control 422, a dynamic range operations touch control 424, a Teravision™ touch control 426, a map operations touch control 428, and a needle guide touch control 428. These exemplary touch controls are described in further detail in connection with FIGS. 4a-4c.

Figure 20A:
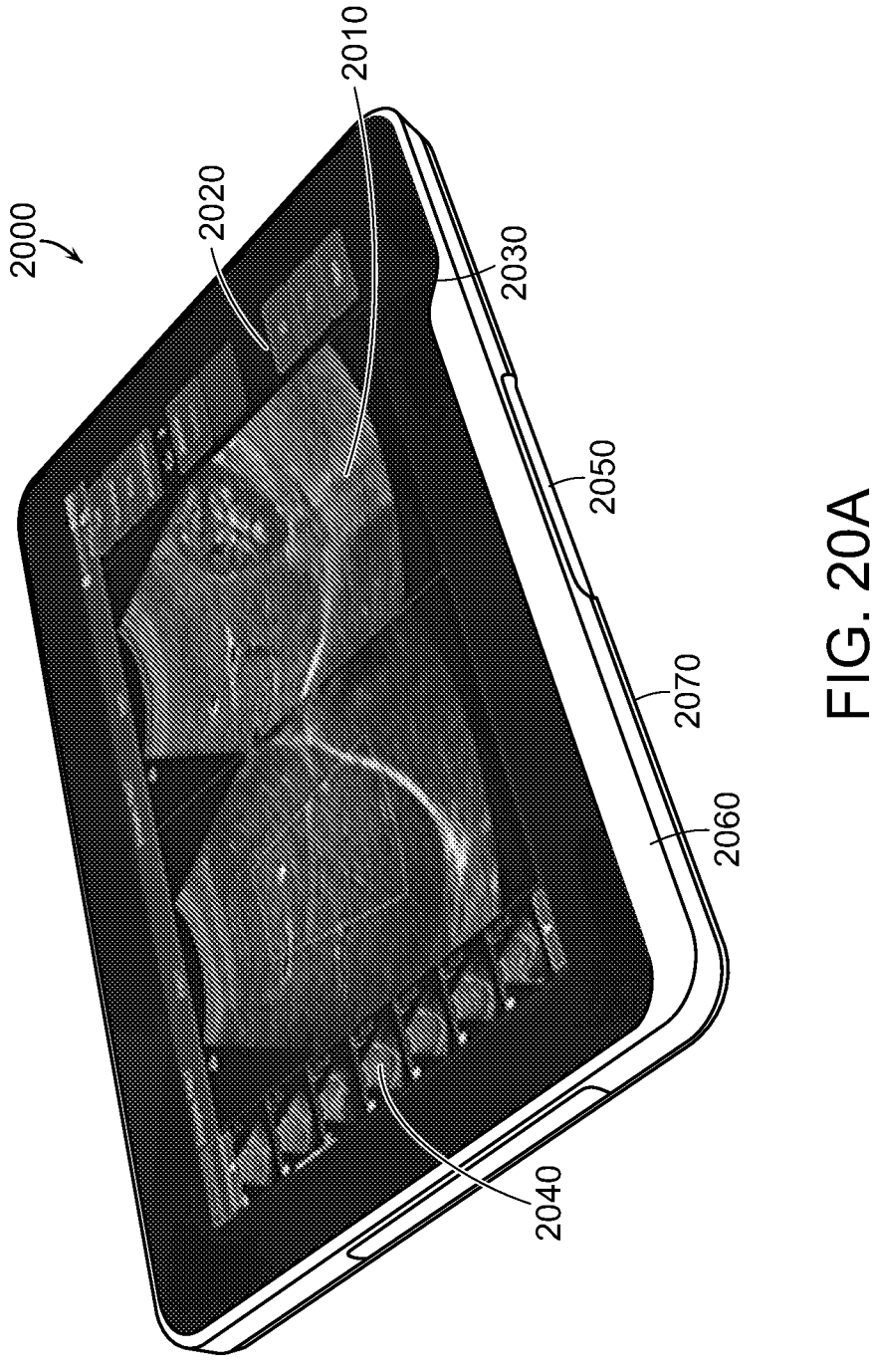
FIGS. 20*a* and 20B are top views of the medical ultrasound imaging systems in accordance with another preferred embodiment of the invention.
Figure 20B:
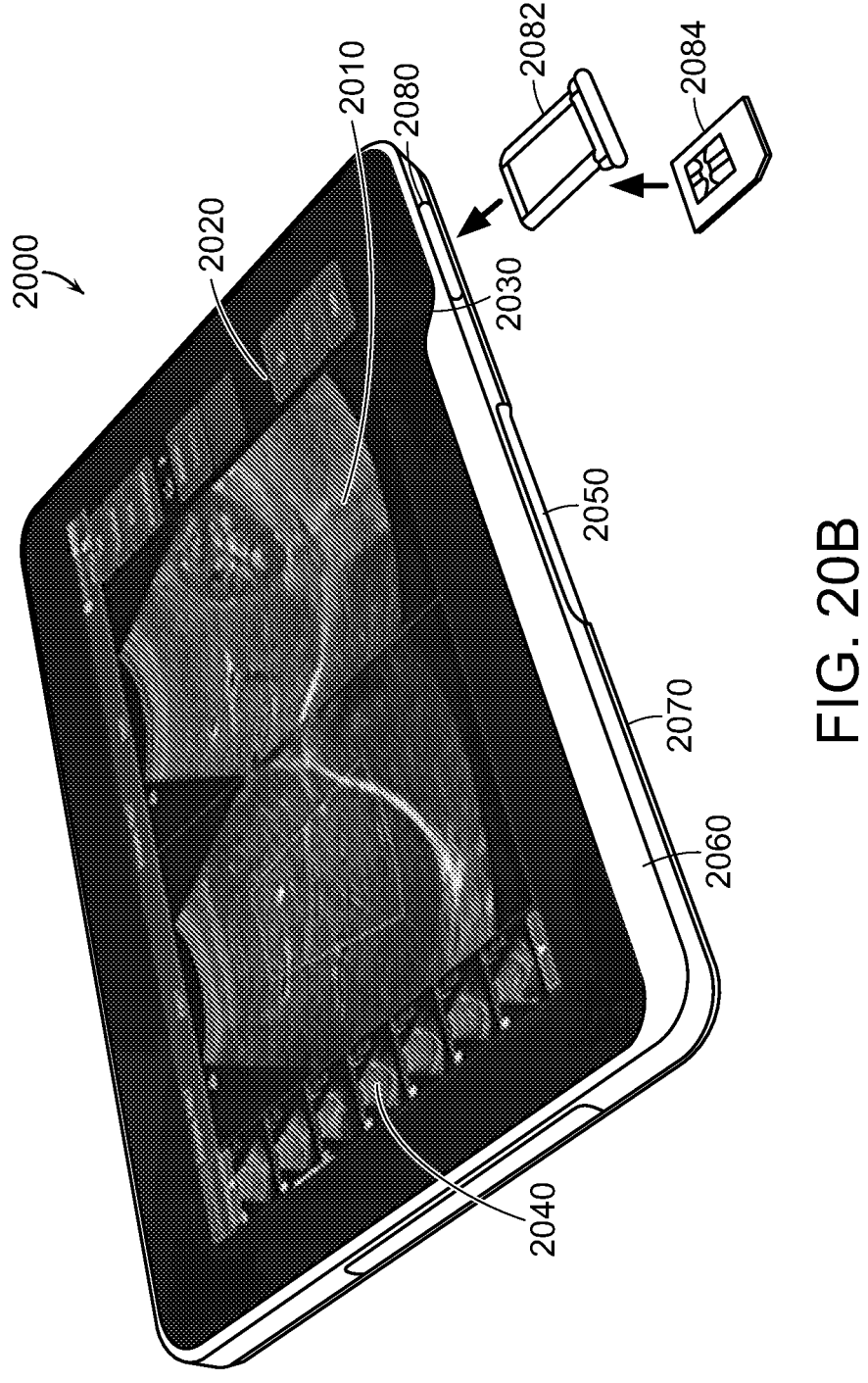

FIG. 20A depicts an illustrative embodiment of exemplary medical ultrasound imaging equipment 2000, implemented in the form factor of a tablet in accordance with the invention. The table may have the dimensions of 12.5"× 1.25"×8.75" or 31.7 cm×3.175 cm×22.22 cm but it may also be in any other suitable form factor having a volume of less than 2500 cm³ and a weight of less than 8 lbs. As shown in FIG. 20, the medical ultrasound imaging equipment 2000, includes a housing 2030, a touch screen display 2010, wherein ultrasound images 2010, and ultra sound data 2040, can be displayed and ultrasound controls 2020, are configured to be controlled by a touchscreen display 2010. The housing 2030, may have a front panel 2060 and a rear panel 2070. The touchscreen display 2010, forms the front panel 2060, and includes a multi-touch LCD touch screen that can recognize and distinguish one or more multiple and or simultaneous touches of the user on the touchscreen display 2010. The touchscreen display 2010 may have a capacitive multi-touch and AVAH LCD screen. For example, the capacitive multi-touch and AVAH LCD screen may enable a user to view the image from multi angles without losing resolution. In another embodiment, the user may utilize a stylus for data input on the touch screen. The tablet can include an integrated foldable stand that permits a user to swivel the stand from a storage position that conforms to the tablet form factor so that the device can lay flat on the rear panel, or alternatively, the user can swivel the stand to enable the tablet to stand at an upright position at one of a plurality of oblique angles relative to a support surface.

Capacitive touchscreen module comprises an insulator for example glass, coated with a transparent conductor, such as indium tin oxide. The manufacturing process may include a bonding process among glass, x-sensor film, y-sensor film and a liquid crystal material. The tablet is configured to allow a user to perform multi-touch gestures such as pinching and stretching while wearing a dry or a wet glove. The surface of the screen registers the electrical conductor making contact with the screen. The contact distorts the screens electrostatic field resulting in measurable changes in capacitance. A processor then interprets the change in the electrostatic field. Increasing levels of responsiveness are enabled by reducing the layers and by producing touch screens with "in-cell" technology. "In-cell" technology eliminates layers by placing the capacitors inside the display. Applying "in-cell" technology reduces the visible distance between the user's finger and the touchscreen target, thereby creating a more directive contact with the content displayed and enabling taps and gestures to have an increase in responsiveness.

FIG. 20A illustrates a tablet system 2000 having a port 2080 to receive a card 2082 having a SIM circuit 2084 mounted thereon.

Figure 21:
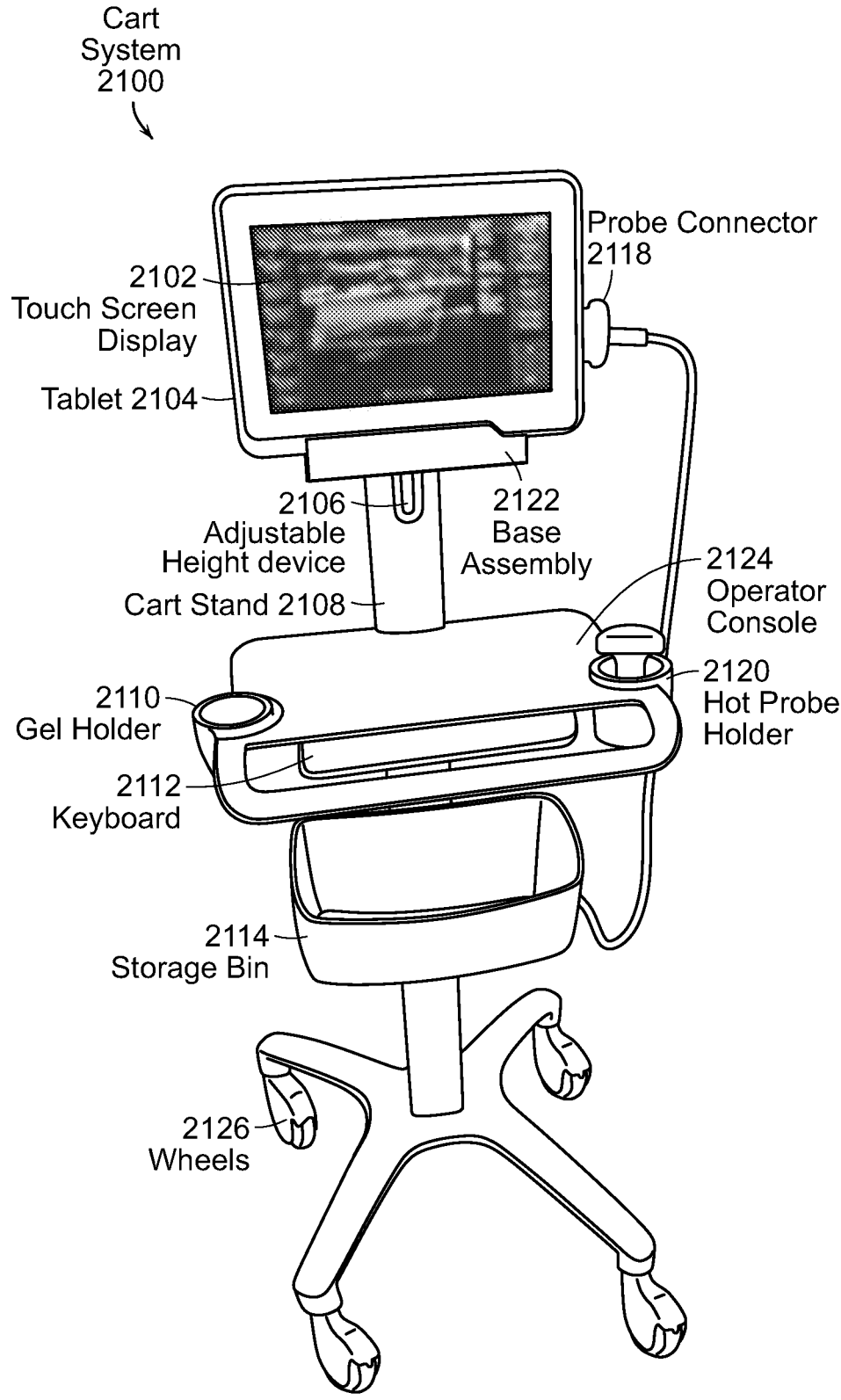
FIG. 21 illustrates a preferred cart system for a tablet ultrasound system in accordance with preferred embodiment 9 of the invention.

FIG. 21 illustrates a preferred cart system for a modular ultrasound imaging system in accordance with the invention. The cart system 2100 uses a base assembly 2122 including a docking bay that receives the tablet. The cart configuration 2100 is configured to dock tablet 2104, including a touch screen display 2102, to a cart 2108, which can include a full operator console 2124. After the tablet 2104, is docked to the cart stand 2108, the system forms a full feature roll about system. The full feature roll about system may include, an adjustable height device 2106, a gel holder 2110, and a storage bin 2114, a plurality of wheels 2116, a hot probe holder 2120, and the operator console 2124. The control devices may include a keyboard 2112 on the operator console 2124 that may also have other peripherals added such as a printer or a video interface or other control devices.

Figure 22:
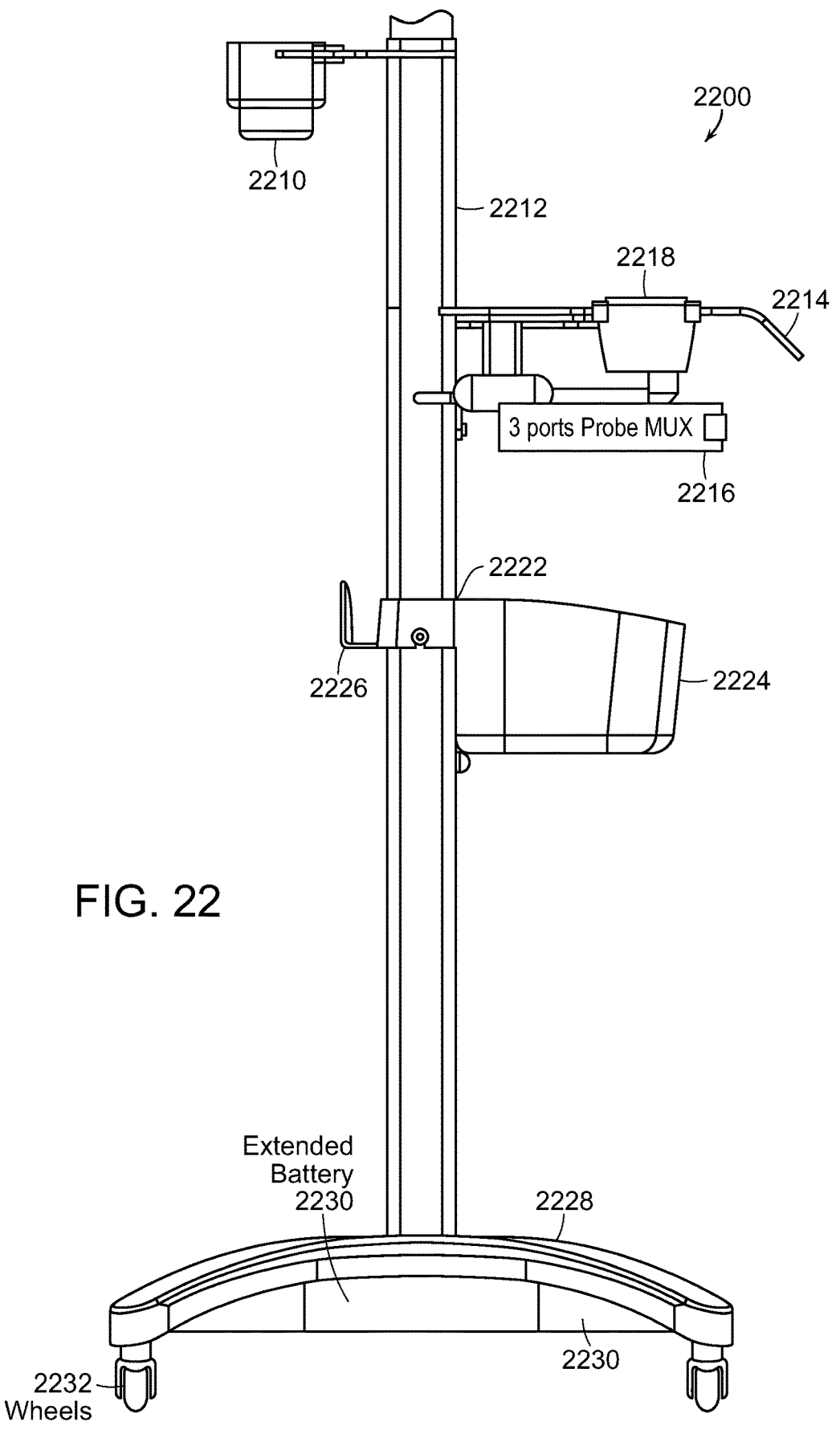
FIG. 22 illustrates preferred cart system for a modular ultrasound imaging system in accordance with preferred embodiments of the invention.

FIG. 22 illustrate a preferred cart system, for use in embodiments with a modular ultrasound imaging system in accordance with the invention. The cart system 2200 may be configured with a vertical support member 2212, coupled to a horizontal support member 2028. An auxiliary device connector 2018, having a position for auxiliary device attachment 2014, may be configured to connect to the vertical support member 2212. A 3 port Probe MUX connection device 2016 may also be configured to connect to the tablet. A storage bin 2224 can be configured to attach by a storage bin attachment mechanism 2222, to vertical support member 2212. The cart system may also include a cord management system 2226, configured to attach to the vertical support member. The cart assembly 2200 includes the support beam 2212 mounted on a base 2228 having wheels 2232 and a battery 2230 that provides power for extended operation of the tablet. The assembly can also include an accessory holder 2224 mounted with height adjustment device 2226. Holders 2210, 2218 can be mounted on beam 2212 or on console panel 2214. The multiport probe multiplex device 2216 connects to the tablet to provide simultaneous connection of several transducer probes which the user can select in sequence with the displayed virtual switch. A moving touch gesture, such as a three finger flick on the displayed image or touching of a displayed virtual button or icon can switch between connected probes.

Figure 23A:
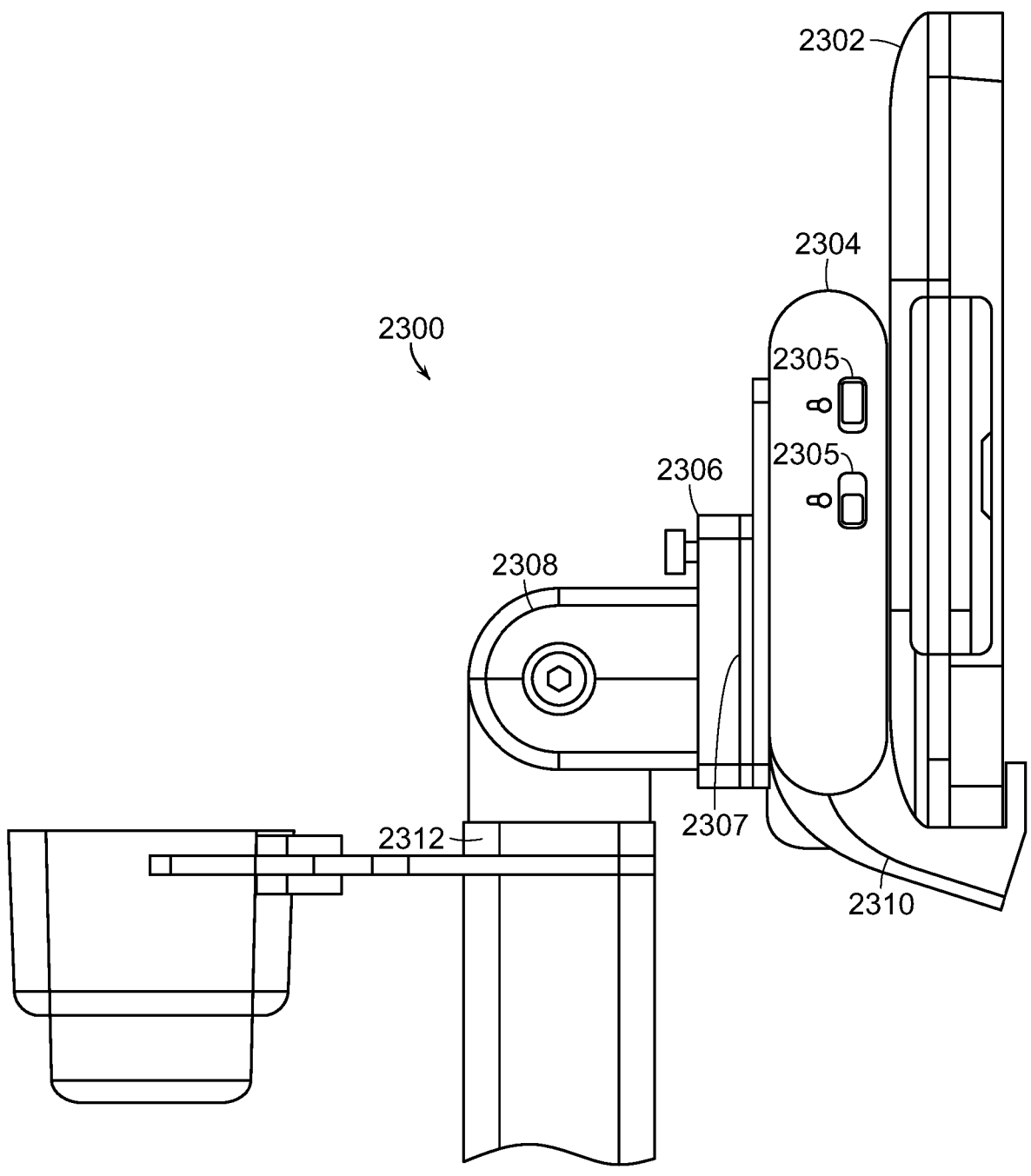
FIGS. 23A and 23B illustrating preferred cart systems for a modular ultrasound imaging system in accordance with preferred embodiments of the invention.

FIG. 23A illustrates preferred cart mount system for a modular ultrasound imaging system in accordance with the invention. Arrangement 2300 depicts the tablet 2302, coupled to the docking station 2304. The docking station 2304 is affixed to the attachment mechanism 2306. The attachment mechanism 2306 may include a hinged member 2308, allowing for the user display to tilted into a user desired position. The attachment mechanism 2306 is attached to the vertical member 2312. A tablet 2302 as described herein can be mounted on the base docking unit 2304 which is mounted to a mount assembly 2306 on top of beam 2212. The base unit 2304 includes cradle 2310, electrical connectors 2305 and a port 2307 to connect to the system 2302 to battery 2230 and multiplexor device 2216.

Figure 23B:
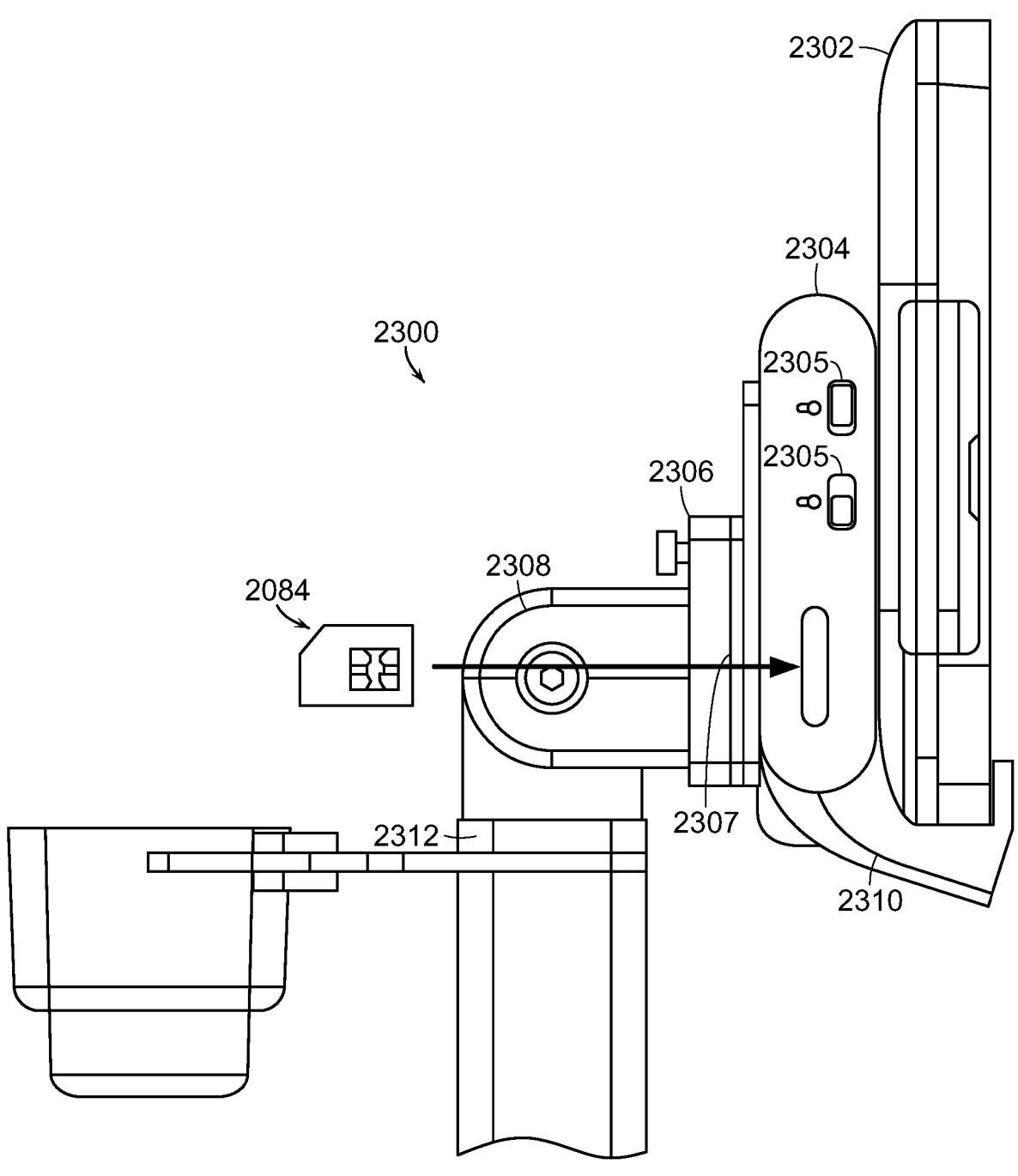

FIG. 23B illustrated a card mounted system in which a SIM card 2084 is inserted into unit 2304.

Figure 24:
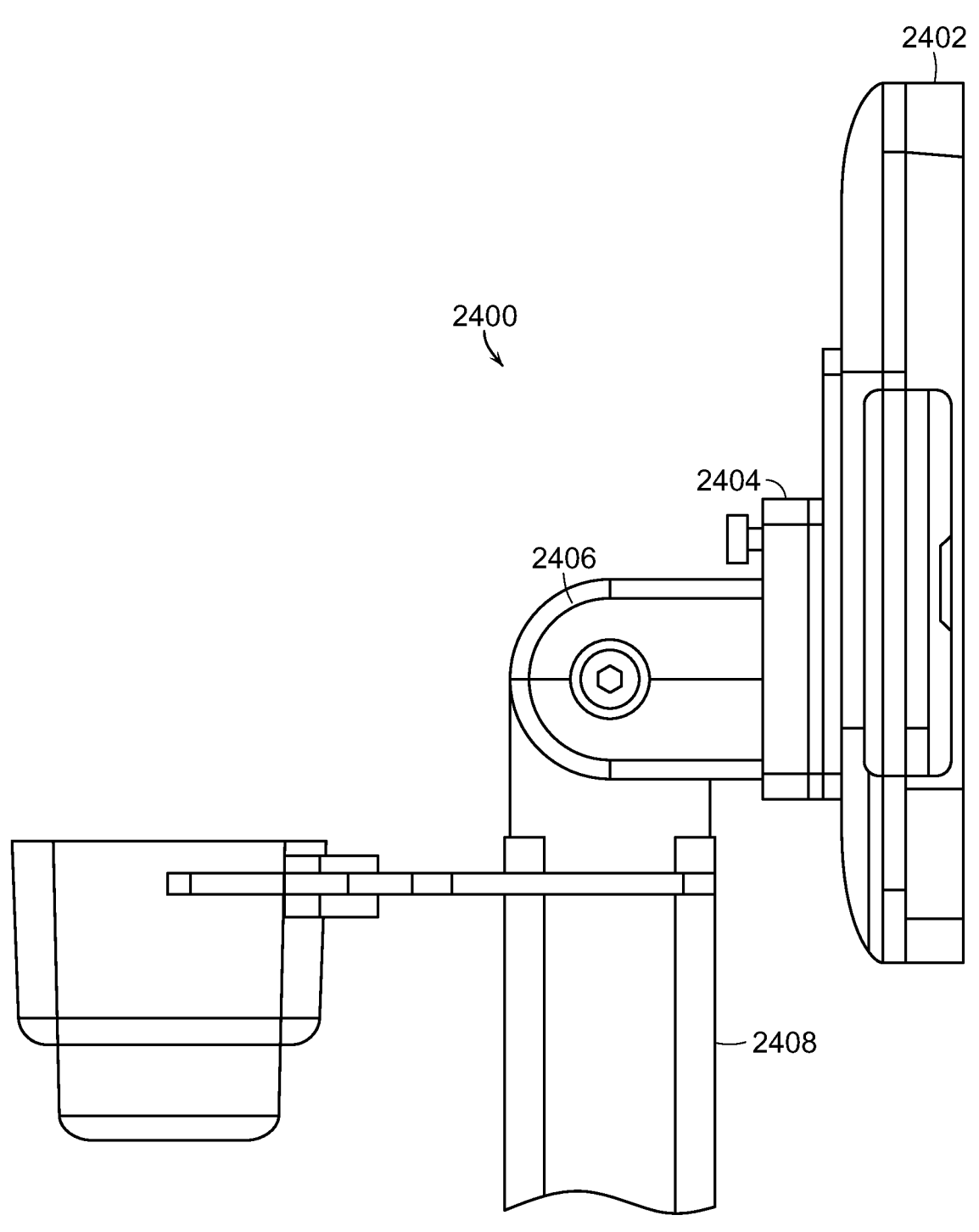
FIG. 24 illustrates preferred cart system for a modular ultrasound imaging system in accordance with preferred embodiments of the invention.

FIG. 24 illustrates preferred cart system 2400 modular ultrasound imaging system in accordance with the invention in which tablet 2402 is connected on mounting assembly 2406 with connector 2404. Arrangement 2400 depicts the tablet 2402, coupled to the vertical support member 2408, via attachment mechanism 2404 without the docking element 2304. Attachment mechanism 2404 may include a hinged member 2406 for display adjustment.

Figures 25A, 25B:
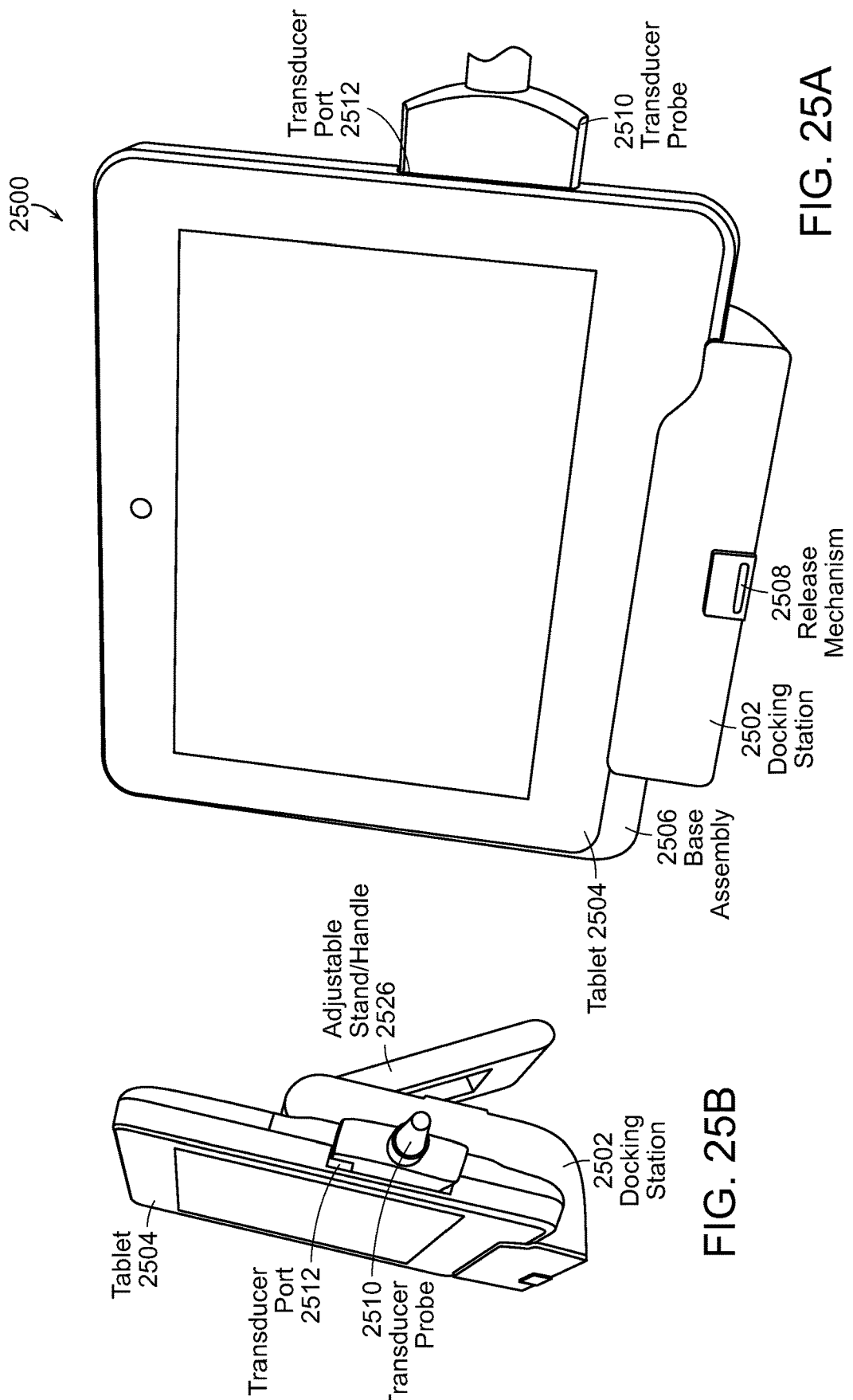
FIGS. 25A-25B illustrate a multifunction docking base for tablet ultrasound device.

FIGS. 25A and 25B illustrate a multi-function docking station. FIG. 25A illustrates docking station 2502, and tablet 2504, having a base assembly 2506, that mates to the docking station 2502. The tablet 2504, and the docking station 2502, may be electrically connected. The tablet 2504 may be released from docking station 2502, by engaging the release mechanism 2508. The docking station 2502 may contain a transducer port 2512, for connection of a transducer probe 2510. The docking station 2502 can contain 3 USB 3.0 ports, a LAN port, a headphone jack and a power connector for charging. FIG. 25B illustrates a side view of the tablet 2504, and docking station 2502, having a stand in accordance with the preferred embodiments of the present invention. The docking station may include an adjustable stand/handle 2526. The adjustable stand/handle 2526 may be tilted for multiple viewing angles. The adjustable stand/handle 2526 may be flipped up for transport purposes. The side view also illustrates a transducer port 2512, and a transducer probe connector 2510.

Figure 26:
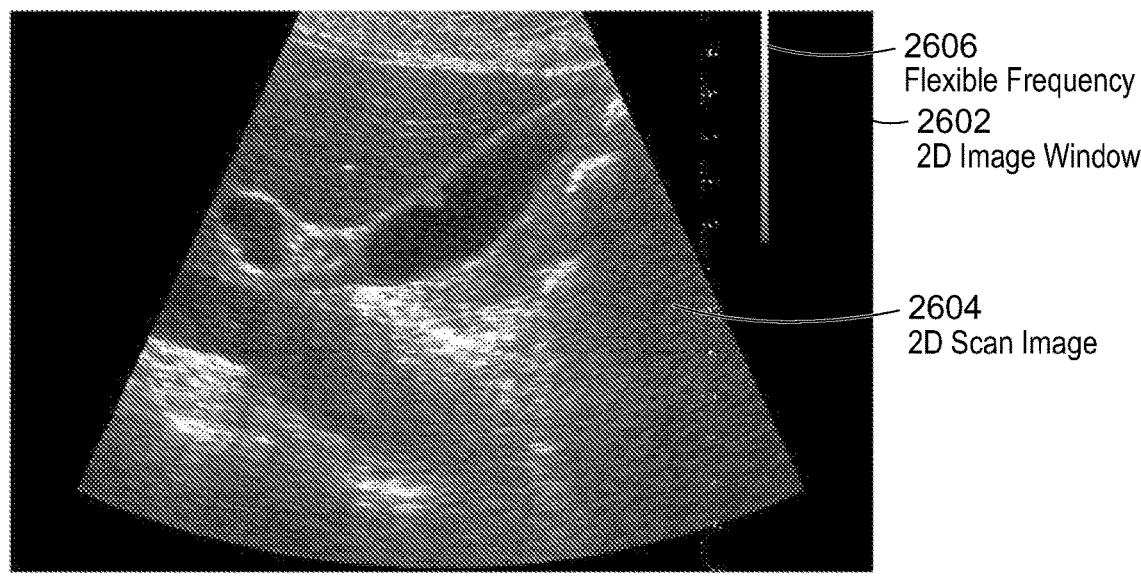
FIG. 26 illustrates a 2D imaging mode of operation with a modular ultrasound imaging system in accordance with the invention.

FIG. 26 illustrates a 2D imaging mode of operation with a modular ultrasound imaging system in accordance with the invention. The touch screen of table 2504 may display images obtained by 2-dimensional transducer probe using a 256 digital beamformer channels. The 2-dimensional image window 2602 depicts a 2-dimensional image scan 2604. The 2-dimensional image may be obtained using flexible frequency scans 2606, wherein the control parameters are represented on the tablet.

Figure 27:
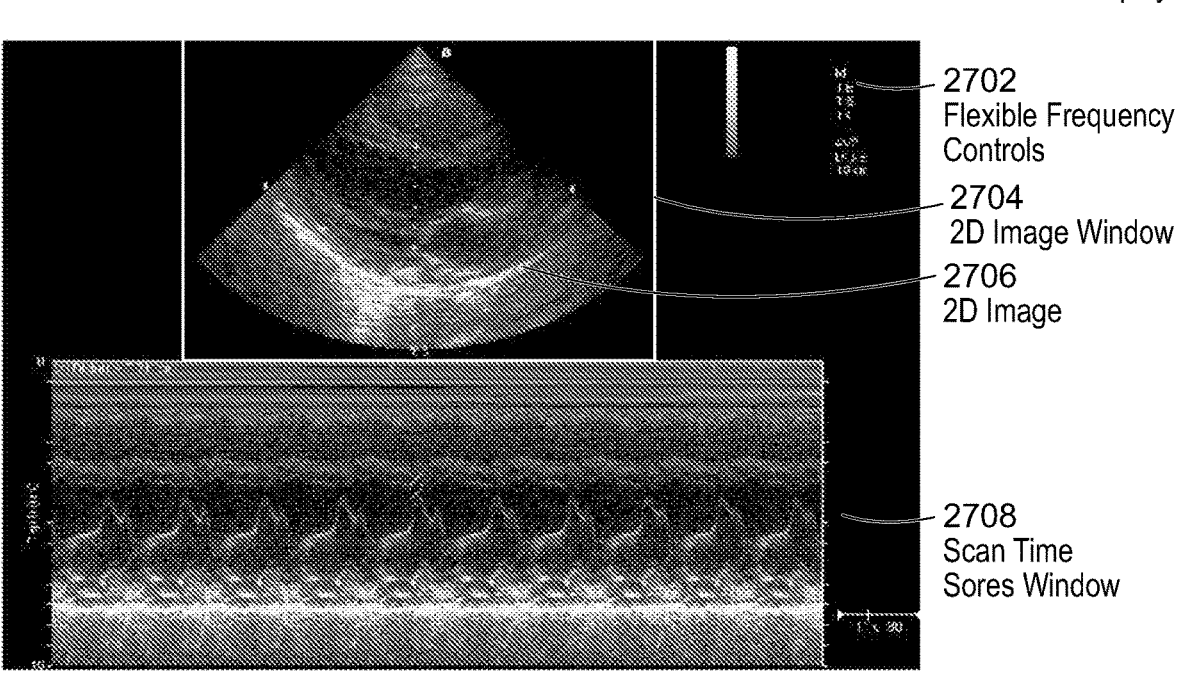
FIG. 27 illustrates a motion mode of operation with a modular ultrasound imaging system in accordance with the invention.

FIG. 27 illustrates a motion mode of operation with a modular ultrasound imaging system in accordance with the invention. The touch screen display of tablet 2700, may display images obtained by a motion mode of operation. The touch screen display of tablet 2700, may simultaneously display 2-dimensional 2706, and motion mode imaging 2708. The touch screen display of tablet 2700, may display a 2-dimensional image window 2704, with a 2-dimensional image 2706. Flexible frequency controls 2702 displayed with the graphical user interface can be used to adjust the frequency from 2 MHz to 12 MHz.

FIG. 28 illustrates a color Doppler mode of operation with a modular ultrasound imaging system in accordance with the invention. The touch screen display of tablet 2800 displays images obtained by color Doppler mode of operation. A 2-dimensional image window 2806 is used as the base display. The color coded information 2808, is overlaid on the 2-dimensional image 2810. Ultrasound-based imaging of red blood cells are derived from the received echo of the transmitted signal. The primary characteristics of the echo signal are the frequency and the amplitude. Amplitude depends on the amount of moving blood within the volume sampled by the ultrasound beam. A high frame rate or high resolution can be adjusted with the display to control the quality of the scan. Higher frequencies may be generated by rapid flow and can be displayed in lighter colors, while lower frequencies are displayed in darker colors. Flexible frequency controls 2804, and color Doppler scan information 2802, may be displayed on the tablet display 2800.

FIG. 29 illustrates a Pulsed wave Doppler mode of operation with a modular ultrasound imaging system in accordance with the invention. The touch screen display of tablet 2900, may display images obtained by pulsed wave Doppler mode of operation. Pulsed wave Doppler scans produce a series of pulses used to analyse the motion of blood flow in a small region along a desired ultrasound cursor called the sample volume or sample gate 2012. The tablet display 2900 may depict a 2-dimensional image 2902, wherein the sample volume/sample gate 2012 is overlaid. The tablet display 2900 may use a mixed mode of operation 2906, to depict a 2-dimensional image 2902, and a time/doppler frequency shift 2910. The time/doppler frequency shift 2910 can be converted into velocity and flow if an appropriate angle between the beam and blood flow is known. Shades of gray 2908, in the time/doppler frequency shift 2910, may represent the strength of signal. The thickness of the spectral signal may be indicative of laminar or turbulent flow. The tablet display 2900 can depict adjustable frequency controls 2904.

Figure 30:
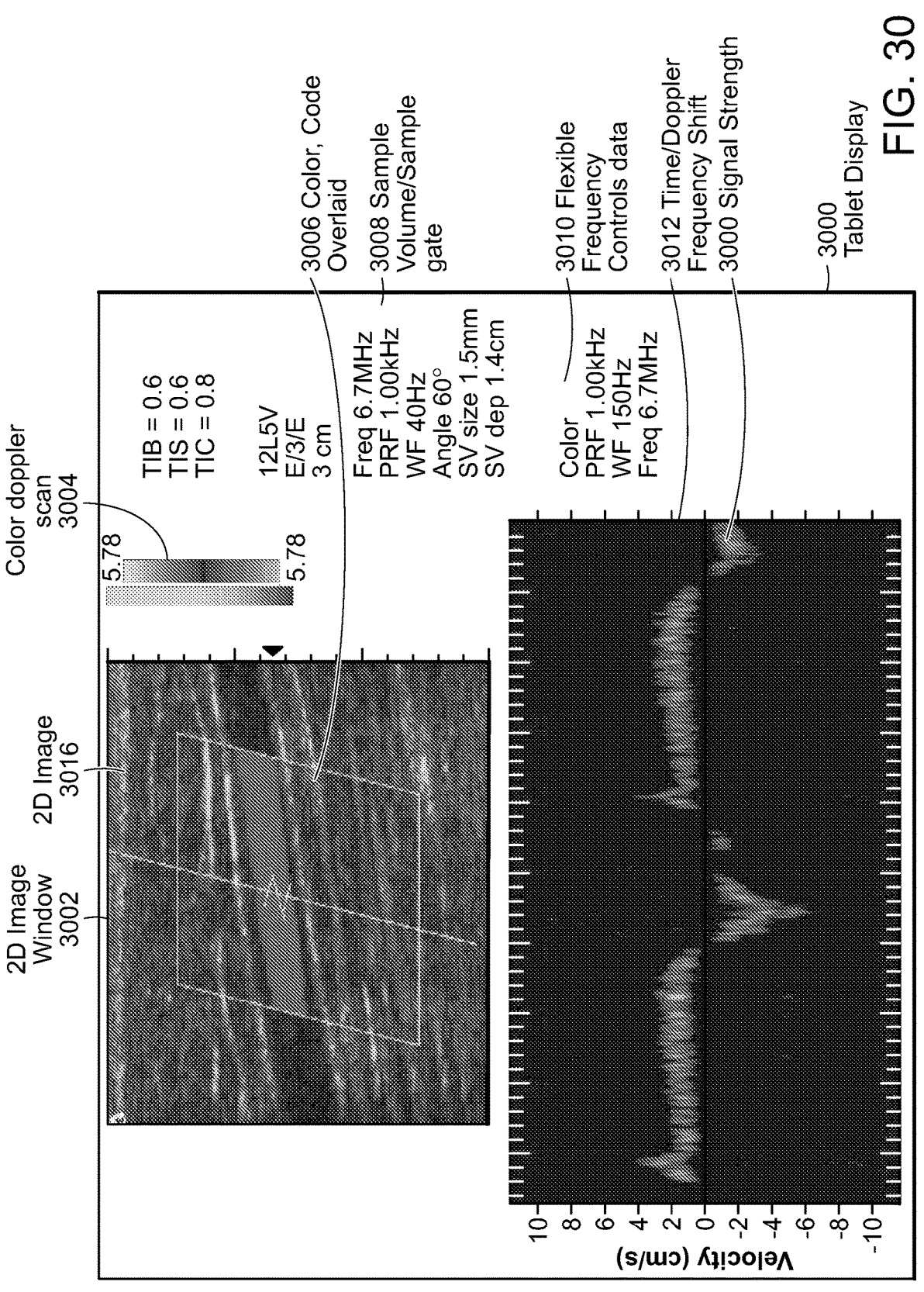
FIG. 30 illustrates a Triplex scan mode of operation with a modular ultrasound imaging system in accordance with the invention.

FIG. 30 illustrates a triplex scan mode of operation with a modular ultrasound imaging system in accordance with the invention. The tablet display 3000 may include a 2-dimensional window 3002, capable of displaying 2-dimensional images alone or in combination with the color Doppler or directional Doppler features. The touch screen display of tablet 3000, may display images obtained by color Doppler mode of operation. A 2-dimensional image window 3002 is used as the base display. The color coded information 3004, is overlaid 3006, on the 2-dimensional image 3016. The pulsed wave Doppler feature may be used alone or in combination with 2-dimensional imaging or the color Doppler imaging. The tablet display 3000 may include a pulsed wave Doppler scan represented by a sample volume/sample gate 3008, overlaid over 2 dimensional images 3016, or the color code overlaid 3006, either alone or in combination. The tablet display 3000 may depict a split screen representing the time/doppler frequency shift 3012. The time/doppler frequency shift 3012 can be converted into velocity and flow if an appropriate angle between the insolating beam and blood flow is known. Shades of gray 3014, in the time/doppler frequency shift 3012, may represent the strength of signal. The thickness of the spectral signal may be indicative of laminar or turbulent flow. The tablet display 3000 also may depict flexible frequency controls 3010.

Figure 31:
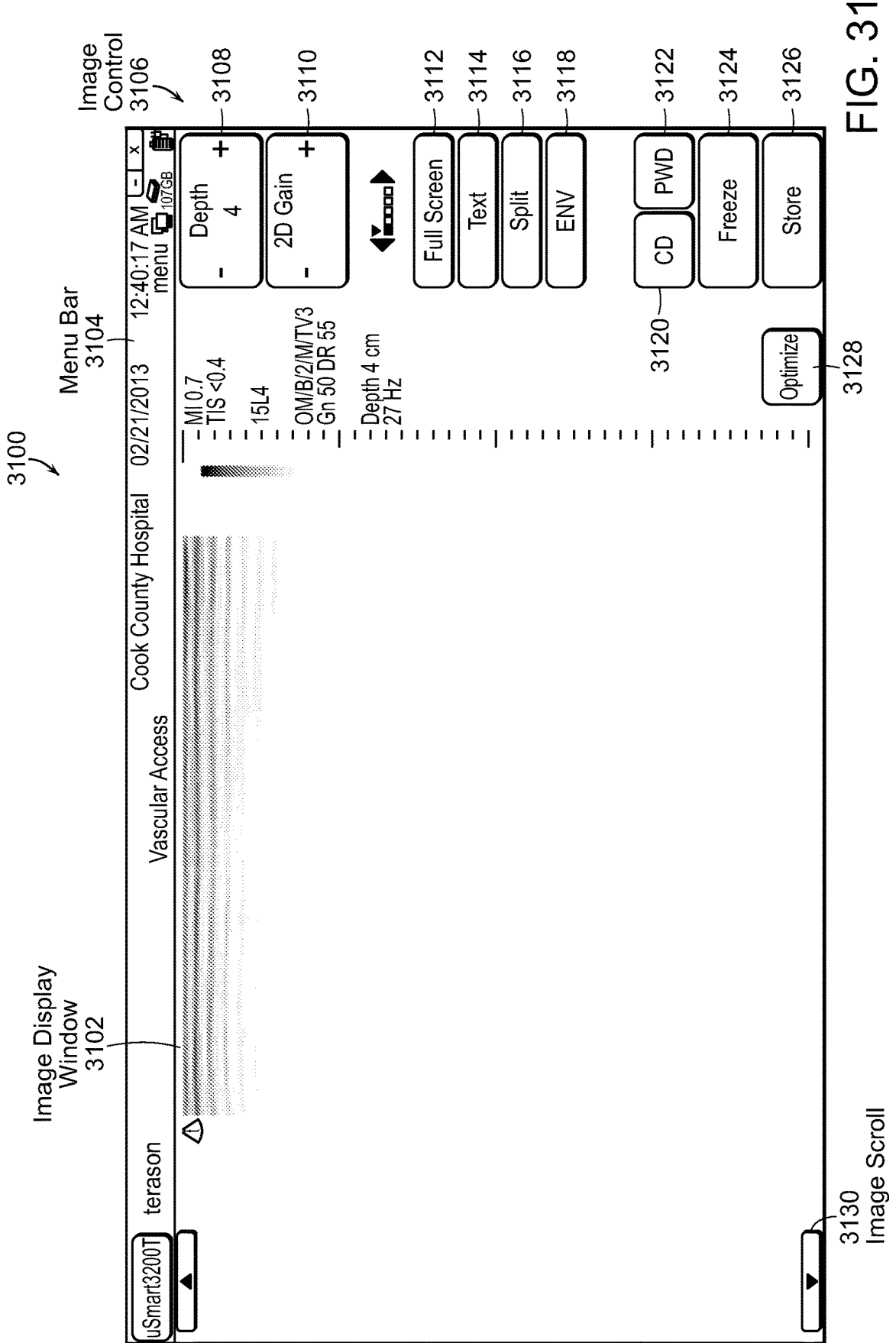
FIG. 31 illustrates a GUI Home Screen interface for a user mode of operation with a modular ultrasound imaging system in accordance with the invention.

FIG. 31 illustrates a GUI home screen interface 3100, for a user mode of operation, with a modular ultrasound imaging system in accordance with the invention. The screen interface for a user mode of operation 3100 may be displayed when the ultrasound system is started. To assist a user in navigating the GUI home screen 3100, the home screen may be considered as including three exemplary work areas: a menu bar 3104, an image display window 3102, and an image control bar 3106. Additional GUI components may be provided on the main GUI home screen 3100, to enable a user to close, resize and exit the GUI home screen and/or windows in the GUI home screen.

The menu bar 3104 enables users to select ultrasound data, images and/or video for display in the image display window 3102. The menu bar may include components for selecting one or more files in a patient folder directly and an image folder directory.

The image control bar 3106 includes touch controls that may be operated by touch and touch gestures applied by the user directly to the surface of the display. Exemplary touch controls may include, but are not limited to a depth control touch controls 3108, a 2-dimensional gain touch control 3110, a full screen touch control 3112, a text touch control 3114, a split screen touch control 3116, a ENV touch control 3118, a CD touch control 3120, a PWD touch control 3122, a freeze touch control 3124, a store touch control 3126, and a optimize touch control 3128.

Figure 32:
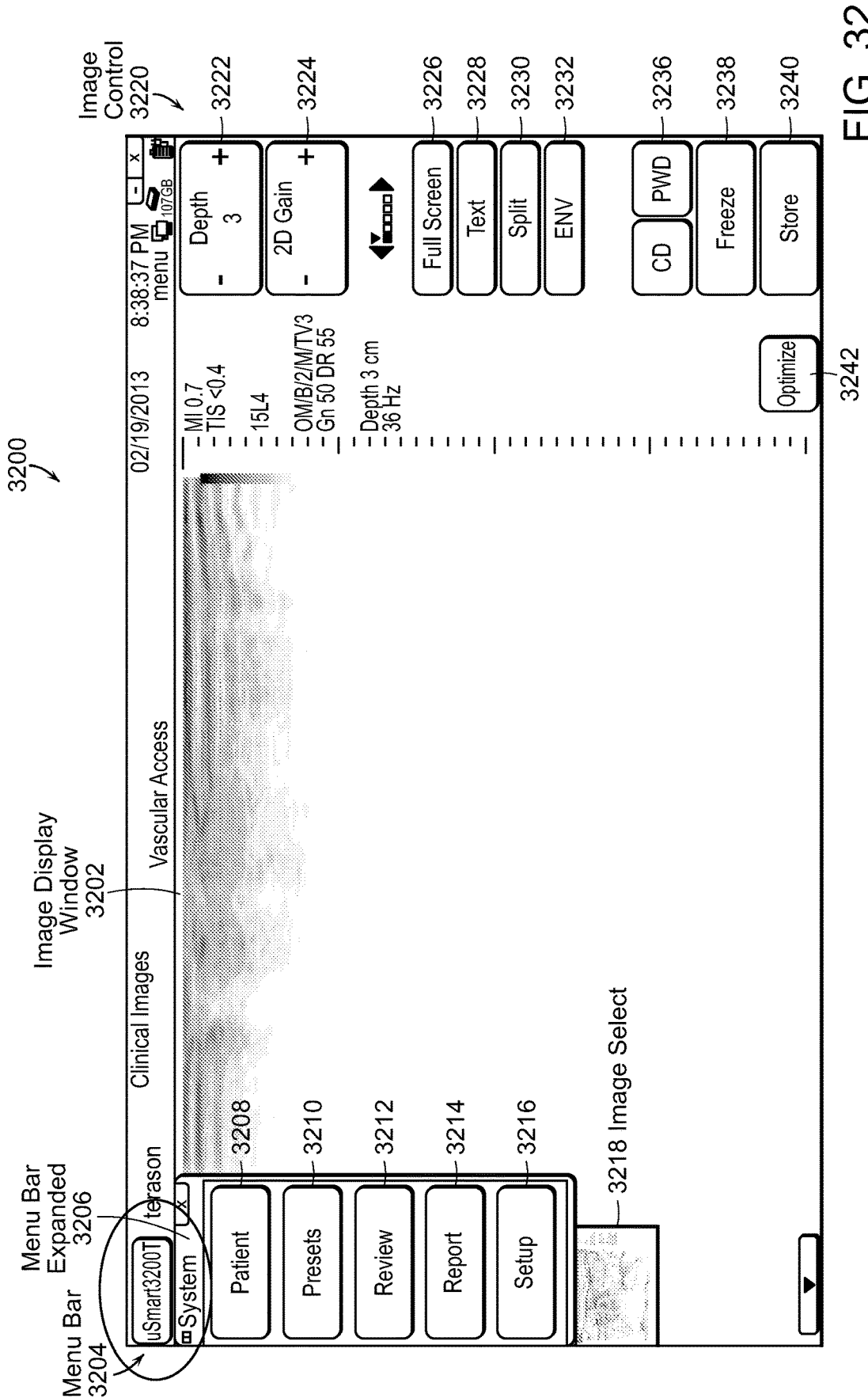
FIG. 32 illustrates a GUI Menu Screen Interface for a user mode of operation with a modular ultrasound imaging system in accordance with the invention.

FIG. 32 illustrates a GUI menu screen interface 3200, for a user mode of operation, with a modular ultrasound imaging system in accordance with the invention. The screen interface for a user mode of operation 3200 may be displayed when the menu selection mode is triggered from the menu bar 3204 thereby initiating operation of the ultrasound system. To assist a user in navigating the GUI home screen 3100, the home screen may be considered as including three exemplary work areas: a menu bar 3204, an image display window 3202, and an image control bar 3220. Additional GUI components may be provided on the main GUI menu screen 3200 to enable a user to close, resize and exit the GUI menu screen and/or windows in the GUI menu screen, for example.

The menu bar 3204 enables users to select ultra sound data, images and/or video for display in the image display window 3202. The menu bar 3204 may include touch control components for selecting one or more files in a patient folder directory and an image folder directory. Depicted in an expanded format, the menu bar may include exemplary touch control such as, a patient touch control 3208, a pre-sets touch control 3210, a review touch control 3212, a report touch control 3214, and a setup touch control 3216.

The image control bar 3220 includes touch controls that may be operated by touch and touch gestures applied by the user directly to the surface of the display. Exemplary touch controls may include, but are not limited to depth control touch controls 3222, a 2-dimensional gain touch control 3224, a full screen touch control 3226, a text touch control 3228, a split screen touch control 3230, a needle visualization ENV touch control 3232, a CD touch control 3234, a PWD touch control 3236, a freeze touch control 3238, a store touch control 3240, and a optimize touch control 3242.

Figure 33:
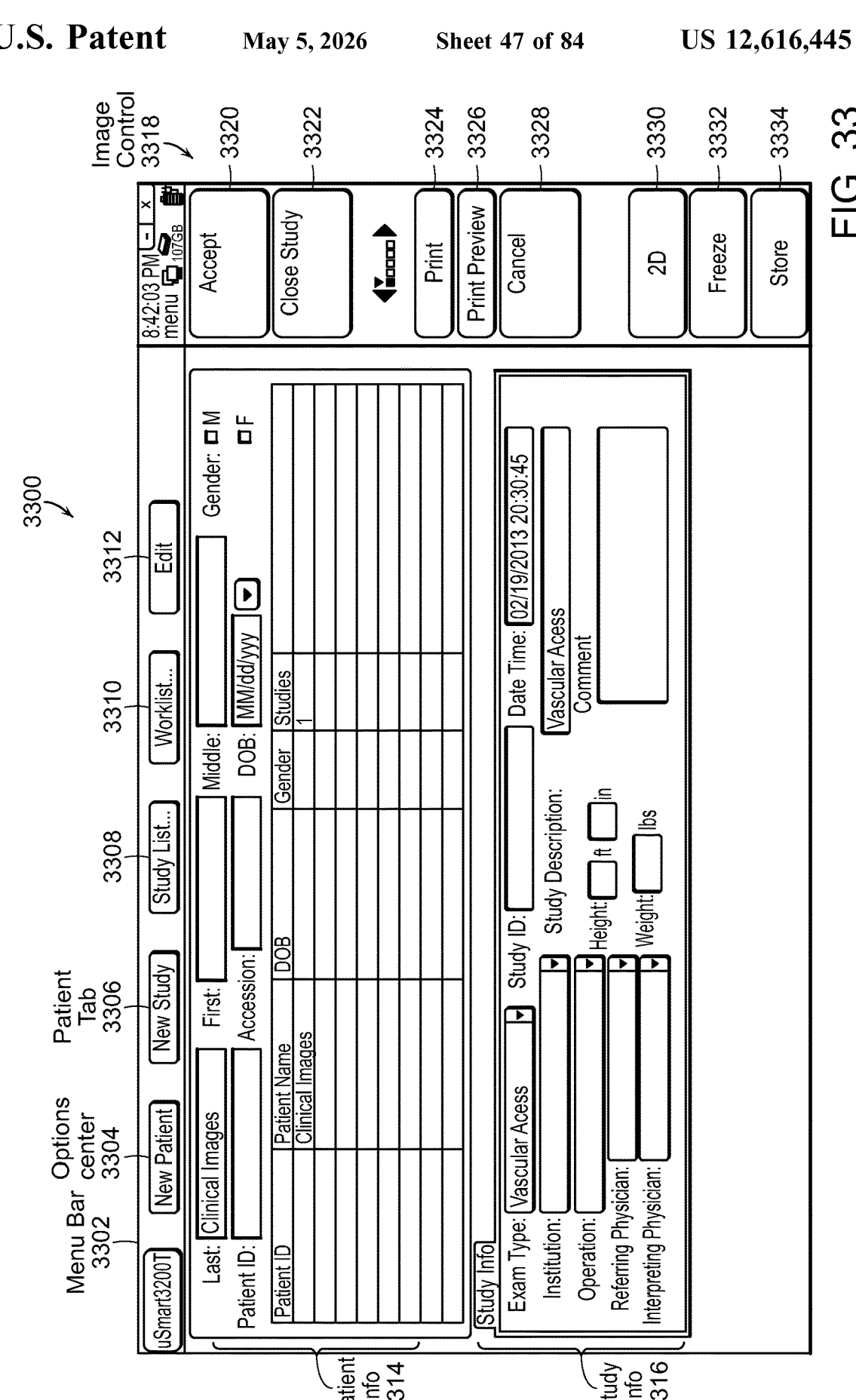
FIG. 33 illustrates a GUI Patient Data Screen Interface for a user mode of operation with a modular ultrasound imaging system in accordance with the invention.

FIG. 33 illustrates a GUI patient data screen interface 3300, for a user mode of operation, with a modular ultrasound imaging system in accordance with the invention. The screen interface for a user mode of operation 3300, may be displayed when the patient selection mode is triggered from the menu bar 3302, when the ultrasound system is started. To assist a user in navigating the GUI patient data screen 3300, the patient data screen may be considered as including five exemplary work areas: a new patient touch screen control 3304, a new study touch screen control 3306, a study list touch screen control 3308, a work list touch screen control 3310, and an edit touch screen control 3312. Within each touch screen control, further information entry fields are available 3314, 3316. For example, patient information section 3314, and study information section 3316, may be used to record data.

Within the patient data screen 3300, the image control bar 3318, includes touch controls that may be operated by touch and touch gestures applied by the user directly to the surface of the display. Exemplary touch controls may include, but are not limited to accept study touch control 3320, close study touch control 3322, print touch control 3324, print preview touch control 3326, cancel touch control 3328, a 2-dimensional touch control 3330, freeze touch control 3332, and a store touch control 3334.

Figure 34:
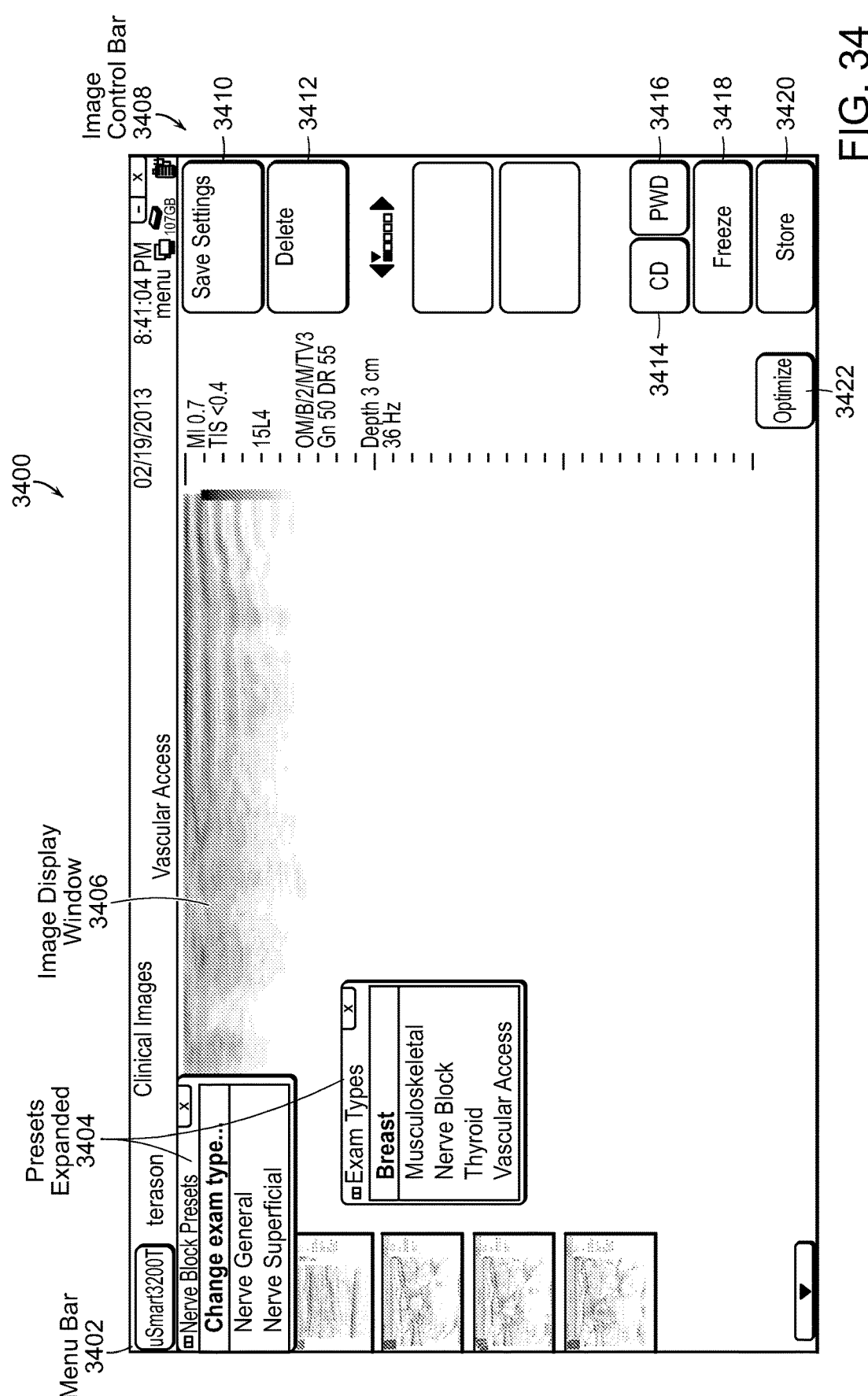
FIG. 34 illustrates a GUI Pre-sets Screen Interface for a user mode of operation with a modular ultrasound imaging system in accordance with the invention.

FIG. 34 illustrates a GUI patient data screen interface 3400, for a user mode of operation with a modular ultrasound imaging system in accordance with the invention. The screen interface for a user mode of operation 3400, may be displayed when the pre-sets selection mode 3404, is triggered from the menu bar 3402, when the ultrasound system is started.

Within the pre-sets screen 3400, the image control bar 3408, includes touch controls that may be operated by touch and touch gestures applied by the user directly to the surface of the display. Exemplary touch controls may include, but are not limited to a save settings touch control 3410, a delete touch control 3412, CD touch control 3414, PWD touch control 3416, a freeze touch control 3418, a store touch control 3420, and a optimize touch control 3422.

Figure 35:
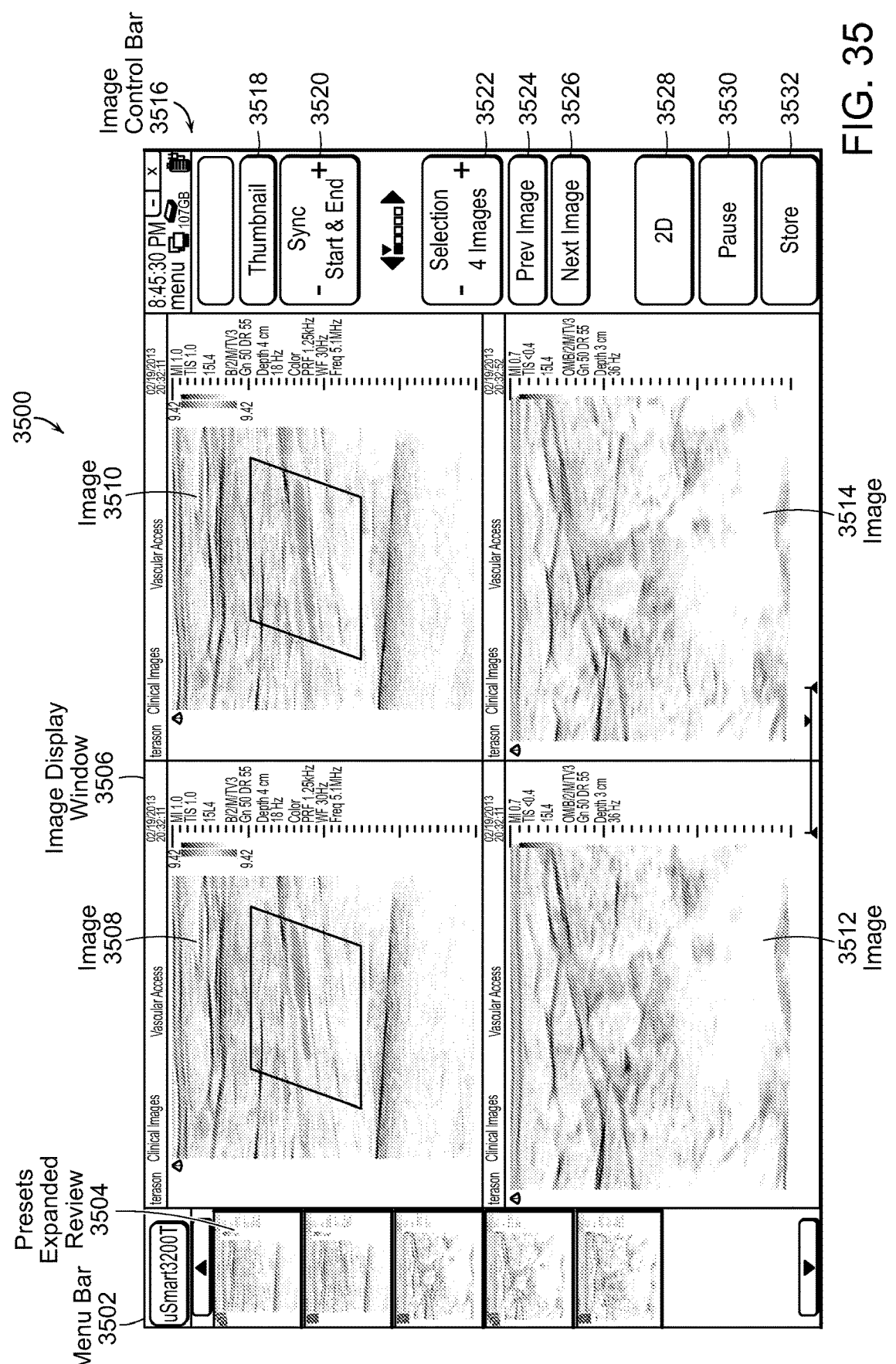
FIG. 35 illustrates a GUI Review Screen Interface for a user mode of operation with a modular ultrasound imaging system in accordance with the invention.

FIG. 35 illustrates a GUI review screen interface 3500, for a user mode of operation, with a modular ultrasound imaging system in accordance with the invention. The screen interface for a user mode of operation 3500, may be displayed when the pre-sets expanded review 3504, selection mode 3404, is triggered from the menu bar 3502, when the ultrasound system is started.

Within the review screen 3500, the image control bar 3516, includes touch controls that may be operated by touch and touch gestures applied by the user directly to the surface of the display. Exemplary touch controls may include, but are not limited to a thumbnail settings touch control 3518, sync touch control 3520, selection touch control 3522, a previous image touch control 3524, a next image touch control 3526, a 2-dimensional image touch control 3528, a pause image touch control 3530, and a store image touch control 3532.

A image display window 3506, may allow the user to review images in a plurality of formats. Image display window 3506, may allow a user to view images 3508, 3510, 3512, 3514, in combination or subset or allow any image 3508, 3510, 3512, 3514, to be viewed individually. The image display window 3506, may be configured to display up to four images 3508, 3510, 3512, 3514, to be viewed simultaneously.

Figure 36:
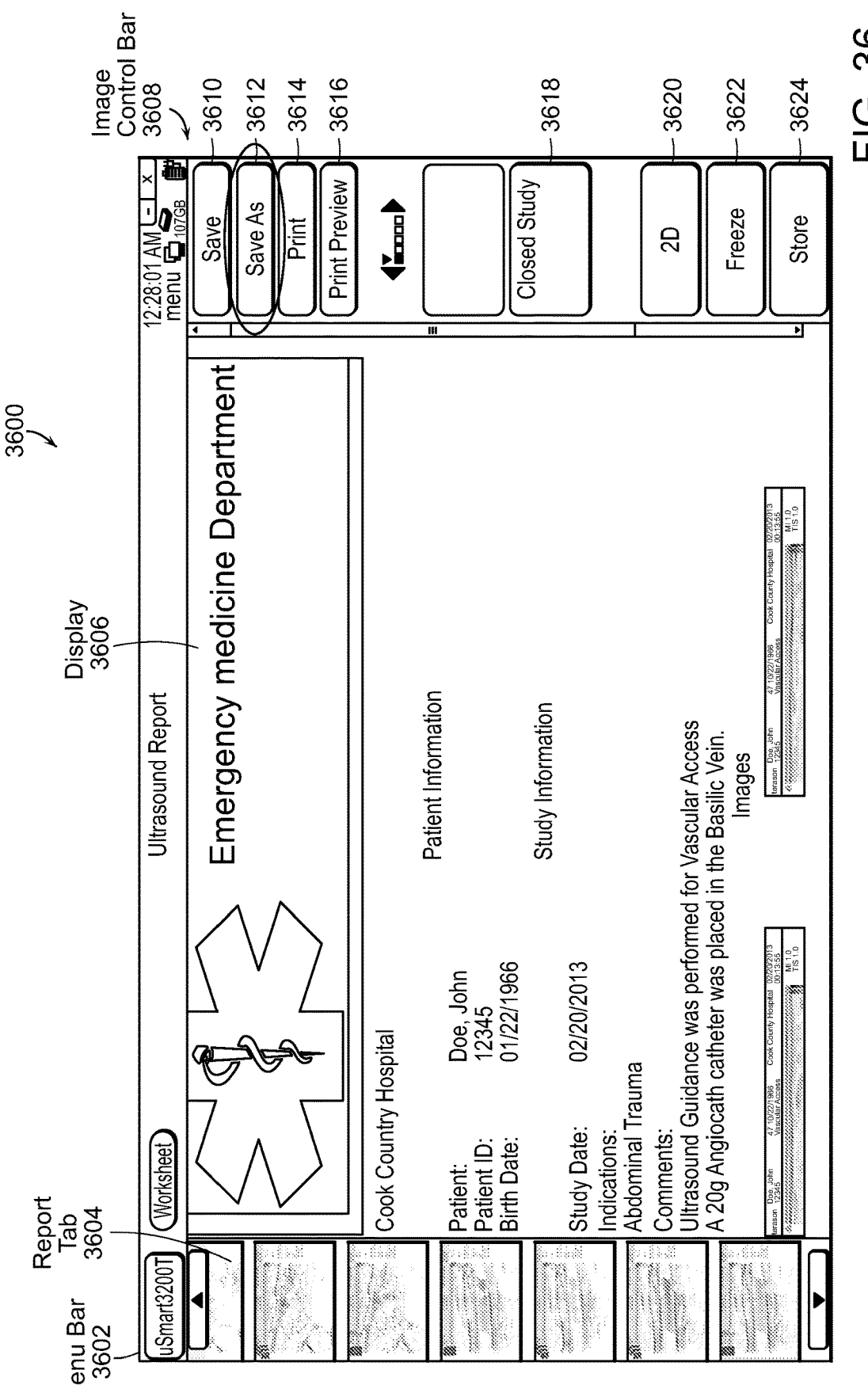
FIG. 36 illustrates a GUI Report Screen Interface for a user mode of operation with a modular ultrasound imaging system in accordance with the invention.

FIG. 36 illustrates a GUI Report Screen Interface for a user mode of operation with a modular ultrasound imaging system in accordance with the invention. The screen interface for a user mode of operation 3600, may be displayed when the report expanded review 3604, is triggered from the menu bar 3602, when the ultrasound system is started. The display screen 3606, contains the ultrasound report information 3626. The user may use the worksheet section within the ultrasound report 3626, to enter in comments, patient information and study information.

Within the report screen 3600, the image control bar 3608, includes touch controls that may be operated by touch and touch gestures applied by the user directly to the surface of the display. Exemplary touch controls may include, but are not limited to a save touch control 3610, a save as touch control 3612, a print touch control 3614, a print preview touch control 3616, a close study touch control 3618, a 2-dimensional image touch control 3620, a freeze image touch control 3622, and a store image touch control 3624.

Figure 37A:
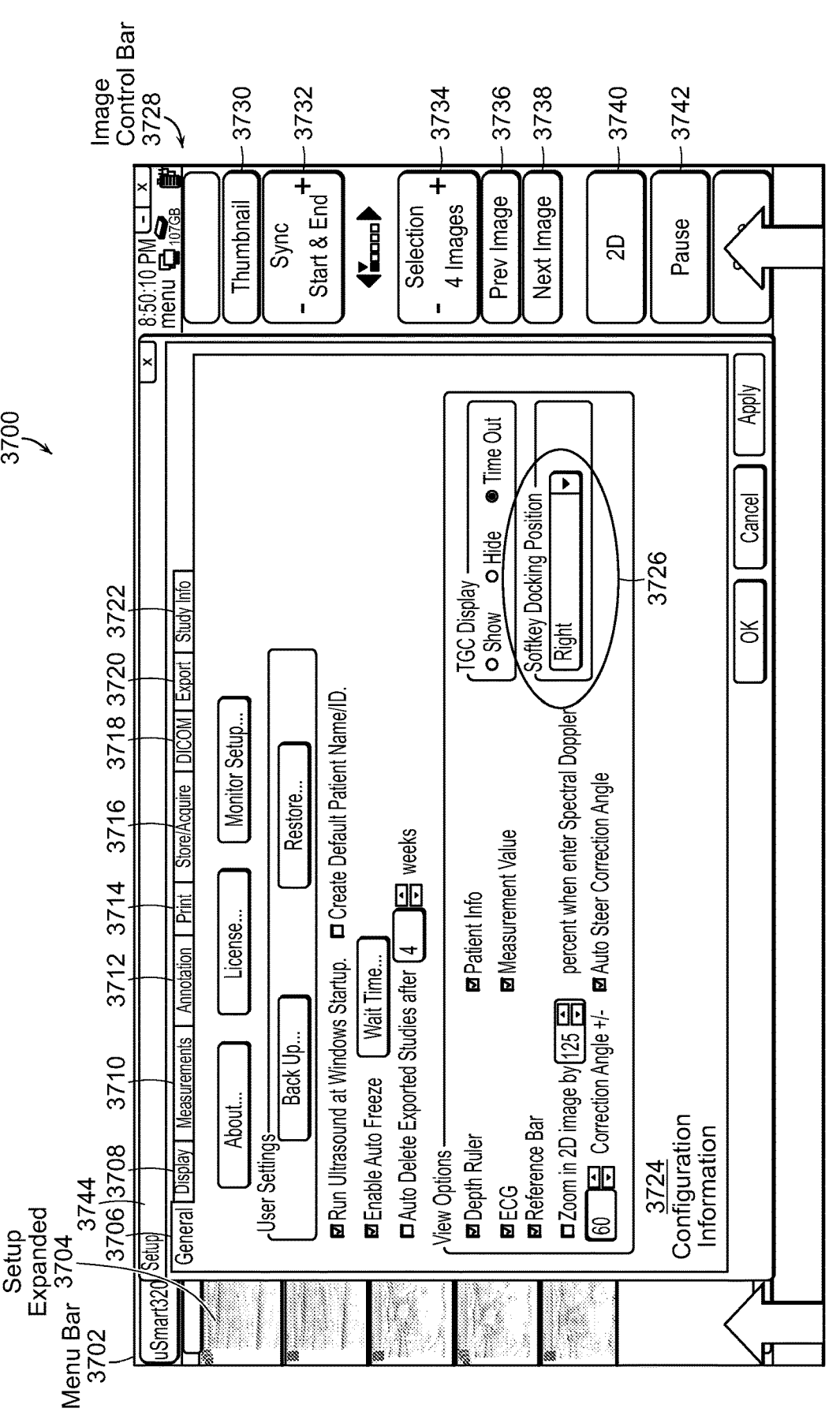
FIGS. 37A-37C illustrates a GUI Setup Display Screen Interface for a user mode of operation with a modular ultrasound imaging system in accordance with the invention.

FIG. 37 illustrates a GUI Setup Screen Interface for a user mode of operation with a modular ultrasound imaging system in accordance with the invention. The screen interface for a user mode of operation 3700, may be displayed when the report expanded review 3704, is triggered from the menu bar 3702, when the ultrasound system is started.

Figure 37B:
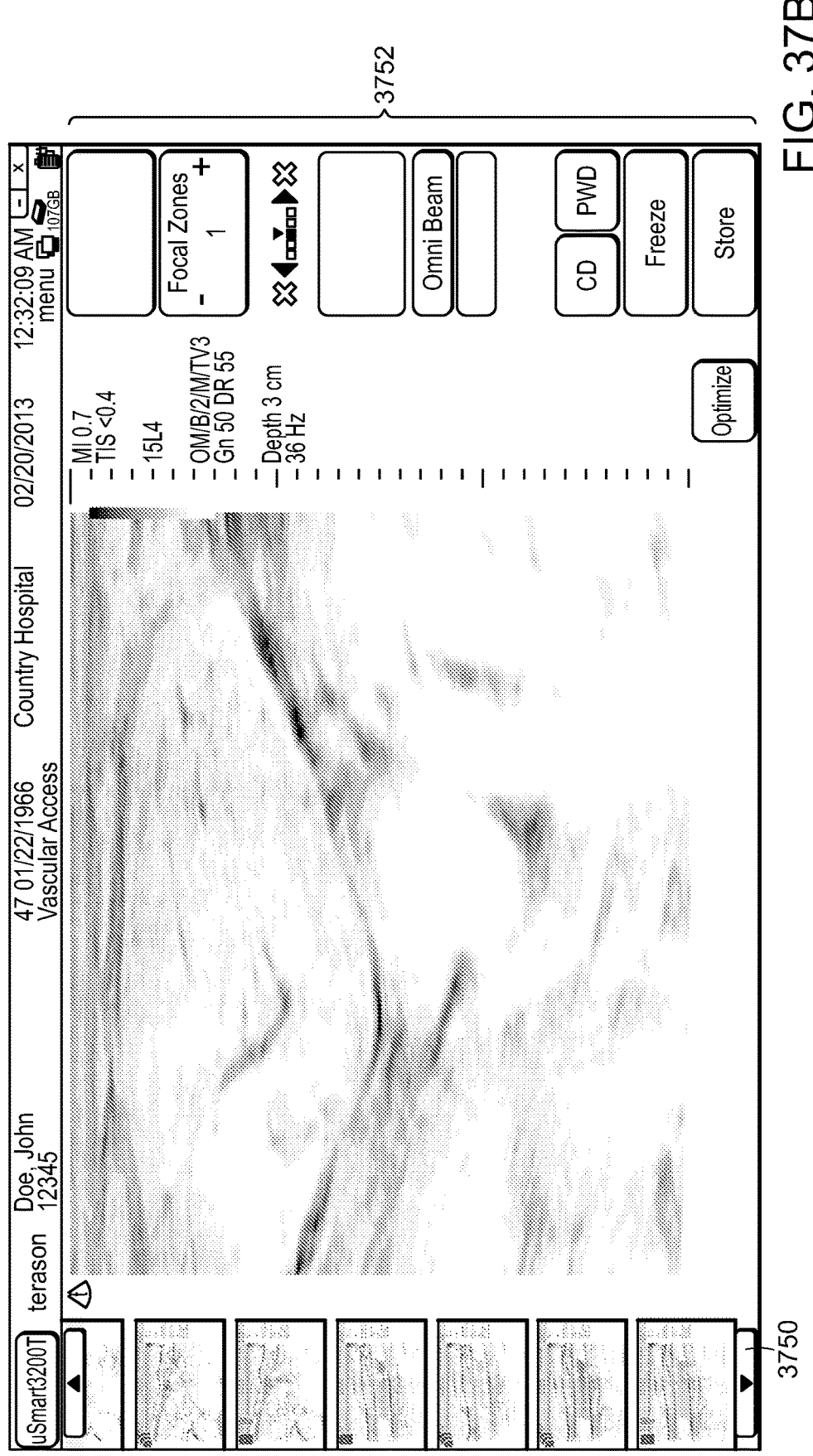
Figure 37C:
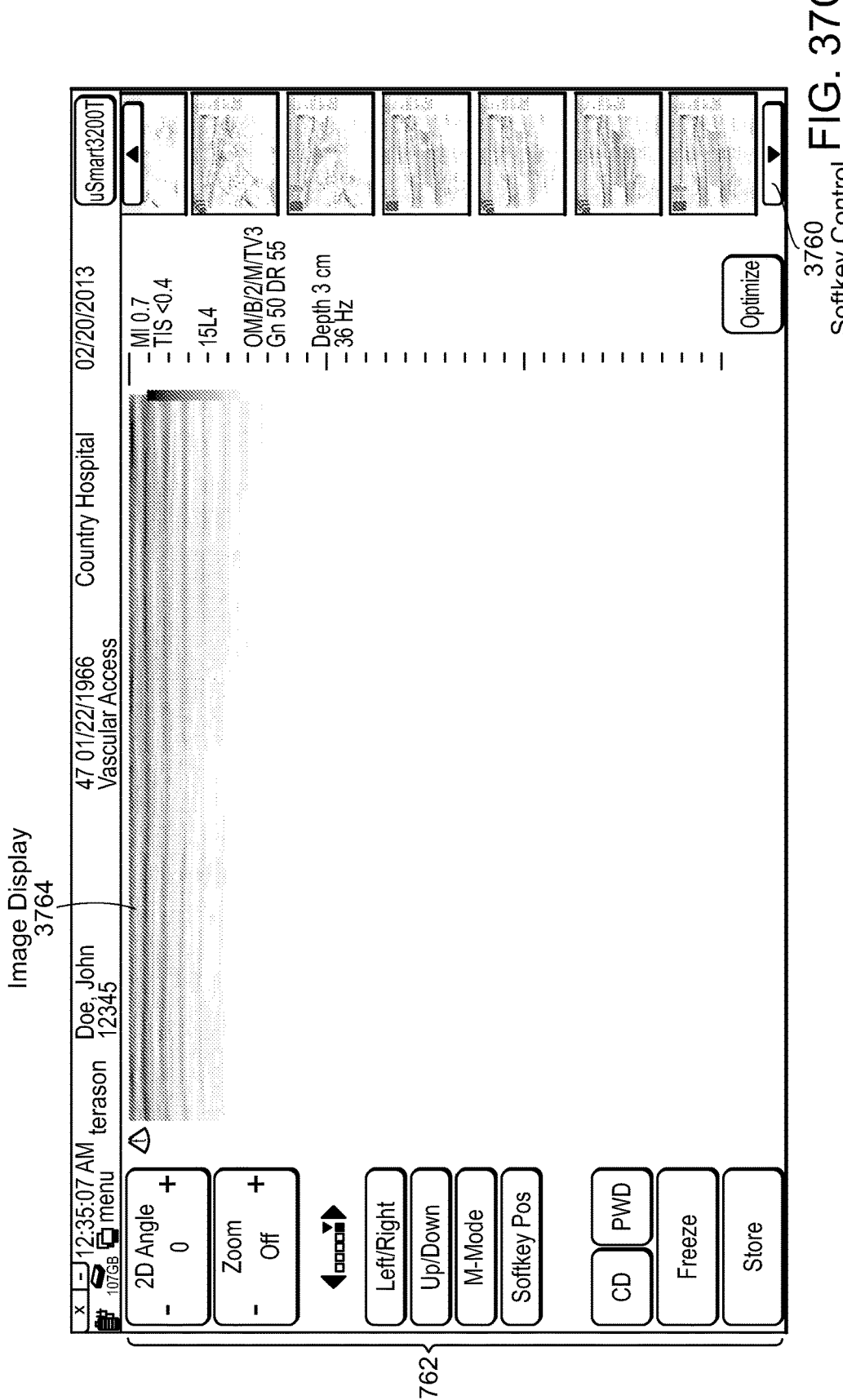

Within the setup expanded screen 3704, the setup control bar 3744, includes touch controls that may be operated by touch and touch gestures, applied by the user directly to the surface of the display. Exemplary touch controls may include, but are not limited to a general touch control 3706, a display touch control 3708, a measurements touch control 3710, annotation touch control 3712, a print touch control 3714, a store/acquire touch control 3716, a DICOM touch control 3718, an export touch control 3720, and a study information image touch control 3722. The touch controls may contain a display screen that allow the user to enter configuration information. For example, the general touch control 3706, contains a configuration screen 3724, wherein the user may enter configuration information. Additionally, the general touch control 3706, contains a section allowing user configuration of the soft key docking position 3726. FIG. 37B depicts the soft key controls 3752, with a right side alignment. FIG. 37B further illustrates that activation of the soft key control arrow 3750, will change the key alignment to the opposite side, in this case, left side alignment. FIG. 37C depicts left side alignment of the soft key controls 3762, the user may activate an orientation change by using the soft key control arrow 3760, to change the position to right side alignment.

Within the review screen 3700, the image control bar 3728, includes touch controls that may be operated by touch and touch gestures applied by the user directly to the surface of the display. Exemplary touch controls may include but are not limited to, a thumbnail settings touch control 3730, sync touch control 3732, selection touch control 3734, a previous image touch control 3736, a next image touch control 3738, a 2-dimensional image touch control 3740, and a pause image touch control 3742.

Figure 38:
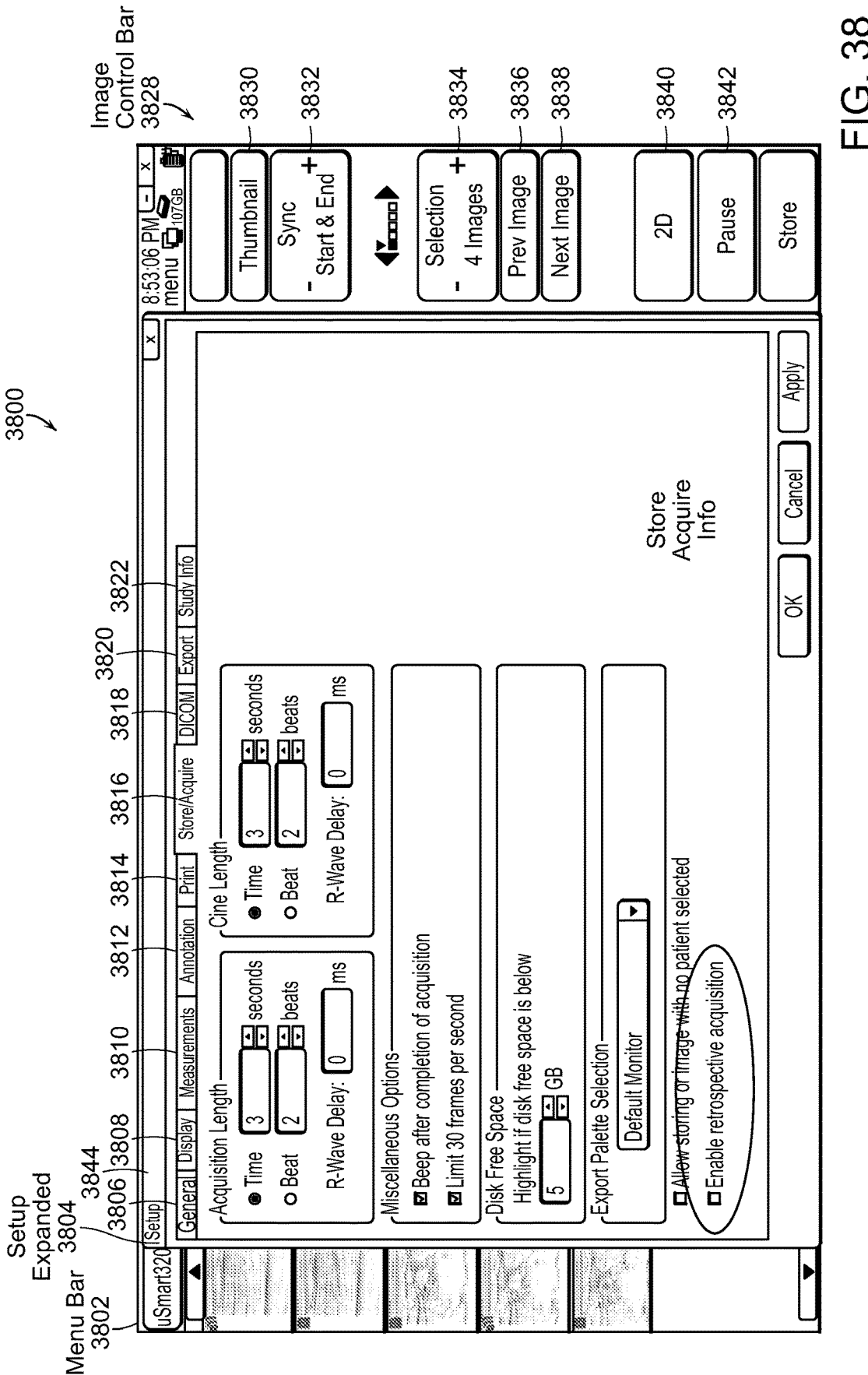
FIG. 38 illustrates a GUI Setup Store/Acquire Screen Interface for a user mode of operation with a modular ultrasound imaging system in accordance with the invention.

FIG. 38 illustrates a GUI Setup Screen Interface for a user mode of operation with a modular ultrasound imaging system in accordance with the invention. The screen interface for a user mode of operation 3800, may be displayed when the report expanded review 3804, is triggered from the menu bar 3802, when the ultrasound system is started.

Within the setup expanded screen 3804, the setup control bar 3844, includes touch controls that may be operated by touch and touch gestures applied by the user directly to the surface of the display. Exemplary touch controls may include, but are not limited to a plurality of icons such as a general touch control 3806, a display touch control 3808, a measurements touch control 3810, annotation touch control 3812, a print touch control 3814, a store/acquire touch control 3816, a DICOM touch control 3818, an export touch control 3820, and a study information image touch control 3822. The touch controls can contain a display screen that allow the user to enter store/acquire information. For example, the store/acquire touch control 3816, contains a configuration screen 3802, wherein the user may enter configuration information. The user can actuate a virtual keyboard allowing the user to enter alphanumeric characters in different touch activated fields. Additionally, the store/acquire touch control 3802, contains a section allowing user enablement of retrospective acquisition 3804. When the user enables the store function, the system is defaulted to store prospective cine loops. If the user enables the enable retrospective capture, the store function may collect the cine loop retrospectively.

Within the setup screen 3800, the image control bar 3828, includes touch controls that may be operated by touch and touch gestures applied by the user directly to the surface of the display. Exemplary touch controls may include, but are not limited to a thumbnail settings touch control 3830, synchronize touch control 3832, selection touch control 3834, a previous image touch control 3836, a next image touch control 3838, a 2-dimensional image touch control 3840, and a pause image touch control 3842.

FIGS. 39A and 39B illustrate an XY bi-plane probe consisting of two one dimensional, multi-element arrays. The arrays may be constructed where one array is on top of the other with a polarization axis of each array being aligned in the same direction. The elevation axis of the two arrays can be at a right angle or orthogonal to one another. Exemplary embodiments can employ transducer assemblies such as those described in U.S. Pat. No. 7,066,887, the entire contents of which is incorporated herein by reference, or transducers sold by Vernon of Tours Cedex, France, for example. Illustrated by FIG. 39A, the array orientation is represented by arrangement 3900. The polarization axis 3908, of both arrays are pointed in the z-axis 3906. The elevation axis of the bottom array, is pointed in y-direction 3902, and the elevation axis of the top array, is in the x-direction 3904.

Further illustrated by FIG. 39B, a one dimensional multi-element array forms an image as depicted in arrangement 3912. A one-dimensional array with an elevation axis 3910, in a y-direction 3914, forms the ultrasound image 3914, on the x-axis 3904, z-axis 3906, plane. A one-dimensional array with the elevation axis 3910, in the x-direction 3904, forms the ultrasound image 3914, on the y-axis 3902, z-axis 3906. A one dimensional transducer array with elevation axis 3910, along a y-axis 3902, and polarization axis 3908, along a z-axis 3906, will result in a ultrasound image 3914, formed along the x 3904 and the z 3906 plane. An alternate embodiment illustrated by FIG. 39C depicts a one-dimensional transducer array with an elevation axis 3920, in a x-axis 904, and a polarization axis 3922, in the z-axis 3906, direction. The ultrasound image 3924, is formed on the y 3902 and the z 3906 plane.

Figure 40:
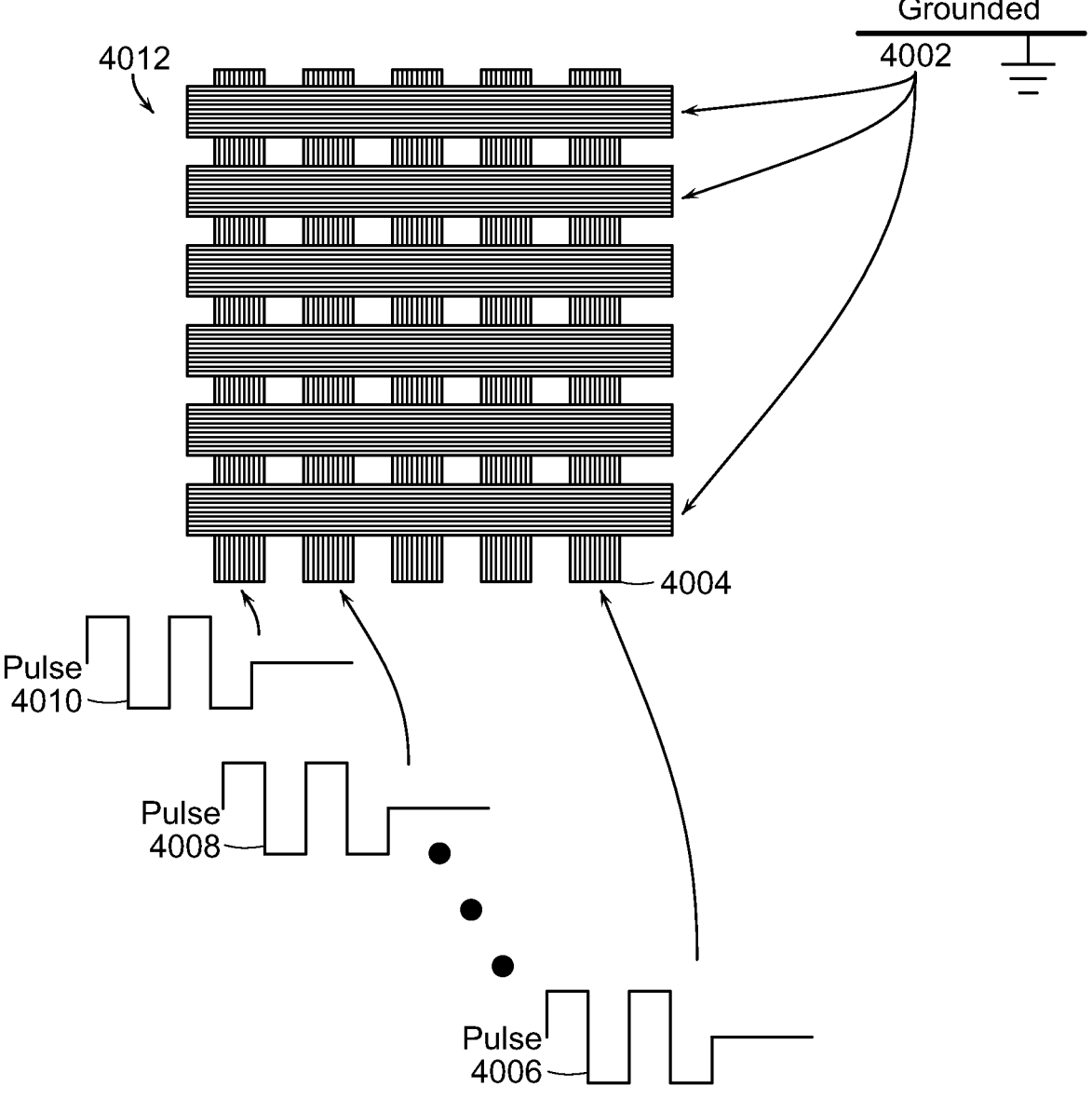
FIG. 40 illustrates the operation of a bi-plane image forming xy-probe.

FIG. 40 illustrates the operation of a bi-plane image forming xy-probe where array 4012 has a high voltage applied for forming images. High voltage driving pulses 4006, 4008, 4010, may be applied to the bottom array 4004, with a y-axis elevation. This application may result in generation of transmission pulses for forming the received image on the XZ plane, while keeping the elements of the top array 4002 at a grounded level. Such probes enable a 3D imaging mode using simpler electronics than a full 2D transducer array. A touchscreen activated user interface as described herein can employ screen icons and gestures to actuate 3D imaging operations. Such imaging operations can be augmented by software running on the tablet data processor that processes the image data into 3D ultrasound images. This image processing software can employ filtering smoothing and/or interpolation operations known in the art.

Beamsteering can also be used to enable 3D imaging operations. A preferred embodiment uses a plurality of 1D sub-array transducers arranged for bi plane imaging.

Figure 41:
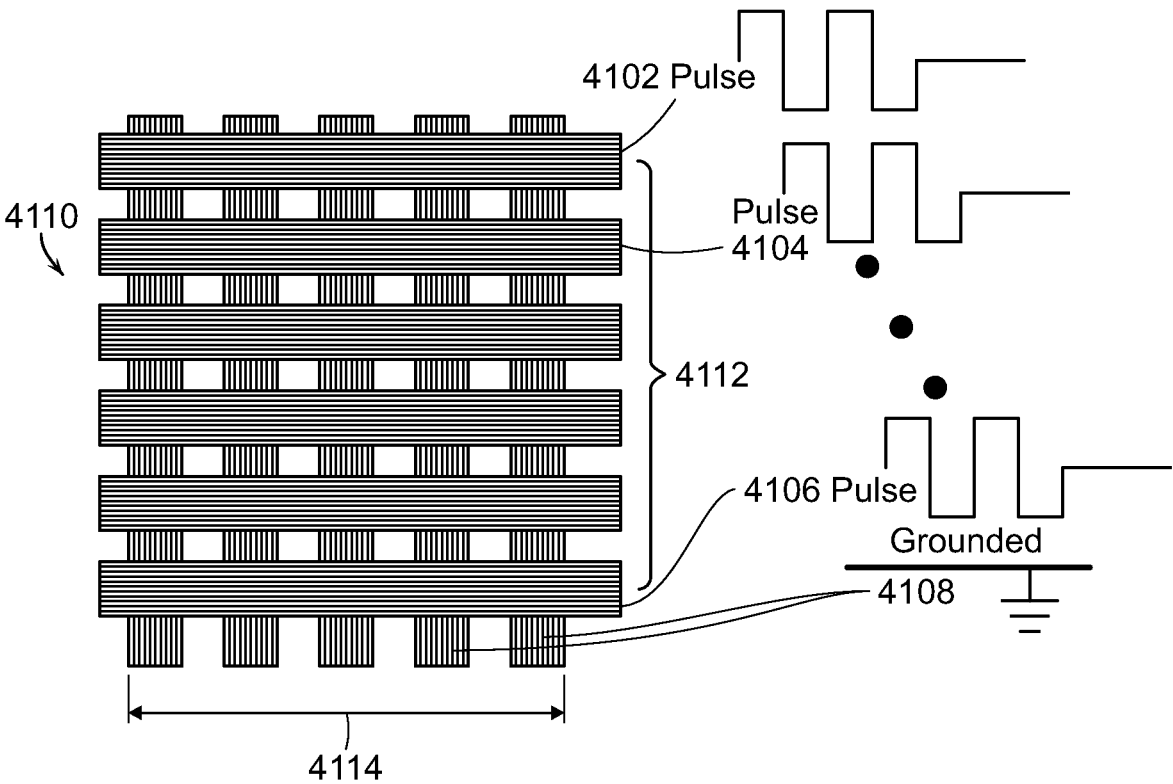
FIG. 41 illustrates the operation of a bi-plane image forming xy-probe.

FIG. 41 illustrates the operation of a bi-plane image forming xy-probe. FIG. 41 illustrates a array 4110, that has a high voltage applied to it for forming images. High voltage pulses 4102, 4104, 4106, may be applied to the top array 4112, with elevation in the x-axis, generating transmission pulses for forming the received image on the yz-plane, while keeping the elements of the bottom array 4014, grounded 4108. This embodiment can also utilize orthogonal 1D transducer arrays operated using sub-array beamforming as described herein.

Figure 42:
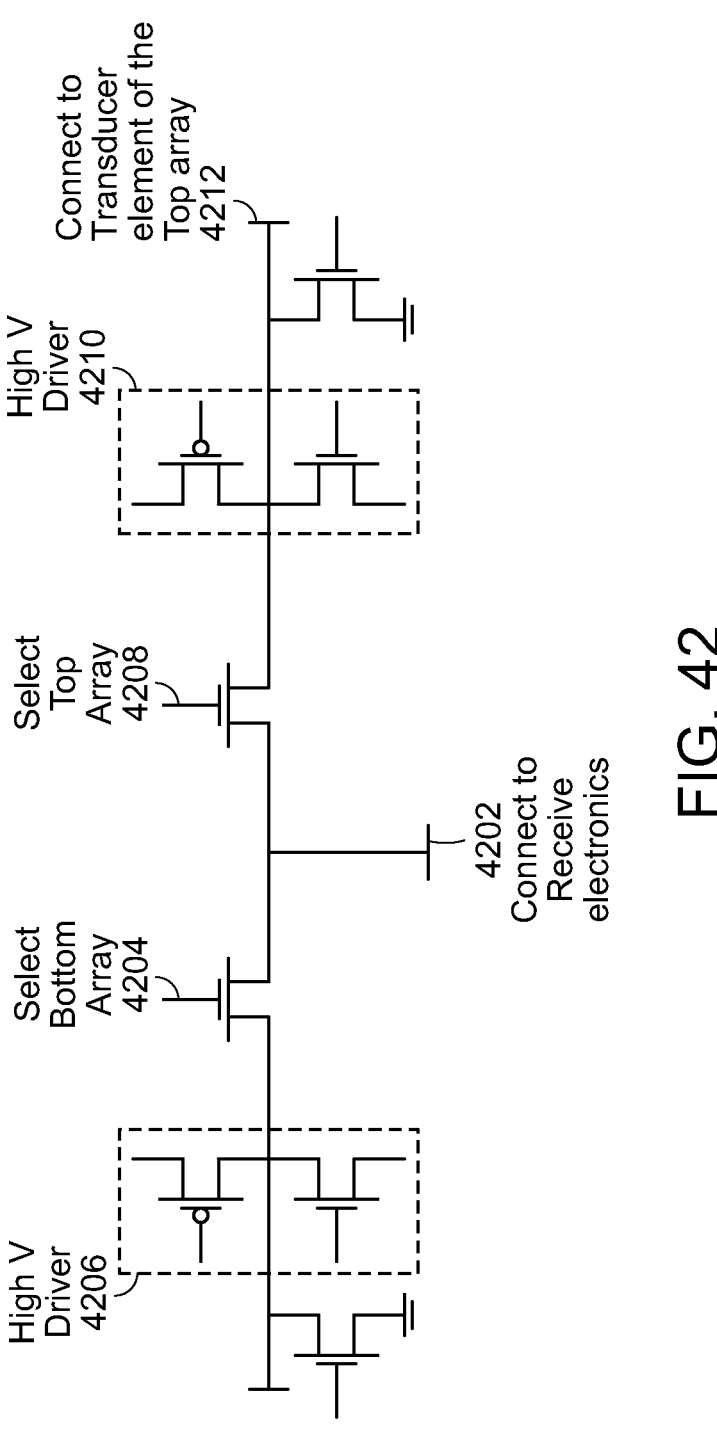
FIG. 42 illustrates a high voltage driver circuit for a bi-plane image forming xy-probe.

FIG. 42 illustrates the circuit requirements of a bi-plane image forming xy-probe. The receive beamforming requirements are depicted for a bi-plane probe. A connection to receive the electronics 4202, is made. Then elements from the select bottom array 4204, and select top array 4208, are connected to share one connect to the receive electronics 4202 channel. A two to one mux circuit can be integrated on the high voltage driver 4206, 4210. The two to one multi-plexor circuit can be integrated into high voltage driver 4206, 4212. One receive beam is formed for each transmit beam. The bi-plane system requires a total of 256 transmit beams for which 128 transmit beams are used for forming a XZ-plane image and the other 128 transmit beams are used for forming a YZ-plane image. A multiple-received beam forming technique can be used to improve the frame rate. An ultrasound system with dual received beam capabilities for each transmit beam provides a system in which two received beams can be formed. The bi-plane probe only needs a total of 128 transmit beams for forming the two orthogonal plane images, in which 64 transmit beams are used to form a XZ-plane image with the other 64 transmit beams for the YZ-plane image. Similarly, for an ultrasound system with a quad or 4 receive beam capability, the probe requires 64 transmit beams to form two orthogonal-plane images.

Figures 43A, 43B:
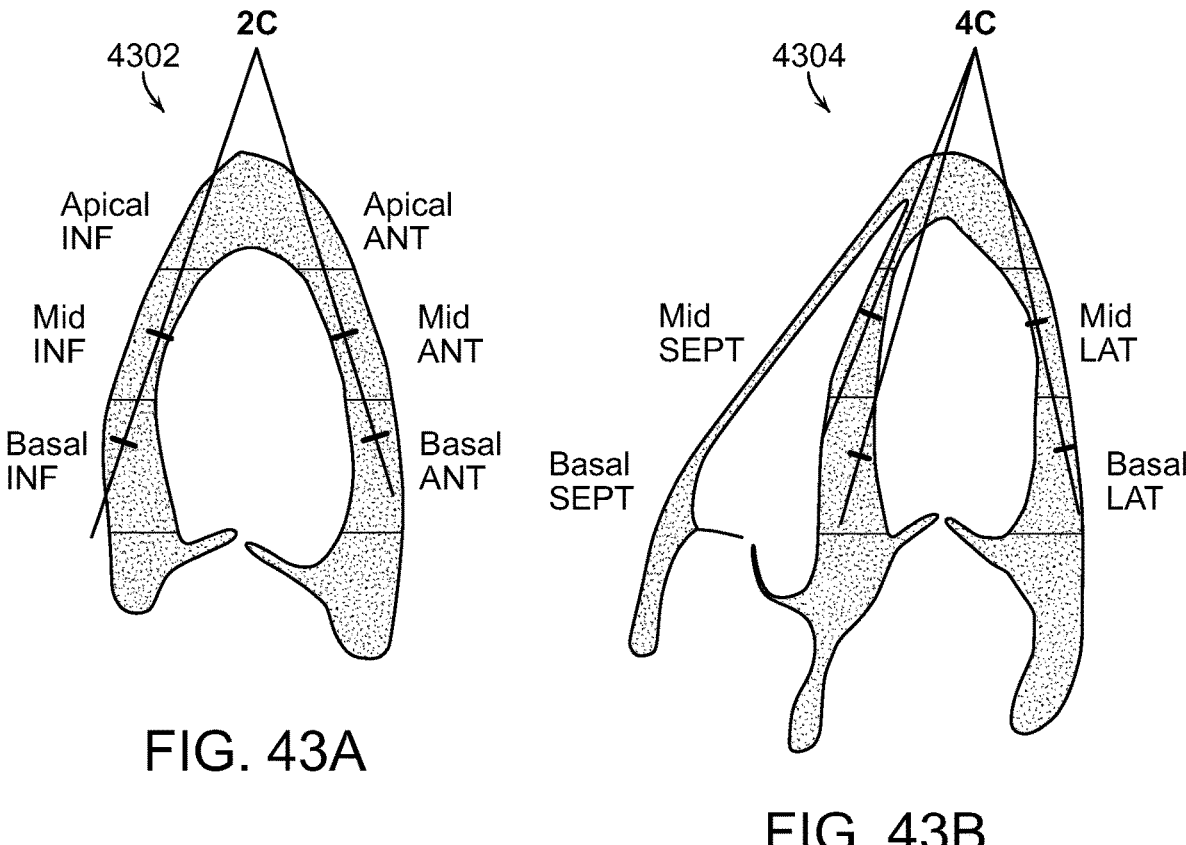
FIGS. 43A-43B illustrate simultaneous bi-plane evaluation of left ventricular condition.

FIGS. 43A-43B illustrate an application for simultaneous bi-plane evaluation. The ability to measure the LV mechanical dyssynchrony with echocardiograph can help identify patients that are more likely to benefit from Cardiac Resynchronization Therapy. LV parameters needed to be quantified are Ts-(lateral-septal), Ts-SD, Ts-peak, etc. The Ts-(lateral-septal) can be measured on a 2D apical 4-chamber view Echo image, while the Ts-SD, Ts-peak (medial), Ts-onset (medial), Ts-peak (basal), Ts-onset (basal) can be obtained on two separated parasternal short-axis views with 6 segments at the level of mitral valve and at the papillary muscle level, respectively, providing a total of 12 segments. FIG. 43A-43B depicts an xy-probe providing apical four chamber 4304, and apicial two chamber 4302 images, to be viewed simultaneously.

Figure 44A:
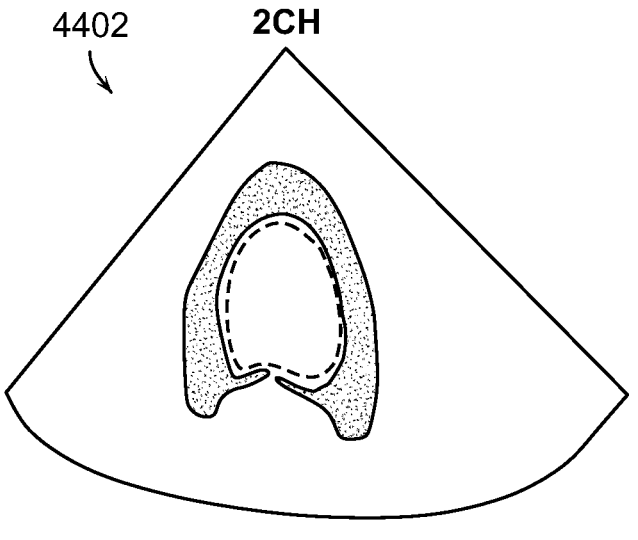
FIGS. 44A and 44B illustrate ejection fraction probe measurement techniques in accordance with preferred embodiments of the invention.
Figure 44B:
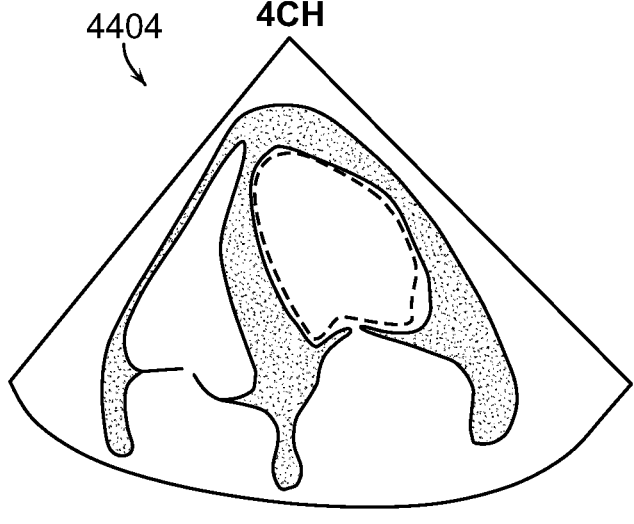

FIGS. 44A-44B illustrate ejection fraction probe measurement techniques. The biplane-probe provides for EF measurement, as visualization of two orthogonal planes ensure on-axis views are obtained. Auto-border detection algorithm, provides quantitative Echo results to select implant responders and guide the AV delay parameter setting. As depicted in FIG. 44 A XY probe acquires real-time simultaneous images from two orthogonal planes and the images 4402, 4404 are displayed on a split screen. A manual contour tracing or automatic boarder tracing technique can be used to trace the endocardial boarder at both end-systole and end-diastolic time from which the EF is calculated. The LV areas in the apical 2CH 4402, and 4CH 4404, views, A1 and A2 respectively, are measured at the end of diastole and the end of systole. The LVEDV, left ventricular end-diastolic volume, and LVESV, left ventricular the end-systole volume, are calculated using the formula:

$$V = \frac{8}{3\pi} \frac{A_1 A_2}{L}.$$

And the ejection fraction is calculated by $$EF = \frac{LVEDV - LVESD}{LVEDV}.$$

In the medical ultrasound industry, almost every ultrasound system can do harmonic imaging, but this is all done by using 2nd harmonics or $f_o$, where $f_o$ is the fundamental frequency. Preferred embodiment of the present invention use higher order harmonics, ie., $3f_o$, $4f_o$, $5f_o$ etc. for ultrasound imaging. Harmonics higher than the 2nd order, provide image quality and spatial resolution that are substantially improved. The advantages of higher order harmonics include improving spatial resolution, minimizing clutter and providing image quality with clear contrast between different tissue structures and clearer edge definition. This technique is based on the generation of harmonic frequencies as an ultrasound wave propagates through tissue. The generation of harmonic frequencies is related to wave attenuation due to nonlinear sound propagation in tissue that results in development of harmonic frequencies that were not present in the transmitted wave. The requirements for achieving this superharmonic imaging are 1) low-noise wideband width linear amplifier; 2) high-voltage, linear transmitter; 3) wide bandwidth transduce; and 4) advanced signal processing.

Figures 45, 46:
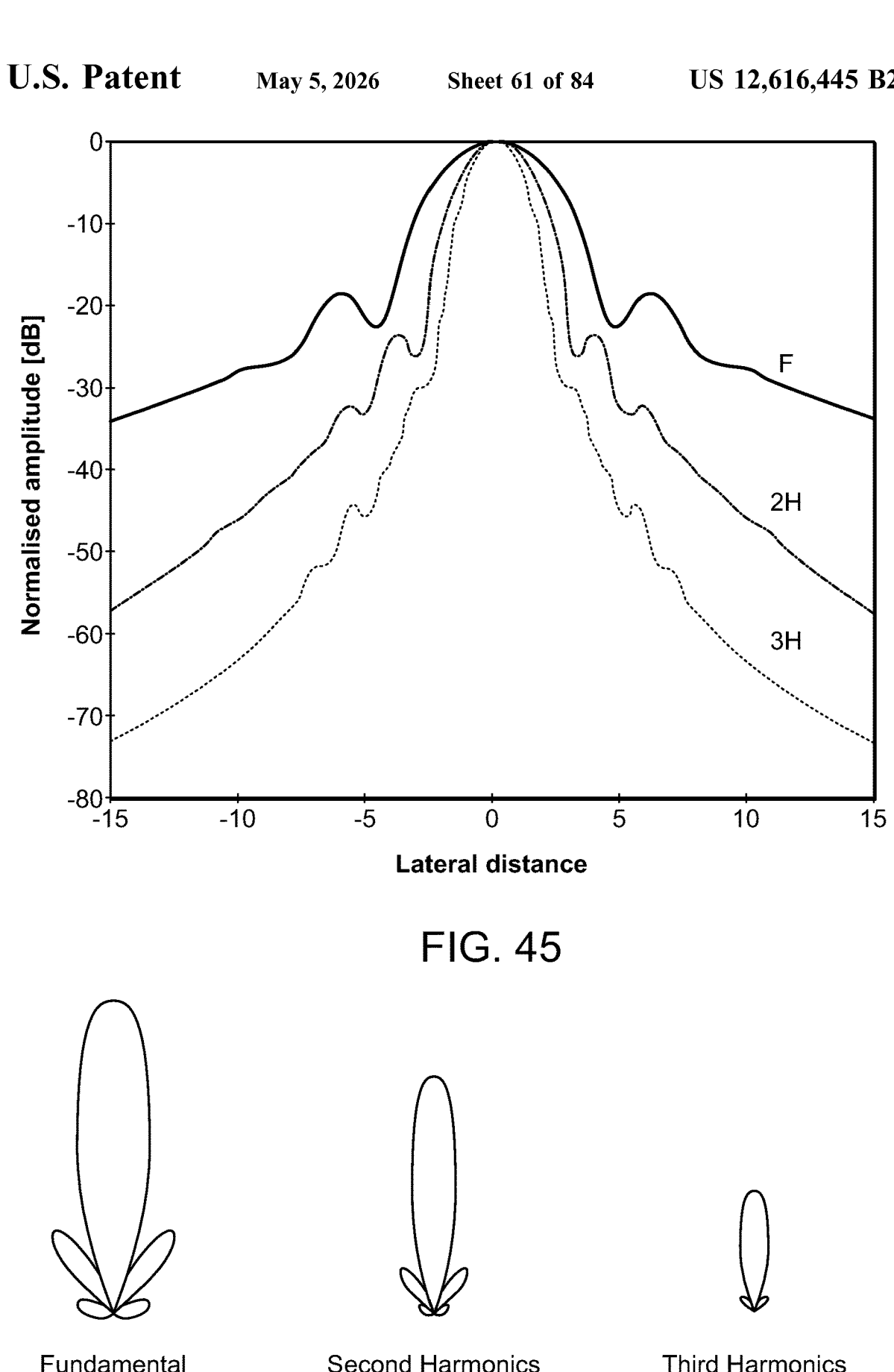
FIG. 45 shows the calculated acoustic pressure level at the fundamental frequency, $2^{nd}$ harmonics frequency and superharmonic frequency in tissue at the focal distance as a function of lateral distance in mm.
FIG. 46 shows the fundamental, $2^{nd}$ and $3^{rd}$ harmonic beam profile.

Due to the nonlinearities of sound wave propagation through tissue; the waveform is gradually attenuated and result in the development of harmonic waveforms which were not present in the original transmitted wave. The nonlinear propagation of ultrasound waves in a tissue like medium can be theoretically calculated using Khokhlov-Zabolotskaya-Kuznetsov, KZK equation. See for example, B. Ward, A. C. Baker and V. F. Humphrey, "Nonlinear propagation applied to the improvement of resolution in Diagnostic medical ultrasound," J. Acoust. Soc. Am., vol. 101, pp 143-163, 1997 the entire contents of which is incorporated herein by reference. The computation is based on the finite-difference approximation and performs in the time domain and the frequency domain. The KZK equation incorporates the combined effects of beam diffraction, energy dissipation due to the attenuation of the medium and wave distortion. As shown in A. Bouakaz, C. T. Lancee, and N. de Jong, "Harmonic Ultrasonic Field of Medical Phased Arrays: Simulations and Measurements," *IEEE Transactions on Ultrasonics, Ferroelectrics and Frequency Control.*, vol. 50, pp. 730-735, 2003, the entire contents of which is incorporated herein by reference, both the diffraction and the non-linearity terms are solved in time domain, whereas the attenuation is accounted for in frequency domain. The calculated acoustic pressure level[2] at the fundamental frequency, $2^{nd}$ harmonics frequency and $3^{rd}$ harmonic frequency in tissue at the focal distance as a function of lateral distance in mm is shown in FIG. 45.

The computation is based on a 3-cycle-Gaussian pulse with a fundamental frequency of 1.7 Mhz for the transmit waveform. The $2^{nd}$ harmonic component was extracted using a band pass filter with a flat response between low and high cut-off frequencies of 2.75 Mhz and 4.02 MHz, respectively. The band pass filter used to extract the superharmonic components with a flat frequency response between 4.35 Mhz, and 9.35 Mhz. The profiles have been scaled to have on-axis amplitudes of 0 dB. As can be seen from FIG. 45, the generation of the superharmonic component is substantially confined to the strongest part of the fundamental beam, even more compared to the 2nd harmonic profile. This has the beneficial effect that the superharmonic beamwidth is much narrower than the 2nd harmonic beamwidth. The beamwidth at the superhamonic frequency is found to be half of the transmitted fundamental beamwidth, whereas the 2nd harmonic beamwidth is only 30% narrower. As shown FIG. 45, for a fundamental beamwidth of 5.3 mm (around the focal point), and 3.5 mm at the 2nd harmonic, the superharmonic component has a beamwidth of less than 2.6 mm. FIG. 46 depicts the normalized axial acoustic beam profile at the fundamental, $2^{nd}$ and $3^{rd}$ harmonic frequencies. It is important to note that the generation of the $3^{rd}$ harmonic is proportional to the product of the amplitudes of the fundamental and $2^{nd}$ harmonic component. Therefore, its generation occurs mainly in the focal region where the fundamental and second harmonic frequencies reach their highest levels. This has the beneficial effect that the superharmonic beamwidth is much narrower than that of the $2^{nd}$ harmonic beamwidth. Furthermore, since the superharmonic energy is substantially concentrated in the central part of the beam, it shows incommensurate reduction in sidelobe energies. This property gives the superhamonic technique the advantage of considerably removing the off-axis echoes coming from scatters located at the edges of the beam. It is obvious that this property is of considerable benefit for diagnostic since most imaging artifacts and aberrations can be caused by the interaction of the ultrasound beam and the sidelobes at the edge of the beamprofile.

Due to the properties that different tissue structures generate different superhamonic responses and the superharmonic beam offers minimum sidelobe pencil beam profile, as a result, the superhamonic image offers the advantages of providing a dramatically clearer and sharper contrast images between the different tissue types and with a much better edge detection. Superharmonic shows a better suppression of reverberations and artifacts especially those occurring at the edges of the beam. With superharmonic, lateral and axial resolution are improved.

Figure 47:
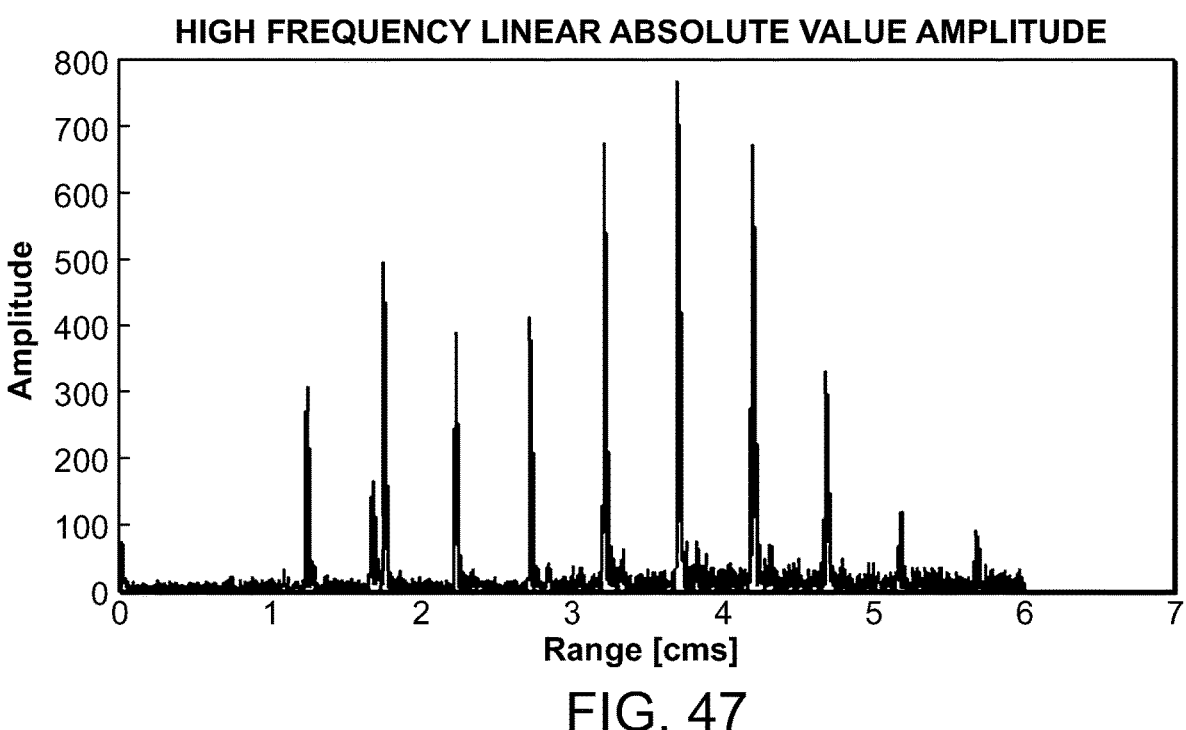
FIG. 47 shows an A-mode plot of the 15 Mhz fundamental image, 15 Mhz transmit waveform, 15 Mhz received A-mode waveform.

A high resolution phantom, GAMMEX 404GS can be used to evaluate the spatial resolution of our system. The size of the reflector, (diameter), that is imbedded in the 404GS Phantom is 100 um. First, a 15 MHz transmit waveform is used to generate 404GS 15 Mhz fundamental phantom image. A-mode plot of the fundamental image is shown in FIG. 47 which also include 15 MHz transmit waveform, and the 15 Mhz received A-mode waveform.

Figure 48:
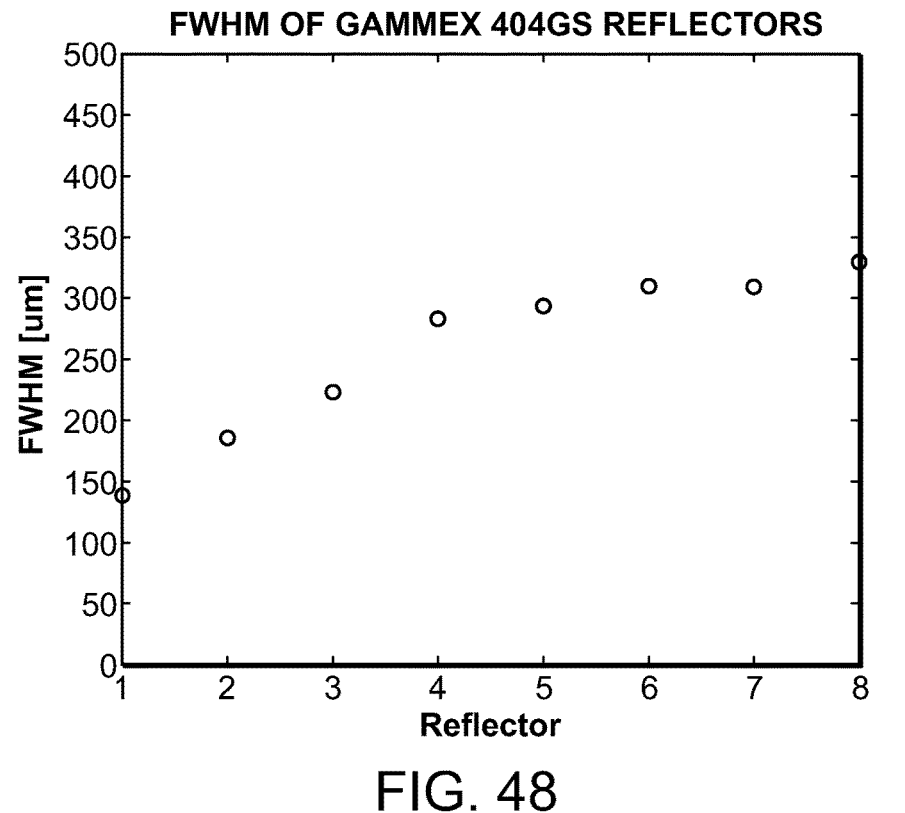
FIG. 48 shows a Full Width Half Magnitude (FWHM), plot of the phantom A-mode image, of the 15 Mhz received fundamental image, 15 Mhz transmit wave form.
Figure 49:
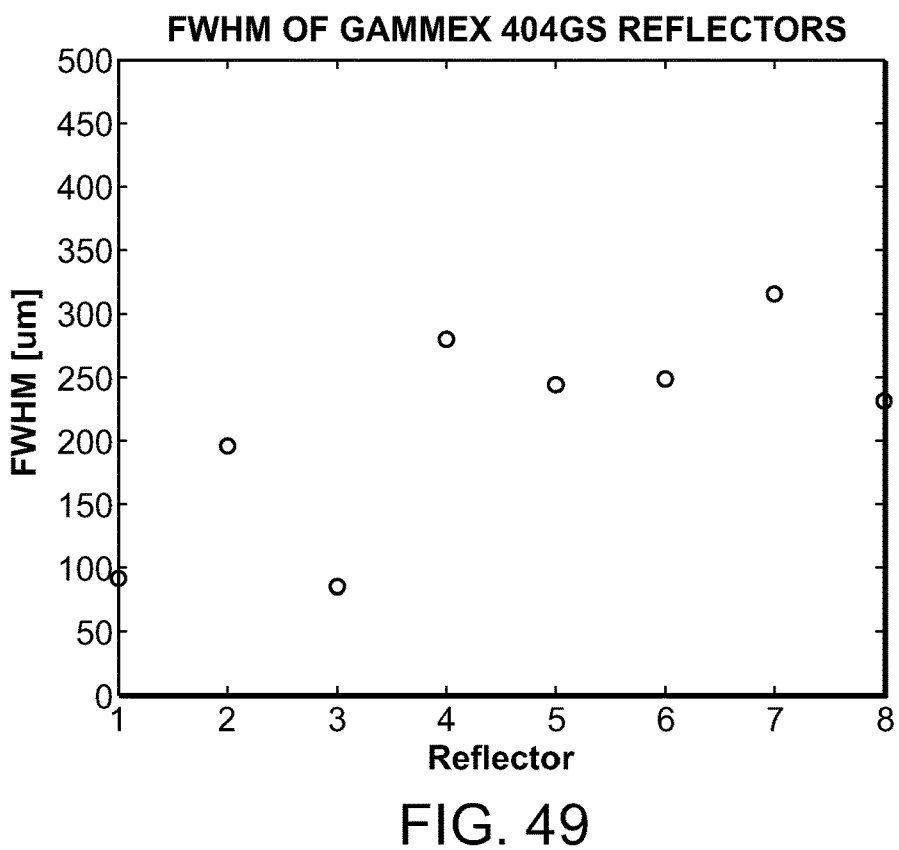
FIG. 49 illustrates use of GAMMAX 4040GS Phamtom, $2^{nd}$ harmonic Full Width Half Magnitude (FWHM) pin dimensions in the axial dimension, 7.5 Mhz transit wave form with 15 Mhz received $2^{nd}$ harmonic image.
Figure 50:
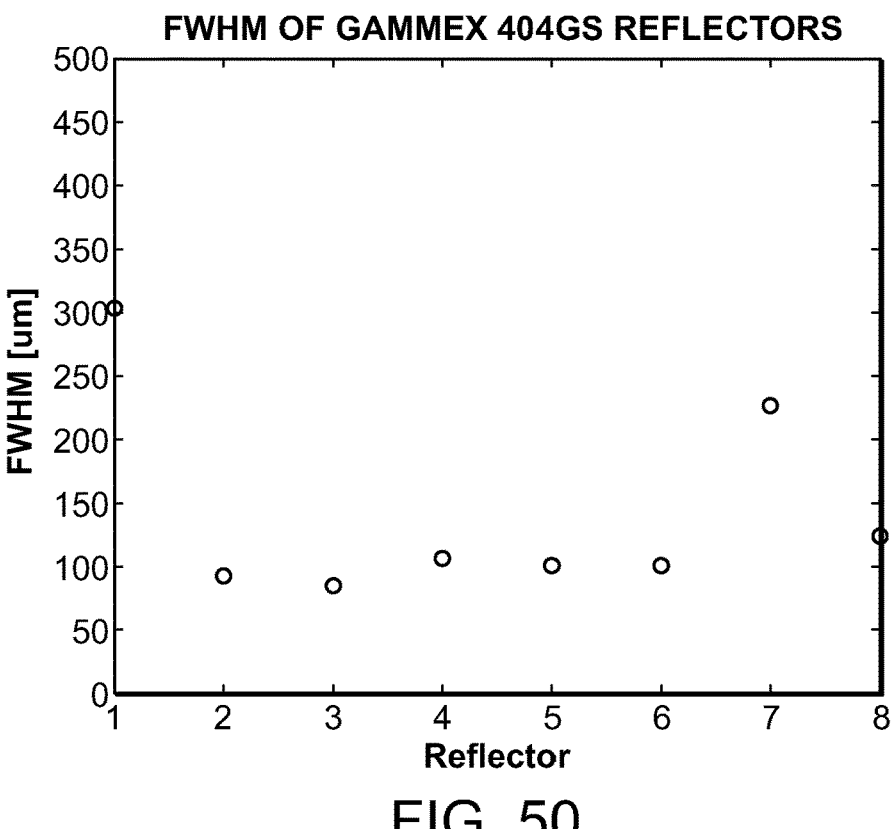
FIG. 50 illustrates use of GAMMAX 4040GS Phamtom, 3rd harmonic FWHM, FULL-WIDTH HALF-MAXIMUM, PIN DIMENSIONS IN THE AXIAL DIMENSION, 5 Mhz transit wave form with 15 Mhz received wave form.

A Full-Width Half Magnitude plot of the 15 Mhz image is used to indicate the spatial resolution of the 100 um pin phantom image. FIG. 48 shows Full Width Half Magnitude (FWHM) plot of the phantom A-mode image, of a 15 MHz received fundamental image, and a 15 MHz transmit wave form.

The spatial resolution compassion of the Full Width Half Maximum (FWHM), measurement results of GAMMAX 404GS Phantom, of the fundamental, $2^{nd}$ harmonic and superhamonic images is listed in the following table:

| | Transmit Waveform | Receive Waveform | Spatial Resolution FWHM | Sidelobe Clutter | Image Quality |
|---|---|---|---|---|---|
| Fundamental | 15 Mhz | 15 Mhz | Poor >200 um | High | Poor |
| $2^{nd}$ Harmonic | 7.5 Mhz | 15 Mhz | Better ~200 um | Lower | Better |
| SuperHarmonic | 5 Mhz | 15 Mhz and above | Best 100 um | Lowest | Best |

Due to the inhomogeneous nature of tissue in a body, it is well known that echo signals received from the reflection of acoustic waves in the tissue are highly non-linear. The nonlinear response of the tissue body results in increasing in the width of the transmitted-received main beam and level of side lobe, which in turn significantly decreases the lateral and contrast resolution of the tissue ultrasound imaging. A further method referred to herein as, Tissue High-Frequency Imaging (THI), or Tissue Mixing Imaging (TMI), or super harmonic imaging, uses the nonlinear response of the propagating wave in tissue, making it possible to minimize these defocusing effects. In medical ultrasound imaging, there is a need for harmonic imaging where the transmitted waveform is of one fundamental frequency $F_0$, and the received signal of interest is a higher harmonic, generally the 2nd harmonic ($2F_0$), or the third harmonic ($3F_0$). The superharmonic image mode combines all higher order harmonic ($>=3f_0$). The harmonic signal of interest is generated by the image targets in the body, and harmonics in the transmitted waveform is not of interest. Therefore it is important to suppress harmonics from the transmitted waveform.

Consider an ultrasound pulser with conventional 3 cycles of square wave. The frequency spectrum of such a waveform has a third harmonic component at about −4 dB below the fundamental frequency, a high third harmonic components in regular square wave, the conventional square wave is therefore not suitable to be used as transmit waveform for higher order harmonic imaging.

Figure 51A:
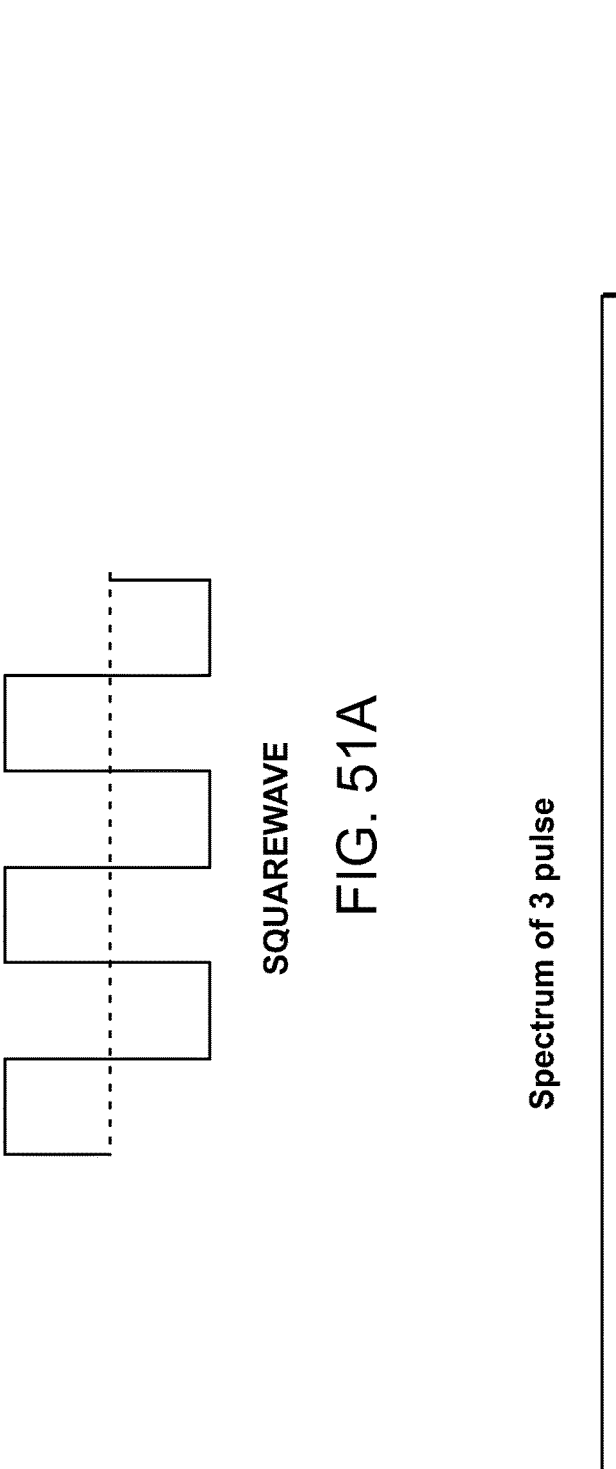
FIGS. 51A and 51B illustrate a frequency spectrum of a square waveform has a third harmonic component at about −4 dB below the fundamental frequency, a high third harmonic components; the conventional square wave is therefore not suitable to be used as transmit waveform for higher order harmonic imaging.
Figure 51B:
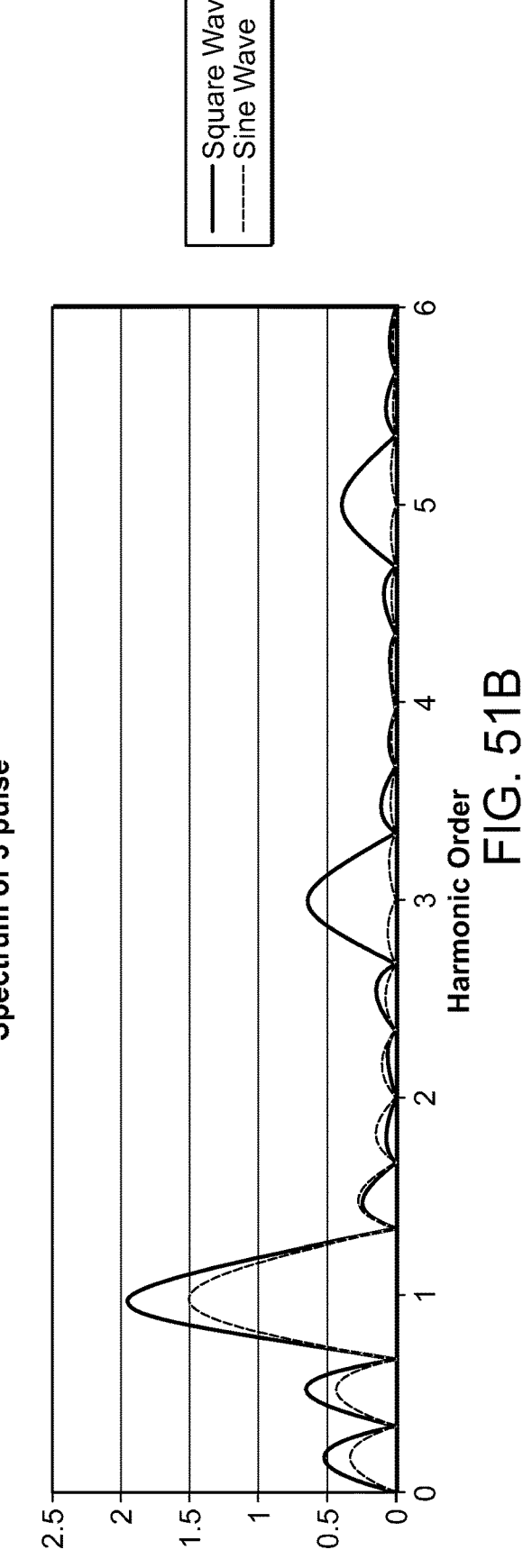

FIGS. 51A and 51B illustrate a square wave and a frequency spectrum of the square waveform having a third harmonic component at about −4 dB below the fundamental frequency, a high third harmonic components; the square wave is therefore not suitable to be used as transmit waveform for higher order harmonic imaging.

Figure 52:
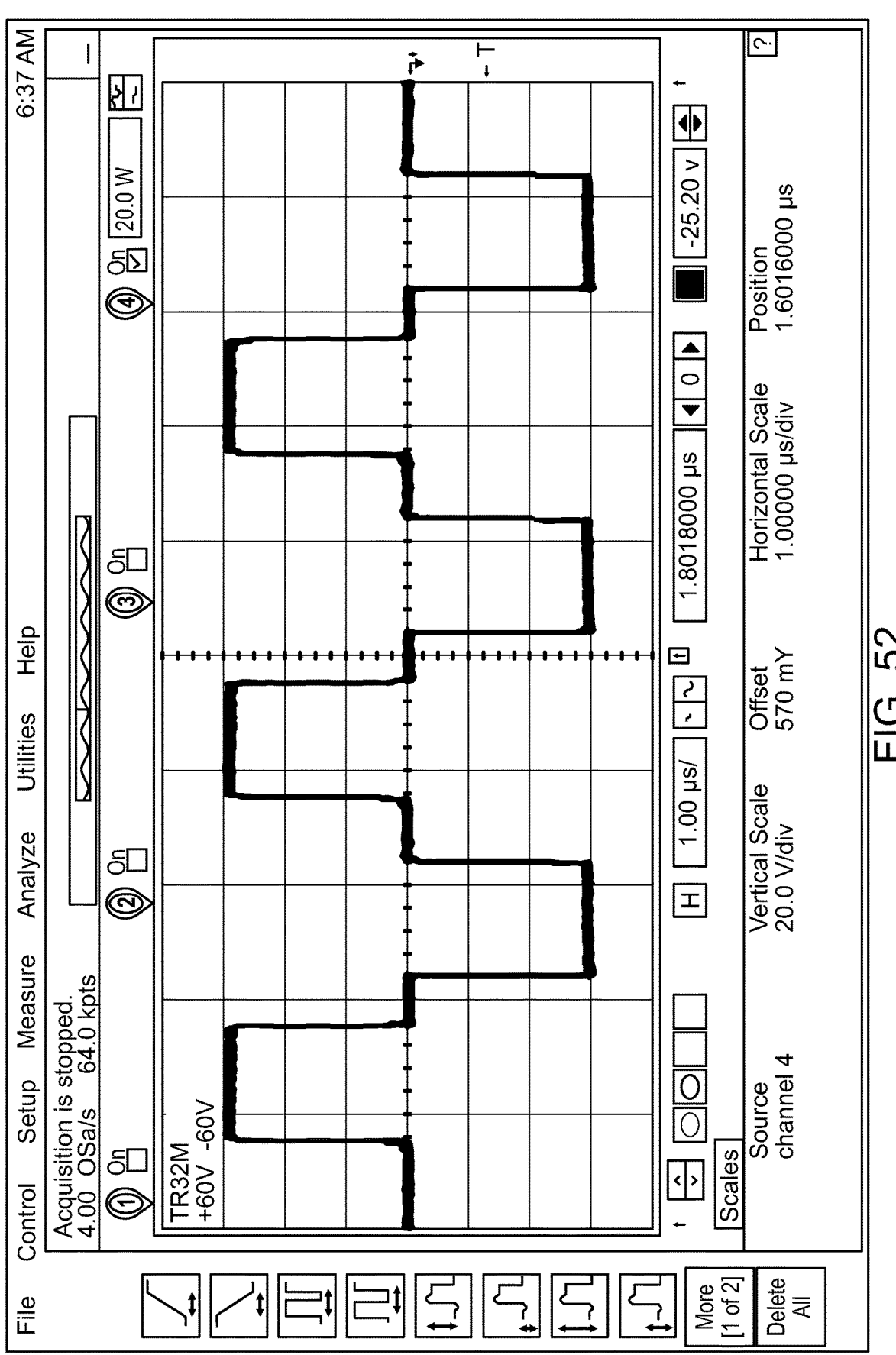
FIG. 52 illustrates a two third waveform.
Figure 53:
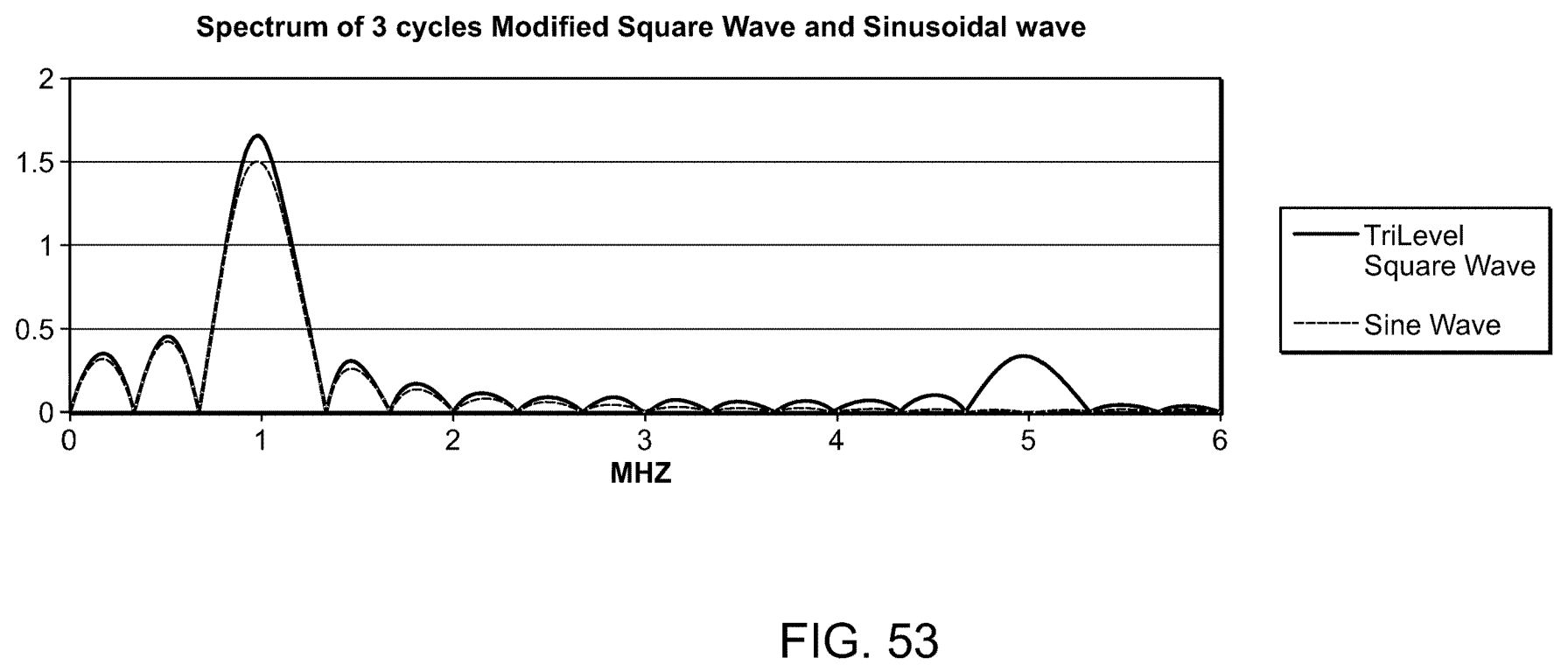

Preferred embodiments hereof use a modified square wave by reducing the pulse high time and pulse low time to two third of the regular square wave. This modified waveform has a much lower third harmonic component than that of a regular square wave, and is close to a pure sinewave. See for example, FIG. 52 that illustrates a two third waveform. FIG. 53 frequency spectrum of a third square waveform and a sine wave. This modified waveform has a much lower third harmonic component than that of a regular square wave, and close to a pure sinewave. The method utilizes two consecutive transmit waveforms; the first and second ultrasound pulses that are alternatively transmitted into the tissue being imaged. The two ultrasound pulses are two-third square waveform in which the first ultrasound pulse differs from the second ultrasound pulse by inverting the transmitted waveforms. The received superharmonic echo signals generated by these pulses are measured and are combined by adding the echo signals generated by each of the ultrasound transmitted pulses.

A ultrasound imaging system includes a wideband amplifier with noise floor, $V_n=0.75$ n V/$\sqrt{Hz}$, bandwidth >22 Mhz.

a two-Third High voltage at 4.5 Mhz transmit waveform, pulse cancellation, and a receive waveform including the $3^{rd}$ harmonic, $4^{th}$ harmonic and $5^{th}$ harmonic frequencies.

Figure 54B:
FIGS. 54A and 54B provide a fundamental image and superharmonic imaging comparison where the superharmonic image is generated by using 4.5 Mhz transmit two third modified waveform with pulse cancellation technique and consists of $3^{rd}$, $4^{th}$ and $5^{th}$ order high harmonics.
Figure 54A:
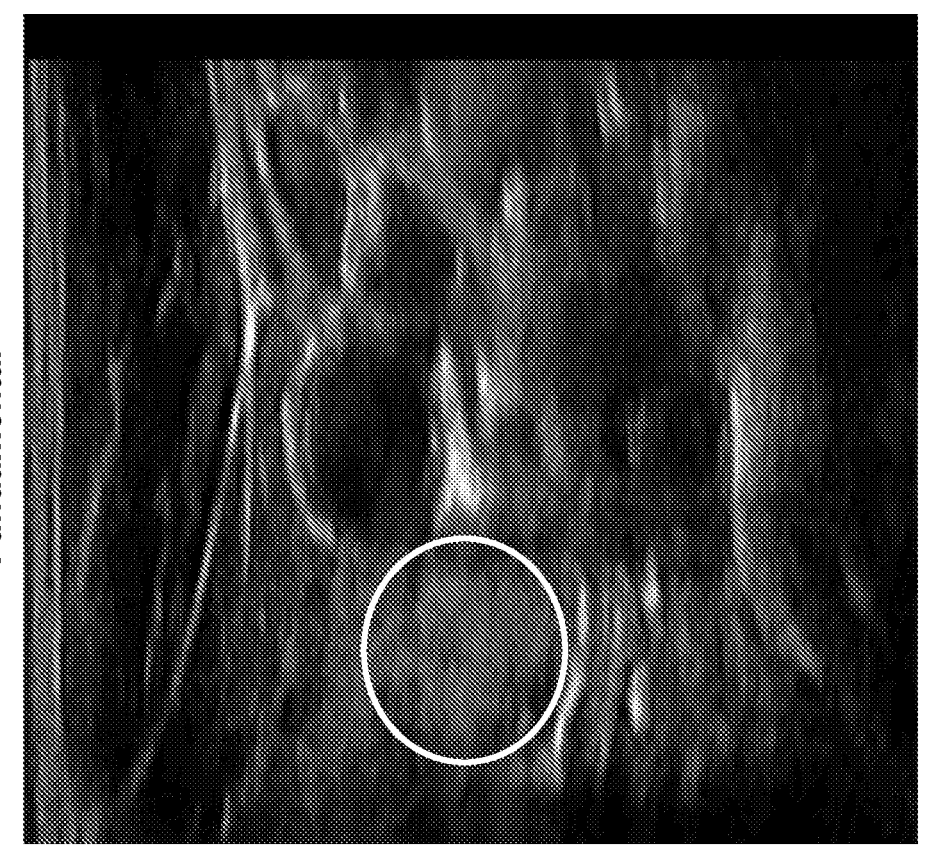

A fundamental image and superharmonic imaging comparison is shown in FIGS. 54A and 54B. Due to the property that different tissue structures such as fat, muscle, carcinoma cells distort the sound wave propagation differently, i.e., different tissue structures attenuate the sound wave differently; as a result the harmonic image can differentiate different tissue structures much better than that of the fundamental images. As can be seen in FIGS. 54A and 54B where, the superharmonic image offers dramatically cleaner and sharper contrast between the different structures being imaged properties. The superharmonic image is generated by using 4.5 Mhz transmit two third modified waveform with pulse cancellation technique and consists of $3^{rd}$, $4^{th}$ and $5^{th}$ order high harmonics.

Figure 55:
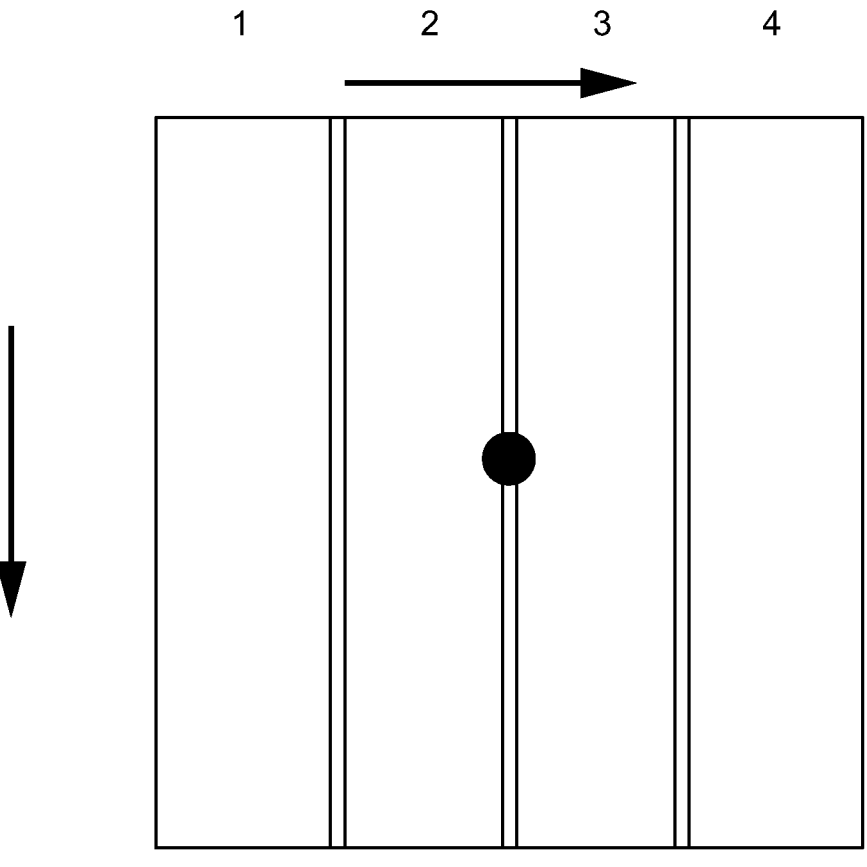
FIG. 55 shows hydrogel pad marked with scanning direction and probe placement. Each rectangle is 50 mm by 200 mm, the transducer is placed at the top of the $1^{st}$ rectangle and free-hand move to the bottom. And the probe is moved to the starting point of the $2^{nd}$ rectangle, start scanning again until the four rectangular area are covered.

It is important to note that the breast ultrasound imaging is very operator dependent. A simple tool with software monitoring is proposed here to guide a sonographer to do a free-hand breast scanning such that the scanning is thoroughly covering the whole breast area without missing any area and it is reproducible. A breast ultrasound transducer can be about 50 mm wide. During scanning, operator free-hand movement of the transducer in a lineal direction covers about 50 mm by 200 mm breast area and then moves the probe to the starting point, offsets the probe in a medial lateral position about 50 mm, repeats the linear scanning again. The imaging procedure repeats until the whole breast area is covered. An acoustic transparent hydrogel pad can be used to ensure the total breast area is covered and the procedure is repeatable. As can be seen in FIG. 55, the hydrogel pad is marked with four overlapping rectangles with transducer placement and scanning direction instruction. Each rectangle is 50 mm wide and 200 mm long, a center dot is used to align the nipple. The scanning is from head to toe, with parallel free-hand scans covering the whole breast. In this example, four parallel overlapping scans can cover the whole breast area.

FIG. 55 shows hydrogel pad marked with scanning direction and probe placement. The transducer is placed at the top of the $1^{st}$ rectangle and free-hand moved to the bottom. The probe is then moved to the starting point of the $2^{nd}$ rectangle and iterated by hand or by an automated controller. It is important that the free-hand movement during the scanning is slow enough that ultrasound frames can be captured as a stream of images each spaced about a sub-mm apart. The system will track the timing from the starting point of each scan row, it will provide "warning beep" if the movement is too fast.

Figure 56:
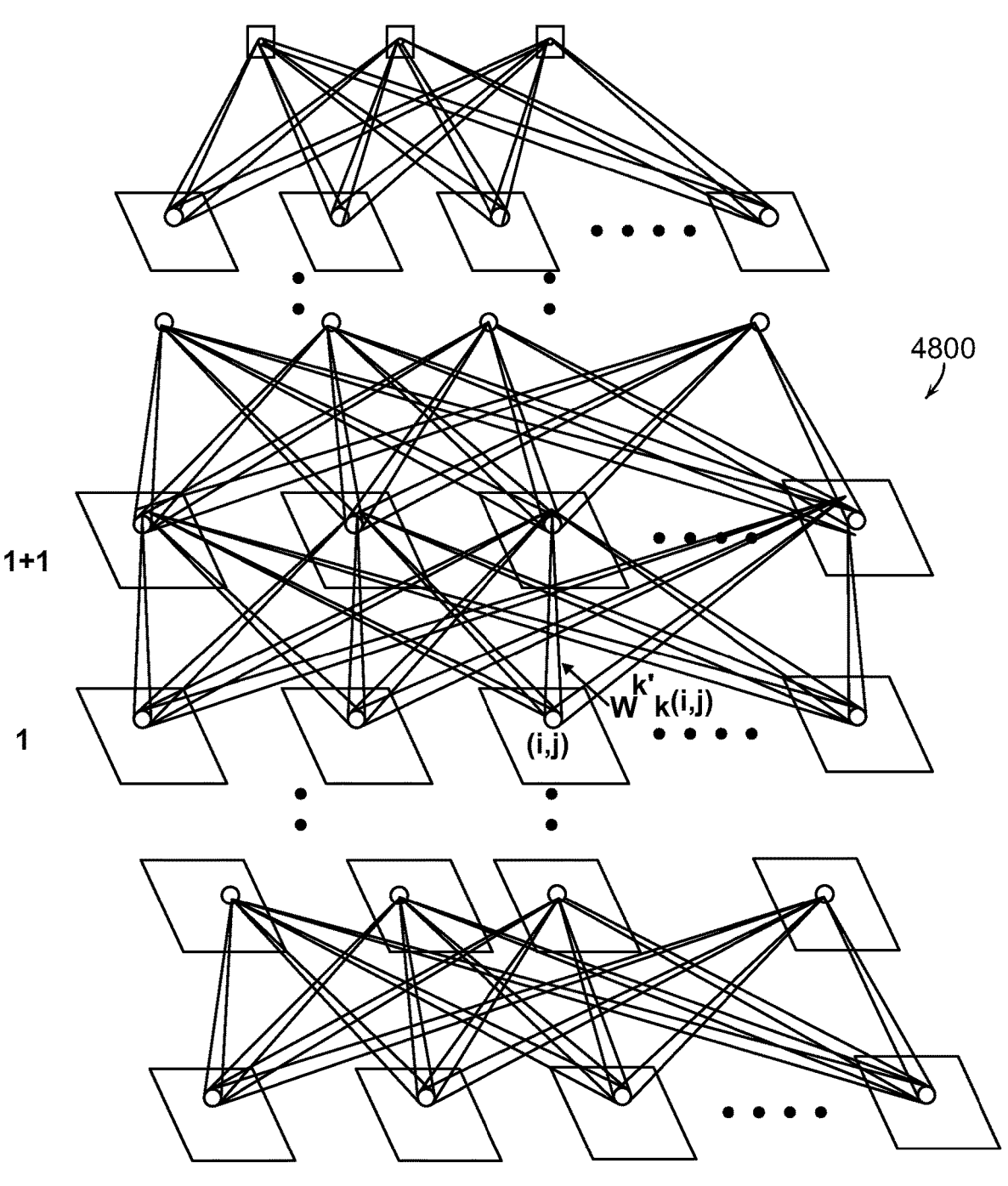
FIG. 56 illustrates a computational neural network model with fully connected artificial neural nodes in accordance with various embodiments of the present application.

A transducer design with 1D image array embedded between two motion guiding arrays mounted in direction normal to the center imaging array. FIG. 56 illustrates linear imaging array embedded between two vertical arrays for motion guidance. The linear array can be embedded between two smaller transducer arrays located normal to the center array. The number of elements of the center imaging array can be 128, 192 or 256. Each of the side arrays can have elements ranging from 16, 24, to 32, etc. The side arrays can be used for monitoring the speed of the free-hand movement, to ensure the operator is using a constant speed and the speed is slow enough to generate ultrasound frames can be captured as a stream of images each spaced about 1 mm or less apart. The array can also be used to ensure the scanning is in a straight line forward movement. When the movement is too fast, or the speed is varying, or the probe is moving in a circular motion, the software sends a warning signal to the operator to adjust the movement.

Artificial intelligence (AI) and Augmented reality (AR) are transforming the medical ultrasound. Medical ultrasound applications using AI and AR can solve critical problems impacting patient outcomes in many diagnostic and therapeutic applications. Ultrasound imaging poses problems that are solved with deep learning because it takes years of training to learn how to read ultrasound images. Clinical studies based on deep learning AI algorithms for automatically detecting the tumor regions and for detecting heart disease to assist medical diagnosis with high sensitivity and specificity have been reported. Augmented reality (AR) fuses optical vision video with ultrasound images providing real-time image guidance to surgeons for improved identification of anatomical structure and enhanced visualization during surgical procedures. Ultrasound system used for image acquisition can employ computer systems with more than 1000GFLOPs (giga floating point operations per second) of processing power to carry out the mathematical computation imposed by the deep learning algorithm, or the computation required for fusing/superimposing an ultrasound image on a user's optical view of an anatomical feature. AI and/or AR can drastically enhance or expand ultrasound imaging applications. A computational enhanced ultrasound system that can acquire real-time ultrasound images and also can carry out the large amount of computations mandated by those algorithms can advance clinical care delivery in cancer treatment and in cancer and heart disease diagnosis. The integration of improvements in portability, reliability, rapidity, ease of use, and affordability of ultrasound systems along with computational capacity for advanced imaging are provided in preferred embodiments herewith.

Ultrasound (US) images have been widely used in the diagnosis and detection of cancer and heart disease, etc. The drawback of applying these diagnostic techniques for cancer detection is the large time consumed in the manual diagnosis of each image pattern by a trained radiologist. While experienced doctors may locate the tumor regions in a US image manually, it is highly desirable to employ algorithms that automatically detect the tumor regions in order to assist medical diagnosis. Automated classifiers substantially upgrade the diagnostic process, in terms of both accuracy and time requirement by distinguishing benign and malignant patterns automatically. Neural networks (NN) play an important role in this respect, especially in the application of breast and prostate cancer detection, for example.

Pulse-coupled neural networks (PCNNs) are a biologically inspired type of neural network. It is a simplified model of a cat's visual cortex with local connections to other neurons. PCNN has the ability to extract edges, segments, and texture information from images. Only a few changes to the PCNN parameters are necessary for effective operation on different types of data. This is an advantage over published image processing algorithms that generally require information about the target before they are effective. An accurate boundary detection algorithm of the prostate in ultrasound images can be obtained to assist radiologists in rendering a diagnosis. To increase the contrast of the ultrasound prostate image, the intensity values of the original images are first adjusted using the PCNN with a median filter. This can be followed by the PCNN segmentation algorithm to detect the boundary of the image. Combining intensity adjustment and segmentation enables the reduction of PCNN sensitivity to the settings of the various PCNN parameters whose optimal selection can be difficult and can vary even for the same problem. The results show that the overall boundary detection overlap accuracy offered by the employed PCNN approach is high compared with other machine learning techniques including Fuzzy C-mean and Fuzzy Type-II.

Ultrasound (US) images have been widely used in the diagnosis of breast cancer in particular. While experienced doctors may locate the tumor regions in a US image manually, it is highly desirable to develop algorithms that automatically detect the tumor regions in order to assist medical diagnosis. An algorithm for automatic detection of breast tumors in US images has been developed by Peng Jiang, Jingliang Peng, Guoquan Zhang, Erkang Cheng, Vasileios Megalooikonomou, Haibin Ling; "Learning-based Automatic Breast Tumor detection and Segmentation in Ultrasound Images", the entire contents of which is incorporated herein by reference. The tumor detection process was formulated as a two step learning problem: tumor localization by bounding box and exact boundary delineation. Specifically, an exemplary method uses an AdaBoost classifier on Harr-like features to detect a preliminary set of tumor regions. The preliminarily detected tumor regions are further screened with a support vector machine (SVM) using quantized intensity features. Finally, the random walk segmentation algorithm is performed on the US image to retrieve the boundary of each detected tumor region. The preferred method has been evaluated on a data set containing 112 breast US images, including histologically confirmed 80 diseased patients and 32 normal patients. The data set contains one image from each patient and the patients are from 31 to 75 years old. These measurements demonstrate that the proposed algorithm can automatically detect breast tumors, with their locations and boundary.

Rheumatic heart disease (RHD) is the most commonly acquired heart disease in young people under the age of 25. It most often begins in childhood as strep throat, and can progress to serious heart damage that kills or debilitates adolescents and young adults, and makes pregnancy hazardous.

Although virtually eliminated in Europe and North America, the disease remains common in Africa, the Middle East, Central and South Asia, the South Pacific, and in impoverished pockets of developed nations. Thirty-three million people around the world are affected by RHD. While RHD can be diagnosed by ultrasound images, such ultrasound images are very user dependent. Typically, it requires very experience sonographer to acquire diagnostic quality ultrasound images. It is beneficial to patients to employ an AI based deep learning algorithm to put ultrasound systems in the hands of general practitioner to diagnose RHD, by training a system with GPU-accelerated deep learning software to provide diagnostic ultrasound images.

A computational neural network model with fully connected artificial neural nodes is shown in FIG. 56. The model comprises L layers with K nodes within each hidden layer. The output of each node in the lower layer is fully connected to the corresponding node in the upper layer with a trainable connecting weight.

As can be seen in FIG. 56, each node is a two dimensional image where (i,j) represents pixel element location; $N_{l,k}$ (i,j) represents the (i,j) pixel value in the $k^{th}$ location of the l layer, $W_{l,k}{}^{k'}$(i,j) represents the connecting weight between the (i,j)$^{th}$ element of the $k^{th}$ location in the l layer with the (i,j) element in the $k'^{th}$ location of the l+1, upper, layer. The pixel value, $N_{l+1,k'}$(i,j), at the $k'^{th}$ location of the upper layer can be computed by summing the products of connecting weights, $W_{l,k}$, to each corresponding nodes at the lower layer and the output values from each of the nodes in the lower, l, layer, $N_{l,k}$ (I,j) for i=1, 2, . . . , I; j=1, 2, . . . , J, i.e., $$N_{l+1,k'}(i, j) = \sum_{k=1}^{K} w_{l,k}^{k'}(i, j) N_{l,k}(i, j)$$

Assume an image size of (1000, 1000), i.e., i=1000, j=1000, in each of the neural nodes in the hidden layer, and there are 500 nodes, k=500, within each hidden layer in this example. It is straightforward to compute the mathematical operations needs to be carried out to compute the values of the nodes on the upper layer from the inputs from the lower layer, i.e., $1 \times 10^9$ floating point operations. For a neural network with 1000 layers, i.e., l=1000, the total number of computations required is $1 \times 10^{12}$ floating point operations, i.e., a processor with 1000GFLOPs is needed to compute the required data using this deep learning artificial neural network in carrying out the RHD clinical evaluation in developing countries. In addition to the ultrasound system, clinicians can carry 76 high-end linux laptops with Nvidia GPUs with more than 1000GFLOPs processing power. Preferred embodiments of the present application include a tablet ultrasound system as described herein which a graphic processing unit is integrated into the tablet or portable system housing and is connected via bus or other high speed/data rate connection to the central processor of the ultrasound system.

Conventional laparoscopes provide a flat representation of the three-dimensional (3D) operating field and are incapable of visualizing internal structures located beneath visible organ surfaces. Computed tomography (CT) and magnetic resonance (MR) images are difficult to fuse in real time with laparoscopic views due to the deformable nature of soft-tissue organs. Utilizing emerging camera technology, a real-time stereoscopic augmented-reality (AR) system has been developed for laparoscopic surgery by merging live laparoscopic ultrasound (LUS) with stereoscopic video. The system creates two important visual cues: (1) perception of true depth with improved understanding of 3D spatial relationships among anatomical structures, and (2) visualization of critical internal structures along with a more comprehensive visualization of the operating field. Using laparoscopic ultrasonography (LUS) is challenging for both novice and experienced ultrasonographers. Laparoscopic cameras have made significant image quality advances in recent years in that high-definition (HD) cameras are now integrated into laparoscopic systems. However, conventional laparoscopes are monocular and capable of providing only a single camera view. The resulting display is thus a flat representation of the three-dimensional (3D) operative field and does not give surgeons a good appreciation of the 3D spatial relationship among the anatomical structures. In addition, despite being rich in surface texture, the laparoscopic video provides no information on internal structures located beneath the visible organ surfaces. Both good depth perception and knowledge of internal structures are of critical importance for the safety and effectiveness of laparoscopic procedures and improved surgical outcomes.

Laparoscopic augmented reality (AR), a method to overlay laparoscopic ultrasound video onto optical video, offers enhanced intraoptive visualization as described in greater detail in Xin Kang, Mahdi Azizian, Emmanuel Wilson, Kyle Wu, Aaron D. Martin, Timothy D. Kane, Craig A. Peters, Kevin Cleary, Raj Shekhar; "Stereoscopic augmented reality for laparoscopic surgery", *Surg Endosc* (2014) 28:2227-

2235, and in Xinyang Liu, Sukryool Kang, William Plishker. George Zaki. Timothy D. Kane, Raj Shekhar; "Laparoscopic stereoscopic augmented reality: toward a clinically viable, electromagnetic tracking solution"; *J. Med. Imag.* 3(4), 045001 (2016), doi: 10.1117/1JMI.3.4.045001, the entire contents of both of these publications being incorporated herein by reference in their entirety.

Intraoperative imaging has the advantage of providing real-time updates of the surgical field and enables AR depiction of moving and deformable organs located in the abdomen, the thorax, and the pelvis. A clinically viable laparoscopic AR system based on EM tracking can be used. The performance of the EM-AR system has been rigorously validated to have clinically acceptable registration accuracy and visualization latency.

Figure 58:
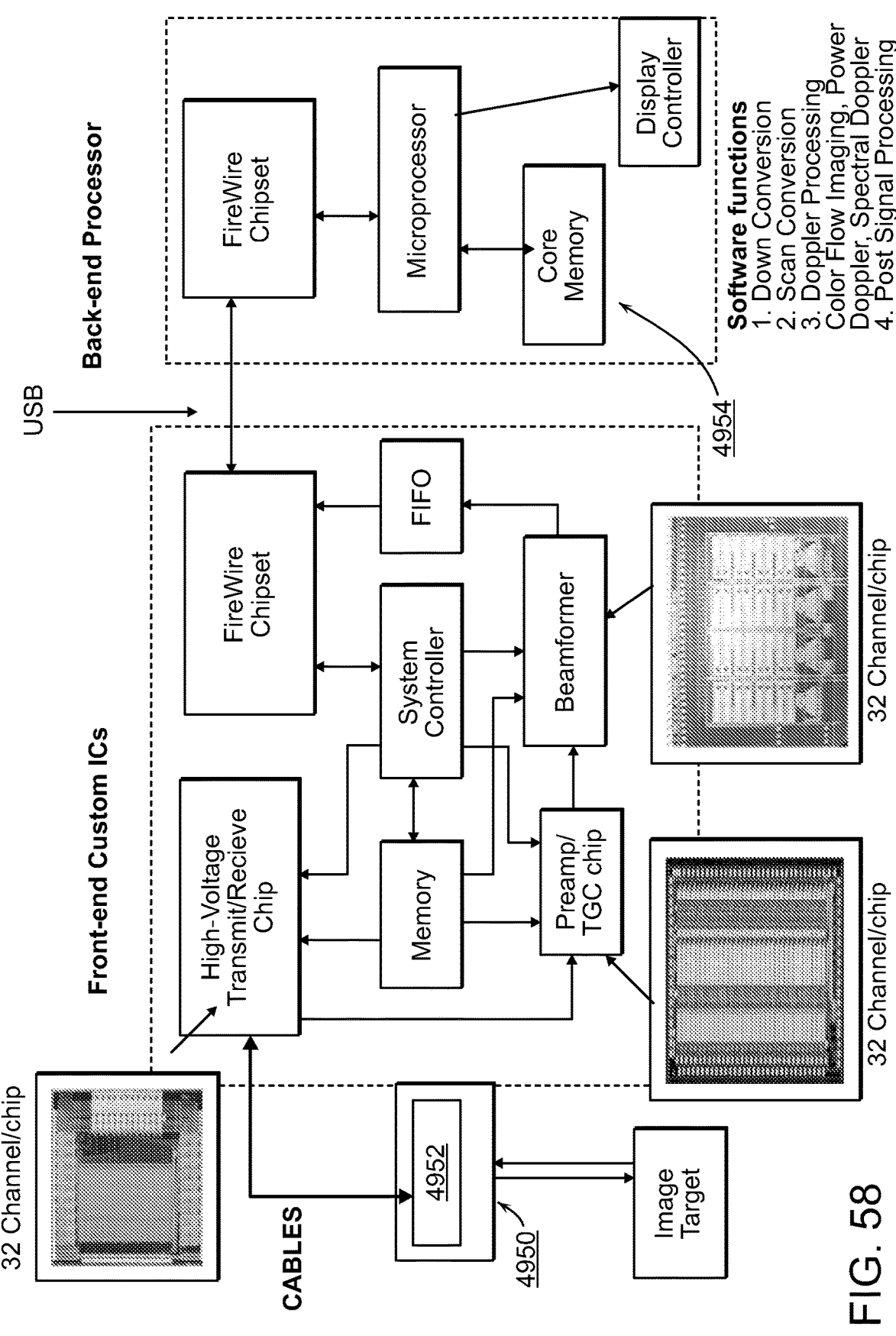
FIG. 58 illustrates a system for performing multi-modal imaging in accordance with various embodiments described herein.

The present system shown in FIG. 58 can perform the procedures illustrated in FIG. 57 wherein a laparoscopic transducer probe 4950 having an EM sensor 4952 can be actuated 4902 using touchscreen operations as described herein. The device can be optionally calibrated 4904 for a specific imaging application and both optical and ultrasound images can be captured 4906 simultaneously or in sequence. The images can be presented in split screen format or merged (overlayed) in video format 4908. The data can be processed 4910 using a neural network to generate diagnostic data. The system includes a core processor and memory 4954 which can comprise an Nvidia graphics processor unit as described previously herein that can be programmed or configured to operate as a neural network. The neural network or networks can be configured for discrete learning algorithms associated with imaging protocals for separate anatomical structures such as the heart, lungs, kidneys, gastrointestinal imaging using an ultrasound laparoscopic probe. The probe 4950 can include an imaging camera such as a CMOS or CCD imaging device. Alternatively, an imaging catheter or probe can be used to generate image data that is connected directly to the portable ultrasound system.

A large number of mathematical computations are required to overlay or to map a laparoscopic ultrasound video on optical video. Let $p_{us}=[x\ y\ 0\ 1]$ represent a point in the LUS, Laparoscopic ultrasound image coordinates, in which the z coordinate is 0. Let $p_{Lap}{}^{u}$ represent the point that $p_{us}$ corresponds to in the undistorted laparoscopic optical video image. If we denote $T_A{}^B$ as the 4×4 transformation matrix from the coordinate system of A to that of B. The relationship between $p_{us}$ and $p_{Lap}{}^{u}$ can be expressed by the following equation.

$$p_{Lap}^{u} \sim K \cdot [I_3\quad 0] \cdot T_{EMS_{Lap}}^{lens} \cdot T_{EMT}^{EMS_{Lap}} \cdot T_{EMS_{US}}^{EMT} \cdot T_{US}^{EMS_{US}} \cdot p_{US}$$

where US refers to the laparoscopic ultrasound image; $EMS_{us}$ refers to the sensor attached to the laparoscopic ultrasound probe; EMT refers to the EM tracking system; $EMS_{Lap}$ refers to the sensor attached to the 3D optical vision scope; lens refers to the camera lens of the 3-D scope; $I_3$ is the unit matrix of size 3; and K is the camera matrix. $T_{us}{}^{EMS_{us}}$ can be obtained from ultrasound calibration; $T_{EMS_{us}}{}^{EMT}$ and $T_{EMT}{}^{EMS_{Lap}}$ can be obtained from tracking data; $T_{EMS_{Lap}}{}^{lens}$ can be obtained from hand-eye calibration; and K can be obtained from camera calibration. $p_{lap}{}^{us}$ can be distorted using lens distortion coefficients also obtained from camera calibration.

It is straightforward to calculate the computational requirement for augmented reality imaging using composite ultrasound and optical video images by mapping one point from the laparoscopic ultrasound image to the corresponding point in the laparoscopic optical video images based on the above equation. Let the camera matrix size be (500, 500) pixels and ultrasound image size of (500,500) pixels. Following the above equation, the total number of computations required is about $1\times10^{12}$ floating point operations, i.e., 1000GFLOPs wherein the graphics processor is used to provide the solution in real-time.

In addition to the ultrasound system used to acquire the laparoscopic ultrasound images, the optical and ultrasound image fusion work was carried out by a laptop computer (Precision M4800, Dell; 4-core 2.9 GHz Intel CPU) with an NVidia GPU Quadro K2100M, 576 cores, with 972.8 GFLOPS processing power. However, a preferred design as described herein uses a computational enhanced ultrasound system. In addition to the Intel Processor CPU, the system can incorporate a multi-core GPU capable of providing more than 1000GFLOPs processing power to accommodate the computing requirements imposed by the AI, AR applications listed above.

Figures 59, 60:
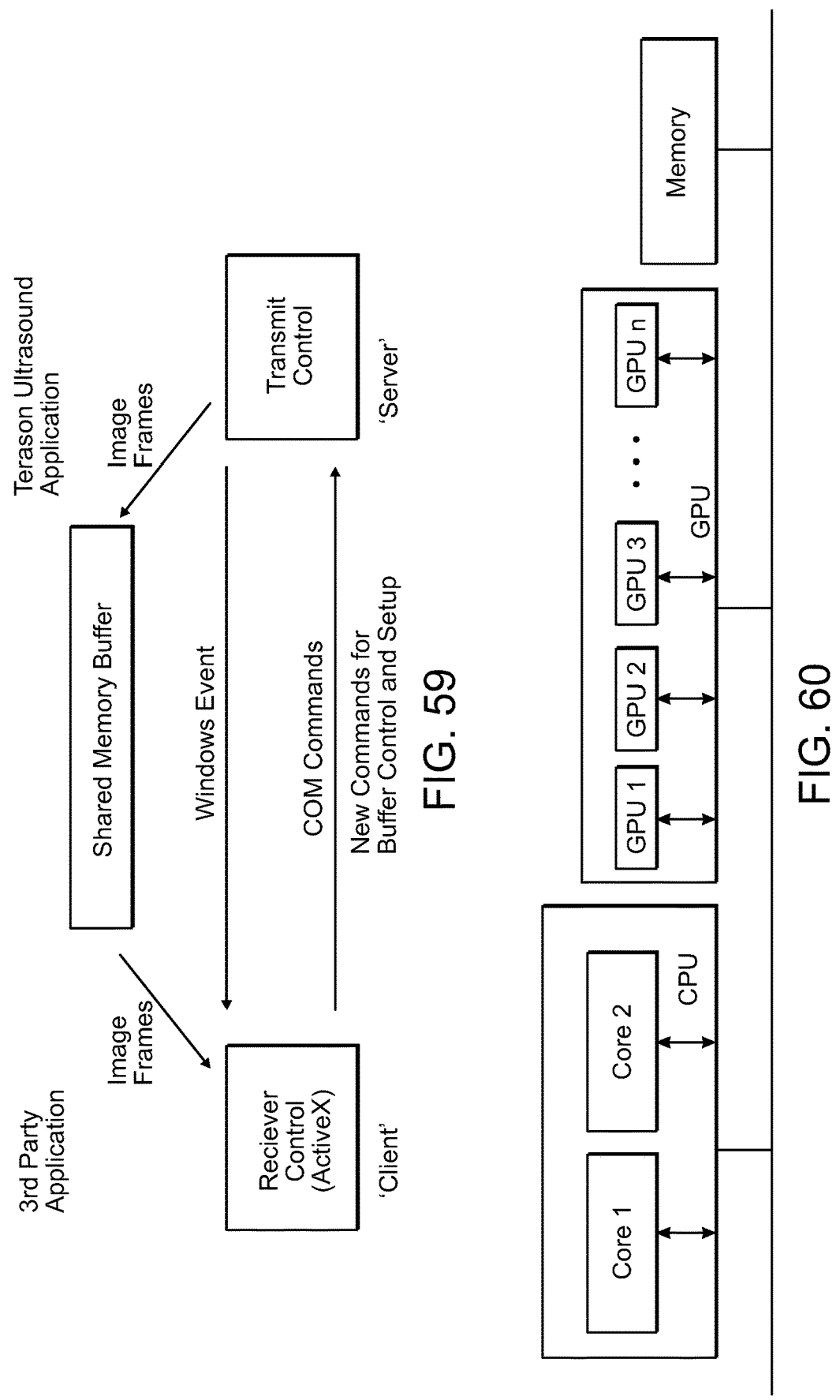
FIG. 59 illustrates the use of a shared memory to provide communication with an external application in accordance with various embodiments described herein.
FIG. 60 depicts a distributed processor system 4954 integrated into an exemplary tablet or laptop ultrasound system.

FIG. 59 illustrates the use of a shared memory to provide communication with an external application. FIG. 60 depicts a distributed processor system or GPU 4954 integrated into a tablet or laptop ultrasound system.

Further to the above, an exemplary portable ultrasound system suitable for use by embodiments of the present invention and shown in FIG. 1B is now further described. It should be appreciated that the description of the exemplary system set forth below is intended for illustration and explanation of system features and not in a limiting sense. It should further be appreciated that modifications to the exemplary system described below that are consistent with the description contained herein are also considered to be within the scope of the present invention.

The exemplary portable ultrasound system produces high resolution images that are intended for use by qualified physicians performing analysis by ultrasound imaging or fluid-flow of the human body. Specific clinical applications and exam types include, but are not limited to: Fetal, Abdominal, Intra-Operative (abdominal, organs and vascular), Pediatrics, Small Organ (Thyroid, Breast, Testes); Neonatal and Adult Cephalic; Trans-rectal, Trans-vaginal, Musculoskeletal (Conventional and Superficial); Cardiac (Adult & Pediatric); Peripheral Vascular.

Conventionally ultrasound has been primarily an operator-dependent imaging technology. The quality of images and the ability to make a correct diagnosis based on scans depend on precise image adjustments and adequate control settings applied during the examination. The exemplary portable ultrasound system provides tools to improve or optimize the image quality during a patient scan for all image modes. This system incorporates a graphical processing unit as described previously herein, as for example, described in FIGS. 9A-9F, and 46-60, without limitation.

The portable ultrasound system can include versions with different levels of features.

The following table lists which scan modes come with each version.

| Mode | Basic | Standard | Advanced | Optional |
|---|---|---|---|---|
| Pulsed-Wave Doppler | | | X | |
| Continuous-Wave Doppler | | X | | X |
| Omni Beam | | | | X |
| DICOM Image Transfer | | | | X |

The portable ultrasound system can deliver 2-dimensional digital imaging using 256 digital beam-forming channels. This imaging mode delivers excellent image uniformity, tissue contrast resolution, and steering flexibility in frequencies from 2 MHz to 12 MHz. The high channel count supports true phased array and high-element count imaging probes. The 2D scan data displays in the 2D Imaging window.

The portable ultrasound system may provide simultaneous 2-dimensional (2D mode) and M-Mode imaging. This combination is valuable for the efficient assessment of moving structures. M-Mode may be used to determine patterns of motion for objects within the ultrasound beam. This mode may be used for viewing motion patterns of the heart. M-Mode displays scan data of the anatomy in the 2D Imaging window, and the motion scan in the time series window.

Color Doppler mode is used to detect the presence, direction, and relative velocity of blood flow by assigning color-coded information to these parameters. The color is depicted in a region of interest (ROI) that is overlaid on the 2D image. Non-inverted flow towards the probe is assigned shades of red, and flow away from the probe displays in shades of blue. The mean Doppler shift is then displayed against a grayscale scan of the structures. All forms of ultrasound-based imaging of red blood cells are derived from the received echo of the transmitted signal. The primary characteristics of this echo signal are its frequency and its amplitude (or power). The frequency shift is determined by the movement of the red blood cells relative to the probe—flow towards the probe produces a higher-frequency signal than flow away from the probe. Amplitude depends on the amount of moving blood within the volume sampled by the ultrasound beam. A high frame rate or high resolution may be applied to control the quality of the scan. Higher frequencies generated by rapid flow are displayed in lighter colors, and lower frequencies in darker colors. For example, the proximal carotid artery is normally displayed in bright red and orange, because the flow is toward the probe, and the frequency (velocity) of flow in this artery is relatively high. By comparison, the flow in the jugular vein displays as blue because it flows away from the probe. The Color Doppler scan data displays in the 2D Imaging window.

A Pulsed-Wave Doppler (PWD) scan produces a series of pulses used to study the motion of blood flow in a small region along a desired scan vector, called the sample volume or sample gate.

The X-axis of the graph represents time, and the Y-axis represents Doppler frequency shift. The shift in frequency between successive ultrasound pulses, caused mainly by moving red blood cells, can be converted into velocity and flow if an appropriate angle between the insonating beam and blood flow is known. Shades of gray in the spectral display represent the strength of the signal. The thickness of the spectral signal is indicative of laminar or turbulent flow (laminar flow typically shows a narrow band of blood flow information). In the portable ultrasound system, Pulsed-Wave Doppler and 2D are shown together in a mixed-mode display. This combination enables a user of the system to monitor the exact location of the sample volume on the 2D image in the 2D Imaging window, while acquiring Pulsed-Wave Doppler data in the Time Series window.

In the 2D scan, the long line lets a user adjust the ultrasound cursor position, the two parallel lines (that look like=) let the user adjust the sample volume (SV) size and depth, and the line that crosses them lets the user adjust the correction angle.

Continuous-Wave Doppler scans display all velocities present over the entire length of the ultrasound cursor. This mode is useful for imaging very high velocities such as those resulting from a leaking heart valve. As with Pulsed-Wave Doppler scans, the X-axis of the graph represents time, and the Y-axis represents Doppler frequency shift.

Figure 61:
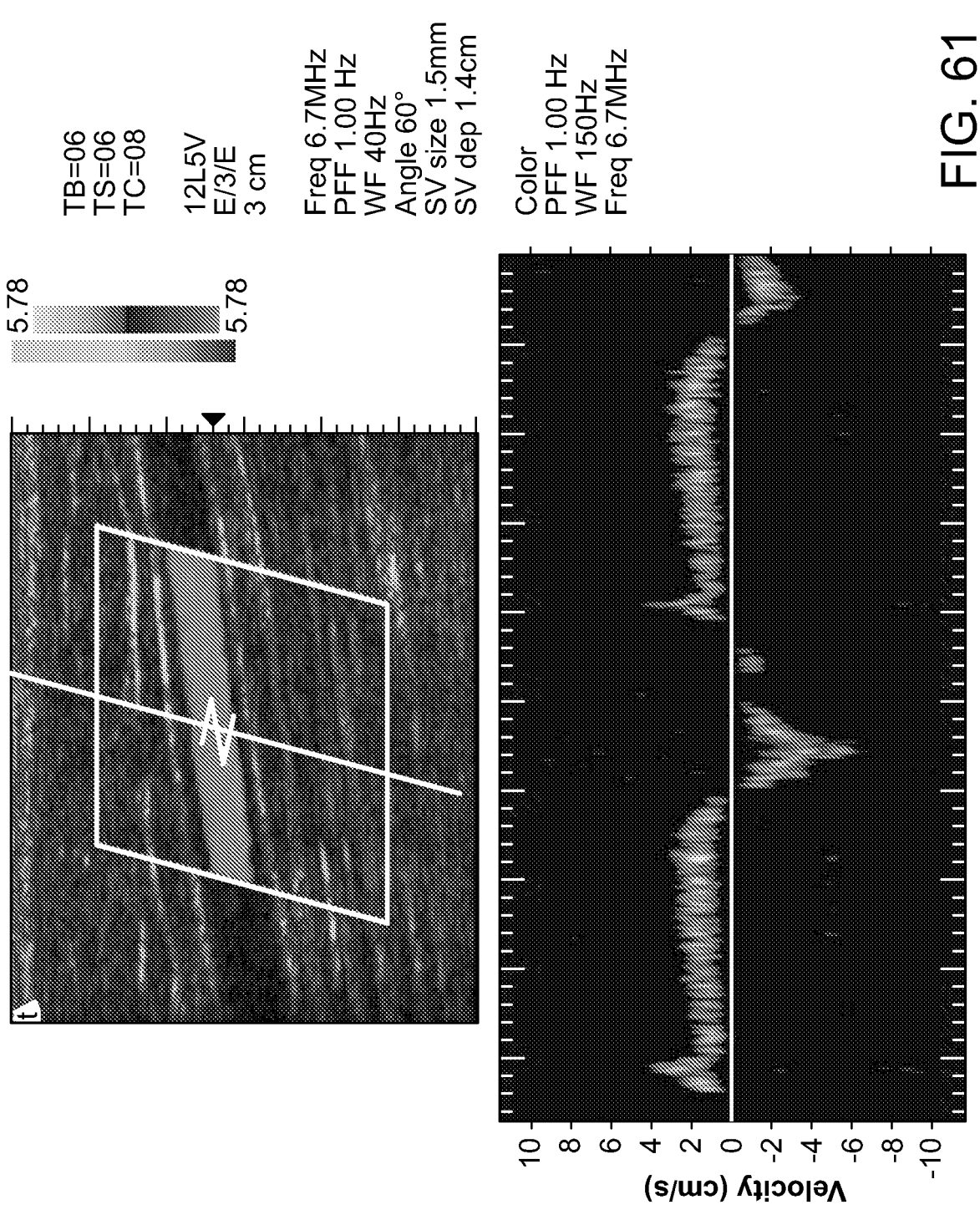
FIG. 61 illustrates a triplex scan image used to perform range gate analysis.

Triplex scan mode combines simultaneous or non-simultaneous Doppler imaging (Color Doppler) with Pulsed-Wave Doppler imaging to view arterial or venous velocity and flow data. Triplex allows a user to perform range-gated assessment of flow. Triplex applications include vascular studies, phlebology, perinatal, and radiology. The following triplex image in FIG. 61 shows the greater saphenous vein.

The exemplary portable ultrasound system may also include an optional image-optimization package that sharpens images. The portable ultrasound system can be configured with needle guides used for tissue biopsy, fluid aspiration, amniocentesis, and catheter placement. The system can also be incorporated into cryoablation (or targeted ablation) and brachytherapy products from other vendors. The portable ultrasound system scans the anatomy or vessel for size, location, and patency, and provides guide lines between which the needle will appear. For biopsy and vascular puncture applications, a needle guide kit directs needles to the proper location for percutaneous vascular punctures and nerve blocks. The needle guide allows a user to direct the needle into the center of a vessel or tissue mass, helping to avoid adjacent vital tissue. A user can see the anatomy in real time before, during, and after the procedure, and can save images and Cine loops for future reference.

For cryoablation or brachytherapy applications, the system may include an insertion template and a stepper or stabilizer. The procedure for these applications is defined by the company that provides those systems. The system software displays the insertion grid and needles on the scan to show the progress of the procedure.

A user can use the needle guides in the following modes: 2D Mode; Color Doppler; M-Mode (Motion Mode). The portable ultrasound system consists of the probe, electronics envelope, and the system software. In the exemplary portable ultrasound system, all of the probes can be used with all scan modes.

When a user start the system software, the Imaging window displays. The Imaging window can include of the 2D window above the Time Series window (if the selected scan mode generates a Time Series window). The 2D window displays in all scan modes; the Time Series window displays only when scanning in M-Mode, PWD mode, CWD mode, or Triplex mode. If a control, button, key, or menu shows in gray, it may indicate that the function is not available for the current circumstances. The Imaging screen may include a status bar at the lower corner.

The status bar may display indicators, including: Network connection which shows if the computer is connected to a network. If there is no connection, a red X shows on the indicator and DICOM status, which shows whether the connection to a DICOM server is active, and whether sending of any studies to the DICOM server has failed. System power shows the remaining charge of the system battery, and whether the AC power supply is connected. In the illustration, the battery is fully charged, and the system is connected to an AC power source. As the battery discharges, the green bands disappear, from right to left. When the battery is almost fully discharged, a single red band shows at the left end of the indicator. When the battery is partly discharged and the AC power supply is connected, a yellow lightning bolt shows on the battery icon. When the battery is full charged and the AC power supply is connected, a power plug icon displays below the battery icon. The Imaging window includes a text display that shows information about the current scan. The image control settings displayed vary, depending on the scan mode and other factors.

Figure 62:
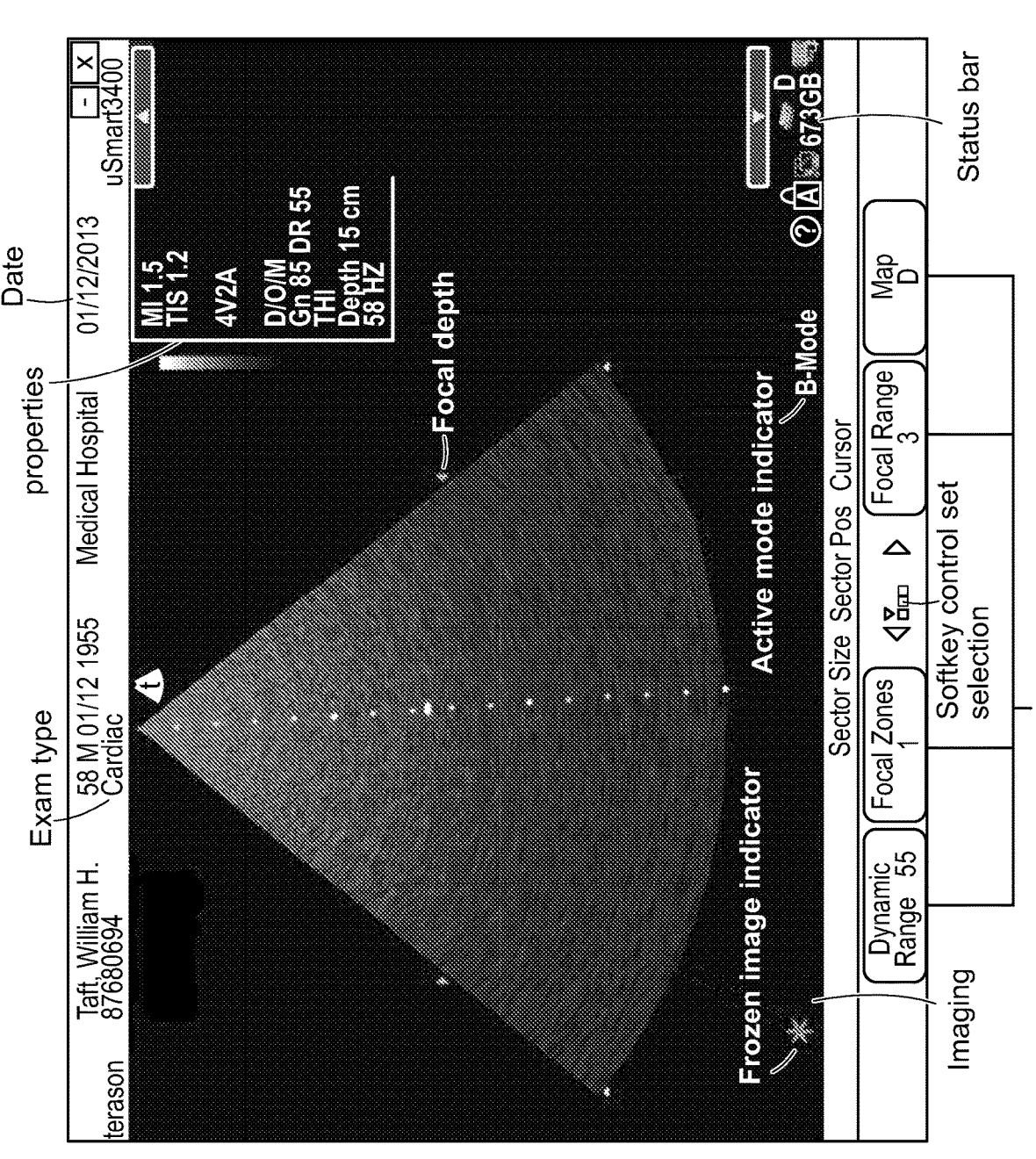
FIG. 62 illustrates an image window display softkey or touch icons.

As pictured in FIG. 62, an exemplary display may include a mechanical index, thermal index, reference bar type, Image Control Settings: Map/Persistence/Scan Frequency// 2D Gain/Dynamic Range, a depth setting, frame rate, scan mode, PRF setting, wall filter setting, color frequency and focal point. In the exemplary portable ultrasound system, the 2D gain display is initially 50. This is not an absolute value; the actual gain changes with different presets, but always displays as 50 initially. When a user change the gain using the Gain knob, the displayed value goes up or down. When the Cardiac exam type is selected, the depth ruler and focal depth indicator are on the ultrasound cursor, as shown in the imaging window figure.

A user can view a saved study in the review window. While reviewing a saved study, a user can add annotations and measurements in the same way as on the Imaging window.

Figure 63:
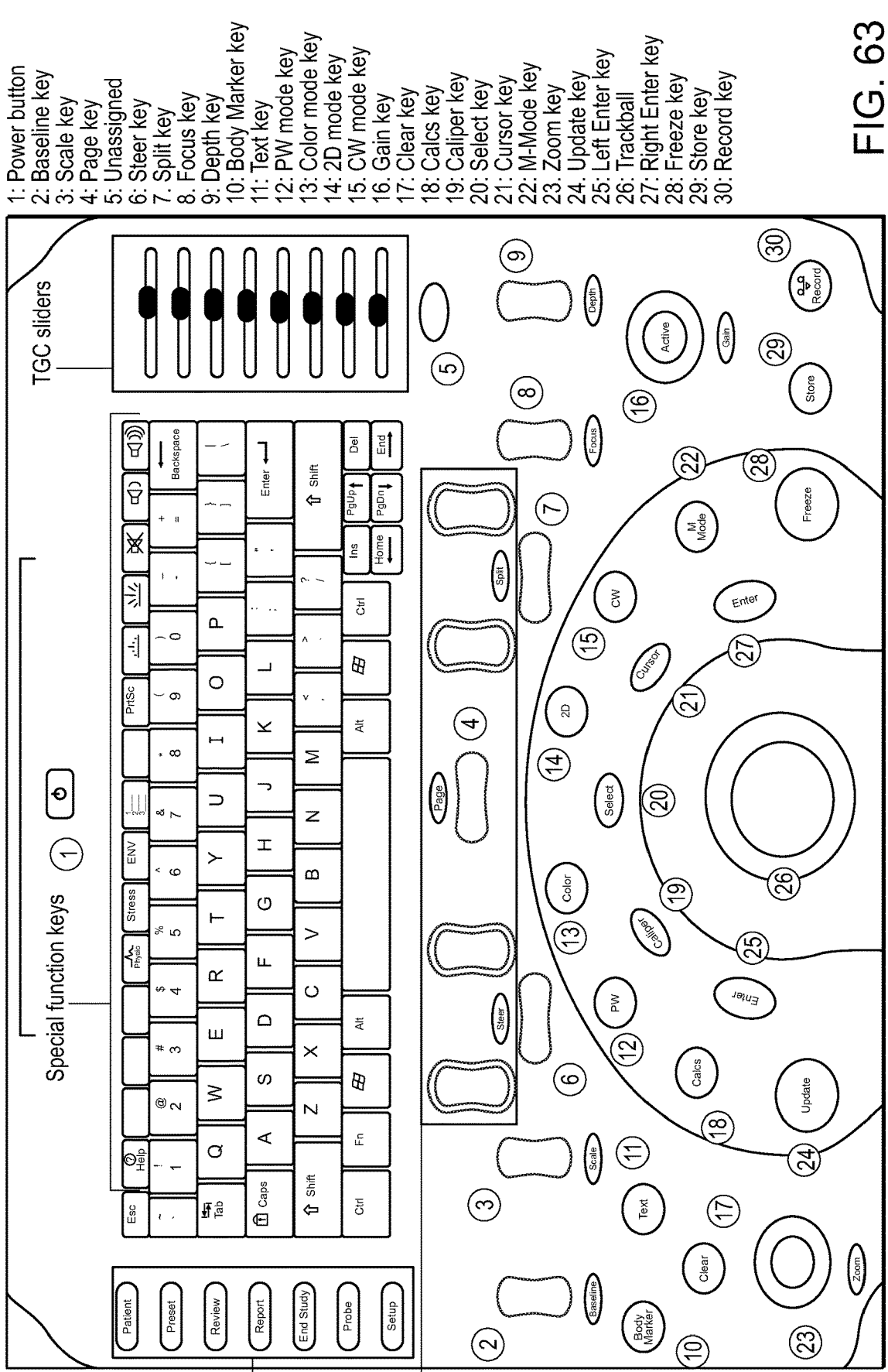
FIG. 63 illustrates a keyboard control panel for a portable ultrasound system.

The exemplary portable ultrasound system includes a console shown in FIG. 63 that houses controls that configure and operate the portable ultrasound system.

1: Power button
2: Baseline key
3: Scale key
4: Page key
5: Unassigned
6: Steer key
7: Split key
8: Focus key
9: Depth key
10: Body Marker key
11: Text key
12: PW mode key
13: Color mode key
14: 2D mode key
15: CW mode key
16: Gain/Active control
17: Clear key
18: Calcs key
19: Caliper key
20: Select key
21: Cursor key
22: M-Mode key
23: Zoom control
24: Update key The console includes an alphanumeric keyboard, a group of system keys, TGC sliders, softkey controls, and numerous controls for ultrasound imaging functions. The numbered Ultrasound Imaging controls in the exemplary console perform the functions listed below:

1. Power: Starts the system and shuts it down.
2. Baseline: Changes the Doppler baseline in PW, CW and Color Doppler modes. Pressing the top of the key moves the baseline up, and pressing the bottom of the key moves it down.
3. Scale: Changes the velocity scale (by changing the PRF) in PW, CW and Color Doppler modes. Pressing the top of the key increases the PRF, and pressing the bottom of the key decreases it.
4. Page: Changes which set of active softkeys are displayed.
5. This key may be unassigned.
6. Steer In 2D, Color Doppler or PWD modes, this key steers the ultrasound signal. Pressing the left end of the key steers left, and pressing the right end steers right.

7. Split: Pressing the left end of the key opens split-screen with the left screen active, or when split screen is already on, makes the left screen active. Pressing the right end of the key opens split-screen with the right screen active or makes the right screen active. Pressing the end of the key that corresponds to the active screen exits split-screen.
8. Focus: Changes the depth of the signal focus. Pressing the top of the key moves the focus up, and pressing the bottom of the key moves it down.
9. Depth: Changes the total image depth. Pressing the top of the key moves the image depth up, and pressing the bottom of the key moves it down.
10. Body Marker Inserts body markers in the scan.
11. Text: Enables text entry and annotation on the scan.
12. PW: Enters and exits Pulsed-wave Doppler mode.
13. Color: Enters and exits Color Doppler mode.
14. 2D: Enters 2D mode.
15. CW: Enters and exits Continuous-wave Doppler mode.
16. Gain/Active: Turning the knob changes the gain. Pushing the Active button toggles between the active scanning modes and the softkeys associated with those modes.
17. Clear: Erases the currently selected annotation or measurement.
18. Calcs: Opens the Calculations menu.
19. Caliper: Starts a generic measurement. Pressing the key repeatedly cycles through available calculations.
20. Select: Chooses a trackball function. The selected function is highlighted in blue above the softkey display.
21. Cursor: Selects and displays or deselects and hides the ultrasound cursor.
22. M-Mode: Enters and exits M-Mode.
23. Zoom: Push to enter ROI box Zoom, or exit Zoom mode. Turn for Quick Zoom
24. Update: Turns updating of the 2D image on and off in PWD and CW modes.
25. Left Enter Selects and deselects items. When the Windows screen is active, the Left Enter key acts like the left button on a mouse.
26. Trackball: Controls movement of the cursor, the ROI, and other features.
27. Right Enter Opens context menus. When the Windows screen is active, the Right Enter key acts like the right button on a mouse.
28. Freeze: Freezes and unfreezes the scan.
29. Store: Stores a single-frame image.
30. Record: Stores a loop.

At the top left of the console is a group of system keys that control what the windows are active. They include: Patient—Opens the Patient window, Preset—Opens the Preset menu, Review—Opens the Review window, Report—Opens the Report window, End Study—Closes the current study, Probe—Opens the Imaging window; Setup—Opens the Setup window.

The keys just below the keyboard control the functions of the softkeys displayed across the bottom of the Imaging window. The softkey functions are dependent on what probe is connected, which scanning mode is chosen, and whether the scan is live or frozen. The illustrations below show examples of the softkeys when the image is live and frozen. The softkeys the system displays depend on the probe that is connected, the selected scan mode, and the selected exam. The display a user sees may differ from the illustrations shown here.

It should be appreciated that in some embodiments, the console controls may be provided via a touchscreen display rather than a being configured in a separate physical housing.

The system can include an ECG module, an ECG lead set—10 sets of electrodes, a Footswitch (Kinessis FS20A-USB-UL), a medical-grade printer and One or more transducer probes. The exemplary portable ultrasound system complies with the *Standard for Real-Time Display of Thermal and Mechanical Acoustic Output Indices on Diagnostic Ultrasound Equipment* (UD3-98). When the relevant output index is below 1.0, the index value is not displayed. When operating in any mode with the Freeze function disabled, the window displays the acoustic output indices relevant to the currently-active probe and operating mode. Minimizing the real-time displayed index values allows the practice of the ALARA principle (exposure of the patient to ultrasound energy at a level that is As Low As Reasonably Achievable).

In the exemplary portable ultrasound system, to choose a scan mode, a user presses the appropriate key on the console:

For 2D, press the 2D key; for M-Mode, press the M Mode key; for Color Doppler, press the Color key; for Pulsed-Wave Doppler, press the PW key; for Continuous-Wave Doppler, press the CW key.

In the exemplary portable ultrasound system, to conduct an ultrasound exam in 2D, Color Doppler, or M-mode, the user completes these steps:

1 Load or create the patient information.

2 Press the console key for the required scan mode:

3 Press the Preset key, then select a preset from the Presets menu.

The system software loads preset image control settings that are optimized for the selected preset and the connected probe. A user can now use the probe to conduct an ultrasound exam. Refer to the appropriate clinical procedure for the exam a user are conducting.

4 If necessary, use the softkeys to adjust the image controls.

5. Press the Freeze key. The softkey controls change to allow printing, measurements, and other functions.

To conduct an exam in Pulsed-Wave Doppler mode, a user may complete these exemplary steps:

1 Conduct an exam in 2D mode,

2 Press the PW key on the console.

3 Move the range gate to the proper location, then press the Left Enter key on the console . . . .

4 Use the softkeys to adjust any image control settings as needed.

Press the Freeze key. The softkey controls change to allow printing, measurements, and other functions.

To conduct an exam in Triplex mode, a user may complete these exemplary steps:

1 Conduct an exam in Color Doppler mode (do not freeze the scan).

2 Press the PW key on the console. The software launches Triplex mode.

3 Move the range gate to the proper location, then press the Left Enter key on the console.

4 Use the softkeys to adjust any image control settings as needed.

Press the Freeze key. The softkey controls change to allow printing, measurements, and other functions.

When a user switches to Triplex mode, both the original 2D scan mode and PWD mode are active. This depends on whether the options are set to simultaneous mode.

Live images are recorded by frame and temporarily stored on the computer. Depending on the mode a user selects, the system records a certain number of frames. For example, 2D mode allows a user to capture up to 10 seconds in a Cine loop.

Pulsed-Wave Doppler (including Triplex) and M-Mode scans only save a single frame for the 2D image, and a user cannot save loops for these scan modes.

When a user freezes a real-time image during a scan, all movement is suspended in the Imaging window. The frozen frame can be saved as a single image file or an image loop. For M-Mode, PWD, and Triplex modes, the software saves the Time Series data and a single 2D image.

A user can unfreeze the frame and return to the live image display at any time. If a user presses the Freeze key without saving the image or image loop, a user loses the temporarily-stored frames.

To freeze the displayed image when performing an ultrasound scan, a user presses the Freeze key. When the scan is frozen, a Freeze icon appears just above the left softkey on the imaging screen. A user can then use the Gain knob or the keyboard arrow keys to move through the frames acquired during the scan.

To start a new scan, a user presses the Freeze key again. If a user does not save the frozen image or loop, starting live scanning erases the frame data. The user saves or prints any needed images before a user acquire new scan data.

Reviewing an image loop is useful for focusing on images during short segments of a scan session. When a user freezes an image, a user can use the Gain knob to review an entire loop, frame by frame, to find a specific frame. A user can also do this when viewing a saved loop by turning the Gain knob until the desired frame displays and pressing the Store key.

To save the entire loop, a user need not select a different frame. All acquired frames are saved in the loop when a user press the Store key.

To view a loop, the user freezes the image and presses the Play softkey. The Play softkey label changes to Pause. The loop plays continuously until a user press the Freeze key or the Pause softkey. A user can track the frames and the number of the current frame in the progress bar at the bottom of the Imaging window.

In 2D and Color modes, the system can acquire loops either prospectively or retrospectively. Prospective acquisition captures a loop of live scan data following the acquire command, while retrospective acquisition saves a loop of a frozen scan.

During live imaging, pressing the Store key tells the system to acquire and save a loop of the scan following the key click. The loop displays in the Thumbnail window at the side of the Main Screen. The default length of the loop is 3 seconds, but this is adjustable, for example, between 1 and 10 seconds in the Acquisition Length section of the Setup Store/Acquire window.

When the beat radio button on the Store/Acquire tab of the Setup window is selected, and the system detects an ECG signal, the acquired loop is a number of heartbeats. A default may be 2 beats, but this also may be adjustable, such as to between 1 and 10 beats in the acquisition length section. If no ECG signal is detected, the acquired loop may be the length set in the Time field, even if the beat radio button is selected. A user can apply an R-wave delay in the Acquisition Length section. A user can also enable a beep that sounds when the acquisition is complete. The default format for loops acquired in this way is .dcm, however, they can also be saved as any of the other available formats. A user may utilize the Export tab on the Setup window to choose a different file format.

When a user views a frozen or live image, a user can use the Zoom tool to enlarge a region of the 2D image. A user cannot use the Zoom tool in the Time Series window. To zoom into the middle of the image the user:

1 Presses the Gain knob until Zoom is selected in the Gain Knob menu.

2 Turns the Gain knob to zoom in or out to the size a user want. To zoom an area that's away from the middle of the image:

To zoom an area that's away from the middle of the image, the user:

1 Presses the Zoom Off softkey.

2 Uses the trackball to move the zoom box to the area a user want larger, and press the Left Enter key.

3 Uses the Gain knob to zoom in or out of that area.

In the exemplary portable ultrasound system, in M-mode and Spectral modes, a user can make the 2D display larger relative to the Time-Series display, and vice-versa.

To resize the scanning displays:

1. Press the Setup key.

2. Click the Display tab.

To make the Time-Series display bigger and the 2D Imaging display smaller, click the S/L radio button in the M-Mode Format or Spectral Format area. To make the 2D display bigger and the Time-Series Imaging display smaller, click the US radio button in the M-Mode Format or Spectral Format area.

3. Click OK to apply the change.

Note: This selection applies whenever a user use the preset that was chosen when a user made the change. When a user use a different preset, the selection does not apply unless a user have also made the change in that preset.

In the exemplary portable ultrasound system, an optional image-optimization package sharpens images produced by the portable ultrasound system. The default configuration starts the software when the portable ultrasound system starts. To change this so the system starts with the optimization software off, a user may make a preset with the TV Level softkey control set to 0. The optimization software level numbers range from 0 to 3. The 0 setting applies no image processing. The larger the number, the more processing is applied to the image. To adjust the optimization level, when live imaging, a user may press the TV Level softkeys until the desired level is set.

The view options section of the general tab on the setup window lets a user add or remove several guides on the scanned image. These guides provide details about the patient. probe, and image control settings.

The system software lets a user split the Imaging screen into two sections to view two current scans for a patient. A user can acquire one scan for the patient, select Split Screen, and then acquire another scan from a different angle or location. Split Screen mode works with the 2D scanning modes (2D and Color Doppler).

When a user enters split screen mode, the system software copies the current settings for the Image Control window to the new screen. A user can then apply any Image Control setting independently to either screen. A user can go live or freeze either screen (only one screen can be live at a time), and a user can use any of the tools and menus with either screen. In addition, a user can scan in different modes in each screen. For example, a user can acquire a 2D scan, enter split screen mode, then acquire a Color Doppler scan in the second screen. The following figure shows an example of a split screen.

The active screen has cyan bars at the top and bottom. To activate the other screen, a user performs one of these actions:

Move the arrow cursor to the desired screen and press the Left Enter key.

Press the Toggle Screen softkey. To exit split screen mode, use any of these methods:

Press the 2D key.

Select a different exam

Select M-Mode, PWD, or Triplex scan modes

Press the Split softkey

When a user exits Split Screen mode by pressing the Split softkey, the system software keeps the acquired data for the active screen (the one with the cyan lines at the top and bottom) and discards the acquired data for the other screen.

Text mode lets a user add text and symbols to an image, using the softkeys. Softkey controls that are available in Text mode include:

Laterality places the word Left or Right on the image. Pressing the Laterality softkey cycles between Left, Right, and no text.

Location opens a menu of body locations, or increments through a list of body locations. If a menu opens, the appropriate item may be clicked to place it on the image.

Anatomy opens a menu of names for different anatomies, or increments through a list of anatomies. If a menu opens, click the appropriate item to place it on the image.

Orientation opens a menu of patient orientations, or increments through a list of patient orientations. If a menu opens, click the appropriate item to place it on the image.

Body Marker opens the Body Marker menu.

Text New starts a new line of text at the home location.

Text Clear deletes all text (including manually typed text and arrows) from the image Home moves the text cursor or selected text to the text home position.

Arrow places an arrow at the text home position, or if there is text on the image, at the middle of the last line of text Set Home sets the text home position. Move the text cursor to the desired location, then press the Set Home softkey.

To enter text mode, press the Text key. The system software places a text cursor (I-beam) on the Imaging screen. The trackball is used to move it to where a user want the new text, and either type the text, or use one of the Text-mode softkeys. When the text is done, press the Left Enter key. If a user added custom text using the Annotation tab of the Setup window, that text shows in the softkey list to which it was added.

A user can also add predefined text, using the softkeys. This lets a user add labels and messages a user needs often, without having to type them each time.

1. Press the Text key on the console, or press the Space bar on the keyboard.

2. Press one of the softkeys for predefined text:

Laterality places the word Left or Right on the image. Pressing the Laterality softkey cycles between Left, Right, and no text.

Location opens a menu of body locations, or increments through a list of body locations. If a menu opens, click the appropriate item to place it on the image.

Anatomy opens a menu of names for different anatomies, or increments through a list of anatomies. If a menu opens, click the appropriate item to place it on the image.

Orientation opens a menu of patient orientations, or increments through a list of patient orientations. If a menu opens, click the appropriate item to place it on the image. Selecting an item with one of the softkeys places it on the image.

A user can place two kinds of arrow on a frozen image: marker arrows and text arrows. The default is marker arrows. A user can place as many arrows as a user want on an image. Marker arrows are short, hollow arrows that indicate a spot on the image. When a user places an arrow (see the procedure below), the arrow is green. A user can use the trackball to move the arrow while it is green. A user can select an arrow by clicking on it. When an arrow is selected, a user can move it with the trackball and rotate it by pressing the Select key, then moving the trackball. To place a marker arrow on an image, complete these steps:

1 Press the Arrow softkey.

2 Use the trackball to move the arrow to where a user want it

3 To rotate the arrow, press the Select key and move the trackball.

4 To place another arrow on the image, press the Arrow softkey.

5 Press the Left Enter key to set the arrows and exit Text mode.

Text arrows are dashed-line arrows that a user can draw from text to a point on the scanned anatomy. A user can also add an arrow without adding text. To use text arrows, a user must make a selection on the Setup/Annotation window.

After placing text on an image, a user can easily move it to any location within the Image Display. To move text, click the text, move it to a new location, and press the Left Enter key. If an arrow is attached to the text, the origin of the arrow also moves.

A user can add an icon to the 2D image that identifies the anatomy of the scan. Body Marker in the Annotation menu opens a window containing several anatomical views based on the current exam. To add a body marker to an image, a user completes these steps:

1 Press the Text key.

2 Press the Body Marker softkey. A body marker displays on the image.

3. If the marker a user wants is not displayed, press the Next Marker or Prev Marker softkey. If another marker is available, it replaces the first marker.

4. When the marker a user want displays, press the Left Enter key.

To change the body marker, complete these steps:

1. Click the body marker. The marker turns green and the softkeys change to the Body Marker set.

2. Press the Next Marker or Prev Marker softkey.

3. When the marker a user want displays, press the Left Enter key.

A user can move the body marker to any location on the image. To move the body marker, complete these steps:

1 Click the body marker to select it.

2 Press the Marker Position softkey.

3 Use the trackball to move the body marker.

4 When the marker is where a user want it, press the Left Enter key twice.

A user can move the orange probe indicator to anywhere on the icon to more precisely indicate the scanned anatomy. To move the orange marker, complete these steps:

1 Click the body marker. The text above the softkey display changes to show Probe Pos is selected.

2 Use the trackball to move the probe indicator to the desired location on the body marker.

3 When the marker is where a user want it, press the Left Enter key.

To rotate the probe indicator to more positions complete these steps:

1. Move the Windows pointer over the body marker. The pointer changes to pointing hand.

2 Press the Select key to highlight Probe Orient in the line above the softkey display.

3 Use the trackball to rotate the probe indicator to the desired orientation on the body marker.

4 Press the Left Enter key to lock the indicator in position.

A set of softkey controls below the Imaging window display the currently available imaging controls. The softkeys are operated by the keys on the console or alternatively using a touchscreen display. When a user select a scan mode, the software configures the softkeys for that mode. The controls displayed vary depending on which probe is connected, and on other selections. Pressing the left and right arrow keys at the left side of the console changes the display to other controls available in the selected mode.

To change a setting, use the toggle keys on the console. Each toggle key controls the setting in one of the softkeys at the bottom of the Imaging window. The position of the key set corresponds to the position of the onscreen button—the leftmost key controls the setting in the leftmost softkey, and so on.

Figure 64:
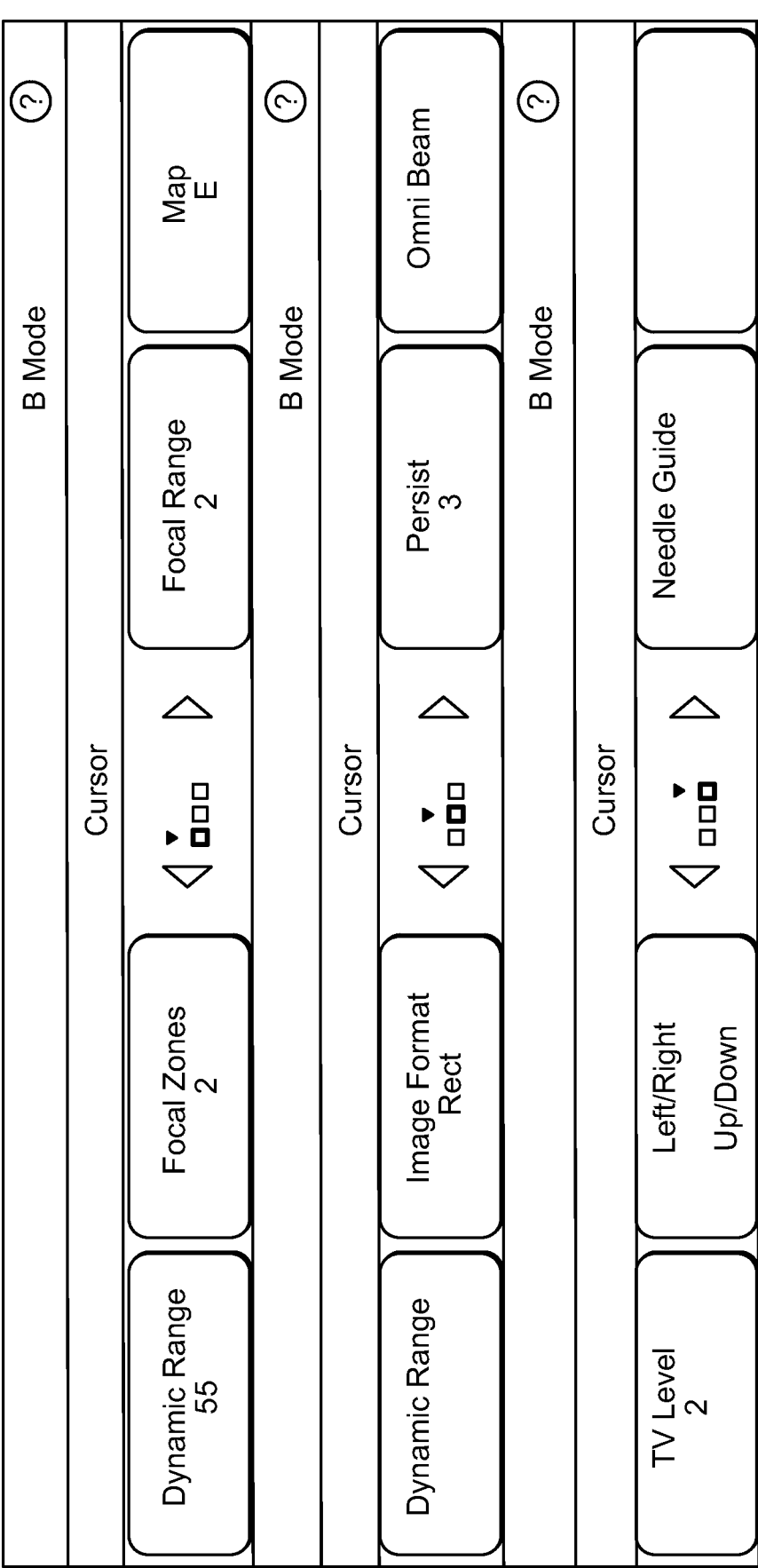
FIG. 64 illustrates a plurality of softkeys displayed on the imaging window.

FIG. 64 illustrates softkeys shown as an example of available 2D image controls. A user can only adjust these image controls during live scanning. When a user freezes a scan, the system software replaces the softkeys with a different set, for printing and making annotations and measurements on the scan image.

The softkey display depends on the probe that is connected, the selected scan mode, and the selected exam. A user can adjust the following 2D image controls during live scanning: Frequency, Scan Depth, Focus depth, Gain, Time Gain Compensation (TGC), Image Format, Omni Beam, Left/Right and Up/Down invert, Colorization, Persistence, Image map, Needle guide, Dynamic range, Software optimization controls.

When a user selects an exam, the system software sets an appropriate frequency for that exam. A user can select an alternate frequency to better suit specific circumstances. In general, a higher transmit frequency yields better 2D resolution, while a lower frequency gives the best penetration. To select high, medium, or low frequency, use the Frequency softkey. The exact frequencies vary, depending on the connected probe. Each frequency has a number of other parameters associated with it, which depend on the type of exam. The selected frequency shows as H, M, or L in a character string in the information to the right of the Imaging window. In the example below, medium frequency is selected.

The Depth key adjusts the field of view. A user can increase the depth to see larger or deeper structures. A user can decrease the depth to enlarge the display of structures near the skin line, or to not display unnecessary areas at the bottom of the window. When a user selects an exam type, the system software enters a preset depth value for the specific exam type and probe. To set the scan depth, use the Depth key. After adjusting the depth, a user may want to adjust the gain, time gain compensation (TGC) curve, and focus control settings. A user can view a depth ruler on the image by selecting Depth Ruler on the General tab of the Setup window.

Figure 65:
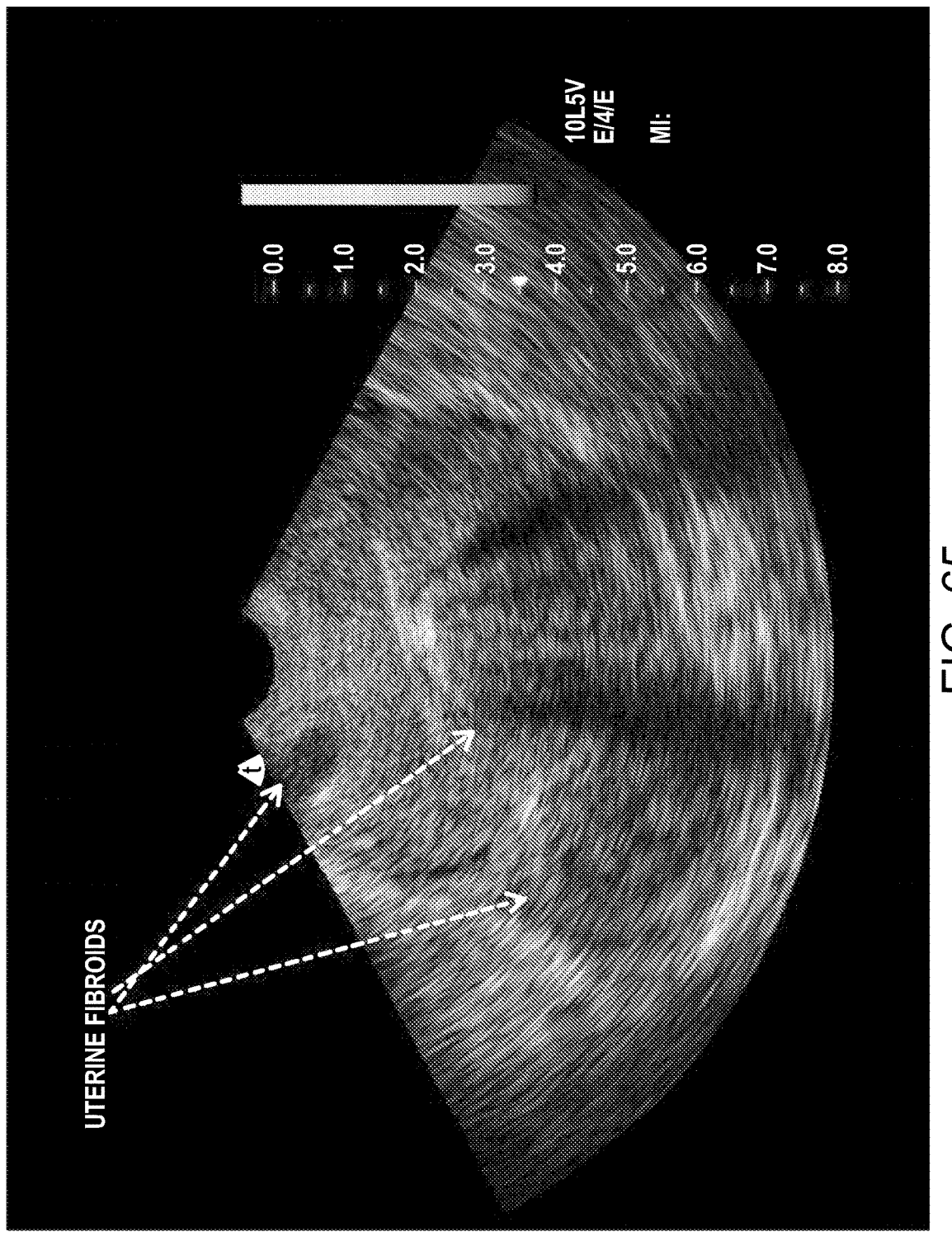
FIG. 65 illustrates imaging of uterine fibroids with arrows and text added.
Figure 66:
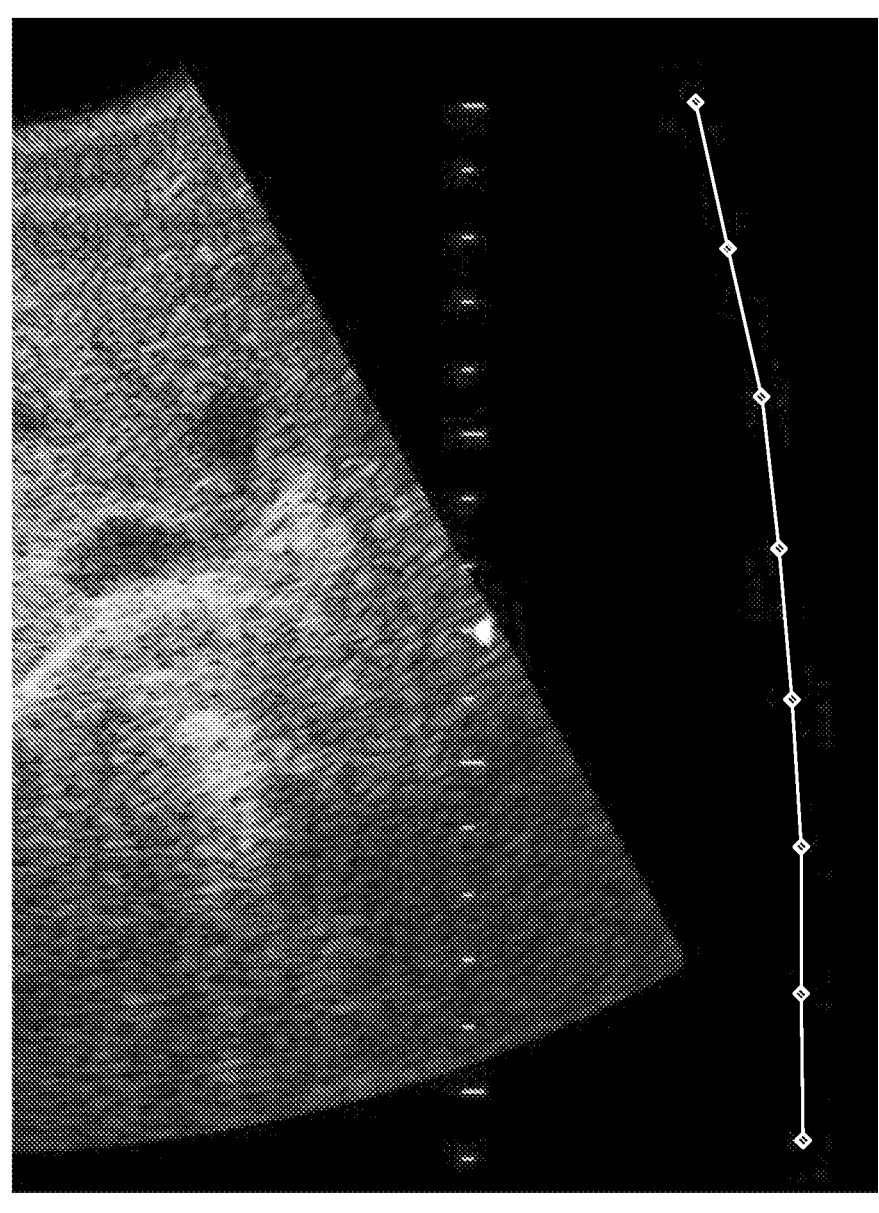
FIG. 66 illustrates a time gain control (TGC) curve as a function of depth.

Focus optimizes the image by increasing the resolution for a specific area. FIG. 65 shows the depth ruler along the right side of the image. A color triangle on the depth ruler indicates the focus depth. This indicator is only visible if a user shows the depth ruler. The depth is also displayed as text in the scan information area. When a user selects an exam type, the software updates the focus value to a preset value for the specific exam type, probe, and frequency. In 2D mode, a user can set up to four focus depths, using the Focal Zones softkey. In all the other modes, a user can set only one focus depth. When a user use more than one focus depth, a user can choose the distribution of the focus depths.

To set the focus depth, a user uses the Focus key. To set multiple focus depths in 2D, a user completes these steps:

1. Use the Focal Zones softkey to select the desired number of focus zones.
2. Use the Focal Range softkey to select a distribution for the focus zones.

The distribution is shown by the spacing of the depth indicators on the depth ruler. The actual spacing of the focus depths depends on the number of points selected and on the depth. Increasing the number of focal zones decreases the frame rate.

2D gain allows a user to increase or decrease amplification of the returning echoes, which increases or decreases the amount of echo information displayed in an image. Adjusting gain may brighten or darken the image if sufficient echo information is generated. When a user adjusts the gain, the system software increases or decreases the overall gain while maintaining the shape of the TGC curve. When a user selects a preset, the system software sets the gain to a preset value for the specific preset and probe. To increase or decrease the gain, the user turns the Gain knob to the right or left.

Scanning tissues at greater depths causes attenuation of the returned signal. The TGC sliders adjust amplification of returning signals to correct for the attenuation. TGC balances the image to equalize the brightness of echoes from near field to far field. The system software rescales the TGC settings when a user change the depth. load a new exam type, select a different frequency, or adjusts the gain setting The TGC slider bar spacing is proportional to the depth. The TGC curve on the image display represents the TGC settings, and appears when a user move one of the sliders. Each slider controls one dot on the curve. A user can adjust the TGC sliders individually as needed. A user drags a slider to the left to decrease the gain, or drags it to the right to increase the gain. To show or hide the TGC curve, press the Setup key, then click the General tab, and select Show, Hide, or Time Out in the TGC box. Select Show to always show the curve, or select Hide to always hide the curve. If a user select Time Out (the default setting), the curve displays briefly when a user start the application or adjust an individual TGC slider.

When using a linear probe, the Image Format softkey lets a user choose an image format of rectangular (Rect) or trapezoidal (Trap). Omni permits electronic steering of the ultrasound beam to acquire scans of an ROI from several directions. Omni works with linear and curved-linear array probes. When Omni is on, the code OM shows in the scan information display, and the focus markers on the depth ruler change. To turn Omni Beam on or off, press the Omni Beam softkey.

Persistence refers to image frame averaging of real-time images or loops. When the persistence rate is high, the image appears less speckled and smoother. However, increasing the persistence rate may produce a blurred image if the tissue is moving when a user freeze the image. When the persistence is low, the opposite is true.

To change the amount of frame averaging, a user presses the Persist softkey to select a value from 0 to 7. The 0 setting represents 0% and 7 represents 100% persistence. The persistence setting displays onscreen as a character in the information text string.

The Map control lets a user choose how grayscale is distributed across the image. Each map emphasizes certain regions of the signal amplitude range. This feature is useful for close viewing of certain anatomical features and for detecting subtle pathologies. The effect of a user map choice is represented by a reference bar to the left of the depth scale on the image.

The needle guide softkey is active only when a probe that supports biopsies or other medical procedures is connected. To display a needle guide, use the softkeys to turn on the needle guide and to select the correct needle guide, if more than one guide is available. Depending on the connected probe, a user may only see one needle guide option. If the bracket for that probe supports more than one angle or depth, options for each supported angle or depth are displayed. To toggle the needle guide on or off, press the Needle Guide softkey. If more than one guide is available, press the Guide Type softkey to select a different guide. To toggle the target indicator on and off, press the Target softkey. Use the trackball to set the target depth. The distance from the probe to the target displays in the upper left corner of the Imaging window.

The Dynamic Range softkey controls the range of acoustic levels displayed in the image, which affects the contrast of the image. A number on the softkey indicates the amount of compression, from 0 to 100. To adjust dynamic range, use the Dynamic Range softkey. The 0 setting gives greatest contrast, and 100 gives the least contrast. To enable or disable the software image enhancement optimization use the TV Level softkey. Using the softkey, a user can set levels of Off, 1, 2, or 3.

Selecting tissue Doppler imaging (TDI) optimizes the image controls for imaging tissue motion. The control settings vary with the selected scan mode. The control values can be adjusted and preset independently of non-TDI settings. TDI is disabled when the image is frozen. TDI works only with the 4V2A probe. To apply tissue Doppler imaging, press the TDI softkey while in 2D mode.

The transmitted ultrasound signal generates harmonics (signals at frequencies that are multiples of the transmitted signal frequency) in tissue. Tissue harmonic imaging processes a returned harmonic signal to enhance the displayed image. The harmonic used for THI is twice the frequency of the transmitted signal. THI is only available when a 4V2A or 5C2A transducer is connected. When a different type of transducer is connected, the THI button does not display. THI is most effective at mid-range depths. Shallow and deep scans do not benefit from THI. When scan depth is 4 cm or more, THI is disabled. To turn THI on or off, tap the THI button in 2D mode.

When a user selects M-Mode, the system software applies a group of preset image settings and changes the available softkey controls. When a user freezes a scan, the system software replaces the imaging softkey controls with controls for measuring features of the M-mode image and for examining frames and playing loops.

When M-mode is chosen, the system software automatically selects the ultrasound cursor, and moving the trackball controls the cursor position. Pressing the Left Enter key deselects the cursor and locks it in place. Pressing the Cursor key selects the ultrasound cursor.

The active button in the center of the gain knob controls which set of imaging controls for the active modes displays. In M-Mode, those are controls for 2D and M-Modes. The currently-selected control set name displays in blue above the softkeys. To select a different control set, press the Active button. In M-mode, the available Gain Knob controls are 2D Gain controls.

The Sweep Speed softkey sets how fast the timeline is scanned across the Time Series window. To set the sweep speed, a user presses the Sweep Speed softkey to select Slow, Medium, or Fast. The tick marks in the Time Series window are closer or farther apart depending on the speed. Each large tick mark represents one second.

To move the ultrasound cursor, a user presses the Cursor key to select the ultrasound cursor, then uses the trackball to move it to a new location. When the cursor is where a user wants it, the Left Enter key is pressed. When the ultrasound cursor is selected, it turns green. When locked in position, it returns to its normal color.

Enabling Anatomical M-Mode with the Anatomic softkey allows a user to rotate and move the scan line vertically. When a user selects Pulsed-Wave Doppler, the system software applies a group of preset image settings and changes the available softkey controls. When a user freeze a Pulsed-Wave scan, the system software replaces the imaging softkey controls with controls for measuring features of the PWD image and for examining frames and playing loops.

The Active button in the center of the Gain knob controls which set of imaging controls for the active modes displays. In PWD mode, those are controls for 2D and Spectral modes. The currently-selected control set is displayed in blue above the softkeys. To select a different control set, press the Active button. Special Trackball Responses to PWD Mode When Pulsed-Wave Doppler mode is chosen, the system software automatically selects the ultrasound cursor and the Sample Volume Gate (SVG), and moving the trackball controls the ultrasound cursor and SVG position. Pressing the Left Enter key sets the ultrasound cursor and SVG in position. Pressing the Cursor key selects the ultrasound cursor and the SVG when in PWD mode.

The system software lets a user choose the sweep speed for Spectral Doppler modes. A slow speed shows more waveforms over time but less detail. A medium speed is suitable for normal use. Fast speed shows fewer waveforms over time but with more detail. The spacing of the ticks along the top of the Time Series window indicates the sweep speed. Each large tick represents one second. When an image is frozen, a user cannot change the setting. The Sweep Speed softkey sets how fast the timeline is scanned across the Time Series window. To set the sweep speed, press the Sweep Speed softkey to select Slow, Medium, or Fast.

The Time Series window shows the velocity of flow in cm/s or kHz. A user can change the units at any time, so long as the cursor angle is 70° or less. To change the velocity display units, press the Output Unit softkey. Pressing the softkey toggles between cm/s and kHz.

Pulse Repetition Frequency defines the velocity range of the display, which manifests as scale. The maximum value (in Hz) for the PRF depends on the specific probe and the location of the sample volume. The PRF should be set high enough to prevent aliasing, and low enough to provide adequate detection of slow blood flow. It may be necessary to vary the PRF during an exam, depending on the speed of the blood flow, or when pathology is present. Aliasing occurs when the frequency of what a user are observing exceeds one half of the sample rate. If the blood is moving faster than the pulse repetition rate, then the waveform on the display will alias, or wrap around, the baseline. A user can only change this setting when viewing a live image, not when an image is frozen. The system software may automatically change the PRF value when a user move the region of interest, to ensure that the maximum PRF value does not exceed its limit. To adjust the PRF value, use the Scale key. The velocity (cm/s) scale to the left of the Time Series window changes in response to the Scale setting, and the PRF value shows in the Scan Properties display. The increment value for each click depends on the current range. For example, if the Scale setting is 4000, each time a user press the up or down softkey, the system software adds or subtracts 500 Hz from that value, until the selected value falls into a lower or higher range. Increasing the PRF also increases the Thermal Index (TI) value. In Triplex scanning only, the PRF value is tied to the setting in 2D mode (Color Doppler). If a user changes the PRF value on one mode, the system software also changes the PRF value on the other mode. This depends on whether a user is scanning in simultaneous or non-simultaneous mode, which is controlled by the Update key.

Doppler systems use a wall filter (high pass frequency filter) to eliminate unwanted low-frequency high-intensity signals (known as clutter) from the display. Clutter can be caused by tissue motion or by rapid movement of the probe. Increasing the wall filter setting reduces the display of low velocity tissue motion. Decreasing the wall filter setting displays more information, but more wall tissue motion.

Use a wall filter setting that is high enough to remove clutter but low enough to display information near the baseline. To adjust the wall filter value, use the Filter softkey. The wall filter range is from 1% to 25% of the PRF, so changing the PRF with the Scale key also changes the range of the wall filter and the increments by which the Filter softkey changes its setting. The increment value for each click depends on the current range. For example, if the wall filter range is 1000 Hz, each time a user click the Filter softkey, the system software adds or subtracts 100 Hz from the filter value.

When using Spectral Doppler, the user should be aware of the Doppler angle-to-flow (the angle between the axis of the ultrasound beam and the plane that the blood flows in). When the ultrasound beam is perpendicular to the flow (90° angle-to-flow), an absent or confusing color pattern displays, even when the flow is normal. An adequate Doppler angle-to-flow is required to obtain useful Spectral Doppler information. In most instances, the more nearly parallel to the flow the Doppler beam is (the lower the angle-to-flow), the better the received signal. Angles less than 60° provide the best quality Spectral Doppler. Electronic steering is useful when the flow is at a poor angle to the Doppler beam. However, it is often also necessary to press on one end of the probe or the other to improve the Doppler angle-to-flow. Electronic steering is available with flat linear-array probes (the 4V2A and 15L4). Curved linear probes are not capable of electronic steering, and depending on the clinical situation, may require that a user press down on one corner of the probe to obtain an adequate angle to flow. The steering angle does not directly affect the calibration of the velocity scale. To select a different steering angle, the user presses the Steer key to get the desired angle. A user can use this control when viewing a live image. When an image is frozen, a user cannot change the setting.

To obtain accurate velocities, a user must maintain Doppler angles of 60° or less. It is often necessary to press on one end of the probe or the other to improve the Doppler angle-to-flow. In the portable ultrasound system, the velocity display in centimeters per second is shown only in the correction angle range between +70° and −70°. At angles greater than 70°, the error in the velocity calculation is too large, and the velocity scale is converted to frequency (in kHz), independent of the correction angle. The flow-direction indicator still shows on the window, for reference. To adjust the correction angle, press the CA softkeys to increase or decrease the angle. The angle setting displays in the image information section of the Imaging window, to the right of the depth scale. To set the correction angle to to 0 or 60°, press the CA+/□□60 softkey or the Steer 0 softkey. The CA+/□□60 softkey toggles the correction angle between −60° and +60° and the Steer 0 softkey sets the angle to 0°.

A user can invert the Pulsed Doppler waveform. The Doppler scale is separated by a zero baseline across the width of the spectral display. The data above the baseline is classified as forward flow. The data below the baseline is classified as reverse flow. When the waveform is inverted, reverse flow displays above the baseline and forward flow is below the baseline. To invert the waveform, the user presses the Invert softkey. A user can only use this control when viewing a live image. When an image is frozen, a user cannot change this setting.

To adjust the ultrasound cursor in the 2D image display, press the Cursor key, use the trackball to move the cursor, and press the Left Enter key to lock the cursor in position.

The sample volume size control adjusts the size of the Doppler region being examined. The lower the value, the narrower the sample size used in the calculation of flow velocity. The sample volume displays along the ultrasound cursor as two parallel lines. The distance between the two parallel lines is the size of the sample volume in millimeters. To adjust the sample volume (SV) size, press the SV Size softkeys. The SV Size displays on the softkey and in the image information area to the right of the depth scale on the Imaging window. A user can set a value from 0.5 to 20 mm (in 0.5 mm increments).

To adjust the position of the sample volume, select it using the Cursor key, then the use the trackball or the touch pad to move it to the desired location. Press the Left Enter key to anchor it.

A user can only use this control when viewing a live image. When an image is frozen, a user cannot adjust the sample volume. Modifying the depth location of the sample volume affects the Thermal Index (TI) value.

The sample volume indicator allows a user to start a scan in a 2D scan mode, set the sample volume location, and switch to Spectral Doppler mode. The sample volume locks in position. When scanning in CD mode, this procedure switches to Triplex mode (if enabled by a user license). To locate the sample volume, in the 2D window, press the Cursor key, then use the trackball to set the gate position.

The PW gain setting (not the 2D gain setting) increases or decreases the amplification of the returning signal (live or playback) for the Time Series display. The gain should be adjusted so that the spectral waveform is bright, but not so high that the systolic window fills in, or other artifacts are created. To adjust the PWD gain, use the Gain knob. Make sure Spectral shows above the softkeys display. A user can adjust gain for live images or saved loops being played. A user cannot adjust the gain for frozen images or paused loops.

Noise Rejection controls rejection of low-level returned signals. Increasing rejection darkens the image background. A number on the softkey indicates the level of noise rejection. To adjust noise rejection, use the Reject softkey. A number on the softkey indicates the level of noise rejection.

The Update key lets a user choose whether or not to continue scanning the anatomy (displayed in the 2D window) while acquiring Spectral Doppler scan data (displayed in the Time Series window). When Update is selected, the key lights up blue, and the system software continuously updates the 2D scan while acquiring Spectral Doppler data. When not selected, the key lights up white and the system software freezes the 2D data while acquiring Spectral Doppler data. The default setting for this key in most exams is selected (continuous scanning of the 2D and Spectral Doppler data). When a user de-selects the Update key (but does not freeze the scan), a user cannot adjust some of the 2D image controls. To toggle the 2D window between live and frozen, press the Update key.

When a user selects Color mode, the system software displays softkeys and a Gain Knob menu for Color mode. The Active button in the center of the Gain knob controls which set of imaging controls displays. In Color mode, those are controls for 2D and Color modes. When Color mode is chosen, the system software automatically selects the ROI Position (ROI Pos), and moving the trackball changes the position. A click of the Select key above the trackball changes control to the ROI Size; and rolling the trackball shrinks or expands the ROI. When the ROI is in the correct position and is the correct size, click the Left Enter key to set the ROI. Pressing the Cursor key selects the ultrasound cursor, and the trackball controls the cursor position.

Figure 67:
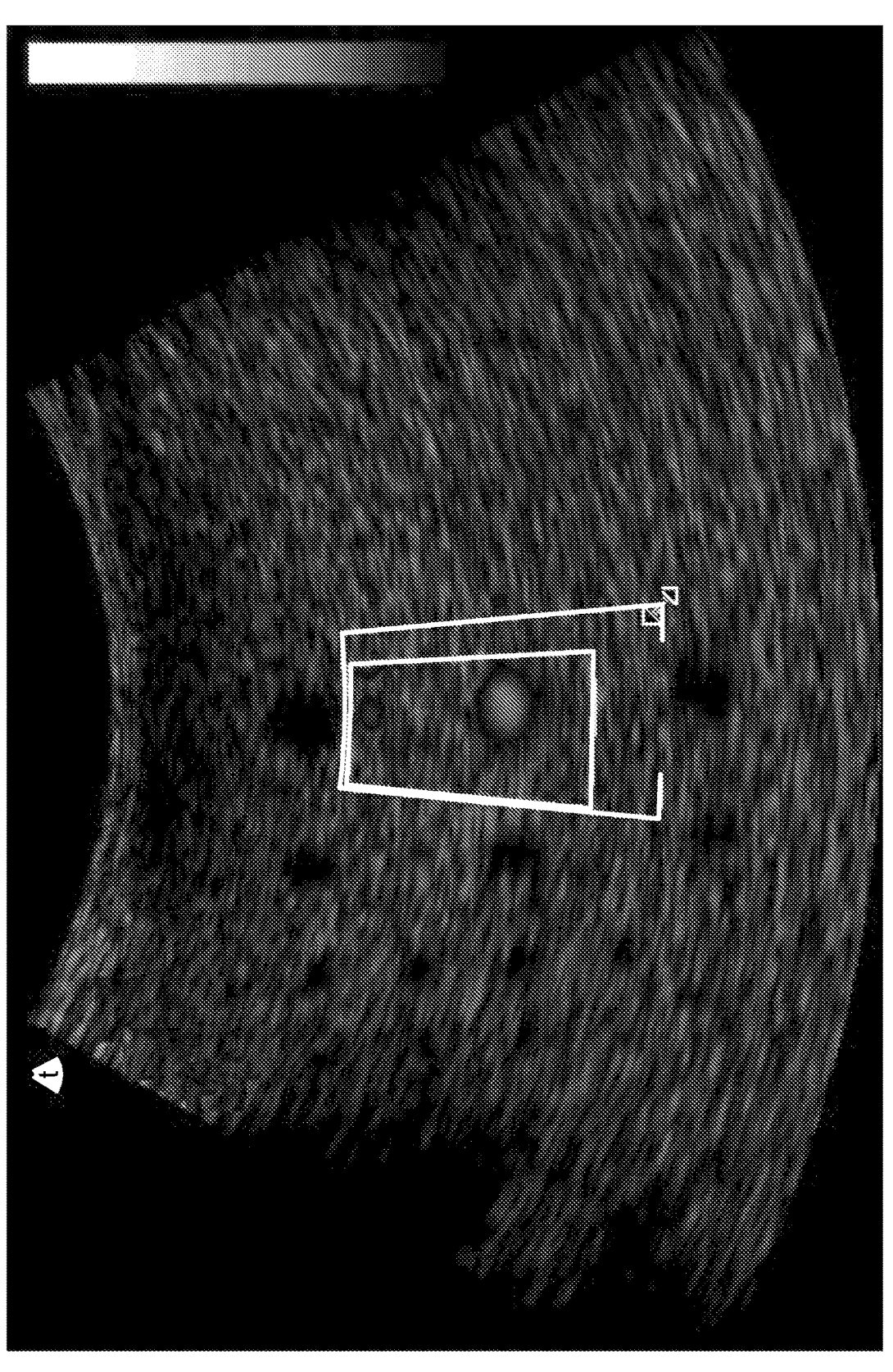
FIG. 67 illustrates a modified ROI window using touch-screen or control panel activations.

The size of the scan area (also referred to as the region of interest, or ROI) is one of the major controls that affect the frame rate. The smaller the scan area, the faster the frame rate. The larger the scan area, the slower the frame rate. A user can move the scan area by pressing the Select key, moving the ROI to a new position, and pressing the Left Enter key to anchor it. Pressing the Select key twice selects the ROI Size, and lets a user resize and reshape it using the trackball or by touch actuation as shown in FIG. 67. A user cannot move or resize the ROI when the image is frozen. To move the region of interest, complete the following steps:

1 Press the Select key to select the ROI. The cursor disappears, and ROI Pos displays in blue above the softkeys.
2 Use the trackball to move the ROI.
3 Press the Left Enter key.

To adjust the size of the region of interest, complete the following steps:

1. Press the Select key twice to select the ROI.

The cursor disappears, the ROI outline becomes a dotted line, and ROI Size displays in blue above the softkeys.

2. Use the trackball to resize the ROI.

The system software may automatically adjust the PRF value when a user move the region of interest to ensure that the maximum PRF is not exceeded for the new depth. Pulse Repetition Frequency defines the velocity range of the display, which manifests as scale. The maximum value (in kHz) for the PRF depends on the specific probe, and the location of the region of interest. The PRF should be set high enough to prevent aliasing, and low enough to provide adequate detection of low flow. It may be necessary to vary the PRF during an exam, depending on the speed of the blood flow, or if pathology is present. Aliasing occurs when the frequency of what a user are observing exceeds one half of the sample rate. If the blood is moving faster than the pulse repetition rate, then the Doppler display will alias, or wrap-around, the baseline. If the PRF is set too high, low-frequency shifts caused by low-velocity flow may not show. As PRF increases, the maximum Doppler shift that can display without aliasing also increases. A user can only use this control when viewing a live image. When an image is frozen, a user cannot change PRF.

To adjust the PRF value, use the Scale key. The increment value for each click depends on the current range. For example, if the PRF setting is 4.0 kHz, each time a user click the right or left arrow, the system software adds or subtracts 500 Hz from that value, until the selected value falls into a lower or higher range. Increasing the PRF also increases the Thermal Index (TI) value.

In Color Doppler, a user can invert the color scale. Normally, the color red is assigned to positive frequency shifts (flow toward the probe), and blue is assigned to negative frequency shifts (flow away from the probe). This color assignment can be reversed by pressing the Invert softkey. Flow toward the probe is always assigned the colors of the top half of the color bar, and flow away from the probe is assigned the colors of the bottom half of the color bar. When a user press the Invert softkey, the Color Doppler reference bar and the color of the scan data within the Region of Interest are both inverted.

Invert may be used when scanning the internal carotid artery (ICA), for example. In general, flow in this vessel goes away from the probe. If Invert is enabled, the ICA flow displays in shades of red. The color bar displays shades of blue on the top half, and shades of red on the bottom.

Doppler systems use a wall filter (high pass frequency filter) to eliminate unwanted low-frequency, high-intensity signals (also known as clutter) from the display. Clutter can be caused by tissue motion or by rapid movement of the probe. Raising the wall filter setting reduces the display of low velocity tissue motion. Lowering the wall filter setting displays more information. However, more wall tissue motion is also displayed. The wall filter setting should be set high enough to ensure that Color Doppler flash artifacts from tissue or wall motion are not displayed, but low enough to display slow flow. If the wall filter is set too high, slower flow may be not seen. Set the wall filter setting higher for applications where there is significant tissue motion, or in instances where the probe is moved rapidly while scanning in Color Doppler mode. Set the wall filter setting lower for small parts or instances where flow is slow but there is not much tissue motion. Use a wall filter setting that is high enough to remove clutter but low enough to display Doppler information near the baseline. To adjust the wall filter value, use the Filter softkey. The current value displays on the softkey and on the Image Information area of the Imaging window (as a number following "WF"). The wall filter range is from 1% to 50% of the Scale value.

Color gain can be increased to correct an inadequate fill of color within a vessel, and decreased to correct an unacceptable amount of color outside of a vessel. A user can adjust the color gain to increase or decrease the amplification of the returning signal being played or displayed. There is no indicator in the scan properties list for Color gain like that for 2D gain. To change the color gain, turn the Gain knob to the left (decrease) or right (increase).

The color priority of the image defines the amount of color displayed over bright echoes, and helps confine color within the vessel walls. Color priority affects the level at which color information overwrites the 2D information. If a user must see more flow in an area of some significant 2D brightness, increase the color priority. To better contain the display of flow within the vessels, decrease the color priority. If the color priority is set to zero, no color is displayed.

To change the color priority, use the Priority softkey. The current Color Priority setting shows on the softkey display.

The color persistence setting determines the amount to be averaged between frames. Increasing the persistence causes the display of flow to persist on the 2D image. Decreasing the persistence allows better detection of short duration jets, and provides a basis for better flow/no flow evaluations. Adjusting color persistence also produces better vessel contour depiction. To change the color persistence, use the Persist softkey. The current Color Persistence setting shows on the softkey display.

Color baseline adjustments are usually unnecessary. The baseline refers to the zero baseline within the Color Doppler image. To adjust it, move the baseline down to display more positive flow (forward) and move the baseline up to display more negative flow (reverse). This adjustment can be used to prevent aliasing in either direction. To move the color baseline, use the Baseline key. The current setting of the baseline shows on the Color Doppler reference bar. A user can see the effect of a user change on the color reference bar. If the bar is not visible, select Setup>General>Reference Bar to add it to the image display.

The Map softkey chooses one of five color maps to show Color Doppler data. A user can configure the color map independently for each exam by selecting an exam, then a color map. When a user selects a different exam, the system software loads the color map for the selected exam. The color maps are designated A through E. Some maps use more colors than others, and some display in a smoother gradient than others. To select a color map, use the Map softkey. The current map letter shows in the softkey display.

Triplex scan mode combines Pulsed-Wave Doppler scanning with Color Doppler scanning. To activate Triplex scanning, select Color Doppler mode, then press the PW key on the console. In Triplex scanning only, the PRF value is tied to the setting on the 2D mode (Color Doppler). If a user changes the PRF value in one mode, the system software also changes the PRF value in the other mode. This depends on whether a user are scanning in simultaneous or non-simultaneous mode, which is controlled by the Update console key. To adjust image controls for Triplex scanning, first adjust the image controls for the 2D scan mode, then go to the Color Doppler window and press the Cursor key to select the PWD ultrasound cursor and Sample Volume location. Some of the 2D image controls cannot be adjusted when scanning in Triplex, so a user must adjust the image controls in 2D mode. A user can only adjust these image controls during live scanning. When a user freeze a scan, the system software replaces the softkeys with a different set, for printing and making annotations and measurements on the scan image. The application adds the Time Series window for PWD to the 2D image.

When scanning in Triplex mode, a user can move the region of interest, adjust its size, or move the range gate. To move the region of interest, complete the following steps:

1. Press the Select key to select the ROI.
2. Use the trackball to move the ROI.
3. Press the Left Enter key.

When Triplex scanning, the PW softkeys are available. The Image Information display shows two PRF values in Triplex mode. The system software sets the Color PRF to an integral fraction ($\frac{1}{2}$, $\frac{1}{3}$, $\frac{1}{4}$, etc.) of the PWD PRF. If a user change the PRF value in one mode, the system software changes the other PRF setting as well. A user can independently set the Wall Filter for the 2D and PWD scans. The Active button in the center of the Gain knob controls which set of imaging controls for the active modes displays. In Triplex mode, those are controls for 2D, Spectral, and Color modes. The currently-selected control set is displayed in blue above the softkeys. To select a different control set, press the Active button.

Measurements accompanying ultrasound images supplement other clinical procedures available to the attending physician. Accuracy of the measurements is determined by the system software and by proper use of medical protocols. When a user freezes a scan, the system software changes the set of available softkey controls and enables the Caliper key. Pressing the Caliper key enables the measurement controls. Repeatedly pressing the Caliper key cycles through the Distance, Trace, and Ellipse measurement options. When a user saves an image, all measurements are saved with the image.

A user can also make measurements on both screens when using Split Screen mode. To obtain a complete set of measurements, a user often has to acquire multiple scans. A user can make as many scans and measurements as required for the study without losing any measurements. Measurements remain on the Imaging window until a user selects a different exam, selects a different scan mode, loads a different patient, presses the Delete softkey, presses the Clear All softkey The default location for the display of measurement results in the exemplary portable ultrasound system is the top left of the image. To move the results to the bottom of the image, press the Results softkey (enabled when a measuring tool is active). A user can also change the default location to the bottom of the image using the Result Display Location radio buttons on the Setup/Measurements window.

When a user chooses an exam preset, the system software makes a default set of measurements available. The default set may vary from one supported probe to another. A user can also add custom measurements to the available lists.

The system loads a set of measurements tailored for the preset a user selects. The measurements are selected using the Calcs key. To select a measurement type, press the Calcs key, and click the desired measurement.

When a user freezes a 2D scan, the system software displays softkeys and a Gain Knob menu for measuring, printing, and playing loops in 2D mode. The Measure function in the 2D window allows measuring Distances; measuring Elliptical, circumference and Area; tracing Areas on the Image; split-Screen Measurements; In general, a user selects what they want to measure from the menu of Measurements.

If a user selects a specific measurement, such as Area, only the softkeys that work with that measurement are available.

To measure a distance in the 2D window, a user completes the following steps:

1 If the image is live, press the Freeze key. The image freezes and the softkey controls change.
2 Press the Caliper key.
3 To measure a detailed area with precision, use the Zoom function to enlarge an area of the 2D scan.
4 Press the Caliper key.
5 Click where a user want to start measuring, move the target cursor, and click where a user want to finish measuring.
6 The system software displays the results in the top left corner of the 2D window.

If a user does not see the measurement value, the user presses the Setup key, then selects General>Measurement Value. To make more than one measurement of the same type on an image, press the appropriate softkey again, then make the additional measurement. When making a series of 2D measurements using the Caliper key, a user can keep the caliper active by checking the Keep caliper active box on the Setup/Measurements window. When the box is checked, a new caliper cursor appears when a user set the end point of a caliper measurement. When a user finishes making measurements, the user saves the image, then presses the Freeze key to turn off caliper measuring.

Figure 68:
FIG. 68 illustrates measurement of an ellipse on an image.

A user can use either the Ellipse softkey or the Trace softkey to measure a circumference on the image as shown in FIG. 68. To measure an oval area, use the Ellipse softkey. To measure the area of an irregular shape, use the Trace softkey. To measure a small area, use the Zoom function before a user measure.

To use the ellipse tool to measure an elliptical area, complete the following steps:

1 If the image is live, press the Freeze key. The image freezes and the softkey controls change.
2 Press the Caliper key.
3 Press the Calcs key. The Measurements menu opens.
4. Select the measurement type by clicking it in the Measurements menu. If a user selects Circumference from the Measurement menu, the Ellipse tool is automatically activated.
5. Position the target cursor at one end of the area that a user want to measure and click.
6. Move the target cursor to the other end of the desired area, and click.
The system software displays a green line and shows the circumference or area values at the top of the image.
7. To adjust the other axis of an ellipse, press the Select key so that Axis is highlighted (above the softkey display), then use the trackball to adjust the width of the ellipse.
8. When the measurement is correct, press the Left Enter key to lock it in. A user cannot change a measurement after locking it in. A user can now make another measurement without deleting the measurements a user locked in.
9. To save the measurements, press the Store Key. The image is saved with all measurements.

Figure 69:
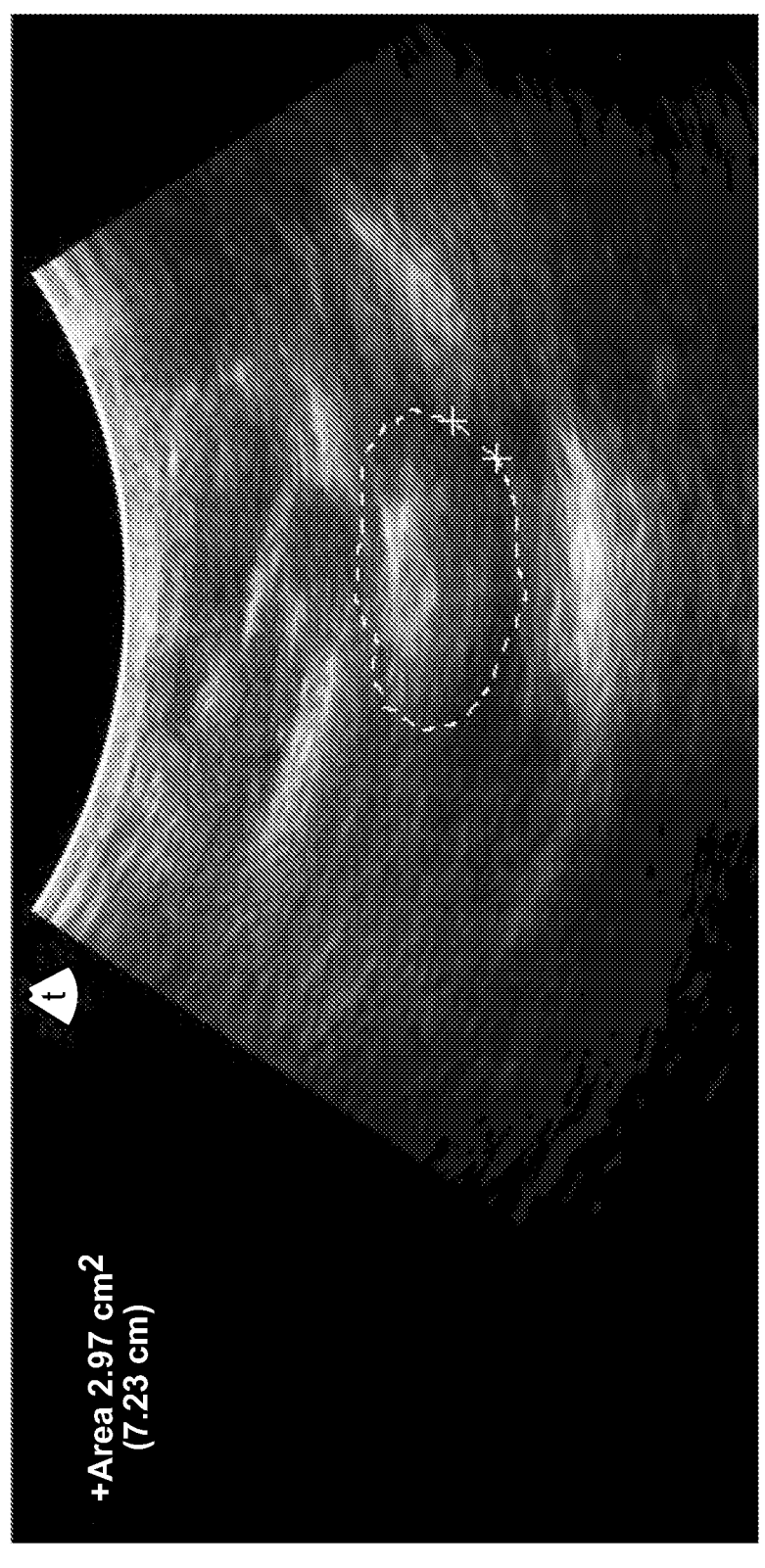
FIG. 69 shows trace measurement of shapes on an image.

The system software lets a user measure an area by tracing the contour of any shape and as a tumor shown in FIG. 69 on an image. A user can also use the Ellipse tool to measure an area A user can use the trace tool to trace an irregular shape by sketching the outline and draw a polygon by clicking on corners of the shape A user can also combine these methods to trace an area on the image.

To trace an outline: a. User clicks to start measuring and b. User uses the trackball to drag the tracing cursor around the object the user want to trace. Then c. when a user trace is nearly complete, press the Left Enter key, and the software completes the loop by drawing a straight line from the current cursor position to the starting point.

When a user presses the Left Enter key, the trace turns white, and can no longer be edited. Before a user clicks the Left Enter key, a user can reverse the track of the cursor to delete parts of the trace.

5. To Edit the Uncompleted Trace:
a. Press the Select key, so that Erase is highlighted above the Softkey display.
b. Use the trackball to erase the unwanted part of the trace, from most recent back toward the beginning.
c. When all the unwanted parts of the trace are erased, press the Select key again, so that Draw is highlighted above the Softkey display.
d. Use the trackball to finish the trace.
e. Press the Left Enter key to complete the trace.

When measuring in Split Screen mode, all measurements are displayed in a single list, even if both screens contain measurements. A user can make a measurement on either screen or across both screens. To make alternating measurements on split screens, a user must Disable Return to live imaging:

1 Press the Setup key.
2 Click the Display tab.
3. Click Return to live imaging on toggle active screen, so that the box is not checked.

This allows a user to make a measurement on one screen, switch to the other screen and make a measurement there, then return to the first screen and make additional measurements. If the box in the Setup/Display window is checked, returning to the first screen makes it live and erases all measurements on it. To make a measurement across both screens:

1 Disable Return to live imaging, as described above.
2 Freeze a scan on one screen.
3 Press the Toggle Screen softkey.
4 Freeze a scan on the other screen.
5 Press the Caliper key repeatedly until the tool a user need displays.
6 Click the start point of the measurement.
7 Click the end point of the measurement.
8 Press the Left Enter key.

When a user freezes an M-mode scan, the system software displays softkeys and a Gain Knob menu for measuring, printing and playing loops in M-mode.

In the Time Series window of an M-Mode scan, a user can measure their heart rate (HR) and the distance (includes time over distance [TD] and Slope values) To measure in the M-Mode Time Series window, complete the following steps:

1 Press the Freeze key.
2 Press the Caliper key until the measurement type a user need displays.
3 Click the target cursor where a user want to start measuring.
4 Move the target cursor and click at the desired end location. The measurement displays at the top left of the Time Series window.

When a user freeze a Pulsed-Wave Doppler or Triplex scan, the system software changes the softkeys to allow measurement, printing, and other functions.

A user can use the CA (correction angle) softkey and the 0/+−60 softkey to adjust the angle on the frozen scan. This function works the same as the Correction Angle on the PWD tab. If a user has added 2D measurements to the Spectral measurement set, a user can perform 2D measurements in Spectral Doppler imaging screens. To make 2D measurements on Spectral Doppler imaging screens, press the Calcs key. Any 2D measurements a user have added to the Spectral measurement set appear in a Measurements menu at the top right corner of the imaging screen.

Figure 70:
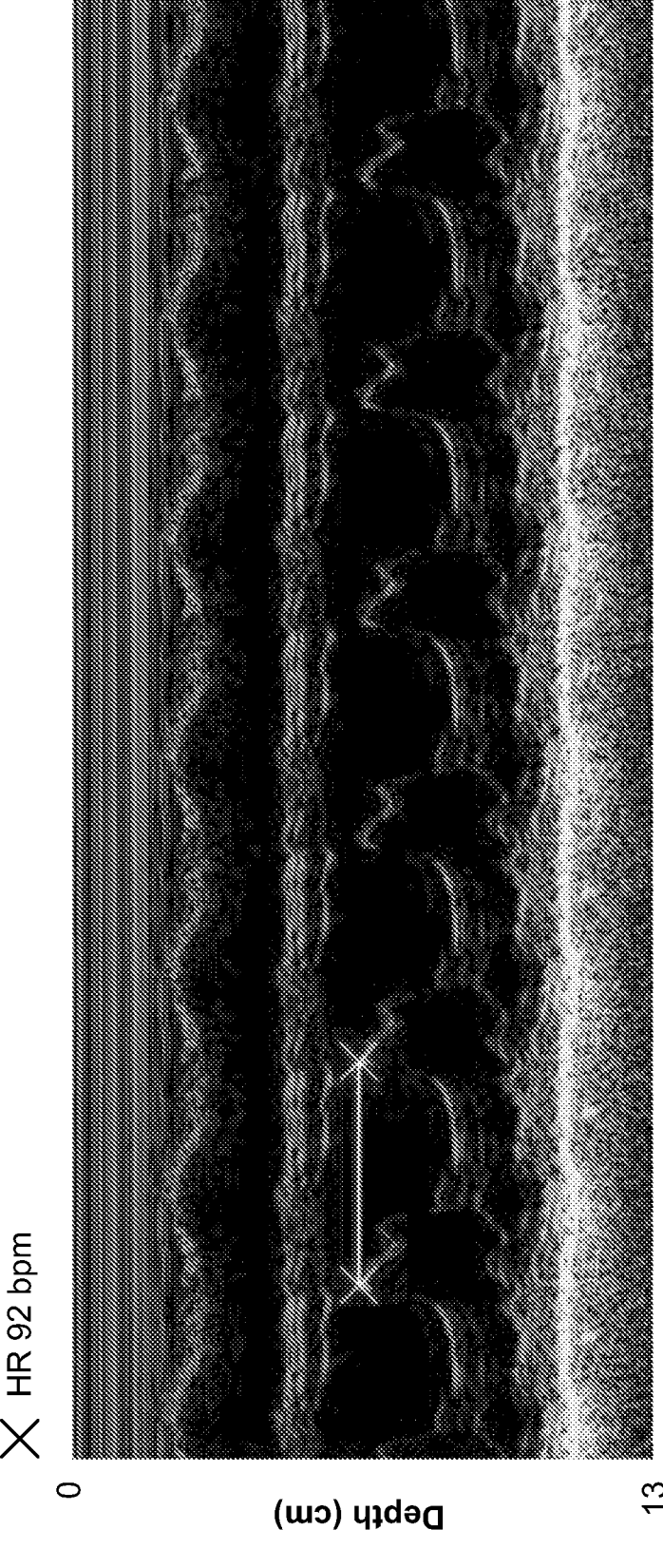
FIG. 70 shows a time series measurement display window.

A user can make any of a number of cardiac measurements and then generate a report. The system software provides Cardiac measurements for the 2D Image Display window, the M-Mode Time Series window, and the PWD/CW Time Series window (See FIG. 70). When a user make a measurement in the 2D Image Display window, the value of the measurement displays at the top left of the window.

Intima Media Thickness (IMT) measurements are useful for diagnosing atherosclerosis, by measuring the thickness of an arterial inner wall. To measure the carotid artery inner wall:

1. Connect a linear probe to the system.
2. In 2D mode, select the Carotid preset.

3. Scan the carotid artery.
4. Freeze the scan.
5. Press the Calcs key. The Measurements menu appears.
6. From the menu, select IMT. A green square displays on the image.
7. Use the trackball to move the green square so that it covers both walls of the artery.

If necessary, press the Select key to allow resizing the box using the trackball. Pressing the Select key once allows horizontal resizing; pressing twice allows vertical resizing. The width of the box displays at the top left of the Imaging window. If the display does not trace the inner walls of the artery correctly, press the Edit softkey, then click the proper location of the wall on the image.

8. Press the Wall softkey to select the anterior wall, the posterior wall, or both. The measurements display at the top left of the Imaging window.

The system software includes default groups of commonly-used measurements that are available in the Measurements menu when an image is frozen. A user can add or remove measurements from groups, and create or delete groups.

The following tables list the measurements that are available for the various scan modes.

a. This calculation is available in CW mode. The Time-Series window must display a velocity range that includes 300 cm/s. Use the Scale softkey to achieve this.
b. This calculation is available in CW mode. The Time-Series window must display a velocity range that includes 200 cm/s. Use the Scale softkey to achieve this.

Figure 71:
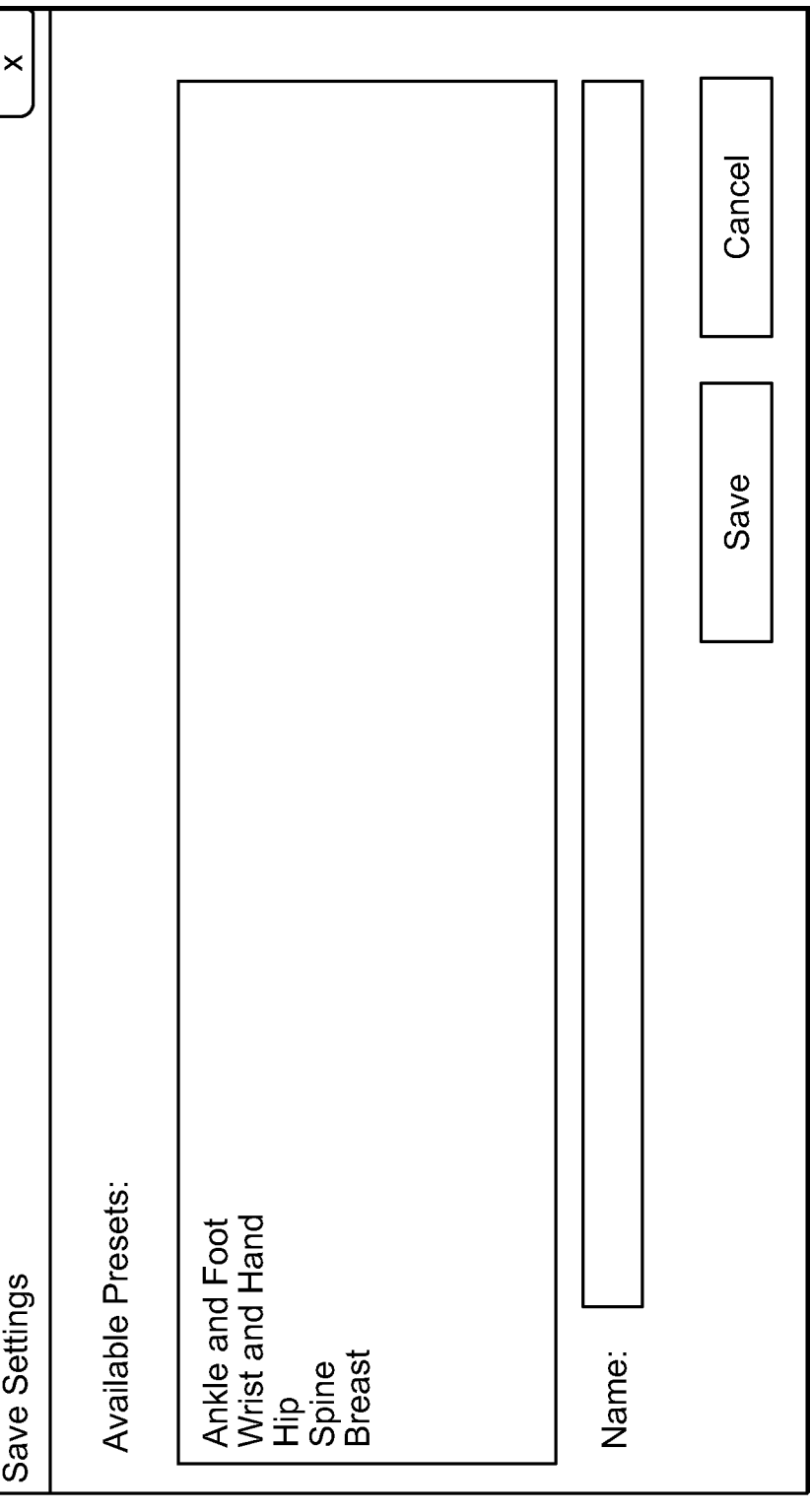
FIG. 71 illustrates an anatomical study preset selection window.

Choosing an exam loads optimized presets for many image control settings, based on the anatomy to be scanned as seen in FIG. 71 including, the probe used, and the scanning mode. The exam presets also specify the measurements appropriate for the exam. A user can use these optimized presets as is, or a user can adjust any of the image control settings as necessary for the specific patient and the specific exam. A user can create additional presets to store sets of image control settings for specific kinds of exams. Customized presets can minimize the number of settings a user must change each time a user performs a specific ultrasound exam.

The portable ultrasound system provides predefined presets for all supported probes. Although several probe models may support the same exam types, the preset image control settings are unique to each probe model. An exam includes predefined image control settings used for high, medium, and low frequencies. When a user selects a frequency range on the console, the system software loads other exam settings optimized for that frequency. When a user selects a different frequency, a user need not reload the preset or load a different preset; the system software automatically updates the settings for the selected frequency. The following table lists the preset exams available for each probe.

The exemplary portable ultrasound system provides customized exam presets for scanning different anatomies. When a user chooses a preset, the system software loads image controls settings that are customized for that anatomy, the chosen scanning mode, and the connected probe. To select a preset, the user chooses it from the Presets menu, highlights the preset by clicking it, then presses the Left Enter key. If a user does not see a preset name that corresponds to the kind of study a user wants to perform, a user can create a custom preset.

The system software displays only those exams supported by the connected probe. If a user creates any custom exams, they show at the bottom of the Exam menu.

In addition to using the provided exam presets, a user can create custom presets. Custom presets include a users own specific modifications to the preset image control settings. A user can then load the custom preset and skip setting the image control parameters. A user can customize any preset to include user specific control settings. A user cannot change the default settings for a system preset. However, a user can edit the image control settings of a system preset, then save it with a different name. To create a preset or to modify an existing custom preset, a user completes these steps:

1 Select the system preset or custom preset that has settings close to the one a user want to create.

2 Modify the image control settings as required. Press the Preset key.

4. Press the Save Settings softkey. The Save Settings window opens. It contains a list of presets, with system presets at the top and custom presets at the bottom.

5. Type a name for the custom preset in the Name: field. The name can be up to 16 characters long. If a user are modifying an existing custom preset, make sure that name is in the field.

6. Click Save. The system software saves the image control settings.

The new preset is now available for use whenever the current probe is connected to the computer. If a user connect a different probe, this new preset is not available.

Images and loops are saved to the Study directory, in the appropriate patient folder. If no patient is associated with a scan, no images or loops can be saved. All images and loops for a given patient saved on the same day are saved in the same study, unless the New Study button in the Patient window is clicked before a later image is saved. A single study cannot include images and loops saved on different days. For Split Screen mode, a user can save the Split Screen image (as a single frame showing both screens). A user can save the Split Screen image as a loop file. When a user does, the system software saves the active screen as an image loop, and the other screen as a single frame.

To Save an Image or Loop, Complete these Steps:

1 Press the Freeze key if viewing a live image.

2 To save an image, press the Store key. A user can also save an image by pressing F8 on the computer keyboard.

3 To save an image loop, press the Store key when live imaging (not frozen).

4 To add the saved image or loop to the report for the current study, place the cursor on the image or loop, press the Right Enter key, and select Add to Report.

5 To delete an image or loop, place the cursor on the image or loop, press the Right Enter key, and select Delete. If a user did not load patient information for an exam, a user cannot save images or loops.

When a user saves an image or loop, a thumbnail of it appears in the area at the right of the Imaging window. When more than 12 images or loops are included in the study, some will be hidden. To view them, click the scroll arrow at the bottom of the thumbnail area. To scroll back up, click the scroll arrow at the top of the thumbnail area. To review a saved image or loop in the current study, double-click the thumbnail of the image or loop. It displays in the Imaging window.

A user can find saved patient studies by using the Study List . . . button on the Patient window.

To find previously-saved studies in the Patient window:

1. Press the Patient key.

2. In the Patient window, click the Study List . . . button. The Study List window opens, displaying a list of saved studies.

3. The default is to show all the studies. To find studies done on a specific day or range of days, click the Study Date menu, and select Today, Last 7 days, Last 30 days, or In date range.

If a user clicks In date range, a box opens where a user can select a range of dates to show studies from.

4. Find the desired study in the list, and click it to select it.

5. Press the Review key. The selected study loads in the Imaging window.

A user can export studies, images to a CD, a DVD, a DICOM server, a USB drive, or another location on a network. When exporting a study, image, or loop, the system creates a uniquely-named subdirectory for each study, image, or loop. A user can export an image onto the computer hard drive or an external drive, as a JPEG, BMP, or AVI format. A user can also attach an image in one of those formats to an email message. The system software allows a user to export an image or loop to external media in any of these formats: AVI, Bitmap, DICOM, JPEG. A user can email image and loop files or include them as graphics in other applications. If a user save images using the JPEG format, the user should be aware of the effects of data compression. By default, the system software uses a lossy JPEG compression algorithm. After compression, some of the image data is gone. When viewed, the compressed image may show artifacts caused by the JPEG compression. The artifacts may also show if a user view the image on a medical viewing station that allows a user to window and level the image. The amount of compression on an image cannot be selected or predicted. One scan may compress at a ratio of 10:1, and another may compress at a ratio of 5:1. It is possible that medically-significant structures could be lost as a result of compression, regardless of the amount of compression. In addition, compression may result in artifacts appearing on the image.

The exemplary portable ultrasound system can aid in performing medical procedures such as biopsies. To perform a biopsy, a user needs a probe, needle, needle guide kit, and bracket. The biopsy feature can be used with the selected probes. When all of the preparatory steps are complete, and a user has recently verified the alignment, perform the biopsy on the patient. The system software displays guide lines for the specific probe, bracket, and needle gauge used in a biopsy or other medical procedure.

The portable ultrasound system software provides two types of needle guides, which are used with different physical needle guides. A needle guide is only available when a probe that supports that guide is connected to the ultrasound system. If more than one needle guide is available for the connected probe, a user must verify that the selected guide matches the hardware installed on the probe. The in-plane guides work with the standard needle guide hardware. These guides are two parallel lines that indicate the path of the needle when the appropriate hardware is used. The transverse guide is a circle that indicates the depth obtained when guide hardware that includes clips to set the angle and depth of insertion is used. To turn off the needle guides, press the lower Needle Guide softkey. If a user were using the transverse needle guide, a user may have to press the lower Needle Guide softkey several times.

Figure 72:
FIG. 72 illustrates a needle visualization using an adjusted transmission frequency.

The portable ultrasound system offers onscreen needle guides, and with particular probes, enhanced imaging of the needle. If a user system is licensed for needle enhancement, the system brightens the needle image as seen in FIG. 72 if all of the following conditions are met; 2D mode is selected; a probe is connected to the system; a patient profile is selected and the N key on the console is pressed.

Pressing the N key displays a solid blue line and a diverging dotted blue line on the scanning window, which mark the limits of needle enhancement. If the point of the needle goes beyond these limits, the part of the needle image that is beyond the limit is not brightened. The dotted line applies to steeper needle insertions. A softkey labeled Needle Lt/Rt toggles between lines angled from upper left to lower right and lines angled from upper right to lower left. When needle enhancement is active, the legend ENV (for Enhanced Needle Visualization) appears in the scan information area at the right side of the imaging window.

To activate needle image enhancement, press the N key on the console.

To perform a biopsy using the in-plane needle guides, complete these steps:

1 Start live imaging.

2 Press the Needle Guide softkey. The needle guide lines show in the Imaging window, along with a warning message.

The warning closes and the system software displays the needle guides and target indicator. The guide lines show a user where the needle should be inserted into the patient. The green target indicator can be moved within the guidelines to the exact location of the biopsy target. The Distance to Target: value then shows exactly how deep the needle must be inserted to reach that target.

The large tick marks on the guide lines are at 1 cm intervals, and the distance between the guide lines is fixed at 1 cm.

4. If the green Target Indicator does not show within the guides, press the Target softkey.

The system software adds the "Distance to Target" value at the top of the image.

5. Use the trackball to move the target indicator to the correct depth. A user cannot move the target outside of the guide lines.

6. Follow the proper medical protocol to complete the biopsy.

The target distance is measured in centimeters and is calculated as the distance from the bottom of the clip to the patients' skin (as indicated by the top of the needle guide lines) plus the distance from the skin line to the target as indicated by the location of the green target indicator. When a user inserts the needle, it should be located near the center of the guidelines. If the needle appears outside of the lines, verify that a user have selected the appropriate needle guide.

To Perform a Biopsy Using the Transverse Needle Guides, Complete these Steps:

1. Start live imaging.

2. Press the Needle Guide softkey. The needle guide lines show in the Imaging window, along with the warning message.

3 Click OK.

4 Press the Guide Type softkey.

A transverse needle guide circle replaces the in-plane needle guides on the Imaging window, and the Needle Guide softkey displays the identification of the guide.

5. If the guide is not the correct one for the clip a user have attached to the hardware guide, press the Guide Type softkey until the correct guide displays.

6. Follow the proper medical protocol to complete the biopsy.

To ensure that the probe and biopsy attachment are accurately aligned, and that the needle path is within the stated specification, a user should periodically conduct a simulation test. To conduct this test, a user must have an assembled biopsy bracket, needle guide, and a water tank. Use 2D to verify the alignment, and do not use the Zoom tool. The needle guides do not show in zoomed displays.

To verify the alignment of the probe and biopsy attachment, complete these steps:

1 If the needle guides are not visible, press the Needle Guide softkey. The biopsy guides appear in the Imaging window.

2 Press the Guide Type softkey to select the needle guide to use for the test. There may be only one guide available for the installed probe.

3 Assemble the bracket, needle guide clip, and gauge insert pin.

4 Insert the needle into the gauge insert pin.

5 Place the needle in a water tank, ensuring that a user do not touch the side or bottom of the water tank (which can bend the needle and produce an inaccurate reading).

6 Verify that the needle appears clearly between the two guidelines.

7 Remove the needle from the biopsy bracket and safely dispose of the needle.

8 Detach the biopsy bracket from the probe.

The system software lets a user make small adjustments to the positioning of the needle guides (used in biopsies) and the insertion grid (used for cryoablation or brachytherapy). When a user receives needle guides, they are already configured and tested for angle and depth. The angle is the number of degrees between the X-axis and the Y-axis (the needle axis). The depth, shown in millimeters, is the point at which the biopsy needle and guide lines intersect the vertical center line of the 2D image.

A user can make marginal changes to the upper and lower limits for angle and depth on the Needle Guide Error Correction dialog box. A user changes to these settings are visible in the needle guidelines, and are saved by the system and used for all biopsies until a user change them again. A user can change the value within these ranges: Angle: –2° to 2° and Depth: –1 mm to 1 mm.

To change the needle guide error correction values for any probe except the biplanar probe, complete these steps:

1 Press the Setup key.

2 Click the Display tab. The Setup Display window opens.

3. In the Needle Guide section, click the Calibration button. The Needle Guide Calibration dialog box opens.

A user can click the Apply button to see the effects of a user choices without closing the dialog box. click the Default button to reset the values to the factory-set values.

1 Next to the Angle Correction field, click the left and right arrows to correct the angle by one or two degrees.

2 Next to the Depth Correction field, click the left and right arrows to correct the depth by plus or minus one millimeter.

3 Click OK to save a user entries and close the dialog box.

DICOM (Digital Imaging and Communications in Medicine) is a format created by NEMA (National Electrical Manufacturers Association) to aid in the distribution and viewing of medical images such as ultrasound scans. If a user has the DICOM option installed on a user portable ultrasound system, a user can: send studies to a DICOM server where they can be used by other applications that support DICOM files and use DICOM Worklist to search the archive of patient studies on the DICOM server, and copy patient info sets to the portable ultrasound system so that exams on the system are identified with the correct patients When a user sends a study to a DICOM server, the system software saves the study in a temporary location on a user computer. The studies are then sent to the server.
To Send a Study to a DICOM Server, Complete these Steps:
1 Load the study (if it was previously saved) or obtain and save a new scan.
2 Press the Export softkey. The Export Selection window opens.
3 In the Export destination: section, make sure the DICOM Server radio button is selected.
4 Click the name of the study a user want to send.
5 Click Export. The portable ultrasound system application sends the study to the configured DICOM server.
When a user export studies to a CD or DVD, a user has the option to include a viewer for DICOM files on the disc. DICOM Worklist is a function of the portable ultrasound system software that connects to a DICOM server using a network service, and generates a list of patient information sets that meet chosen criteria. Worklist finds patient records based on parameters set in the Setup>DICOM>Query window.

To prepare for an ultrasound exam, the ultrasound technician queries Worklist using parameters that include the patient's information. The query reruns a worklist of all the patient information sets that meet the criteria. The ultrasound technician selects a patient's record on the worklist, and the exam is automatically attached to that patient's information (the Patient Info window is populated with the selected patient's information.) The technician can also use Worklist to obtain the patient information from the DICOM server and apply the information to a current exam. There are two available types of Worklist queries: auto queries and manual queries.

Auto queries run periodically when the ultrasound system is on, and return a list of patient info sets that match the criteria set in the Query window as a broad query. For example, an auto query can be set up to return a list of ultrasound exams that are scheduled on the current date. The facility's scheduling administrator enters an ultrasound exam for a patient into DICOM, and when the scheduled date arrives, the Worklist auto query collects the patient info and adds it to the worklist.

Manual queries can take two forms: broad queries, and patient-based queries. Broad queries search all records on the DICOM server, using the parameters chosen in the Options window. Broad queries are preset groups of parameters. They can be used as they are, or modified with different parameters, or applied to patient-based queries.

Patient-based queries search the records using a patient name, accession number, or Patient ID. They can be further limited to the parameters in a broad query.

A user can make a broad query that searches all the patient records and returns all the patient info sets that match the criteria, or a patient-specific query that searches for a specific patient's info set. A patient-specific query can use the same criteria as a broad query, returning only those info sets that match both the criteria in the broad query and some data specific to the patient.

The checkbox controls whether toggling between split screens makes the active screen live or not. When the box is unchecked, toggling between the screens leaves them both frozen. Pressing the Freeze key makes the active window live. Toggling to the other screen and back freezes both screens again. When the box is checked, toggling between windows makes the active window live, even if it was previously frozen using the Freeze key.

When they are selected, Spectral Doppler modes normally open updating both the Time Series display and the 2D display simultaneously. This is the default, and is the Simultaneous selection on the Setup Display window. Selecting Non-Simultaneous causes Spectral Doppler modes to open with the 2D display frozen. Whichever radio button is selected, pressing the Update key toggles the 2D display between live and frozen.

This section includes a checkbox that shows or hides the Target Indicator and a button that opens the Needle Guide Calibration window. Needle guide calibration is used exclusively with the biopsy/medical procedures options.

These radio buttons set the relative sizes of the 2D display and the Time-Series display on the Imaging window.
S/L makes the 2D display half the height of the Time-Series display
Equal makes the 2D display the same height as the Time-Series display
L/S makes the 2D display twice the height of the Time-Series display
This chooses the thermal index that is displayed on the scanning window.
TIS is the Soft Tissue index; and TIB is the Bone index; TIC is the Cranial index.

When this box is checked, toggling from one split-screen view to the other makes the selected view live. When the box is not checked, both views remain frozen when toggling from one to the other, until the Freeze key is pressed.

When a user press the Setup key, then click the Measurement tab, the Setup window lets a user choose which measurements appear on the menu accessed by the Calcs key on frozen images. The Setup Measurement window also includes controls for choosing the size of the measurement cursor, the tables used in calculating obstetric measurements, and the port used to send measurements to another location. The Volume Calculation Coefficient selection chooses either the standard PI/6 ellipsoid coefficient, or a custom value. The default for the Custom selection is 0.479, another commonly used value, but a user can enter any value.

The above devices and methods can be used with conventional ultrasound systems.

Preferred embodiments are used in a touchscreen actuated tablet display system as described herein. Touch actuated icons can be employed such that gestures can be used to control the imaging procedure.

It is noted that the operations described herein are purely exemplary, and imply no particular order. Further, the operations can be used in any sequence, when appropriate, and/or can be partially used. Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2, etc., or by rounded-off approximations thereof, unless otherwise specified.

With the above illustrative embodiments in mind, it should be understood that such embodiments can employ various computer-implemented operations involving data transferred or stored in computer systems. Such operations are those requiring physical manipulation of physical quantities. Typically, though not necessarily, such quantities take the form of electrical, magnetic, and/or optical signals capable of being stored, transferred, combined, compared, and/or otherwise manipulated.

Further, any of the operations described herein that form part of the illustrative embodiments are useful machine operations. The illustrative embodiments also relate to a device or an apparatus for performing such operations. The apparatus can be specially constructed for the required purpose, or can incorporate general-purpose computer devices selectively activated or configured by a computer program stored in the computer. In particular, various general-purpose machines employing one or more processors coupled to one or more computer readable media can be used with computer programs written in accordance with the teachings disclosed herein, or it may be more convenient to construct a more specialized apparatus to perform the required operations.

The foregoing description has been directed to particular illustrative embodiments of this disclosure. It will be apparent, however, that other variations and modifications may be made to the described embodiments, with the attainment of some or all of their associated advantages. Moreover, the procedures, processes, and/or modules described herein may be implemented in hardware, software, embodied as a computer-readable medium having program instructions, firmware, or a combination thereof. For example, one or more of the functions described herein may be performed by a processor executing program instructions out of a memory or other storage device.

It will be appreciated by those skilled in the art that modifications to and variations of the above-described systems and methods may be made without departing from the inventive concepts disclosed herein. Accordingly, the disclosure should not be viewed as limited except as by the scope and spirit of the appended claims.

The invention claimed is:

1. A portable medical ultrasound imaging device comprising:

a transducer probe housing a transducer array; and a portable tablet housing mounted on a cart, the portable tablet housing having a computer in the portable tablet housing, the computer including a central processing unit performing a scan conversion operation and at least one memory, a field programmable gate array (FPGA) to control transmit signals emitted by the transducer array, wherein the portable tablet housing is powered by a battery, and a touchscreen display that displays an ultrasound image, the touchscreen display positioned on the portable tablet housing and including a touch actuated focal zone control and a focal range control;

wherein the touchscreen display displays a user interface enabling a user selection of a preset group of image control settings associated with an anatomical structure from among a plurality of presets for separate anatomical structures, and wherein each of the separate anatomical structures is associated with an imaging protocol performed by a separate machine learning algorithm;

a graphics processor in the portable tablet housing that is connected to the central processing unit wherein the graphics processor is configured to perform more than 1000 giga floating point operations per second to execute a machine learning algorithm based on the user selection using ultrasound image data in response to a touch actuated input on the touchscreen display, the machine learning algorithm to generating computed real time ultrasound images, wherein the generated computed real time ultrasound images are displayed on the touchscreen display; and an ultrasound beamformer processing circuit that receives image data from the transducer array, the ultrasound beamformer processing circuit being communicably connected to the computer.

2. The device of claim 1 wherein the graphics processor is connected to a core memory in the housing.

3. The device of claim 1 wherein the transducer array comprises a bi plane transducer array.

4. The device of claim 1 wherein the probe further comprises a laparoscopic imaging device.

5. The device of claim 1 further comprising a camera mounted with the probe wherein images generated by the camera are processed by the graphics processor.

6. The device of claim 1 wherein the graphics processor is configured to operate a neural network to perform a machine learning operation.

7. The device of claim 1, wherein the computer receives an input from the touchscreen display, the input being received at the first location inside a region of a virtual window in an ultrasound image display area on the touchscreen display.

8. The device of claim 7 wherein the input corresponds to a press gesture against the touch screen display.

9. The device of claim 1 wherein the transducer array comprises a plurality of transducer arrays in one or more transducer probe housings, at least one transducer array having a least 64 transducer elements, each operated by a probe beamformer processing circuit.

10. The device of claim 7 wherein the computer fixes a first cursor at the first location inside the region of the virtual window in response to a second input from the touch screen display.

11. The device of claim 10 wherein the computer performs at least one measurement on the ultrasound image based at least in part on the first cursor at the first location.

12. The device of claim 1 wherein the computer receives an input from a keyboard control panel or virtual control panel.

13. The device of claim 1 wherein the computer is connected to a shared memory.

14. The device of claim 10 wherein the computer displays a second cursor at a second location inside the region of the virtual window in response to a third input from the touch screen display.

15. The device of claim 14 wherein the computer processes at least one measurement with the ultrasound image based at least in part on the respective locations of the first and second cursors inside the region of the virtual window.

16. The device of claim 14 wherein the computer receives a fourth further input from the touchscreen display, the fourth further input being received inside the region of the virtual window.

17. The device of claim 16 wherein the fourth further input corresponds to a press and drag gesture against the touch screen display.

18. The device of claim 1 further comprising a bus connecting the graphics processor to the central processing unit (CPU).

19. The device of claim 18 further comprising a neural network that processes image data.

20. The device of claim 1 wherein the transducer array is connected to the housing with a transducer connector.

21. The device of claim 1 wherein the housing has a volume of less than 2500 cubic centimeters.

22. The device of claim 1 wherein the portable tablet housing mounts on a cart such that a plurality of transducers can be communicatively connected to the portable tablet housing.

23. The device of claim 22 wherein a multiplexor on the cart electrically connects to the portable tablet housing to connect to a plurality of transducer arrays.

24. The device of claim 23 wherein the portable tablet housing is detachable from the cart and mounted to a stand.

25. The device of claim 23 wherein the multiplexor can be switched using a touch gesture.

26. A method of operating a cart mounted medical ultrasound imaging device, the medical ultrasound imaging device comprising a transducer probe, a portable tablet housing having a computer system including a central processing unit in the portable tablet housing, the computer including at least one processor and at least one memory, a battery, a touchscreen display for displaying an ultrasound image, an ultrasound beamformer processing circuit disposed in the portable tablet housing, and a graphics processing unit in the portable tablet housing communicably coupled to the central processing unit, the graphics processing unit configured to perform more than 1000 giga floating point operations per second, the method comprising the steps of:

displaying on the touchscreen display a user interface enabling a user selection of a preset group of image control settings associated with an anatomical structure from among a plurality of presets for separate anatomical structures, and wherein each of the separate anatomical structures is associated with an imaging protocol performed by a separate machine learning algorithm;

receiving, at the computer, an input from the touchscreen display;

actuating a transmission of ultrasound pulses with a transducer array in the transducer probe wherein a field programmable gate array (FPGA) controls said transmission;

performing a beamforming operation to generate ultrasound image data; and performing a machine learning computational process to adjust ultrasound image data with a neural network using the graphics processing unit in response to a further touchscreen actuated input from the touchscreen display to display computed real time ultrasound images.

27. The method of claim 26 further comprising receiving, at the computer, a second input from the touch screen display.

28. The method of claim 27 wherein the second input corresponds to a double tap gesture against the touch screen display.

29. The method of claim 27 further comprising in response to the second input from the touch screen display, displaying a first cursor inside a region of a virtual window displaying a magnified image.

30. The method of claim 29 further comprising performing, by the computer, at least one measurement on the ultrasound image based at least in part on the first cursor at the first location.

31. The method of claim 30 further comprising in response to a third further input from the touch screen display, displaying a second cursor at a second location inside the region of the virtual window.

32. The method of claim 31 further comprising performing, by the computer, at least one measurement on the ultrasound image based at least in part on the respective locations of the first and second cursors inside the region of the virtual window.

33. The method of claim 31 further comprising receiving, at the computer, a fourth further input from the touchscreen display, the fourth further input being received inside the region of the virtual window.

34. The method of claim 33 wherein the fourth further input corresponds to a press and drag gesture against the touch screen display.

35. The method of claim 33 further comprising in response to the fourth further input from the touch screen display, providing a connecting line on the touch screen display extending from the first cursor across at least a portion of the ultrasound image to a second location inside the region of the virtual window.

36. The method of claim 26 wherein the transducer probe includes an electromagnetic (EM) sensor, the portable housing has a tablet form factor and a front panel, the computer including a touch screen display for displaying an ultrasound image, the touch screen display being disposed on the front panel, the touch screen display and the ultrasound beamformer processing circuit being communicably coupled to the computer, the method further comprising the steps of:

receiving ultrasound image data and camera image data of a region of interest.

* * * * *